United States Patent
Hubbell et al.

(10) Patent No.: US 10,821,157 B2
(45) Date of Patent: *Nov. 3, 2020

(54) GLYCOTARGETING THERAPEUTICS

(71) Applicants: Ecole Polytechnique Federale de Lausanne (EPFL), Lausanne (CH); Anokion SA, Ecublens (CH)

(72) Inventors: Jeffrey A. Hubbell, Chicago, IL (US); Stephane Kontos, Chavannes-Renens (CH); Kristen Marie Lorentz, Chavannes-Pres-Renens (CH); David Scott Wilson, Lausanne (CH); Shuning Gai, Gland (CH)

(73) Assignees: ANOKION SA, Ecublens (CH); ECOLE POLYTECHNIQUE FEDERALE DE LAUSANNE ("EPFL"), Lausanne (CH)

( * ) Notice: Subject to any disclaimer, the term of this patent is extended or adjusted under 35 U.S.C. 154(b) by 127 days.

This patent is subject to a terminal disclaimer.

(21) Appl. No.: 14/627,297

(22) Filed: Feb. 20, 2015

(65) Prior Publication Data

US 2016/0015821 A1    Jan. 21, 2016

Related U.S. Application Data

(60) Provisional application No. 61/942,942, filed on Feb. 21, 2014.

(51) Int. Cl.
| | | |
|---|---|---|
| A61K 39/00 | (2006.01) | |
| A61K 39/385 | (2006.01) | |
| A61K 38/38 | (2006.01) | |
| A61K 39/35 | (2006.01) | |
| A61K 47/54 | (2017.01) | |
| A61K 38/28 | (2006.01) | |

(52) U.S. Cl.
CPC .............. *A61K 38/38* (2013.01); *A61K 38/28* (2013.01); *A61K 39/001* (2013.01); *A61K 39/35* (2013.01); *A61K 39/385* (2013.01); *A61K 47/549* (2017.08); *A61K 47/555* (2017.08); *A61K 2039/555* (2013.01); *A61K 2039/577* (2013.01); *A61K 2039/60* (2013.01); *A61K 2039/6093* (2013.01); *A61K 2039/627* (2013.01); *C07K 2319/01* (2013.01)

(58) Field of Classification Search
None
See application file for complete search history.

(56) References Cited

U.S. PATENT DOCUMENTS

| | | |
|---|---|---|
| 4,671,958 A | 6/1987 | Rodwell et al. |
| 4,741,900 A | 5/1988 | Alvarez et al. |
| 4,859,449 A | 8/1989 | Mattes |
| 4,867,973 A | 9/1989 | Goers et al. |
| 4,950,738 A | 8/1990 | King et al. |
| 5,086,002 A | 2/1992 | Hillyard et al. |
| 5,140,104 A | 8/1992 | Coughlin et al. |
| 5,156,840 A | 10/1992 | Goers et al. |
| 5,162,512 A | 11/1992 | King et al. |
| 5,227,165 A | 7/1993 | Domb et al. |
| 5,227,293 A | 7/1993 | Stengelin et al. |
| 5,346,696 A | 9/1994 | Kim et al. |
| 5,358,857 A | 10/1994 | Stengelin et al. |
| 5,470,570 A | 11/1995 | Taylor et al. |
| 5,487,890 A | 1/1996 | Taylor et al. |
| 5,681,571 A | 10/1997 | Holmgren et al. |
| 5,698,679 A | 12/1997 | Nemazee et al. |
| 5,718,915 A | 2/1998 | Virtanen et al. |
| 5,879,679 A | 3/1999 | Taylor et al. |
| 5,885,808 A | 3/1999 | Spooner et al. |
| 5,886,143 A | 3/1999 | Theodore et al. |
| 5,948,639 A | 9/1999 | Gimeno et al. |
| 5,985,826 A | 11/1999 | Theodore et al. |
| 5,994,104 A | 11/1999 | Anderson et al. |
| 5,997,861 A | 12/1999 | Virtanen et al. |
| 6,022,564 A | 2/2000 | Takechi et al. |
| 6,090,925 A | 7/2000 | Woiszwillo et al. |
| 6,120,770 A | 9/2000 | Adams et al. |
| 6,153,203 A | 11/2000 | Holmgren et al. |
| 6,217,869 B1 | 4/2001 | Meyer et al. |
| 6,224,794 B1 | 5/2001 | Amsden et al. |
| 6,264,950 B1 | 7/2001 | Staerz |
| 6,322,796 B1 | 11/2001 | Holmgren et al. |
| 6,365,163 B1 | 4/2002 | Holmgren et al. |
| 6,379,699 B1 | 4/2002 | Virtanen et al. |
| 6,488,927 B2 | 12/2002 | Muzykantov et al. |
| 6,512,103 B1 | 1/2003 | Dairaghi et al. |
| 6,562,347 B1 | 5/2003 | Kwak et al. |
| 6,703,488 B1 | 3/2004 | Burton et al. |

(Continued)

FOREIGN PATENT DOCUMENTS

| | | |
|---|---|---|
| CN | 102791293 A | 11/2012 |
| CN | 103282380 A | 9/2013 |

(Continued)

OTHER PUBLICATIONS

Dieterich et al., Nat. Med. 3:797-801 (1997).*
Loma et al., Curr. Neuropharmac. 9:409-416 (2011) (Year: 2011).*
Meyer et al., Diabetes Care 26:1655-1656 (2003) (Year: 2003).*
See "Integer", Meriam-Webster, available online at https://www.merriam-webster.com/dictionary/integer, 12 pages (2019) (Year: 2019).*

(Continued)

*Primary Examiner* — Thea D'Ambrosio

(74) *Attorney, Agent, or Firm* — Knobbe, Martens, Olson & Bear, LLP

(57) ABSTRACT

Glycotargeting therapeutics are useful in the treatment of transplant rejection, autoimmune disease, food allergy, and immune response against a therapeutic agent.

26 Claims, 9 Drawing Sheets

Figure 1A:
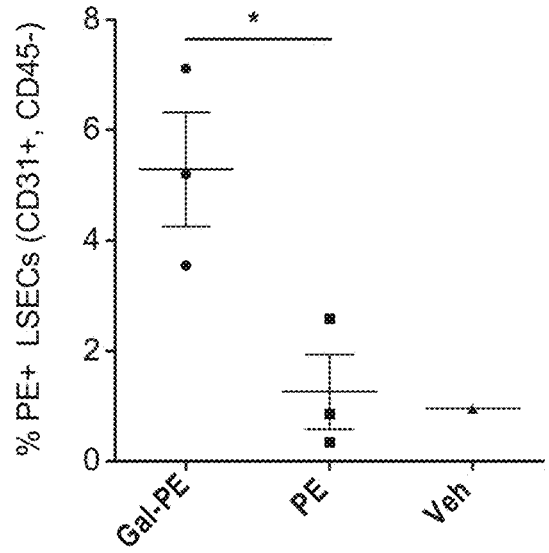
Figure 1B:
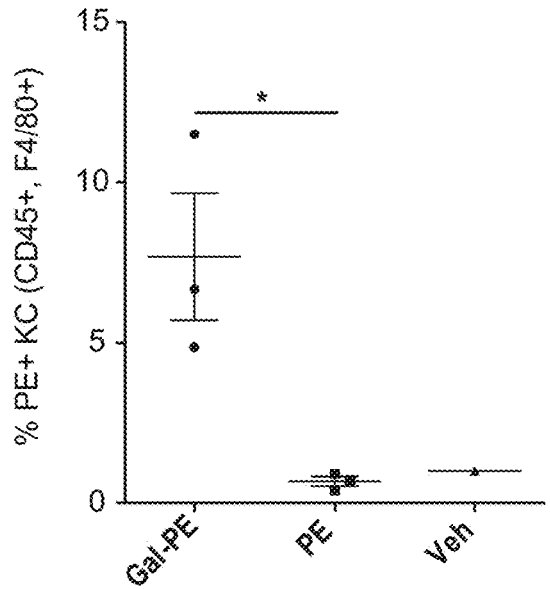
Figure 1C:
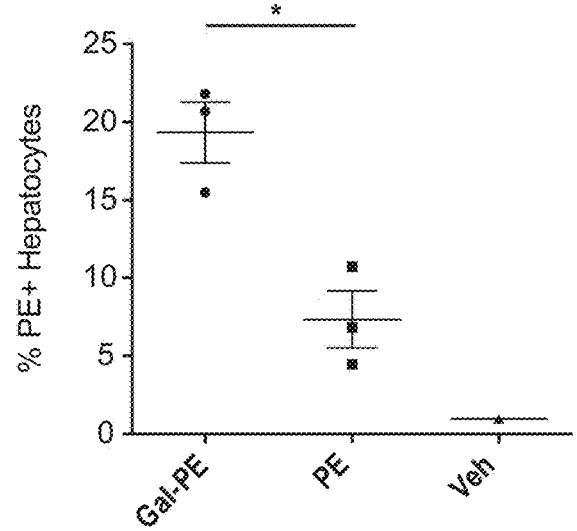
Figure 1D:
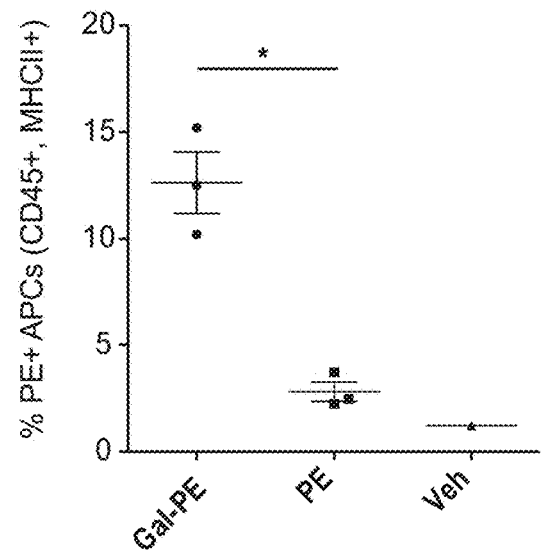

Specification includes a Sequence Listing.

(56) References Cited

U.S. PATENT DOCUMENTS

| | | |
|---|---|---|
| 6,737,057 B1 | 5/2004 | Zaghouani et al. |
| 6,814,964 B2 | 11/2004 | Virtanen et al. |
| 6,905,688 B2 | 6/2005 | Rosen et al. |
| 6,953,675 B2 | 10/2005 | Leung et al. |
| 7,041,287 B2 | 5/2006 | Muzykantov et al. |
| 7,132,475 B2 | 11/2006 | Hubbel et al. |
| 7,144,569 B1 | 12/2006 | Anderson et al. |
| 7,148,329 B1 | 12/2006 | Figdor et al. |
| 7,172,760 B2 | 2/2007 | Muzykantov et al. |
| 7,175,988 B2 | 2/2007 | Roschke et al. |
| 7,192,582 B2 | 3/2007 | Hudson et al. |
| 7,285,642 B2 | 10/2007 | Figdor et al. |
| 7,420,040 B2 | 9/2008 | Young et al. |
| 7,420,041 B2 | 9/2008 | Young et al. |
| 7,541,180 B2 | 6/2009 | Valiante et al. |
| 7,585,508 B1 | 9/2009 | Prendergast |
| 7,612,180 B2 | 11/2009 | Goldenberg et al. |
| 7,704,943 B2 | 4/2010 | Griffin et al. |
| 7,704,964 B2 | 4/2010 | Delcayre et al. |
| 7,786,267 B2 | 8/2010 | Zurawski et al. |
| 7,811,809 B2 | 10/2010 | Heyduk et al. |
| 7,837,997 B2 | 11/2010 | Muzykantov et al. |
| 7,884,190 B2 | 2/2011 | Cohen et al. |
| 7,888,460 B2 | 2/2011 | Anderson et al. |
| 7,892,743 B2 | 2/2011 | Owen et al. |
| 7,932,294 B2 * | 4/2011 | Satyam ............... C07C 323/12 514/707 |
| 7,994,283 B2 | 8/2011 | Valiante et al. |
| 8,007,805 B2 | 8/2011 | George et al. |
| 8,021,689 B2 | 9/2011 | Reddy et al. |
| 8,057,798 B2 | 11/2011 | Zurawski et al. |
| 8,058,400 B2 | 11/2011 | Figdor et al. |
| 8,058,406 B2 | 11/2011 | Mi et al. |
| 8,105,599 B2 | 1/2012 | Figdor et al. |
| 8,236,934 B2 | 8/2012 | Banchereau et al. |
| 8,252,902 B2 | 8/2012 | Barbas et al. |
| 8,273,357 B2 | 9/2012 | Hacohen et al. |
| 8,277,812 B2 | 10/2012 | Iannacone et al. |
| 8,318,912 B2 | 11/2012 | Simon |
| 8,323,696 B2 | 12/2012 | Hubbel et al. |
| 8,329,144 B2 | 12/2012 | Anderson et al. |
| 8,333,973 B2 | 12/2012 | Muzykantov et al. |
| 8,343,497 B2 | 1/2013 | Shi et al. |
| 8,343,498 B2 | 1/2013 | Alexis et al. |
| 8,425,910 B2 | 4/2013 | Mi et al. |
| 8,449,888 B2 | 5/2013 | Zurawski et al. |
| 8,507,237 B2 | 8/2013 | Hermet et al. |
| 8,518,410 B2 | 8/2013 | Zurawski et al. |
| 8,551,476 B2 | 10/2013 | Mi et al. |
| 8,562,998 B2 | 10/2013 | Shi et al. |
| 8,580,253 B2 | 11/2013 | Rubin-Bejerano et al. |
| 8,586,052 B2 | 11/2013 | Zurawski et al. |
| 8,591,905 B2 | 11/2013 | von Andrian et al. |
| 8,592,364 B2 | 11/2013 | Swartz et al. |
| 8,613,903 B2 | 12/2013 | Goldenberg et al. |
| 8,617,823 B2 | 12/2013 | Rubin-Bejerano et al. |
| 8,637,028 B2 | 1/2014 | Alexis et al. |
| 8,673,293 B2 | 3/2014 | Martin et al. |
| 8,685,408 B2 | 4/2014 | Tartour et al. |
| 8,722,047 B2 | 5/2014 | Goldenberg et al. |
| 8,728,481 B2 | 5/2014 | Banchereau et al. |
| 8,889,140 B2 | 11/2014 | Lee et al. |
| 8,906,381 B2 | 12/2014 | Iannacone et al. |
| 8,932,595 B2 | 1/2015 | Iannacone et al. |
| 8,961,991 B2 | 2/2015 | Zurawski et al. |
| 8,992,917 B2 | 3/2015 | Goldenberg et al. |
| 9,005,903 B2 | 4/2015 | Rubin-Bejerano et al. |
| 9,066,984 B2 | 6/2015 | Mi et al. |
| 9,102,730 B2 | 8/2015 | Zurawski et al. |
| 9,102,734 B2 | 8/2015 | Zurawski et al. |
| 9,187,561 B2 | 11/2015 | Goldenberg et al. |
| 9,216,156 B2 | 12/2015 | Fleury et al. |
| 9,233,072 B2 | 1/2016 | Alexis et al. |
| 9,234,040 B2 | 1/2016 | Zurawski et al. |
| 9,260,692 B2 | 2/2016 | Martin et al. |
| 9,308,280 B2 | 4/2016 | Shi et al. |
| 9,326,939 B2 | 5/2016 | Paulson et al. |
| 9,416,186 B2 | 8/2016 | Zurawski et al. |
| 9,439,859 B2 | 9/2016 | Alexis et al. |
| 9,453,074 B2 | 9/2016 | Oh et al. |
| 9,457,047 B2 | 10/2016 | Rubin-Bejerano et al. |
| 9,474,717 B2 | 10/2016 | von Andrian et al. |
| 10,046,056 B2 | 8/2018 | Hubbell et al. |
| 2002/0004037 A1 | 1/2002 | Koteliansky et al. |
| 2002/0038002 A1 | 3/2002 | Zaghouani |
| 2002/0081298 A1 | 6/2002 | Zaghouani |
| 2002/0103343 A1 | 8/2002 | Taylor et al. |
| 2002/0187131 A1 | 12/2002 | Hawiger et al. |
| 2002/0193572 A1 | 12/2002 | Leung et al. |
| 2003/0022826 A1 | 1/2003 | Haynes |
| 2003/0082643 A1 | 5/2003 | Hudson et al. |
| 2003/0103967 A1 | 5/2003 | Zaghouani |
| 2003/0104045 A1 | 6/2003 | Virtanen et al. |
| 2003/0175921 A1 | 9/2003 | Barbas et al. |
| 2003/0190676 A1 | 10/2003 | Barbas et al. |
| 2003/0211078 A1 | 11/2003 | Heavner |
| 2004/0052815 A1 | 3/2004 | Lycke |
| 2004/0077843 A1 | 4/2004 | Burton et al. |
| 2004/0146948 A1 | 7/2004 | Britton et al. |
| 2004/0147721 A1 | 7/2004 | Valiante |
| 2004/0185057 A1 | 9/2004 | Kirkby et al. |
| 2004/0197314 A1 | 10/2004 | Delcayre et al. |
| 2004/0258688 A1 | 12/2004 | Hawiger et al. |
| 2005/0031628 A1 | 2/2005 | George et al. |
| 2005/0053579 A1 | 3/2005 | Galipeau et al. |
| 2005/0113297 A1 | 5/2005 | Francois et al. |
| 2005/0118168 A1 | 6/2005 | Figdor et al. |
| 2005/0201973 A1 | 9/2005 | Virtanen et al. |
| 2005/0203022 A1 | 9/2005 | Gotwals et al. |
| 2005/0220804 A1 | 10/2005 | Figdor et al. |
| 2005/0250936 A1 | 11/2005 | Oppermann et al. |
| 2006/0034864 A1 | 2/2006 | Zaghouani |
| 2006/0127929 A1 | 6/2006 | Swager et al. |
| 2006/0153881 A1 | 7/2006 | Narum et al. |
| 2006/0173168 A1 | 8/2006 | Carlock et al. |
| 2006/0178299 A1 | 8/2006 | Anderson et al. |
| 2006/0257412 A1 | 11/2006 | Bowdish et al. |
| 2006/0280679 A1 | 12/2006 | Bowdish et al. |
| 2007/0059794 A1 | 3/2007 | Ideno et al. |
| 2007/0111222 A1 | 5/2007 | Chasm et al. |
| 2007/0122409 A1 | 5/2007 | Zaghouani |
| 2007/0190615 A1 | 8/2007 | Cohen et al. |
| 2007/0218053 A1 | 9/2007 | Zaghouani |
| 2008/0031899 A1 | 2/2008 | Reddy et al. |
| 2008/0131428 A1 | 6/2008 | Young et al. |
| 2008/0175971 A1 | 6/2008 | Anderson et al. |
| 2008/0160041 A1 | 7/2008 | Figdor et al. |
| 2008/0178299 A1 | 7/2008 | Merkle et al. |
| 2008/0206262 A1 | 8/2008 | Banchereau et al. |
| 2008/0213267 A1 | 9/2008 | Young et al. |
| 2008/0227707 A1 | 9/2008 | Carlock et al. |
| 2008/0233143 A1 | 9/2008 | Jackson et al. |
| 2008/0241170 A1 | 10/2008 | Zurawski et al. |
| 2008/0254044 A1 | 10/2008 | Zurawski |
| 2008/0261262 A1 | 10/2008 | Godfrin |
| 2008/0274092 A1 | 11/2008 | Godfrin et al. |
| 2008/0305104 A1 | 12/2008 | Young et al. |
| 2008/0318852 A1 | 12/2008 | Anderson et al. |
| 2009/0004218 A1 | 1/2009 | Hacohen et al. |
| 2009/0017039 A1 | 1/2009 | Mi et al. |
| 2009/0123467 A1 | 5/2009 | Bedi et al. |
| 2009/0130104 A1 | 5/2009 | Muzykantov et al. |
| 2009/0142263 A1 | 6/2009 | Young et al. |
| 2009/0149656 A1 | 6/2009 | Singaram et al. |
| 2009/0181011 A1 | 7/2009 | Zaghouani |
| 2009/0191118 A1 | 7/2009 | Young et al. |
| 2009/0202622 A1 | 8/2009 | Fleury et al. |
| 2009/0269285 A1 | 10/2009 | Anderson et al. |
| 2009/0280132 A1 | 11/2009 | Zaghouani |
| 2009/0317381 A1 | 12/2009 | Plaut et al. |
| 2009/0324538 A1 | 12/2009 | Wong et al. |
| 2010/0003266 A1 | 1/2010 | Simon |
| 2010/0003338 A1 | 1/2010 | Hubbell et al. |
| 2010/0015131 A1 | 1/2010 | Mi et al. |

(56) References Cited

U.S. PATENT DOCUMENTS

| | | |
|---|---|---|
| 2010/0055189 A1 | 3/2010 | Hubbell et al. |
| 2010/0092425 A1 | 4/2010 | Von Andrian et al. |
| 2010/0098718 A1 | 4/2010 | Valiante |
| 2010/0129392 A1 | 5/2010 | Shi et al. |
| 2010/0129439 A1 | 5/2010 | Alexis et al. |
| 2010/0129820 A1 | 5/2010 | Kool et al. |
| 2010/0222407 A1 | 9/2010 | Segura et al. |
| 2010/0233251 A1 | 9/2010 | Von Adrian et al. |
| 2010/0239575 A1 | 9/2010 | Banchereau et al. |
| 2010/0285015 A1 | 11/2010 | Muzykantov et al. |
| 2010/0291080 A1 | 11/2010 | Lee et al. |
| 2010/0291082 A1 | 11/2010 | Zurawski |
| 2010/0297114 A1 | 11/2010 | Zurawski |
| 2010/0310612 A1 | 12/2010 | DuFour et al. |
| 2010/0316620 A1 | 12/2010 | Bourgeaux et al. |
| 2010/0322929 A1 | 12/2010 | Zurawski et al. |
| 2010/0330115 A1 | 12/2010 | Zurawski et al. |
| 2011/0014171 A1 | 1/2011 | Bourgeaux et al. |
| 2011/0033426 A1 | 2/2011 | Martin et al. |
| 2011/0044912 A2 | 2/2011 | Anderson et al. |
| 2011/0045049 A1 | 2/2011 | Rubin-Bejerano et al. |
| 2011/0064709 A1 | 3/2011 | Miller et al. |
| 2011/0064754 A1 | 3/2011 | Taylor et al. |
| 2011/0082075 A1 | 4/2011 | Prendergast |
| 2011/0091493 A1 | 4/2011 | Mohamadzadeh et al. |
| 2011/0105379 A1 | 5/2011 | Shulman et al. |
| 2011/0123536 A1 | 5/2011 | Chermann et al. |
| 2011/0143994 A1 | 6/2011 | Lycke |
| 2011/0177532 A1 | 7/2011 | Rubin-Bejerano et al. |
| 2011/0200632 A1 | 8/2011 | Jackson et al. |
| 2011/0206759 A1 | 8/2011 | Swartz et al. |
| 2011/0268804 A1 | 11/2011 | Shi et al. |
| 2011/0268805 A1 | 11/2011 | Alexis et al. |
| 2011/0293644 A1 | 12/2011 | Anderson et al. |
| 2011/0311542 A1 | 12/2011 | Mi et al. |
| 2012/0004643 A1 | 1/2012 | Zurawski et al. |
| 2012/0009140 A1 | 1/2012 | Godfrin et al. |
| 2012/0014960 A1 | 1/2012 | Mi et al. |
| 2012/0027808 A1 | 2/2012 | Iannacone |
| 2012/0039989 A1 | 2/2012 | Hubbell et al. |
| 2012/0058180 A1 | 3/2012 | Kren et al. |
| 2012/0076831 A1 | 3/2012 | Miller et al. |
| 2012/0087890 A1 | 4/2012 | Iannacone et al. |
| 2012/0107301 A1 | 5/2012 | Bowdish et al. |
| 2012/0121570 A1 | 5/2012 | Godfrin |
| 2012/0121592 A1 | 5/2012 | Oh et al. |
| 2012/0128635 A1 | 5/2012 | Gregory et al. |
| 2012/0129210 A1 | 5/2012 | Bourgeaux et al. |
| 2012/0178139 A1 | 7/2012 | Hubbell et al. |
| 2012/0207745 A1 | 8/2012 | Godfrin et al. |
| 2012/0237513 A1 | 9/2012 | Zurawski et al. |
| 2012/0276095 A1 | 11/2012 | Langermann et al. |
| 2012/0282281 A1 | 11/2012 | Banchereau et al. |
| 2013/0004427 A1 | 1/2013 | El-Sayed et al. |
| 2013/0022634 A1 | 1/2013 | Lycke |
| 2013/0053543 A1 | 2/2013 | Davis et al. |
| 2013/0059299 A1 | 3/2013 | Parr et al. |
| 2013/0071413 A1 | 3/2013 | Simon |
| 2013/0078216 A1 | 3/2013 | Dunlevy et al. |
| 2013/0078267 A1 | 3/2013 | Anderson et al. |
| 2013/0101463 A1 | 4/2013 | Mambrini et al. |
| 2013/0115230 A1 | 5/2013 | Simon |
| 2013/0129790 A1 | 5/2013 | Alexis et al. |
| 2013/0164364 A1 | 6/2013 | Paulson et al. |
| 2013/0171074 A1 | 7/2013 | Barbas et al. |
| 2013/0171233 A1 | 7/2013 | Paulson et al. |
| 2013/0236533 A1 | 9/2013 | Von Adrian et al. |
| 2013/0287810 A1 | 10/2013 | Mohamadzadeh et al. |
| 2013/0287857 A1 | 10/2013 | Von Adrian et al. |
| 2013/0295120 A1 | 11/2013 | Zurawski et al. |
| 2013/0318648 A1 | 11/2013 | Anderson et al. |
| 2013/0323786 A1 | 12/2013 | Mi et al. |
| 2013/0336991 A1 | 12/2013 | Mi et al. |
| 2014/0037736 A1 | 2/2014 | Shi et al. |
| 2014/0079728 A1 | 3/2014 | Jackson et al. |
| 2014/0127198 A1 | 5/2014 | Zurawski et al. |
| 2014/0127301 A1 | 5/2014 | Alexis et al. |
| 2014/0134168 A1 | 5/2014 | Zurawski et al. |
| 2014/0199315 A1 | 7/2014 | Mi et al. |
| 2014/0205630 A1 | 7/2014 | Tartour |
| 2014/0212445 A1 | 7/2014 | Martin et al. |
| 2014/0227268 A1 | 8/2014 | Banchereau et al. |
| 2014/0234344 A1 | 8/2014 | Banchereau et al. |
| 2014/0308238 A1 | 10/2014 | Rubin-Bejerano et al. |
| 2014/0314865 A1 | 10/2014 | Von Adrian et al. |
| 2014/0377291 A1 | 12/2014 | Fischbach et al. |
| 2015/0104478 A1 | 4/2015 | Lee et al. |
| 2015/0166659 A1 | 6/2015 | Goldenberg et al. |
| 2015/0191730 A1 | 7/2015 | Levy et al. |
| 2015/0250862 A1 | 9/2015 | Cantor et al. |
| 2015/0299329 A1 | 10/2015 | Zurawski et al. |
| 2015/0307545 A1 | 10/2015 | Jackson et al. |
| 2016/0015821 A1 | 1/2016 | Hubbell et al. |
| 2016/0022792 A1 | 1/2016 | Zurawski et al. |
| 2016/0024212 A1 | 1/2016 | Goldenberg et al. |
| 2016/0031988 A1 | 2/2016 | Zurawski et al. |
| 2016/0058792 A1 | 3/2016 | Quintana et al. |
| 2016/0060324 A1 | 3/2016 | Paulson et al. |
| 2016/0060358 A1 | 3/2016 | Hay |
| 2016/0083468 A1 | 3/2016 | Mi et al. |
| 2016/0108096 A1 | 4/2016 | Thompson et al. |
| 2016/0243248 A1* | 8/2016 | Hubbell ............ A61K 47/48092 |
| 2016/0346384 A1 | 12/2016 | Porcelli et al. |
| 2016/0375126 A1 | 12/2016 | Oh et al. |
| 2017/0007708 A1* | 1/2017 | Hubbell ............ A61K 47/48092 |
| 2017/0020926 A1 | 1/2017 | Mata-Fink et al. |
| 2017/0066825 A1 | 3/2017 | Hubbell et al. |
| 2017/0066828 A1 | 3/2017 | Goldenberg et al. |
| 2017/0121379 A1 | 5/2017 | Zhang et al. |
| 2017/0137513 A1 | 5/2017 | Vallera et al. |
| 2017/0252417 A1 | 9/2017 | Irvine et al. |
| 2017/0296636 A9 | 10/2017 | Hubbell et al. |
| 2017/0320933 A1 | 11/2017 | Mannie |
| 2017/0326213 A1 | 11/2017 | Jajosky et al. |
| 2018/0000916 A1 | 1/2018 | Zurawski et al. |
| 2018/0094071 A1 | 4/2018 | Zurawski et al. |
| 2018/0100011 A1 | 4/2018 | Hubbell et al. |
| 2018/0104284 A1 | 4/2018 | Wallecha et al. |
| 2018/0117171 A1 | 5/2018 | Mooney et al. |
| 2018/0271986 A1 | 9/2018 | Hubbell et al. |
| 2018/0303951 A1 | 10/2018 | Hubbell et al. |
| 2019/0382479 A1 | 12/2019 | Hubbell et al. |
| 2020/0101146 A1 | 4/2020 | Hubbell et al. |
| 2020/0101169 A1 | 4/2020 | Hubbell et al. |
| 2020/0121762 A1 | 4/2020 | Hubbell et al. |
| 2020/0129601 A1 | 4/2020 | Hubbell et al. |
| 2020/0129625 A1 | 4/2020 | Hubbell et al. |
| 2020/0129629 A1 | 4/2020 | Hubbell et al. |

FOREIGN PATENT DOCUMENTS

| | | |
|---|---|---|
| CN | 103547272 A | 1/2014 |
| EP | 0119650 | 9/1984 |
| EP | 0175617 | 10/1991 |
| EP | 0088695 | 6/1992 |
| EP | 0173629 | 6/1992 |
| EP | 0480041 | 6/1993 |
| EP | 0308208 | 12/1993 |
| EP | 0251455 | 5/1994 |
| EP | 0294294 | 5/1995 |
| EP | 0789715 | 8/1997 |
| EP | 0808366 | 11/1997 |
| EP | 0722340 | 4/1998 |
| EP | 0505357 | 3/1999 |
| EP | 0602290 | 8/1999 |
| EP | 0978564 | 2/2000 |
| EP | 1012308 | 6/2000 |
| EP | 630407 | 8/2000 |
| EP | 1046651 | 10/2000 |
| EP | 1301541 | 4/2003 |
| EP | 0743856 | 7/2003 |
| EP | 1370588 | 12/2003 |
| EP | 1292621 | 9/2006 |
| EP | 1838734 | 10/2007 |

(56) References Cited

FOREIGN PATENT DOCUMENTS

| | | |
|---|---|---|
| EP | 1853313 | 11/2007 |
| EP | 1028978 | 1/2008 |
| EP | 1086137 | 6/2008 |
| EP | 1938836 | 7/2008 |
| EP | 1440156 | 8/2008 |
| EP | 1619208 | 10/2008 |
| EP | 1996701 | 12/2008 |
| EP | 1045861 | 3/2009 |
| EP | 2125012 | 12/2009 |
| EP | 1516881 | 6/2010 |
| EP | 2238986 | 10/2010 |
| EP | 2315779 | 5/2011 |
| EP | 1417229 | 6/2011 |
| EP | 2344185 | 7/2011 |
| EP | 2394657 | 12/2011 |
| EP | 2394661 | 12/2011 |
| EP | 2406290 | 1/2012 |
| EP | 2428226 | 3/2012 |
| EP | 2478917 | 7/2012 |
| EP | 2066294 | 10/2012 |
| EP | 2527363 | 11/2012 |
| EP | 2598120 | 6/2013 |
| EP | 2618817 | 7/2013 |
| EP | 2620157 | 7/2013 |
| EP | 2630967 | 8/2013 |
| EP | 1904104 | 9/2013 |
| EP | 1991564 | 9/2013 |
| EP | 2115129 | 11/2013 |
| EP | 2684889 | 1/2014 |
| EP | 1443963 | 5/2014 |
| EP | 1664270 | 5/2014 |
| EP | 2115002 | 8/2014 |
| EP | 1605974 | 11/2014 |
| EP | 1850832 | 12/2014 |
| EP | 2114985 | 12/2014 |
| EP | 2283358 | 4/2015 |
| EP | 2213742 | 1/2016 |
| EP | 2982695 | 2/2016 |
| EP | 2983791 | 2/2016 |
| EP | 2989123 | 3/2016 |
| EP | 2346528 | 4/2016 |
| EP | 2406286 | 5/2016 |
| EP | 2205273 | 9/2016 |
| EP | 3091034 | 11/2016 |
| EP | 2406288 | 12/2016 |
| EP | 2406289 | 2/2017 |
| EP | 2217269 | 4/2017 |
| EP | 2344186 | 4/2017 |
| EP | 2630966 | 4/2017 |
| JP | 2003-519619 | 6/2003 |
| JP | 2004-526452 | 9/2004 |
| JP | 2007-510915 | 4/2007 |
| JP | 2007-312776 | 12/2007 |
| JP | 2009-505049 | 2/2009 |
| JP | 2009-060894 | 3/2009 |
| JP | 2009-149664 | 7/2009 |
| JP | 2013-516967 | 5/2013 |
| JP | 2018-072431 | 8/2018 |
| WO | WO 1991/008770 | 6/1991 |
| WO | 9205801 | 4/1992 |
| WO | WO 92/22310 | 12/1992 |
| WO | WO 1995/06737 | 3/1995 |
| WO | 9522977 | 8/1995 |
| WO | WO 1996/023882 | 8/1996 |
| WO | WO 1996/040245 | 12/1996 |
| WO | 9806737 | 2/1998 |
| WO | WO 1999/036437 | 7/1999 |
| WO | WO 2000/074717 | 12/2000 |
| WO | WO 2001/022995 | 4/2001 |
| WO | WO 2001/025793 | 4/2001 |
| WO | WO 2002/004522 | 1/2002 |
| WO | WO 2002/072799 A | 9/2002 |
| WO | WO 2002/083262 A | 10/2002 |
| WO | WO 2003/066820 | 8/2003 |
| WO | WO 2003/104273 | 12/2003 |
| WO | WO 2004/034966 A2 | 4/2004 |
| WO | WO 2004/035619 | 4/2004 |
| WO | WO 2004/098645 | 11/2004 |
| WO | WO 2005/045436 A | 5/2005 |
| WO | WO 2005/105129 | 11/2005 |
| WO | WO 2006/002382 | 1/2006 |
| WO | WO 2006/016247 | 2/2006 |
| WO | WO 2006/093524 | 9/2006 |
| WO | WO 2007/008300 | 1/2007 |
| WO | WO 2007/017556 A | 2/2007 |
| WO | 2007097934 | 8/2007 |
| WO | WO 2007/098254 | 8/2007 |
| WO | WO 2007/099387 | 9/2007 |
| WO | WO 2007/099446 | 9/2007 |
| WO | 2007150020 | 12/2007 |
| WO | 2008063849 | 5/2008 |
| WO | WO 2008/063849 | 5/2008 |
| WO | WO 2009/019317 | 2/2009 |
| WO | 2009056332 | 5/2009 |
| WO | 2009078796 | 6/2009 |
| WO | WO 2009/086552 | 7/2009 |
| WO | 2010045518 | 4/2010 |
| WO | WO 2010/060155 | 6/2010 |
| WO | 2010085509 | 7/2010 |
| WO | WO 2010/076517 | 7/2010 |
| WO | 2011012715 | 2/2011 |
| WO | 2011051346 | 5/2011 |
| WO | WO 2011/086143 | 7/2011 |
| WO | WO 2011/092715 | 8/2011 |
| WO | 2012021512 | 2/2012 |
| WO | WO 2012/021512 | 2/2012 |
| WO | WO 2012/057671 | 5/2012 |
| WO | WO 2012/083185 | 6/2012 |
| WO | WO 2012/112690 | 8/2012 |
| WO | WO 2012/167088 | 12/2012 |
| WO | 2013121296 | 8/2013 |
| WO | WO 2013/160865 | 10/2013 |
| WO | WO 2014/011465 | 1/2014 |
| WO | WO 2014/023709 | 2/2014 |
| WO | WO 2014/052545 | 4/2014 |
| WO | WO 2014/135528 | 9/2014 |
| WO | WO 2014/169255 | 10/2014 |
| WO | WO 2015/140648 | 9/2015 |
| WO | WO 2015/157595 | 10/2015 |
| WO | WO 2015/171863 | 11/2015 |
| WO | WO 2015/175957 | 11/2015 |
| WO | WO 2016/022971 | 2/2016 |
| WO | WO 2016/044655 | 3/2016 |
| WO | WO 2016/044661 | 3/2016 |
| WO | WO 2016/070050 | 5/2016 |
| WO | WO 2016/210447 | 12/2016 |
| WO | WO 2017/015141 | 1/2017 |
| WO | WO 2017/023779 | 2/2017 |
| WO | WO 2017/025889 | 2/2017 |
| WO | WO 2017/041053 | 3/2017 |
| WO | WO2017/044308 | 3/2017 |
| WO | WO 2017/046652 | 3/2017 |
| WO | WO 2017/058996 | 4/2017 |
| WO | WO 2017/066484 | 4/2017 |
| WO | WO 2017/109134 | 6/2017 |
| WO | WO 2017/112899 | 6/2017 |
| WO | WO 2017/139498 | 8/2017 |
| WO | WO 2017/139787 | 8/2017 |
| WO | WO 2017/192785 | 11/2017 |
| WO | WO 2017/192786 | 11/2017 |
| WO | WO 2018/232176 | 12/2018 |
| WO | WO 2019/098682 | 5/2019 |
| WO | WO 2019/191079 | 10/2019 |
| WO | WO 2019/0215590 | 11/2019 |

OTHER PUBLICATIONS

U.S. Appl. No. 16/724,067, filed Dec. 2019, Hubbell et al.*
U.S. Appl. No. 16/723,914, filed Dec. 2019, Hubbell et al.*
U.S. Appl. No. 16/723,774, filed Dec. 2019, Hubbell et al.*
U.S. Appl. No. 16/723,757, filed Dec. 2019, Hubbell et al.*
"cMET-HGF Binding Peptide #65,", XP002717161, Retrieved From EBI Accession No. GSP:ADS33412 (Dec. 2, 2004).

(56) References Cited

OTHER PUBLICATIONS

"SubName: Full=Putative Integron Gene Cassette Protein; Flags: Fragment;", XP002717159, Retrieved From EBI Accession No. UNIPROT:B0BIT0, Database Accession No. B0BIT0 (Feb. 26, 2008).
"SubName: Full=Putative Transcriptional Regulator, ArsR Family;", XP002717163, Retrieved From EBI Accession No. UNIPROT:D2RZT2, Database Accession No. D2RZT2 (Mar. 2, 2010).
"SubName: Full=Putative Uncharacterized Protein;", XP002717158, Retrieved From EBI Accession No. Uniprot: C0NJE0, Database Accession No. CONJE0 (May 5, 2009).
"SubName: Full=Putative Uncharacterized Protein;", XP002717160, Retrieved From EBI Accession No. UNIPROT:B9PUP0, Database Accession No. B9PUP0 (Mar. 24, 2009).
"SubName: Full=Uncharacterized Protein;", XP002717157, Retrieved From EBI Accession No. UNIPROT:B5E9K2 Database Accession No. B5E9K2 (Oct. 14, 2008).
Bigbee et al., "Binding specificities of eight monoclonal antibodies to human glycophorin A—studies with McM, and MkEn(UK) variant human erythrocytes and M- and MNv-type chimpanzee erythrocytes," Dec. 1, 1984, J. Immunol., 133(6): 3149-3155 (1984).
Craig et al., "Processing of C3b-Opsonized Immune Complexes Bound to Non-Complement Receptor 1 Sites on Red Cells: Phagocytosis, Transfer and Associations with CR1," J. Immunol.
Crispe et al., "Cellular and molecular mechanisms of liver tolerance," Immunol Rev., 213: 101-118 (2006).
Di Lorenzo et al., "Translational Mini-Review Series on Type 1 Diabetes: Systemic analysis of T cell epitopes in autoimmune diabetes," 2007, Clin Exp Immunol, vol. 148: 1-146.
Gorovits et al., "Proposed mechanism of off-target toxicity for antibody-drug conjugates driven by mannose receptor uptake," Cancer Immunol Immunother (2013) 62:217-233.
Gorzelany et al., "Protein replacement therapies for rare diseases: a breeze for regulatory approval?" Science Translational Medicine 5, 178fs10 (2013).
International Search Report and Written Opinion from corresponding PCT Application No. PCT/IB2013/000684, 12 pages, dated Jul. 9, 2013.
International Search Report for Application No. PCT/EP2014/054161 dated May 26, 2014.
International Search Report and Written Opinion from corresponding PCT Application No. PCT/US2011/047078, 13 pages, dated May 1, 2012.
Janeway et al., Immuno Biology, 8th Edtition, Garland Science (2012) pp. 150-151.
Janeway et al., "The complement system and innate immunity," Immunology: the Immune System in Health and Disease, 5th Edition. New York: Garland Science (2001).
Murphy, "Antigen Recognition by B-Cell and T-cell Receptors," 2012, Janeway's Immuno Biology, 8th Edition, Chapter 4, Garland Science Taylor & Francis Goup, London and New York.
Kravtzoff et al., "Tolerance Evaluation of L-asparaginase loaded in red blood cells," 1996, Eur J Clin Pharmacol, vol. 51: 221-225.
La Rosa, et al., "The Innate Immune System in Allograft Rejection and Tolerance," J. Immunol., 2007, 178:7503-7509.
Li et al., "Targeting self- and foreign antigens to dendritic cells via Dc-Asgpr generates IL-10pproducing suppressive CD4+ T cells," Jan. 2, 2012, Journal of Experimental Medicine 209, 109-121 (2012).
Lutterotti, A. et al., "Antigen-Specific Tolerance by Autologous Myelin Peptide-Coupled Cells: A Phase 1 Trial in Multiple Sclerosis," Science Translational Medicine 5, 188ra75-188ra75 (2013).
Manidyala, S. et al, "Glycomimetic ligands for the human asialoglycoprotein receptor" J. Am Chem. Soc. Feb. 1, 2012, 134(4), pp. 1978-1981.
Nardin et al., "How are immune complexes bound to the primate erythrocyte complement receptor transferred to acceptor phagocytic cells," Mol. Immunol.
Qin, et al., Preparation and bioactivity of anti-hum red blood cell ScFv and CSFV E@ bifunctional fusion protein, Chin J. Biotech Jan. 25, 2010: 26(1): 28-34, Chinese Journal of Biotechnology (2010).
Reinagel et al., "The Primate Erythrocyte Complement Receptor (CR1) as a Priveleged Site: Binding of Immunoglobulin G to Erythrocyte CR1 Does Not Target Erythrocytes for Phagocytosis," 1997, Blood, vol. 89: p. 1068-1077.
Rigopoulou et al., "Asialoglycoprotein receptor (ASGPR) as target autoantigen in liver autoimmunity: Lost and found," Autoimmunity Reviews, 12 (2012) 260-269.
Saibeni et al., "Antibodies to tissue-type plasminogen activator (t-PA) in patients with inflammatory bowel disease: high prevalence, interactions with functional domains of t-PA and possible implications in thrombosis," J. Thrombosis and Haemostasis, 4:1510-1516 (2006).
Sakaguchi et al., "Regulatory T Cells and Immune Tolerance," Cell 133, May 30, 2008, 775-787.
Sehon et al., the Pharmacology and Toxicology of Proteins, Proceedings of Cetus—UCLA Symposium Held at Lake Tahoe, Ca, 2/21-28, 1987, Alan r. Liss, Inc.—New York.
Shan et al., "Structural Basis for Gluten Intolerance in Celiac Sprue," Science, 297, 2275 (2002).
St. Clair et al., "New Reagents on the Horizon for Immune Tolerance," Sep. 20, 2006, Annu. Rev. Med. 2007. 58:329-46.
Supplementary European Search Report from corresponding PCT Application No. PCT/US2011047078, 21 Pages, dated Jan. 22, 2014.
Taneja et al., "Lessons from animal models for human autoimmune diseases," Sep. 1, 2001, Nature Immunology, vol. 2, No. 9, 781-784 (Sep. 2001).
Trahtenherts, A. et al, "An internalizing antibody specific for the human asialoglycoprotein receptor" Hybridoma, vol. 28, No. 4, Aug. 1, 2009.
Updike et al., "Infusion of red blood cell-loaded asparaginase in monkey: Immunologic, metabolic, and toxicologic consequences," 1983, J Lab Clin Med, vol. 101(5): p. 679-691.
Wan, "Regulatory T cells: immune suppression and beyond," May 1, 2010, Cell Mol Immunol. May 2010; 7(3):204-210.
Zhao, X. et al "Construction and characterization of an anti-asialoglycoprotein receptor single-chain variable-fragment-targeted melittin" Biotechnol Appl. Biochem, Nov.-Dec. 2011; 58(6): pp. 405-411.
Coulstock et al., "Liver-targeting of interferon-alpha with tissue-specific domain antibodies" PLOS ONE, Public Library of Science, US, vol. 8, No. 2, Jan. 1, 2013.
Ducan, R. Development of HPMA copolymer-anticancer conjugates: Clinical experience and lessons learnt. Advanced Drug Delivery Reviews 61 (2009) pp. 1131-1148.
Grimm et al., "Memory of tolerance and induction of regulatory T cells by erythrocyte-targeted antigens." Scientific Reports, 5:159907.
Hasselberg et al, "ADP-ribosylation controls the outcome of tolerance or enhanced priming following mucosal immunization" The Journal of Immunology, Aug. 24, 2016.
Julyan et al "Preliminary clinical study of the distribution of HPMA copolymers bearing doxorubicin and galactosamine" Journal of Controlled Release 57 (1999) pp. 281-290.
Kopecek et al. "HPMA copolymers: Origins, early developments, present, and future." Advanced Drug Delivery Reviews 62, (2010) pp. 122-149.
Lorentz et al., "Engineered binding to erythrocytes induces immunological tolerance to E. coli asparaginase." Sci. Adv. 2015.
Magnani et al., "Red blood cells as an antigen-delivery system," Biotechnol Appl Biochem. Oct. 1992;16(2):188-94.
Meager et al., "Anti-cytokine autoantibodies in autoimmunity: preponderance of neutralizing autoantibodies against interferon-alpha, interferon-omega and interleukin-12 in patients with thymoma and or myasthenia gravis" Clinical and Experimental Immunology, Wiley-Blackwell Publishing Ltd, GB, vol. 132, No. 1, Apr. 1, 2003.
Seymour et al., "Hepatic Drug Targeting: Phase I evaluation of polymer-bound doxorubicin" Journal of Clinical Oncology, vol. 20, No. 6, Mar. 15, 2002, pp. 1668-1676.

(56) References Cited

OTHER PUBLICATIONS

Seymour et al., "N-(2-Hydroxypropyl)methacrylamide copolymers targeted to the hepatocyte galactose-receptor: pharmacokinetics in DBA2 mice." Br. J. Cancer (1991) 63, pp. 859-866.
Yoo et al., "N-Acetylgalactosamino dendrons as clearing agents to enhance liver targeting of model antibody-fusion protein." Bioconjugate Chemistry, vol. 24, No. 12, Dec. 18, 2013, pp. 2088-2103.
Miller et al.,"Antigen-specific tolerance strategies for the prevention and treatment of autoimmune disease." Nature Reviews Immunology 7(9):665-677, (Sep. 2007).
Moghimi et al., "Stealth liposomes and long circulating nanoparticles: critical issues in pharmacokinetics, opsonization and protein-binding properties." Progress in Lipid Research, vol. 42(6):463-478 (2003).
Mohandas et al.,"Red cell membrane: past, present, and future." Blood, vol. 112(10):3939-3948 (Nov. 15, 2008).
Mueller, "Mechanisms maintaining peripheral tolerance." Nature Immunology, vol. 11(1):21-27 (Jan. 2010).
Murray et al., "The Mouse Immune Response to Carrier Erythrocyte Entrapped Antigens", Vaccine, 24:6129-6139, (2006).
Muzykantov, "Drug Delivery by Red Blood Cells: Vascular Carriers Designed by Mother Nature", Expert Opinion Drug Delivery, 7(4):403-427, (Apr. 2010).
O'Neil et al., "Extracellular matrix binding mixed micelles for drug delivery applications." Journal of Control Release, vol. 137(2):146-151, (Mar. 27, 2009).
Parmeggiani et al., "Designed armadillo repeat proteins as general peptide-binding scaffolds: consensus design and computational optimization of the hydrophobic core." Journal of Molecular Biology, vol. 376(5):1282-1304 (2008).
Pasut et al.,"PEG conjugates in clinical development or use as anticancer agents: An overview." Advanced Drug Delivery Reviews, vol. 61(13):1177-1188 (2009).
Reddy et al., "In vivo targeting of dendritic cells in lymph nodes with polypropylene sulfide) nanoparticles." Journal of Controlled Release, vol. 112(1):26-34, (Mar. 10, 2006).
Reddy et al., "Exploiting lymphatic transport and complement activation in nanoparticle vaccines." Nature Biotechnology, vol. 25(10):1159-1164 (Oct. 2007).
Rice et al., "Directed evolution of a biterminal bacterial display scaffold enhances the display of diverse peptides." Protein Engineering, Design & Selection, vol. 21(7):435-442 (2008).
Rockey et al., "Synthesis and radiolabeling of chelator-RNA aptamer bioconjugates with copper-64 for targeted molecular imaging." Bioorganic & Medicinal Chemistry, vol. 19(13):4080-4090 (2011).
Ruoslahti et al.,"Targeting of drugs and nanoparticles to tumors." Journal of Cell Biology, vol. 188(6):759-768 (2010).
Rybak et al., "The extra-domain A of fibronectin is a vascular marker of solid tumors and metastases." Cancer Research, vol. 67(22)10948-10957 (2007).
Saint-Lu N et al., "Targeting the allergen to oral dendritic cells with mucoadhesive chitosan particles enhances tolerance induction.", Allergy, vol. 64(7)1003-1013 (2009).
Sampson, "Aptamers and SELEX: the technology.", World Patent Information, vol. (25):123-129 (2003).
Savla et al., "Tumor targeted quantum dot-mucin 1 aptamer-doxorubicin conjugate for imaging and treatment of cancer.", Journal of Controlled Release, vol. 153(1):16-22 (Feb. 20, 2011).
Schliemann et al., "In vivo biotinylation of the vasculature in B-cell lymphoma identifies BST-2 as a target for antibody-based therapy.", Vascular Blood, vol. 115(3):736-744 (Jan. 21, 2010).
Sehon et al., "Conversion of Antigens to Tolerogenic Derivatives by Conjugation with Monomethoxypolyethylene Clycol", The Pharmacology and Toxicology of Proteins, pp. 205-219 (1987).
Sheridan, "Fresh from the biologic pipeline—2009." Nature Biotechnology, vol. 28(4):307-310 (Apr. 2010).
Silverman et al., "Engineered cystine-knot peptides that bind vβ3 integrin with antibody-like affinities.", Journal of Molecular Biology, vol. 385(4):1064-1075 (Jan. 30, 2009).

Spitzer et al., "ScFv-Mediated in Vivo Targeting of DAF to Erythrocytes Inhibits Lysis by Complement", Molecular Immunology, vol. 40:911-919 (Oct. 30, 2003).
Steiner et al., "Efficient selection of DARPins with sub-nanomolar affinities using SRP phage display.", Journal of Molecular Biology, vol. 382(5):1211-1227 (2008).
Thijssen et al.,"Galectin-1 is essential in tumor angiogenesis and is a target for antiangiogenesis therapy.", Proceeding of the Natinoal Academy Sciences, vol. 103(43):15975-15980 (2006).
Thomson et al., "Antigen-presenting cell function in the tolerogenic liver environment.", National Reviews Immunology, vol. 10(11):753-766 (Nov. 2010).
Tobio et al., "Stealth PLA-PEG Nanoparticles as Protein Carriers for Nasal Administration", Pharmaceutical Research, 15(2):270-275, (1998).
Turley et al., "Prospects for Antigen-Specific Tolerance Based Therapies for the Treatment of Multiple Sclerosis", Results and Problems in Cell Differentiation, 51:217-235, (2010).
Van Der Vlies et al., "Synthesis of pyridyl disulfide-functionalized nanoparticles for conjugating thiol-containing small molecules, peptides, and proteins.", Bioconjugate Chemistry, vol. 21(4):653-662 (2010).
Velluto et al., "PEG-b-PPS Diblock Copolymer Aggregates for Hydrophobic Drug Solubilization and Release: Cyclosporin A as an Example", Molecular Pharmaceutics, 11 Pages, (May 2, 2008).
Vogl et al.,"Review on transarterial chemoembolization in hepatocellular carcinoma: Palliative, combined, neoadjuvant, bridging, and symptomatic indications.", European Journal Radiology, vol. 72(3):505-516 (2009).
Walker et al.,"Anti-serum albumin domain antibodies in the development of highly potent, efficacious and long-acting interferon." Protein Engineering Design & Selection, vol. 23(4):271-278 (2010).
Weisser et al.,"Applications of single-chain variable fragment antibodies in therapeutics and diagnostics." Biotechnology Advances, vol. 27(4):502-520 (2009).
Wilson et al., "Rapid Whole Blood Assay for HIV-1 Seropositivity Using an Fab-Peptide Conjugate", Journal of Immunological Methods, vol. 138:111-119 (1991).
Yamazaki et al., "CD8+ CD205+ splenic dendritic cells are specialized to induce Foxp3+ regulatory T cells.", Journal of Immunology, vol. 181(10):6923-6933 (2008).
Zaitsev et al., "Targeting of a Mutant Plasminogen Activator to Circulating Red Blood Cells for Prophylactic Fibrinolysis", The Journal of Pharmacology and Experimental Therapeutics, 332(3):1022-1031 and 976, (Nov. 30, 2009).
Albert et al., "Immature dendritic cells phagocytose apoptotic cells via vβ5 and CD36, and cross-present antigens to cytotoxic T lymphocytes." Journal of Experimental Medicine, vol. 188(7):1359-1368 (Oct. 5, 1998).
Arnaboldi et al., "Suppression of Th1 and Th17, but not Th2, responses in a CD8+ T cell-mediated model of oral tolerance." Mucosal Immunology, vol. 2(5):427-438 (Sep. 2009).
Bailon et al.,"Rational design of a potent, long-lasting form of interferon: A 40 kDa branched polyethylene glycol-conjugated interferon -2a for the treatment of hepatitis C." Bioconjugate Chemistry, vol. 12(2):195-202 (2001).
Brack et al., "Tumor-targeting properties of novel antibodies specific to the large isoform of tenascin-C." Clinic Cancer Research, vol. 12(10):3200-3208 (May 15, 2006).
Bursch et al., "Langerhans cells are not required for the CD8 T cell response to epidermal self-antigens." Journal of Immunology, vol. 182(8):4657-4664 (Apr. 15, 2009).
Cao et al., "Molecular Beacon Aptamers for Protein Monitoring in Real-Time and in Homogeneous Solutions", Current Proteomics, 2:31-40, (2005).
Chasis et al., "Signal Transduction by Glycophorin A: Role of Extracellular and Cytoplasmic Domains in a Modulatable Process", The Journal of Cell Biology,107:1351-1357, (Oct. 1988).
Chiarantini et al., "Red Blood Cells as Delivery System for Recombinant HSV-1 Glycoprotein B: Immunogenicity and Protection in Mice", Vaccine,15(3):276-280, (1997).

(56) References Cited

OTHER PUBLICATIONS

Dane et al., "Isolation of cell specific peptide ligands using fluorescent bacterial display libraries." Journal of Immunological Methods, vol. 309(1-2):120-129, (Jan. 11, 2006).
Darrah et al., "IL-10 production differentially influences the magnitude, quality, and protective capacity of Th1 responses depending on the vaccine platform." Journal of Experimental Medicine, vol. 207(7):1421-1433 (2010).
Dennis et al., "Albumin Binding as a General Strategy for Improving the Pharmacokinetics of Proteins." Journal of Biological Chemistry, vol. 277(38):35035-35043 (Sep. 20, 2002).
Devalapally et al., "Poly(ethylene oxide)-modified Poly(beta-amino ester) Nanoparticles as a pH-sensitive System for Tumor-targeted Delivery of Hydrophobic Drugs: Part 3. Therapeutic Efficacy and Safety Studies in Ovarian Cancer Xenograft Model", Cancer Chemotherapy Pharmacology, 59:477-484, (2007).
Dhalluin et al.,"Structural and biophysical characterization of the 40 kDa PEG-interferon-2a and its individual positional isomers." Bioconjugate Chemistry, vol. 16(3):504-517 (2005).
Dienst et al.,"Specific occlusion of murine and human tumor vasculature by VCAM-1-targeted recombinant fusion proteins." Journal of the National Cancer Institute, vol. 97(10):733-747, (2005).
"EPFL School of Life Sciences—Annual Report SV 2011" 156 Pages (Dec. 31, 2011).
Ferguson et al., "Armed response: How dying cells influence T-cell functions." Immunology Review, vol. 241 (1):77-88 (May 2011).
Fife et al.,"Insulin-induced remission in new-onset NOD mice is maintained by the PD-1-PD-L1 pathway." The Journal of Experimental Medicine, vol. 203(12):2737-2747, (Nov. 27, 2006).
Fishburn, "The pharmacology of PEGylation: balancing PD with PK to generate novel therapeutics." Journal of Pharmaceutical Sciences vol. 97(10):4167-4183 (Oct. 10, 2008).
Fonsatti et al.,"Targeting cancer vasculature via endoglin/CD105: A novel antibody-based diagnostic and therapeutic strategy in solid tumours." Cardiovascular Research, vol. 86(1):12-19, (2010).
Gadaleta et al.,"Trans-arterial chemoembolization as a therapy for liver tumours: New clinical developments and suggestions for combination with angiogenesis inhibitors." Critical Reviews in Oncology/Hematology, vol. 80:40-53 (2011).
Gao et al.,"In situ growth of a stoichiometric PEG-like conjugate at a protein's N-terminus with significantly improved pharmacokinetics." Proceedings of the National Academy Sciences vol. 106(36):15231-15236 (Sep. 8, 2009).
Getts et al. "Have We Overestimated the Benefit of Human(ized) Antibodies?" Landes Bioscience, 2(6):682-694, (Nov./Dec. 2010).
Getz et al. "Protease-Resistant Peptide Ligands From a Knottin Scaffold Library", ACS Chemical Biology, 8 Pages, (May 26, 2011).
Godsel et al., "Prevention of autoimmune myocarditis through the induction of antigen-specific peripheral immune tolerance." Circulation vol. 103(12):1709-1714 (2001).
Green et al., "Immunogenic and tolerogenic cell death." National Review of Immunology vol. 9(5):353-363, (May 2009).
Hackel et al., "Picomolar affinity fibronectin domains engineered utilizing loop length diversity, recursive mutagenesis, and loop shuffling." Journal of Molecular Biolology, vol. 381(5):1238-1252, (Sep. 19, 2008).
Hall et al.,"Identification of peptide ligands facilitating nanoparticle attachment to erythrocytes." Biotechnology Progess, vol. 23(3):749-754 (2007).
Holz et al., "CD8+ T cell tolerance following antigen recognition on hepatocytes." Journal of Autoimmunity, vol. 34 (1):15-22 (2010).
Huang et al.,"Tumor infarction in mice by antibody-directed targeting of tissue factor to tumor vasculature." Science, vol. 275(5299):547-550 (Jan. 24, 1997).
Huang et al.,"Characterization of polyethylene glycol and PEGylated products by LC/MS with postcolumn addition of amines." Analytical Chemistry, vol. 81(2):567-577 (Jan. 15, 2009).

Ichikawa et al., "Hepatic stellate cells function as regulatory bystanders." Journal of Immunology, vol. 186 (10):5549-5555 (May 15, 2011).
Keefe et al., "Aptamers as therapeutics." Nature Reviews Drug Discovery, vol. 9(7):537-550 (2010).
Kenrick et al., "Bacterial Display Enables Efficient and Quantitative Peptide Affinity Maturation", Protein Engineering Design & Selection, vol. 23(1):9-17 (2010).
Khandelwal et al., "Assessment of survival of aging erythrocyte in circulation and attendant changes in size and CD147 expression by a novel two step biotinylation method." Experimental Gerontology, vol. 41(9):855-861 (Aug. 4, 2006).
Kina et al., "The Monoclonal Antibody TER-119 Recognizes a Molecule Associated with Glycophorin A and Specifically Marks the Late Stages of Murine Erythroid Lineage", British Journal of Haematolgy, vol. 109:280-287 (2000).
Kontos et al., "Improving Protein Pharmacokinetics by Engineering Erythrocyte Affinity", Molecular Pharmaceutics, 7(6):2141-2147, (Sep. 10, 2010).
Kontos, "Engineering Erythrocyte Affinity for Improved Pharmacokinetics and Immune Tolerogenesis", 1 Page (2011) (Abstract Only).
Kontos, "Engineering Erythrocyte Affinity for Improved Pharmacokinetics and Immune Tolerogenesis", 106 Page (Apr. 27, 2011).
Kontos et al., "Engineering Antigens for in Situ Erythrocyte Binding Induces T-Cell Deletion", PNAS (Dec. 17, 2012).
Krebber et al., "Reliable Cloning of Functional Antibody Variable domains from Hybridomas and Spleen Cell Repertoires Employing a Reengineered Phage Display System", Journal of Immunological Methods, vol. 201:35-55 (1997).
Langer et al., "Optimization of the Preparation Process for Human Serum Albumin (HSA) Nanoparticles", International Journal of Pharmaceutics, 257:169-180, (2003).
Lee et al., "Aptamers as Molecular Recognition Elements for Electrical Nanobiosensors", Analytical and Bioanalytical Chemistry, 390:1023-1032, (2008).
Lee et al., "Signaling pathways downstream of pattern-recognition receptors and their cross talk." Annual Review of Biochemistry, vol. 76:447-480 (Feb. 28, 2007).
Liu et al., "Functional Nucleic Acid Sensors", Chemical Reviews, vol. 109(5):1948-1998, (May 2009).
Liu et al., "Immune tolerance after delivery of dying cells to dendritic cells in situ." Journal of Experimental Medicine, vol. 196(8):1091-1097 (Oct. 21, 2002).
Luo et al.,"ECDI-fixed allogeneic splenocytes induce donor-specific tolerance for long-term survival of islet transplants via two distinct mechanisms." Proceedings of National Academy of Science, vol. 105(38):14527-14532 (Sep. 23, 2008).
Lutolf et al., "Systematic modulation of Michael-type reactivity of thiols through the use of charged amino acids." Bioconjugate Chemistry vol. 12(6):1051-1056 (2001).
Lutolf et al., "Synthesis and Physicochemical Characterization of End-Linked Poly(ethylene glycol)-co-peptide Hydrogels Formed by Michael-Type Addition" Biomacromolecules, 4:713-722, (Feb. 1, 2003).
Maluccio et al.,"Transcatheter arterial embolization with only particles for the treatment of unresectable hepatocellular carcinoma." Journal of Vascular and Interventional Radiology, vol. 19(6):862-869 (2008), (synopsis only).
Maynard et al.,"Antibody engineering." Annual Review of Biomedical Engineering, vol. 2:339-376 (2000).
Ahmed et al., "Carbohydrate-based materials for targeted delivery of drugs and genes to the liver." Nanomedicine (Lond.) (205) 10(14), 2263-2288.
Jewett et al., "Cu-free click cycloaddition reactions in chemical biology," Chem Soc Rev. Apr. 2010; 39(4): 1272-1279.
Kim et al "Imaging and therapy of liver fibrosis using bioreducible polyethylenimine/siRNA complexes conjugated with N-acetylglucosamine as a targeting moiety" Biomaterials 34:6504-6514 (2013).
King et al. "Antibody responses to bee melittin (Api m 4) and hornet antigen 5 (Dol m 5) in mice treated with the dominant T-cell Epitope peptides" Journal of Allergy and Clinical Immunology, vol. 101, Issue 3, Mar. 1998, pp. 397-403.

(56) References Cited

OTHER PUBLICATIONS

Kim et el., "Specific Binding of Glucose-derivatized Polymers to the Asialoglycoprotein Receptor of Mouse Primary Hepatocytes." The Journal of Biological Chemistry, vol. 276, No. 38, pp. 35312-35319, Sep. 21, 2001.

Lepenies et al., "Targeting C-type lectin receptors with multivalent carbohydrate ligands." Adv. Drug Deliv. Rev. (2013).

Liu et al. "Hapten may play an important role in food allergen-related intestinal immune inflammation," North American Journal of Medical Sciences, vol. 3. No. 3. (Mar. 2011).

Medina et al., "Targeting hepatic cancer cells with pegylated dendrimers displaying N-acetylgalactosamine and SP94 peptide ligands" Advanced Healthcare Materials, vol. 2, Issue 10, pp. 1337-1350, Oct. 2013.

Sørensen et al., "Role of sialic acid for platelet life span: exposure of β-galactose results in the rapid clearance of platelets from the circulation by asialoglycoprotein receptor-expressing liver macrophages and hepatocytes." Blood, Aug. 20, 2009. vol. 114, No. 8.

Sun, et al, "Comparison between Ovalbumin and Ovalbumin Peptide 323-339 Responses in Allergic Mice: Humoral and Celluler Aspects," Scandinavian Journal of Immunology, vol. 71: 329-335 (Jan. 2010).

Andre et al., "Determination of modulation of ligand properties of synthetic complex-type biantennary N-glycans by introduction of bisecting GlcNAc in silico, in vitro and in vivo" Eur. J. Biochem. 2004;271(1):118-134.

Geng et al., "Site-directed conjugation of "clicked" glycopolymers for form glycoprotein mimics: binding to mammalian lectin and induction of immunological function." J Am Chem Soc. Dec. 12, 2007;129(49):15156-63.

Gupta et al., "Expression, purification, and characterization of an anti-RBCFab-p24 fusion protein for hemagglutination-based rapid detection of antibodies to HIV in whole blood." Protein Expression and Purification 26 (2002) 162-170.

Jones et al., "Localization of Pectic Galactan in Tomato Cell Walls Using a Monoclonal Antibody Specific to (1->4)-β-D-Galactan" Plant Physiol. 1997; 113:1405-1412.

Lehrman et al., "The Binding of Fucose-containing Glycoproteins by Hepatic Lectins" The Journal of Biological Chemistry Jun. 5, 1986; 261, 7426-7432.

Nishikawa et al. "Galactosylated proteins are recognized by the liver according to the surface density of galactose moieties" The American journal of physiology Jun. 1995; 268(5 Pt 1):G849-56, Abstract.

Staud et al., "Liver uptake and hepato-biliary transfer of galactosylated proteins in rats are determined by the extent of galactosylation" Biochimica et Biophysica Acta May 1999; 1427(2):183-192, Abstract.

Taylor et al., "Anti-glycophorin single-chain Fv fusion to low-affinity mutant erythropoietin improves red blood cell-lineage specificity", Protein Engineering, Design & Selection, vol . 23, No. 4 pp. 251-260, 2010.

Zhong et al., Biomacromalecules 14:3723-3730 (2013).

Wang et al., J Polymer Sci. 49:3280-3290 (2011).

Qin et al., Bioconjugate Chem. 22:1503-1512 (2011).

Bielekova et al., "Expansion and Functional Relevance of High-Avidity Myelin-Specific CD4 T Cells in Multiple Sclerosis," J Immunol 2004; 172:3893-3904.

Dornmair Klaus et al: "T-cell-mediated autoimmunity: Novel techniques to characterize autoreactive T-cell receptors", American Journal of Pathology, vol. 163, No. 4, Oct. 2003 (Oct. 2003), pp. 1215-1226, ISSN: 0002-9440.

Folgori A et al: "A general strategy to identify mimotopes of pathological antigens using only random peptide libraries and huamn sera", EMBO (European Molecular Biology Organization) Journal, vol. 13, No. 9, May 1, 1994 (May 1, 1994), pp. 2236-2243, ISSN: 0261-4189.

Granoff et al., "A Novel Mimetic Antigen Eliciting Protective Antibody to Neisseria meningitidis" J Immunol 2001; 167:6487-6496.

Mamidyala, et al., "Glycomimetic Ligands for the Human Asialoglycoprotein Receptor", Journal of the American Chemical Society, Jan. 24, 2012, vol. 134, p. 1978-1981.

Kontos, S: "Engineering Erythrocyte Affinity for Improved Pharmacokinetics and Immune Tolerogenesis", Thesis Ecole polytechnique federale de Lausanne EPFL , Jun. 23, 2011, 106 pages.

Moreau et al, "PEPOP: Computational design of immunogenic peptides" BioMed Central, Jan. 30, 2008, 15 pages.

Seamons et al. Immune Tolerance to Myelin Proteins (Immunologic Research 2003; 28/3:201-221).

Teitelbaum et al., Immunomodulation of experimental autoimmune encephalomyelitis by oral administration of copolymer 1. Pro. Natl. Acad. Sci. USA vol. 96, pp. 3842-3847, Mar. 1999.

Tye-Din, et al. "Comprehensive, Quantitive Mapping of T Cell Epitopes in Gluten in Celiac Disease", www.ScienceTranslationalMedicine.org, Jul. 21, 2010, vol. 2 Issue 41, in 14 pages.

Yeste Ada et al: "Antigen Microarrays for the Study of Autoimmune Diseases", Clinical Chemistry, vol. 59, No. 7, Jul. 2013 (Jul. 2013), pp. 1036-1044, ISSN: 0009-9147(print).

Ciccocioppo, R. et al, "The immune recognition of gluten in coeliac disease", British Society for Immunology, Clinical and Experimental Immunology, Feb. 1, 2005, pp. 408-416.

Immunogenic, Definition of Immunogenic by Merriam-Webster, https://www.merriam-webster.com/dictionary/immunogenic[May 10, 2019 11:59:27 AM], retrieved on May 10, 2019, in 9 pages.

Dominguez-Soto, et al., "The DC-SIGN-related lectin LSECtin mediates antigen capture and pathogen binding by human myeloid cells" www.bloodjournal.org. Immunobiology, Jun. 15, 2007, vol. 109, No. 12, pp. 5337-5345.

Gurwitz, "Peptide Mimetics: Fast-Forward Look" Drug Development Research 78:231-235, Year 2017.

Kontos, et al., "Engineering antigen-specific immunological tolerance", www.sciencedirect.com, Current Opinion in Immunology, Jul. 8, 2015, 35:80-88.

Baker, et al. "Hybrid Insulin Peptides are Autoantigens in Type 1 Diabetes", Diabetes, Sep. 2019, vol. 68, pp. 1830-1840.

Caja et al., "Antibodies in celiac disease: implications beyond diagnostics," Cellular & Molecular Immunology (2011) 8, 103-109.

Lobst et al., "Selective Sugar Binding to the Carbohydrate Recognition Domains of the Rat Hepatic and Macrophage Asialoglycoprotein Receptors." The Journal of Biological Chemistry, vol. 271, No. 12, Issue Mar. 22, 1996, 6686-6693.

Mitea, C. et al., "A Universal Approach to Eliminate Antigenic Properties of Alpha-Gliadin Peptides in Celiac Disease." PLoS One, vol. 5, Issue 12, e15637, pp. 1-9, Dec. 2010.

Nakayama, et al., "Determining Antigen Specificity of Human Islet Infiltrating T Cells in Type 1 Diabetes", Frontiers in Immunology, Mar. 8, 2019, vol. 10, pp. 1-7.

Rajpal, Arvind, et al. "A general method for greatly improving the affinity of antibodies by using combinatorial libraries", PNAS, www.pnas.org/cgi/doi/10.1073/pnas.0503543102, vol. 102 No. 24, pp. 8466-8471, Jun. 14, 2005.

Shen "A galactosamine-mediated drug delivery carrier for targeted liver cancer therapy" Pharmacological Research 64 (2011) 410-419.

Wilson, D.B., "Kent et al. Replying to: D.B. Wilson", Nature, 438, 2005.

Wu, Herren, "Simultaneous Humanization and Affinity Optimization of Monoclonal Antibodies", Methods in Molecular Biology, vo. 207: Recombinant Antibodies for Cancer Therapy: Methods and Protocols, Tolowa, NJ, pp. 197-212, Jan. 1, 2003.

https://en.wikipedia.org/wiki/Tenecteplase, accessed Apr. 13, 2020, printed Apr. 23, 2020 in 4 pages.

https://en.wikipedia.org/wiki/Reteplase accessed Apr. 13, 2020, printed Apr. 23, 2020 in 2 pages.

\* cited by examiner

SEQUENCE LISTING

```
<160> NUMBER OF SEQ ID NOS: 31

<210> SEQ ID NO 1
<211> LENGTH: 6
<212> TYPE: PRT
<213> ORGANISM: Artificial Sequence
<220> FEATURE:
<223> OTHER INFORMATION: Synthetic His tag

<400> SEQUENCE: 1

His His His His His His
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic fragment

<400> SEQUENCE: 2

Gly Gly Gly Ser
1

<210> SEQ ID NO 3
<211> LENGTH: 20
<212> TYPE: PRT
<213> ORGANISM: Homo sapiens

<400> SEQUENCE: 3

Met Glu Thr Asp Thr Leu Leu Leu Trp Val Leu Leu Leu Trp Val Pro
1               5                   10                  15

Gly Ser Thr Gly
            20

<210> SEQ ID NO 4
<211> LENGTH: 22
<212> TYPE: PRT
<213> ORGANISM: Homo sapiens
```

<400> SEQUENCE: 4

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 5
<211> LENGTH: 110
<212> TYPE: PRT
<213> ORGANISM: Homo sapiens

<400> SEQUENCE: 5

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 6
<211> LENGTH: 585
<212> TYPE: PRT
<213> ORGANISM: Homo sapiens

<400> SEQUENCE: 6

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

```
Arg Tyr Phe Asn Gln Leu Ser Thr Gly Leu Asp Met Val Gly Leu Ala
            180                 185                 190
Ala Asp Trp Leu Thr Ser Thr Ala Asn Thr Asn Met Phe Thr Tyr Glu
        195                 200                 205
Ile Ala Pro Val Phe Val Leu Leu Glu Tyr Val Thr Leu Lys Lys Met
    210                 215                 220
Arg Glu Ile Ile Gly Trp Pro Gly Gly Ser Gly Asp Gly Ile Phe Ser
225                 230                 235                 240
Pro Gly Gly Ala Ile Ser Asn Met Tyr Ala Met Met Ile Ala Arg Phe
                245                 250                 255
Lys Met Phe Pro Glu Val Lys Glu Lys Gly Met Ala Ala Leu Pro Arg
            260                 265                 270
Leu Ile Ala Phe Thr Ser Glu His Ser His Phe Ser Leu Lys Lys Gly
        275                 280                 285
Ala Ala Ala Leu Gly Ile Gly Thr Asp Ser Val Ile Leu Ile Lys Cys
    290                 295                 300
Asp Glu Arg Gly Lys Met Ile Pro Ser Asp Leu Glu Arg Arg Ile Leu
305                 310                 315                 320
Glu Ala Lys Gln Lys Gly Phe Val Pro Phe Leu Val Ser Ala Thr Ala
                325                 330                 335
Gly Thr Thr Val Tyr Gly Ala Phe Asp Pro Leu Leu Ala Val Ala Asp
            340                 345                 350
Ile Cys Lys Lys Tyr Lys Ile Trp Met His Val Asp Ala Ala Trp Gly
        355                 360                 365
Gly Gly Leu Leu Met Ser Arg Lys His Lys Trp Lys Leu Ser Gly Val
    370                 375                 380
Glu Arg Ala Asn Ser Val Thr Trp Asn Pro His Lys Met Met Gly Val
385                 390                 395                 400
Pro Leu Gln Cys Ser Ala Leu Leu Val Arg Glu Glu Gly Leu Met Gln
                405                 410                 415
Asn Cys Asn Gln Met His Ala Ser Tyr Leu Phe Gln Gln Asp Lys His
            420                 425                 430
Tyr Asp Leu Ser Tyr Asp Thr Gly Asp Lys Ala Leu Gln Cys Gly Arg
        435                 440                 445
His Val Asp Val Phe Lys Leu Trp Leu Met Trp Arg Ala Lys Gly Thr
    450                 455                 460
Thr Gly Phe Glu Ala His Val Asp Lys Cys Leu Glu Leu Ala Glu Tyr
465                 470                 475                 480
Leu Tyr Asn Ile Ile Lys Asn Arg Glu Gly Tyr Glu Met Val Phe Asp
                485                 490                 495
Gly Lys Pro Gln His Thr Asn Val Cys Phe Trp Tyr Ile Pro Pro Ser
            500                 505                 510
Leu Arg Thr Leu Glu Asp Asn Glu Glu Arg Met Ser Arg Leu Ser Lys
        515                 520                 525
Val Ala Pro Val Ile Lys Ala Arg Met Met Glu Tyr Gly Thr Thr Met
    530                 535                 540
Val Ser Tyr Gln Pro Leu Gly Asp Lys Val Asn Phe Phe Arg Met Val
545                 550                 555                 560
Ile Ser Asn Pro Ala Ala Thr His Gln Asp Ile Asp Phe Leu Ile Glu
                565                 570                 575
Glu Ile Glu Arg Leu Gly Gln Asp Leu
            580                 585
```

<210> SEQ ID NO 7
<211> LENGTH: 355
<212> TYPE: PRT
<213> ORGANISM: Homo sapiens

<400> SEQUENCE: 7

Met Asp Phe Leu His Arg Asn Gly Val Leu Ile Ile Gln His Leu Gln
1               5                   10                  15

Lys Asp Tyr Arg Ala Tyr Tyr Thr Phe Leu Asn Phe Met Ser Asn Val
            20                  25                  30

Gly Asp Pro Arg Asn Ile Phe Phe Ile Tyr Phe Pro Leu Cys Phe Gln
        35                  40                  45

Phe Asn Gln Thr Val Gly Thr Lys Met Ile Trp Val Ala Val Ile Gly
    50                  55                  60

Asp Trp Leu Asn Leu Ile Phe Lys Trp Ile Leu Phe Gly His Arg Pro
65                  70                  75                  80

Tyr Trp Trp Val Gln Glu Thr Gln Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ala Ser Cys Val Trp Tyr Val Met Val Thr
        115                 120                 125

Ala Ala Leu Ser His Thr Val Cys Gly Met Asp Lys Phe Ser Ile Thr
    130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190

Phe Glu His Thr Pro Gly Ile Gln Thr Ala Ser Leu Gly Thr Tyr Leu
        195                 200                 205

Lys Thr Asn Leu Phe Leu Phe Leu Phe Ala Val Gly Phe Tyr Leu Leu
    210                 215                 220

Leu Arg Val Leu Asn Ile Asp Leu Leu Trp Ser Val Pro Ile Ala Lys
225                 230                 235                 240

Lys Trp Cys Ala Asn Pro Asp Trp Ile His Ile Asp Thr Thr Pro Phe
                245                 250                 255

Ala Gly Leu Val Arg Asn Leu Gly Val Leu Phe Gly Leu Gly Phe Ala
            260                 265                 270

Ile Asn Ser Glu Met Phe Leu Leu Ser Cys Arg Gly Gly Asn Asn Tyr
        275                 280                 285

Thr Leu Ser Phe Arg Leu Leu Cys Ala Leu Thr Ser Leu Thr Ile Leu
    290                 295                 300

Gln Leu Tyr His Phe Leu Gln Ile Pro Thr His Glu Glu His Leu Phe
305                 310                 315                 320

Tyr Val Leu Ser Phe Cys Lys Ser Ala Ser Ile Pro Leu Thr Val Val
                325                 330                 335

Ala Phe Ile Pro Tyr Ser Val His Met Leu Met Lys Gln Ser Gly Lys
            340                 345                 350

Lys Ser Gln
        355

<210> SEQ ID NO 8
<211> LENGTH: 304

<212> TYPE: PRT
<213> ORGANISM: Homo sapiens

<400> SEQUENCE: 8

```
Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
        195                 200                 205

Lys Ser His Gly Arg Thr Gln Asp Glu Asn Pro Val Val His Phe Phe
210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
        275                 280                 285

Lys Leu Gly Gly Arg Asp Ser Arg Ser Gly Ser Pro Met Ala Arg Arg
290                 295                 300
```

<210> SEQ ID NO 9
<211> LENGTH: 247
<212> TYPE: PRT
<213> ORGANISM: Homo sapiens

<400> SEQUENCE: 9

```
Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45
```

-continued

```
Val Glu Leu Pro Cys Arg Ile Ser Pro Gly Lys Asn Ala Thr Gly Met
 50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Ala Ala Met Glu Leu Lys Val
130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
    210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 10
<211> LENGTH: 277
<212> TYPE: PRT
<213> ORGANISM: Homo sapiens

<400> SEQUENCE: 10

Met Gly Leu Leu Glu Cys Cys Ala Arg Cys Leu Val Gly Ala Pro Phe
 1               5                  10                  15

Ala Ser Leu Val Ala Thr Gly Leu Cys Phe Phe Gly Val Ala Leu Phe
                 20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
        50                  55                  60

Ile His Ala Phe Gln Tyr Val Ile Tyr Gly Thr Ala Ser Phe Phe Phe
 65                  70                  75                  80

Leu Tyr Gly Ala Leu Leu Leu Ala Glu Gly Phe Tyr Thr Thr Gly Ala
                 85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175
```

Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
            195                 200                 205

Val Leu Pro Trp Asn Ala Phe Pro Gly Lys Val Cys Gly Ser Asn Leu
210                 215                 220

Leu Ser Ile Cys Lys Thr Ala Glu Phe Gln Met Thr Phe His Leu Phe
225                 230                 235                 240

Ile Ala Ala Phe Val Gly Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
            275

<210> SEQ ID NO 11
<211> LENGTH: 20
<212> TYPE: PRT
<213> ORGANISM: Homo sapiens

<400> SEQUENCE: 11

Lys Tyr Leu Ala Thr Ala Ser Thr Met Asp His Ala Arg His Gly Phe
1               5                   10                  15

Leu Pro Arg His
            20

<210> SEQ ID NO 12
<211> LENGTH: 16
<212> TYPE: PRT
<213> ORGANISM: Homo sapiens

<400> SEQUENCE: 12

Glu Asn Pro Trp His Phe Phe Lys Asn Ile Val Thr Pro Arg Thr Pro
1               5                   10                  15

<210> SEQ ID NO 13
<211> LENGTH: 19
<212> TYPE: PRT
<213> ORGANISM: Homo sapiens

<400> SEQUENCE: 13

Leu Ser Arg Phe Ser Trp Gly Ala Glu Gly Gln Arg Pro Gly Phe Gly
1               5                   10                  15

Tyr Gly Gly

<210> SEQ ID NO 14
<211> LENGTH: 25
<212> TYPE: PRT
<213> ORGANISM: Homo sapiens

<400> SEQUENCE: 14

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 15
<211> LENGTH: 20
<212> TYPE: PRT
<213> ORGANISM: Homo sapiens -continued

<400> SEQUENCE: 15

Gly Gln Phe Arg Val Ile Gly Pro Arg His Pro Ile Arg Ala Leu Val
1               5                   10                  15

Gly Asp Glu Val
            20

<210> SEQ ID NO 16
<211> LENGTH: 20
<212> TYPE: PRT
<213> ORGANISM: Homo sapiens

<400> SEQUENCE: 16

Met Glu Val Gly Trp Tyr Arg Pro Pro Phe Ser Arg Trp His Leu Tyr
1               5                   10                  15

Arg Asn Gly Lys
            20

<210> SEQ ID NO 17
<211> LENGTH: 16
<212> TYPE: PRT
<213> ORGANISM: Homo sapiens

<400> SEQUENCE: 17

His Cys Leu Gly Lys Trp Leu Gly His Pro Asp Lys Phe Val Gly Ile
1               5                   10                  15

<210> SEQ ID NO 18
<211> LENGTH: 118
<212> TYPE: PRT
<213> ORGANISM: Homo sapiens

<400> SEQUENCE: 18

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
                20                  25                  30

Leu Thr Val Ile Leu Gly Val Leu Leu Leu Ile Gly Cys Trp Tyr Cys
            35                  40                  45

Arg Arg Arg Asn Gly Tyr Arg Ala Leu Met Asp Lys Ser Leu His Val
        50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 19
<211> LENGTH: 529
<212> TYPE: PRT
<213> ORGANISM: Homo sapiens

<400> SEQUENCE: 19

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
                20                  25                  30

```
Lys Glu Cys Cys Pro Pro Trp Ser Gly Asp Arg Ser Pro Cys Gly Gln
     35                  40                  45

Leu Ser Gly Arg Gly Ser Cys Gln Asn Ile Leu Leu Ser Asn Ala Pro
 50                  55                  60

Leu Gly Pro Gln Phe Pro Phe Thr Gly Val Asp Asp Arg Glu Ser Trp
 65                  70                  75                  80

Pro Ser Val Phe Tyr Asn Arg Thr Cys Gln Cys Ser Gly Asn Phe Met
                 85                  90                  95

Gly Phe Asn Cys Gly Asn Cys Lys Phe Gly Phe Trp Gly Pro Asn Cys
                100                 105                 110

Thr Glu Arg Arg Leu Leu Val Arg Arg Asn Ile Phe Asp Leu Ser Ala
            115                 120                 125

Pro Glu Lys Asp Lys Phe Phe Ala Tyr Leu Thr Leu Ala Lys His Thr
        130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
            180                 185                 190

Glu Ile Trp Arg Asp Ile Asp Phe Ala His Glu Ala Pro Ala Phe Leu
        195                 200                 205

Pro Trp His Arg Leu Phe Leu Leu Arg Trp Glu Gln Glu Ile Gln Lys
    210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
                260                 265                 270

Gln Ile Val Cys Ser Arg Leu Glu Glu Tyr Asn Ser His Gln Ser Leu
            275                 280                 285

Cys Asn Gly Thr Pro Glu Gly Pro Leu Arg Arg Asn Pro Gly Asn His
        290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr
                340                 345                 350

Gly Ile Ala Asp Ala Ser Gln Ser Ser Met His Asn Ala Leu His Ile
            355                 360                 365

Tyr Met Asn Gly Thr Met Ser Gln Val Gln Gly Ser Ala Asn Asp Pro
        370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
        435                 440                 445
```

```
Tyr Ser Tyr Leu Gln Asp Ser Asp Pro Asp Ser Phe Gln Asp Tyr Ile
    450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
        515                 520                 525

Leu

<210> SEQ ID NO 20
<211> LENGTH: 661
<212> TYPE: PRT
<213> ORGANISM: Homo sapiens

<400> SEQUENCE: 20

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285
```

```
Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
    610                 615                 620

Phe Ser Val Pro Gln Leu Pro His Ser Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 21
<211> LENGTH: 323
<212> TYPE: PRT
<213> ORGANISM: Homo sapiens

<400> SEQUENCE: 21
```

```
Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
        115                 120                 125

Gly Ala Gly Ile Leu Tyr Leu Val Thr Pro Pro Ser Val Val Gly Gly
    130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
        195                 200                 205

Gly Ala Ser Met Asn Pro Ala Arg Ser Phe Gly Pro Ala Val Ile Met
    210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
            260                 265                 270

Thr Lys Gly Ser Tyr Met Glu Val Glu Asp Asn Arg Ser Gln Val Glu
        275                 280                 285

Thr Asp Asp Leu Ile Leu Lys Pro Gly Val Val His Val Ile Asp Val
    290                 295                 300

Asp Arg Gly Glu Glu Lys Lys Gly Lys Asp Gln Ser Gly Glu Val Leu
305                 310                 315                 320

Ser Ser Val

<210> SEQ ID NO 22
<211> LENGTH: 405
<212> TYPE: PRT
<213> ORGANISM: Homo sapiens

<400> SEQUENCE: 22

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45
```

Val Leu Val Asp Pro Asp Leu Val Lys Gly Lys Lys Val Tyr Val Thr
 50                  55                  60

Leu Thr Cys Ala Phe Arg Tyr Gly Gln Glu Asp Ile Asp Val Ile Gly
 65                  70                  75                  80

Leu Thr Phe Arg Arg Asp Leu Tyr Phe Ser Arg Val Gln Val Tyr Pro
                 85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405

<210> SEQ ID NO 23
<211> LENGTH: 1247
<212> TYPE: PRT
<213> ORGANISM: Homo sapiens

<400> SEQUENCE: 23

Met Met Arg Glu Trp Val Leu Leu Met Ser Val Leu Leu Cys Gly Leu

```
1               5                   10                  15
Ala Gly Pro Thr His Leu Phe Gln Pro Ser Leu Val Leu Asp Met Ala
                20                  25                  30
Lys Val Leu Leu Asp Asn Tyr Cys Phe Pro Glu Asn Leu Leu Gly Met
                35                  40                  45
Gln Glu Ala Ile Gln Ala Ile Lys Ser His Glu Ile Leu Ser Ile
                50                  55                  60
Ser Asp Pro Gln Thr Leu Ala Ser Val Leu Thr Ala Gly Val Gln Ser
65              70                  75                  80
Ser Leu Asn Asp Pro Arg Leu Val Ile Ser Tyr Glu Pro Ser Thr Pro
                85                  90                  95
Glu Pro Pro Pro Gln Val Pro Ala Leu Thr Ser Leu Ser Glu Glu Glu
                100                 105                 110
Leu Leu Ala Trp Leu Gln Arg Gly Leu Arg His Glu Val Leu Glu Gly
                115                 120                 125
Asn Val Gly Tyr Leu Arg Val Asp Ser Val Pro Gly Gln Glu Val Leu
                130                 135                 140
Ser Met Met Gly Glu Phe Leu Val Ala His Val Trp Gly Asn Leu Met
145                 150                 155                 160
Gly Thr Ser Ala Leu Val Leu Asp Leu Arg His Cys Thr Gly Gly Gln
                165                 170                 175
Val Ser Gly Ile Pro Tyr Ile Ile Ser Tyr Leu His Pro Gly Asn Thr
                180                 185                 190
Ile Leu His Val Asp Thr Ile Tyr Asn Arg Pro Ser Asn Thr Thr Thr
                195                 200                 205
Glu Ile Trp Thr Leu Pro Gln Val Leu Gly Glu Arg Tyr Gly Ala Asp
                210                 215                 220
Lys Asp Val Val Val Leu Thr Ser Ser Gln Thr Arg Gly Val Ala Glu
225                 230                 235                 240
Asp Ile Ala His Ile Leu Lys Gln Met Arg Arg Ala Ile Val Val Gly
                245                 250                 255
Glu Arg Thr Gly Gly Gly Ala Leu Asp Leu Arg Lys Leu Arg Ile Gly
                260                 265                 270
Glu Ser Asp Phe Phe Phe Thr Val Pro Val Ser Arg Ser Leu Gly Pro
                275                 280                 285
Leu Gly Gly Gly Ser Gln Thr Trp Glu Gly Ser Gly Val Leu Pro Cys
                290                 295                 300
Val Gly Thr Pro Ala Glu Gln Ala Leu Glu Lys Ala Leu Ala Ile Leu
305                 310                 315                 320
Thr Leu Arg Ser Ala Leu Pro Gly Val Val His Cys Leu Gln Glu Val
                325                 330                 335
Leu Lys Asp Tyr Tyr Thr Leu Val Asp Arg Val Pro Thr Leu Leu Gln
                340                 345                 350
His Leu Ala Ser Met Asp Phe Ser Thr Val Val Ser Glu Glu Asp Leu
                355                 360                 365
Val Thr Lys Leu Asn Ala Gly Leu Gln Ala Ala Ser Glu Asp Pro Arg
                370                 375                 380
Leu Leu Val Arg Ala Ile Gly Pro Thr Glu Thr Pro Ser Trp Pro Ala
385                 390                 395                 400
Pro Asp Ala Ala Ala Glu Asp Ser Pro Gly Val Ala Pro Glu Leu Pro
                405                 410                 415
Glu Asp Glu Ala Ile Arg Gln Ala Leu Val Asp Ser Val Phe Gln Val
                420                 425                 430
```

-continued

```
Ser Val Leu Pro Gly Asn Val Gly Tyr Leu Arg Phe Asp Ser Phe Ala
            435                 440                 445

Asp Ala Ser Val Leu Gly Val Leu Ala Pro Tyr Val Leu Arg Gln Val
        450                 455                 460

Trp Glu Pro Leu Gln Asp Thr Glu His Leu Ile Met Asp Leu Arg His
465                 470                 475                 480

Asn Pro Gly Gly Pro Ser Ser Ala Val Pro Leu Leu Ser Tyr Phe
                485                 490                 495

Gln Gly Pro Glu Ala Gly Pro Val His Leu Phe Thr Thr Tyr Asp Arg
            500                 505                 510

Arg Thr Asn Ile Thr Gln Glu His Phe Ser His Met Glu Leu Pro Gly
            515                 520                 525

Pro Arg Tyr Ser Thr Gln Arg Gly Val Tyr Leu Leu Thr Ser His Arg
        530                 535                 540

Thr Ala Thr Ala Ala Glu Glu Phe Ala Phe Leu Met Gln Ser Leu Gly
545                 550                 555                 560

Trp Ala Thr Leu Val Gly Glu Ile Thr Ala Gly Asn Leu Leu His Thr
                565                 570                 575

Arg Thr Val Pro Leu Leu Asp Thr Pro Glu Gly Ser Leu Ala Leu Thr
            580                 585                 590

Val Pro Val Leu Thr Phe Ile Asp Asn His Gly Glu Ala Trp Leu Gly
            595                 600                 605

Gly Gly Val Val Pro Asp Ala Ile Val Leu Ala Glu Ala Leu Asp
        610                 615                 620

Lys Ala Gln Glu Val Leu Glu Phe His Gln Ser Leu Gly Ala Leu Val
625                 630                 635                 640

Glu Gly Thr Gly His Leu Leu Glu Ala His Tyr Ala Arg Pro Glu Val
                645                 650                 655

Val Gly Gln Thr Ser Ala Leu Leu Arg Ala Lys Leu Ala Gln Gly Ala
            660                 665                 670

Tyr Arg Thr Ala Val Asp Leu Glu Ser Leu Ala Ser Gln Leu Thr Ala
        675                 680                 685

Asp Leu Gln Glu Val Ser Gly Asp His Arg Leu Leu Val Phe His Ser
        690                 695                 700

Pro Gly Glu Leu Val Val Glu Glu Ala Pro Pro Pro Pro Ala Val
705                 710                 715                 720

Pro Ser Pro Glu Glu Leu Thr Tyr Leu Ile Glu Ala Leu Phe Lys Thr
                725                 730                 735

Glu Val Leu Pro Gly Gln Leu Gly Tyr Leu Arg Phe Asp Ala Met Ala
            740                 745                 750

Glu Leu Glu Thr Val Lys Ala Val Gly Pro Gln Leu Val Arg Leu Val
        755                 760                 765

Trp Gln Gln Leu Val Asp Thr Ala Ala Leu Val Ile Asp Leu Arg Tyr
770                 775                 780

Asn Pro Gly Ser Tyr Ser Thr Ala Ile Pro Leu Leu Cys Ser Tyr Phe
785                 790                 795                 800

Phe Glu Ala Glu Pro Arg Gln His Leu Tyr Ser Val Phe Asp Arg Ala
                805                 810                 815

Thr Ser Lys Val Thr Glu Val Trp Thr Leu Pro Gln Val Ala Gly Gln
            820                 825                 830

Arg Tyr Gly Ser His Lys Asp Leu Tyr Ile Leu Met Ser His Thr Ser
        835                 840                 845
```

```
Gly Ser Ala Ala Glu Ala Phe Ala His Thr Met Gln Asp Leu Gln Arg
850                 855                 860

Ala Thr Val Ile Gly Glu Pro Thr Ala Gly Ala Leu Ser Val Gly
865                 870                 875                 880

Ile Tyr Gln Val Gly Ser Ser Pro Leu Tyr Ala Ser Met Pro Thr Gln
                885                 890                 895

Met Ala Met Ser Ala Thr Thr Gly Lys Ala Trp Asp Leu Ala Gly Val
                900                 905                 910

Glu Pro Asp Ile Thr Val Pro Met Ser Glu Ala Leu Ser Ile Ala Gln
                915                 920                 925

Asp Ile Val Ala Leu Arg Ala Lys Val Pro Thr Val Leu Gln Thr Ala
930                 935                 940

Gly Lys Leu Val Ala Asp Asn Tyr Ala Ser Ala Glu Leu Gly Ala Lys
945                 950                 955                 960

Met Ala Thr Lys Leu Ser Gly Leu Gln Ser Arg Tyr Ser Arg Val Thr
                965                 970                 975

Ser Glu Val Ala Leu Ala Glu Ile Leu Gly Ala Asp Leu Gln Met Leu
                980                 985                 990

Ser Gly Asp Pro His Leu Lys Ala Ala His Ile Pro Glu Asn Ala Lys
                995                 1000                1005

Asp Arg Ile Pro Gly Ile Val Pro Met Gln Ile Pro Ser Pro Glu
    1010            1015            1020

Val Phe Glu Glu Leu Ile Lys Phe Ser Phe His Thr Asn Val Leu
    1025            1030            1035

Glu Asp Asn Ile Gly Tyr Leu Arg Phe Asp Met Phe Gly Asp Gly
    1040            1045            1050

Glu Leu Leu Thr Gln Val Ser Arg Leu Leu Val Glu His Ile Trp
    1055            1060            1065

Lys Lys Ile Met His Thr Asp Ala Met Ile Ile Asp Met Arg Phe
    1070            1075            1080

Asn Ile Gly Gly Pro Thr Ser Ser Ile Pro Ile Leu Cys Ser Tyr
    1085            1090            1095

Phe Phe Asp Glu Gly Pro Pro Val Leu Leu Asp Lys Ile Tyr Ser
    1100            1105            1110

Arg Pro Asp Asp Ser Val Ser Glu Leu Trp Thr His Ala Gln Val
    1115            1120            1125

Val Gly Glu Arg Tyr Gly Ser Lys Lys Ser Met Val Ile Leu Thr
    1130            1135            1140

Ser Ser Val Thr Ala Gly Thr Ala Glu Glu Phe Thr Tyr Ile Met
    1145            1150            1155

Lys Arg Leu Gly Arg Ala Leu Val Ile Gly Glu Val Thr Ser Gly
    1160            1165            1170

Gly Cys Gln Pro Pro Gln Thr Tyr His Val Asp Asp Thr Asn Leu
    1175            1180            1185

Tyr Leu Thr Ile Pro Thr Ala Arg Ser Val Gly Ala Ser Asp Gly
    1190            1195            1200

Ser Ser Trp Glu Gly Val Gly Val Thr Pro His Val Val Val Pro
    1205            1210            1215

Ala Glu Glu Ala Leu Ala Arg Ala Lys Glu Met Leu Gln His Asn
    1220            1225            1230

Gln Leu Arg Val Lys Arg Ser Pro Gly Leu Gln Asp His Leu
    1235            1240            1245
```

```
<210> SEQ ID NO 24
<211> LENGTH: 33
<212> TYPE: PRT
<213> ORGANISM: Triticum aestivum

<400> SEQUENCE: 24

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 25
<211> LENGTH: 33
<212> TYPE: PRT
<213> ORGANISM: Artificial Sequence
<220> FEATURE:
<223> OTHER INFORMATION: Synthetic

<400> SEQUENCE: 25

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 26
<211> LENGTH: 18
<212> TYPE: PRT
<213> ORGANISM: Triticum aestivum

<400> SEQUENCE: 26

Gln Gln Tyr Pro Ser Gly Gln Gly Ser Phe Gln Pro Ser Gln Gln Asn
1               5                   10                  15

Pro Gln

<210> SEQ ID NO 27
<211> LENGTH: 12
<212> TYPE: PRT
<213> ORGANISM: Triticum aestivum

<400> SEQUENCE: 27

Gln Pro Phe Pro Gln Pro Glu Gln Pro Phe Pro Trp
1               5                   10

<210> SEQ ID NO 28
<211> LENGTH: 519
<212> TYPE: PRT
<213> ORGANISM: Homo sapiens

<400> SEQUENCE: 28

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80
```

```
Ser Ser Leu Arg Asp Ile Leu Asn Gln Ile Thr Lys Pro Asn Asp Val
            85                  90                  95

Tyr Ser Phe Ser Leu Ala Ser Arg Leu Tyr Ala Glu Glu Arg Tyr Pro
        100                 105                 110

Ile Leu Pro Glu Tyr Leu Gln Cys Val Lys Glu Leu Tyr Arg Gly Gly
    115                 120                 125

Leu Glu Pro Ile Asn Phe Gln Thr Ala Ala Asp Gln Ala Arg Glu Leu
130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
    210                 215                 220

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
                245                 250                 255

Ser Ile Ile Asn Phe Glu Lys Leu Thr Glu Trp Thr Ser Ser Asn Val
            260                 265                 270

Met Glu Glu Arg Lys Ile Lys Val Tyr Leu Pro Arg Met Lys Met Glu
        275                 280                 285

Glu Lys Tyr Asn Leu Thr Ser Val Leu Met Ala Met Gly Ile Thr Asp
    290                 295                 300

Val Phe Ser Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
                325                 330                 335

Ala Gly Arg Glu Val Val Gly Ser Ala Glu Ala Gly Val Asp Ala Ala
            340                 345                 350

Ser Val Ser Glu Glu Phe Arg Ala Asp His Pro Phe Leu Phe Cys Ile
        355                 360                 365

Lys His Ile Ala Thr Asn Ala Val Leu Phe Phe Gly Arg Cys Val Ser
    370                 375                 380

Pro Gly Gly Gly Ser Glu Val Gln Leu Leu Glu Ser Gly Gly Gly Leu
385                 390                 395                 400

Val Gln Pro Gly Gly Ser Leu Arg Leu Ser Cys Ala Ala Ser Gly Phe
                405                 410                 415

Thr Phe Glu Lys Tyr Ala Met Ala Trp Val Arg Gln Ala Pro Gly Lys
            420                 425                 430

Gly Leu Glu Trp Val Ser Arg Ile Ser Ala Arg Gly Val Thr Thr Tyr
        435                 440                 445

Tyr Ala Asp Ser Val Lys Gly Arg Phe Thr Ile Ser Arg Asp Asn Ser
    450                 455                 460

Lys Asn Thr Leu Tyr Leu Gln Met Asn Ser Leu Arg Ala Glu Asp Thr
465                 470                 475                 480

Ala Val Tyr Tyr Cys Ala Ser His Lys Arg His Glu His Thr Arg Phe
                485                 490                 495
```

Asp Ser Trp Gly Gln Gly Thr Leu Val Thr Val Ser Ser Gly Gly Gly
            500                 505                 510

Ser His His His His His His
        515

<210> SEQ ID NO 29
<211> LENGTH: 519
<212> TYPE: PRT
<213> ORGANISM: Synthetic Fusion protein

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Lys Tyr
            20                  25                  30

Ala Met Ala Trp Val Arg Gln Ala Pro Gly Lys Gly Leu Glu Trp Val
        35                  40                  45

Ser Arg Ile Ser Ala Arg Gly Val Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Lys Arg His Glu His Thr Arg Phe Asp Ser Trp Gly Gln
            100                 105                 110

Gly Thr Leu Val Thr Val Ser Ser Gly Gly Gly Ser Gly Ser Ile Gly
        115                 120                 125

Ala Ala Ser Met Glu Phe Cys Phe Asp Val Phe Lys Glu Leu Lys Val
130                 135                 140

His His Ala Asn Glu Asn Ile Phe Tyr Cys Pro Ile Ala Ile Met Ser
145                 150                 155                 160

Ala Leu Ala Met Val Tyr Leu Gly Ala Lys Asp Ser Thr Arg Thr Gln
                165                 170                 175

Ile Asn Lys Val Val Arg Phe Asp Lys Leu Pro Gly Phe Gly Asp Ser
            180                 185                 190

Ile Glu Ala Gln Cys Gly Thr Ser Val Asn Val His Ser Ser Leu Arg
        195                 200                 205

Asp Ile Leu Asn Gln Ile Thr Lys Pro Asn Asp Val Tyr Ser Phe Ser
210                 215                 220

Leu Ala Ser Arg Leu Tyr Ala Glu Glu Arg Tyr Pro Ile Leu Pro Glu
225                 230                 235                 240

Tyr Leu Gln Cys Val Lys Glu Leu Tyr Arg Gly Gly Leu Glu Pro Ile
                245                 250                 255

Asn Phe Gln Thr Ala Ala Asp Gln Ala Arg Glu Leu Ile Asn Ser Trp
            260                 265                 270

Val Glu Ser Gln Thr Asn Gly Ile Ile Arg Asn Val Leu Gln Pro Ser
        275                 280                 285

Ser Val Asp Ser Gln Thr Ala Met Val Leu Val Asn Ala Ile Val Phe
290                 295                 300

Lys Gly Leu Trp Glu Lys Ala Phe Lys Asp Glu Asp Thr Gln Ala Met
305                 310                 315                 320

Pro Phe Arg Val Thr Glu Gln Glu Ser Lys Pro Val Gln Met Met Tyr
                325                 330                 335

Gln Ile Gly Leu Phe Arg Val Ala Ser Met Ala Ser Glu Lys Met Lys
            340                 345                 350

```
Ile Leu Glu Leu Pro Phe Ala Ser Gly Thr Met Ser Met Leu Val Leu
            355                 360                 365

Leu Pro Asp Glu Val Ser Gly Leu Glu Gln Leu Glu Ser Ile Ile Asn
        370                 375                 380

Phe Glu Lys Leu Thr Glu Trp Thr Ser Ser Asn Val Met Glu Glu Arg
385                 390                 395                 400

Lys Ile Lys Val Tyr Leu Pro Arg Met Lys Met Glu Glu Lys Tyr Asn
                405                 410                 415

Leu Thr Ser Val Leu Met Ala Met Gly Ile Thr Asp Val Phe Ser Ser
            420                 425                 430

Ser Ala Asn Leu Ser Gly Ile Ser Ser Ala Glu Ser Leu Lys Ile Ser
            435                 440                 445

Gln Ala Val His Ala Ala His Ala Glu Ile Asn Glu Ala Gly Arg Glu
        450                 455                 460

Val Val Gly Ser Ala Glu Ala Gly Val Asp Ala Ala Ser Val Ser Glu
465                 470                 475                 480

Glu Phe Arg Ala Asp His Pro Phe Leu Phe Cys Ile Lys His Ile Ala
                485                 490                 495

Thr Asn Ala Val Leu Phe Phe Gly Arg Cys Val Ser Pro Gly Gly Gly
            500                 505                 510

Ser His His His His His His
            515

<210> SEQ ID NO 30
<211> LENGTH: 908
<212> TYPE: PRT
<213> ORGANISM: Artificial Sequence
<220> FEATURE:
<223> OTHER INFORMATION: Synthetic Fusion Protein

<400> SEQUENCE: 30

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190
```

```
Thr Gln Ala Met Pro Phe Arg Val Thr Glu Gln Ser Lys Pro Val
        195                 200                 205

Gln Met Met Tyr Gln Ile Gly Leu Phe Arg Val Ala Ser Met Ala Ser
    210                 215                 220

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
                245                 250                 255

Ser Ile Ile Asn Phe Glu Lys Leu Thr Glu Trp Thr Ser Ser Asn Val
                260                 265                 270

Met Glu Glu Arg Lys Ile Lys Val Tyr Leu Pro Arg Met Lys Met Glu
                275                 280                 285

Glu Lys Tyr Asn Leu Thr Ser Val Leu Met Ala Met Gly Ile Thr Asp
                290                 295                 300

Val Phe Ser Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
                325                 330                 335

Ala Gly Arg Glu Val Val Gly Ser Ala Glu Ala Gly Val Asp Ala Ala
                340                 345                 350

Ser Val Ser Glu Glu Phe Arg Ala Asp His Pro Phe Leu Phe Cys Ile
                355                 360                 365

Lys His Ile Ala Thr Asn Ala Val Leu Phe Phe Gly Arg Cys Val Ser
                370                 375                 380

Pro Gly Gly Gly Ser Glu Val Gln Leu Leu Glu Ser Gly Gly Gly Leu
385                 390                 395                 400

Val Gln Pro Gly Gly Ser Leu Arg Leu Ser Cys Ala Ala Ser Gly Phe
                405                 410                 415

Thr Phe Glu Lys Tyr Ala Met Ala Trp Val Arg Gln Ala Pro Gly Lys
                420                 425                 430

Gly Leu Glu Trp Val Ser Arg Ile Ser Ala Arg Gly Val Thr Thr Tyr
                435                 440                 445

Tyr Ala Asp Ser Val Lys Gly Arg Phe Thr Ile Ser Arg Asp Asn Ser
450                 455                 460

Lys Asn Thr Leu Tyr Leu Gln Met Asn Ser Leu Arg Ala Glu Asp Thr
465                 470                 475                 480

Ala Val Tyr Tyr Cys Ala Ser His Lys Arg His Glu His Thr Arg Phe
                485                 490                 495

Asp Ser Trp Gly Gln Gly Thr Leu Val Thr Val Ser Ser Gly Gly Gly
                500                 505                 510

Ser Gly Ser Ile Gly Ala Ala Ser Met Glu Phe Cys Phe Asp Val Phe
                515                 520                 525

Lys Glu Leu Lys Val His His Ala Asn Glu Asn Ile Phe Tyr Cys Pro
530                 535                 540

Ile Ala Ile Met Ser Ala Leu Ala Met Val Tyr Leu Gly Ala Lys Asp
545                 550                 555                 560

Ser Thr Arg Thr Gln Ile Asn Lys Val Val Arg Phe Asp Lys Leu Pro
                565                 570                 575

Gly Phe Gly Asp Ser Ile Glu Ala Gln Cys Gly Thr Ser Val Asn Val
                580                 585                 590

His Ser Ser Leu Arg Asp Ile Leu Asn Gln Ile Thr Lys Pro Asn Asp
                595                 600                 605
```

Val Tyr Ser Phe Ser Leu Ala Ser Arg Leu Tyr Ala Glu Glu Arg Tyr
610                 615                 620

Pro Ile Leu Pro Glu Tyr Leu Gln Cys Val Lys Glu Leu Tyr Arg Gly
625                 630                 635                 640

Gly Leu Glu Pro Ile Asn Phe Gln Thr Ala Ala Asp Gln Ala Arg Glu
            645                 650                 655

Leu Ile Asn Ser Trp Val Glu Ser Gln Thr Asn Gly Ile Ile Arg Asn
            660                 665                 670

Val Leu Gln Pro Ser Ser Val Asp Ser Gln Thr Ala Met Val Leu Val
            675                 680                 685

Asn Ala Ile Val Phe Lys Gly Leu Trp Glu Lys Ala Phe Lys Asp Glu
690                 695                 700

Asp Thr Gln Ala Met Pro Phe Arg Val Thr Glu Gln Glu Ser Lys Pro
705                 710                 715                 720

Val Gln Met Met Tyr Gln Ile Gly Leu Phe Arg Val Ala Ser Met Ala
                725                 730                 735

Ser Glu Lys Met Lys Ile Leu Glu Leu Pro Phe Ala Ser Gly Thr Met
            740                 745                 750

Ser Met Leu Val Leu Leu Pro Asp Glu Val Ser Gly Leu Glu Gln Leu
            755                 760                 765

Glu Ser Ile Ile Asn Phe Glu Lys Leu Thr Glu Trp Thr Ser Ser Asn
770                 775                 780

Val Met Glu Glu Arg Lys Ile Lys Val Tyr Leu Pro Arg Met Lys Met
785                 790                 795                 800

Glu Glu Lys Tyr Asn Leu Thr Ser Val Leu Met Ala Met Gly Ile Thr
                805                 810                 815

Asp Val Phe Ser Ser Ser Ala Asn Leu Ser Gly Ile Ser Ser Ala Glu
            820                 825                 830

Ser Leu Lys Ile Ser Gln Ala Val His Ala Ala His Ala Glu Ile Asn
            835                 840                 845

Glu Ala Gly Arg Glu Val Val Gly Ser Ala Glu Ala Gly Val Asp Ala
850                 855                 860

Ala Ser Val Ser Glu Glu Phe Arg Ala Asp His Pro Phe Leu Phe Cys
865                 870                 875                 880

Ile Lys His Ile Ala Thr Asn Ala Val Leu Phe Phe Gly Arg Cys Val
                885                 890                 895

Ser Pro Gly Gly Gly Ser His His His His His
            900                 905

<210> SEQ ID NO 31
<211> LENGTH: 395
<212> TYPE: PRT
<213> ORGANISM: Homo sapiens

<400> SEQUENCE: 31

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
                20                  25                  30

Ala Ile Met Ser Ala Leu Ala Met Val Tyr Leu Gly Ala Lys Asp Ser
            35                  40                  45

Thr Arg Thr Gln Ile Asn Lys Val Val Arg Phe Asp Lys Leu Pro Gly
        50                  55                  60

Phe Gly Asp Ser Ile Glu Ala Gln Cys Gly Thr Ser Val Asn Val His
65                  70                  75                  80

```
Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
               100                 105                 110

Ile Leu Pro Glu Tyr Leu Gln Cys Val Lys Glu Leu Tyr Arg Gly Gly
           115                 120                 125

Leu Glu Pro Ile Asn Phe Gln Thr Ala Ala Asp Gln Ala Arg Glu Leu
       130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
               165                 170                 175

Ala Ile Val Phe Lys Gly Leu Trp Glu Lys Ala Phe Lys Asp Glu Asp
           180                 185                 190

Thr Gln Ala Met Pro Phe Arg Val Thr Glu Gln Glu Ser Lys Pro Val
       195                 200                 205

Gln Met Met Tyr Gln Ile Gly Leu Phe Arg Val Ala Ser Met Ala Ser
   210                 215                 220

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
               245                 250                 255

Ser Ile Ile Asn Phe Glu Lys Leu Thr Glu Trp Thr Ser Ser Asn Val
           260                 265                 270

Met Glu Glu Arg Lys Ile Lys Val Tyr Leu Pro Arg Met Lys Met Glu
       275                 280                 285

Glu Lys Tyr Asn Leu Thr Ser Val Leu Met Ala Met Gly Ile Thr Asp
   290                 295                 300

Val Phe Ser Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
               325                 330                 335

Ala Gly Arg Glu Val Val Gly Ser Ala Glu Ala Gly Val Asp Ala Ala
           340                 345                 350

Ser Val Ser Glu Glu Phe Arg Ala Asp His Pro Phe Leu Phe Cys Ile
       355                 360                 365

Lys His Ile Ala Thr Asn Ala Val Leu Phe Phe Gly Arg Cys Val Ser
   370                 375                 380

Pro Gly Gly Gly Ser His His His His His
385                 390                 395
```

GLYCOTARGETING THERAPEUTICS

CROSS-REFERENCE TO RELATED APPLICATION

This application claims priority from provisional application U.S. Ser. No. 61/942,942 filed Feb. 21, 2014, entitled "GLYCOTARGETING THERAPEUTICS," which is hereby incorporated by reference.

THE NAMES OF THE PARTIES TO A JOINT RESEARCH AGREEMENT

The claimed invention was made by, on behalf of, and/or in connection with one or more of the following parties to a joint research agreement between: Ecole Polytechnique Federale de Lausanne (EPFL) and Anokion SA. The agreement was in effect on and before the date the claimed invention was made, and the claimed invention was made as a result of activities undertaken within the scope of the agreement.

FIELD OF THE DISCLOSURE

The field of the disclosure relates to pharmaceutically acceptable compositions that are useful in the treatment of transplant rejection, autoimmune disease, food allergy, and immune response against a therapeutic agent.

BACKGROUND OF THE DISCLOSURE

Applications US 2012/0039989, US 2012/0178139 and WO 2013/121296 describe the targeting of antigens to erythrocytes to take advantage of the erythrocytes' role in antigen presentation for tolerization. Notwithstanding the positive results generated to date with this approach, the possibility of alternative approaches has remained of interest.

SUMMARY OF THE DISCLOSURE

An aspect of the disclosure provides a composition comprising a compound of Formula 1:

$$X{-}[Y{-}Z]_m \qquad \text{Formula 1}$$

where:
  m is an integer from about 1 to 100;
  X comprises an antigen against which a patient develops an unwanted immune response, or a tolerogenic portion thereof; or
  X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy;
  Y comprises a linker moiety; and
  Z comprises a liver-targeting moiety.
  Z can also comprise galactose, galactosamine or N-acetylgalactosamine, for example, conjugated at its C1, C2 or C6 to Y.
  Y can be Y is selected from N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, and nitrophenoxy poly(ethylene glycol)ester linkers.
  Y can also comprise: an antibody, antibody fragment, peptide or other ligand that specifically binds X; a disulfanyl ethyl ester; a structure represented by one of Formulae Ya to Yp:

Formula Ya

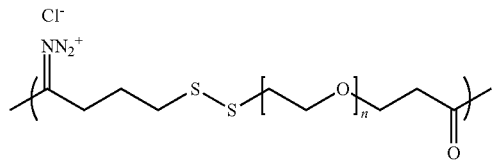

Formula Yb

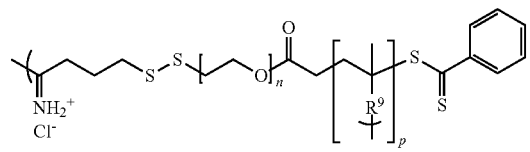

Formula Yc

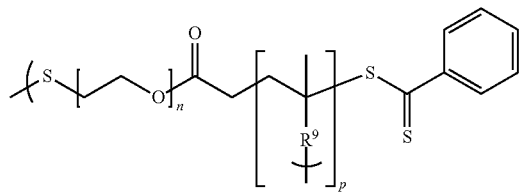

Formula Yd

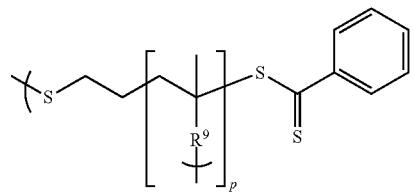

Formula Ye

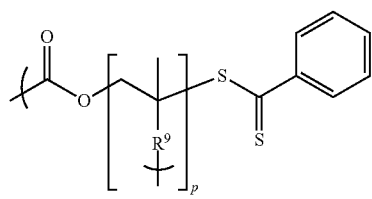

Formula Yf

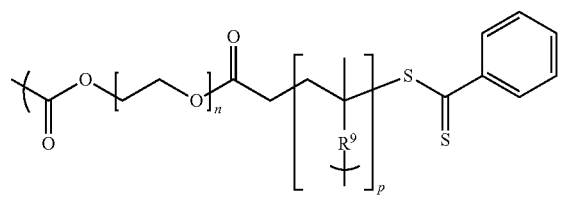

Formula Yg
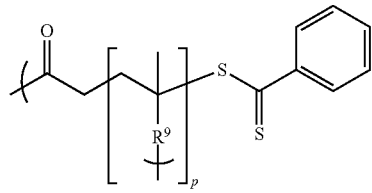
Formula Yh
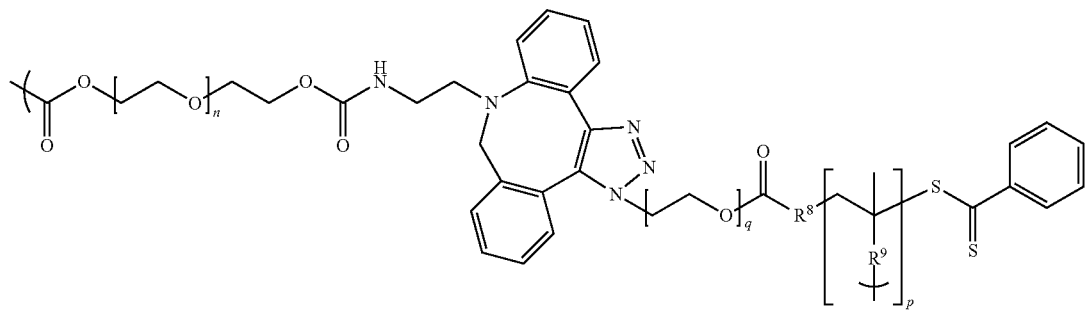
Formula Yi
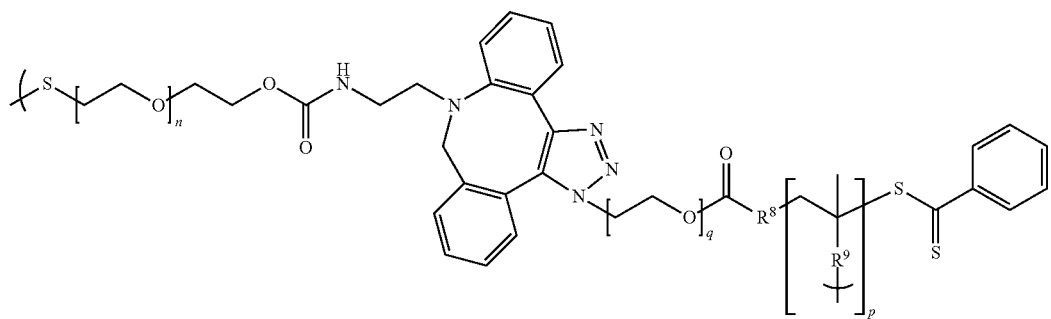
Formula Yj
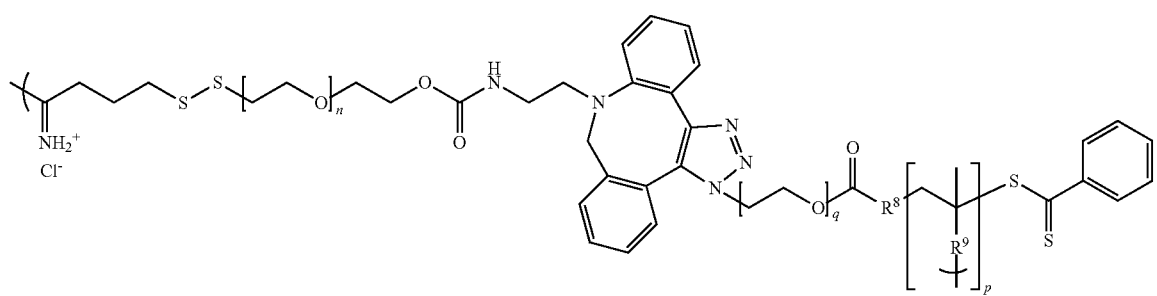
Formula Yk
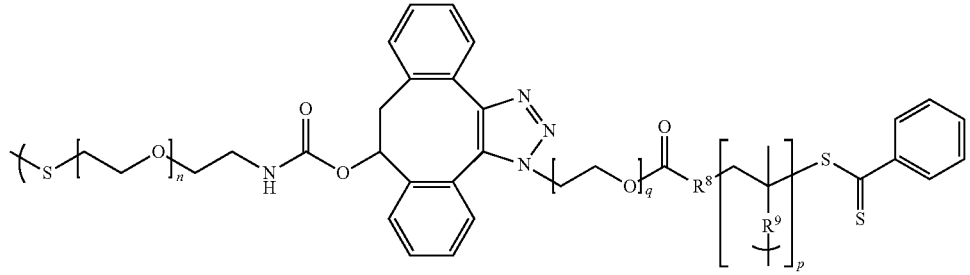

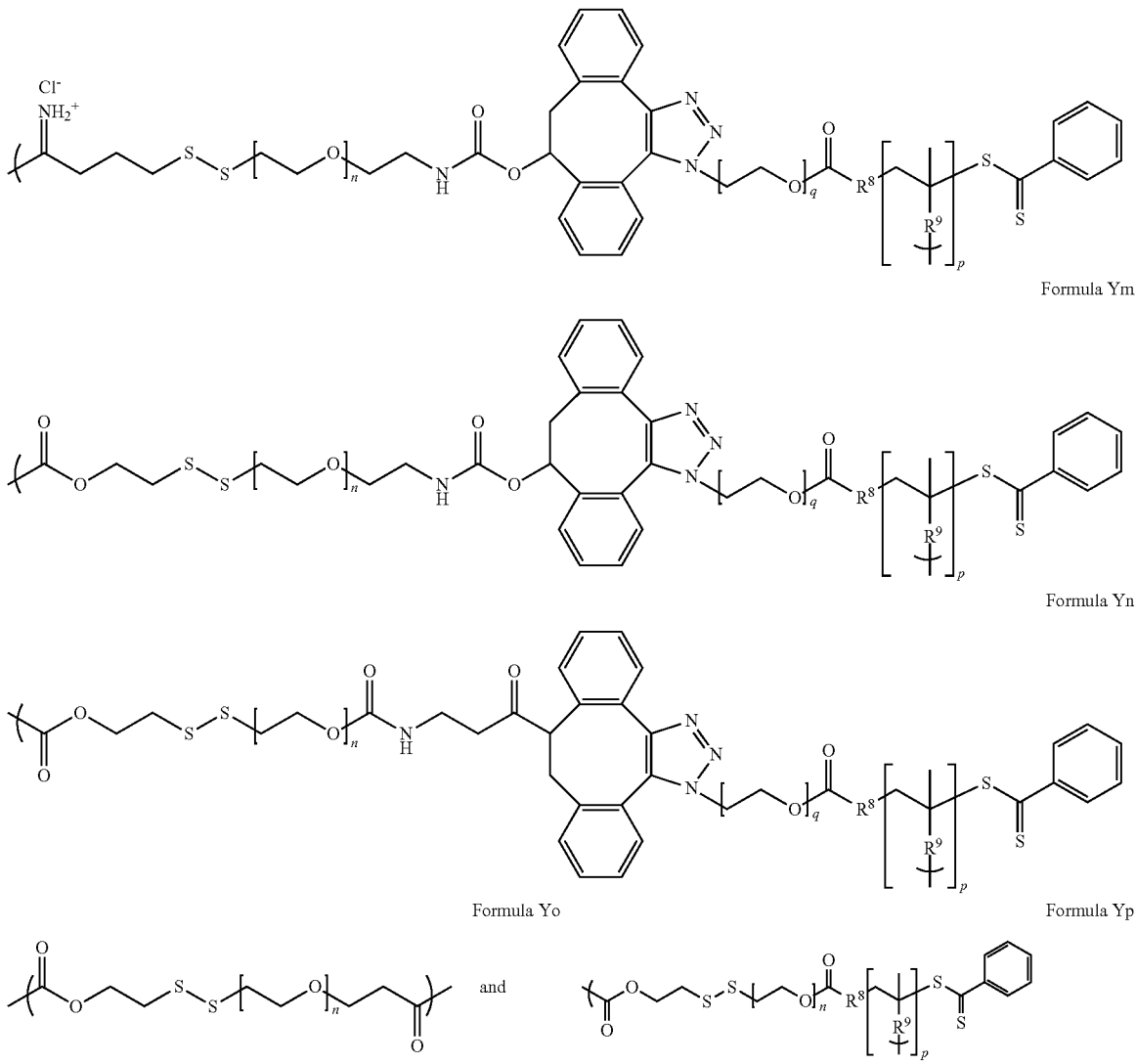

Formula YL, Formula Ym, Formula Yn, Formula Yo, Formula Yp or has a portion represented by Formula Y'-CMP:

Formula Y'-CMP

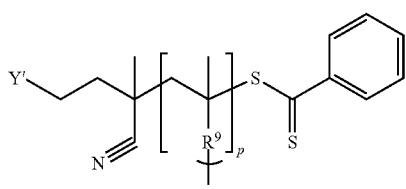

where: the left bracket "(" indicates the bond between X and Y; the right or bottom bracket and ")" indicates the bond between Y and Z; n is an integer from about 1 to 100; p is an integer from about 2 to 150; q is an integer from about 1 to 44; $R^8$ is —$CH_2$— or —$CH_2$—$CH_2$—$C(CH_3)(CN)$—; $R^9$ is a direct bond or —$CH_2$—$CH_2$—NH—C(O)—; and Y' represents the remaining portion of Y.

In another aspect of the above, n is about 40 to 80, p is about 10 to 100, q is about 3 to 20, $R^8$ is —$CH_2$—$CH_2$—$C(CH_3)(CN)$—; and when $R^9$ is —$CH_2$—$CH_2$—NH—C(O)—, Z is galactose or N-acetylgalactosamine conjugated at its C1.

In still another aspect of the above, Y comprises Formula Ya, Formula Yb, Formula Yh, Formula Yi, Formula Yk, Formula Ym or Formula Yn, particularly Formula Ya, Formula Yb, Formula Ym or Formula Yn.

X can further comprise: a foreign transplant antigen against which transplant recipients develop an unwanted immune response; a foreign food, animal, plant or environmental antigen against which patients develop an unwanted immune response; a foreign therapeutic agent against which patients develop an unwanted immune response; or a synthetic self-antigen against the endogenous version of which patients develop an unwanted immune response, or a tolerogenic portion thereof.

The disclosure also pertains to a method of treatment for an unwanted immune response against an antigen by administering to a mammal in need of such treatment an effective amount of a composition comprising a compound of Formula 1 as discussed above. In such method the composition can be administered for clearance of a circulating protein or peptide or antibody that specifically binds to antigen moiety X, which circulating protein or peptide or antibody is causatively involved in transplant rejection, immune response against a therapeutic agent, autoimmune disease, hypersensitivity and/or allergy. The composition can be administered in an amount effective to reduce a concentration of the antibodies that are causatively involved in transplant rejection, immune response against a therapeutic agent, autoimmune disease, hypersensitivity and/or allergy in blood of the patient by at least 50% w/w, as measured at a time between about 12 to about 48 hours after the administration. The composition can administered for tolerization of a patient with respect to antigen moiety X.

Yet another aspect of the disclosure provides a composition comprising a compound of Formula 2:

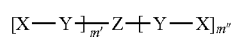

Formula 2

$$[X-Y]_{m'}Z[Y-X]_{m''}$$

where: m' is zero or an integer from about 1 to 10, m" is zero or an integer from about 1 to 10, and the sum of m'+m" is an integer from about 1 to 10 but is at least 1; each X is a foreign antigen or self-antigen against which a patient develops an unwanted immune response, or a tolerogenic portion thereof; each Y is a linker moiety or a direct bond, or an antibody, antibody fragment, peptide or other ligand that specifically binds X; and Z is a liver-targeting moiety, provided that X is not interferon, Ribavirin, Nexavar/Sorafenib, Erbitus/Cetuximab, Avastatin/bevacizumab or Herceptin/trastuzumab when m'+m" equals 1 and Z is DOM 26h-196-61

In the above aspect involving Formula 2, Z can comprise an ASGPR-targeted antibody, an ASGPR-targeted antibody fragment, an ASGPR-targeted peptide, an ASGPR-targeted scFv, or another ASGPR ligand. Y can be a linker having an immunoproteosome cleavage site. X can comprise a group of related antigens against which a patient develops an unwanted immune response or a group of tolerogenic fragments thereof. For example, X can be selected from the groups comprising:

- two or more of insulin, proinsulin, preproinsulin, glutamic acid decarboxylase-65 GAD-67, glucose-6 phosphatase 2, insulinoma-associated protein 2, insulinoma-associated protein 23, ICA69, ICA12, carboxypeptidase H, Imogen 38, GLIMA 38, chromogranin-A, HSP-60, caboxypeptidase E, peripherin, glucose transporter 2, hepatocarcinoma-intestine-pancreas/pancreatic associated protein, S1001, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5;
- two or more of myelin basic protein, myelin oligodendrocyte glycoprotein, myelin proteolipid protein, SEQ ID NO:11, SEQ ID NO:12, SEQ ID NO:13, SEQ ID NO:14, SEQ ID NO:15, SEQ ID NO:16, and SEQ ID NO:17; and
- two or more of SEQ ID NO:24, SEQ ID NO:25, SEQ ID NO:26, and SEQ ID NO:27.

The disclosure also pertains to a method of treatment for an unwanted immune response against an antigen by administering to a mammal in need of such treatment an effective amount of a composition comprising a compound of Formula 2 as discussed above. In such method the composition can be administered for clearance of a circulating protein or peptide or antibody that specifically binds to antigen moiety X, which circulating protein or peptide or antibody is causatively involved in transplant rejection, immune response against a therapeutic agent, autoimmune disease, hypersensitivity and/or allergy. The composition can be administered in an amount effective to reduce a concentration of the antibodies that are causatively involved in transplant rejection, immune response against a therapeutic agent, autoimmune disease, hypersensitivity and/or allergy in blood of the patient by at least 50% w/w, as measured at a time between about 12 to about 48 hours after the administration. The composition can administered for tolerization of a patient with respect to antigen moiety X.

BRIEF DESCRIPTION OF THE DRAWINGS

FIG. 1A is a graph showing galactose conjugation (F1aA-PE-$m_4$-$n_{80}$ (Gal-PE)) preferentially targets OVA to sinusoidal endothelia cells of the liver (LSECs).

FIG. 1B is a graph showing galactose conjugation (F1aA-PE-$m_4$-$n_{80}$ (Gal-PE)) preferentially targets OVA to Kupffer cells of the liver (KC).

FIG. 1C is a graph showing galactose conjugation (F1aA-PE-$m_4$-$n_{80}$ (Gal-PE)) preferentially targets OVA to hepatocytes of the liver.

FIG. 1D is a graph showing galactose conjugation (F1aA-PE-$m_4$-$n_{80}$ (Gal-PE)) preferentially targets OVA to other antigen-presenting cells of the liver (APCs).

FIG. 2 is a graph showing proliferation of OTI CD8+ T cells in mice treated with F1aA-OVA-$m_4$-$n_{80}$ (Gal-OVA), OVA or saline (i.e. naïve).

FIG. 3A is a graph showing the percentage of OT-I $CD8^+$ T cells presenting surface markers PD-1+ in generations of proliferating T cells treated with saline, OVA or F1aA-OVA-$m_4$-$n_{80}$ (GAL-OVA).

FIG. 3B is a graph showing the percentage of OT-I $CD8^+$ T cells presenting surface markers Annexin-V+ in generations of proliferating T cells treated with saline, OVA or F1aA-OVA-$m_4$-$n_{80}$ (GAL-OVA).

FIG. 4 is a graph showing galactose conjugation (F1aA-OVA-$m_4$-$n_{80}$ (Gal-OVA)) decreases the immunogenicity of OVA as determined by OVA-specific antibody titers (shown in Ab titers $\log^{-1}$).

FIG. 5 shows that F1aA-OVA-$m_4$-$n_{80}$ (Gal-OVA) is able to deplete OVA-specific antibodies from the serum.

FIG. 6 shows that F1aA-OVA-$m_4$-$n_{80}$ (mGal-OVA), F1b-OVA-$m_1$-$n_{44}$-$p_{34}$ (pGal-OVA), and N'-DOM-$Gly_3$Ser-OVA-$Gly_3$Ser-6×His-C' (Dom-OVA) are able to mitigate the OVA-specific immune response in draining lymphnodes after intradermal challenge with OVA and the adjuvant LPS.

FIG. 7A shows the characterization of F1aA-OVA-$m_4$-$n_{80}$ and F1b-OVA-$m_1$-$n_{44}$-$p_{34}$ by Size-exclusion HPCL traces of F1aA-OVA-$m_4$-$n_{80}$ (magenta), F1b-OVA-$m_1$-$n_{44}$-$p_{34}$ (blue) and unconjugated OVA (black). Shift to the left represents an increase in molecular weight.

FIG. 7B shows the characterization of F1aA-OVA-$m_4$-$n_{80}$ and F1b-OVA-$m_1$-$n_{44}$-$p_{34}$ by Polyacrylamide gel demonstrating increased molecular weight after OVA conjugation: (1.) Unconjugated OVA, (2.) F1aA-OVA-$m_4$-$n_{80}$ and (3.) F1b-OVA-$m_1$-$n_{44}$-$p_{34}$.

FIG. 8 is a graph showing the normalized quantity of N-OVA-$Gly_3$Ser-6×His-C(OVA), N-DOM-$Gly_3$Ser-OVA-$Gly_3$Ser-6×His-C (DOM-OVA), or N-OVA-$Gly_3$Ser-DOM-$Gly_3$Ser-6×His-C(OVA-DOM) in the circulation of mice after injection as an i.v. bolus.

Figure 9A:
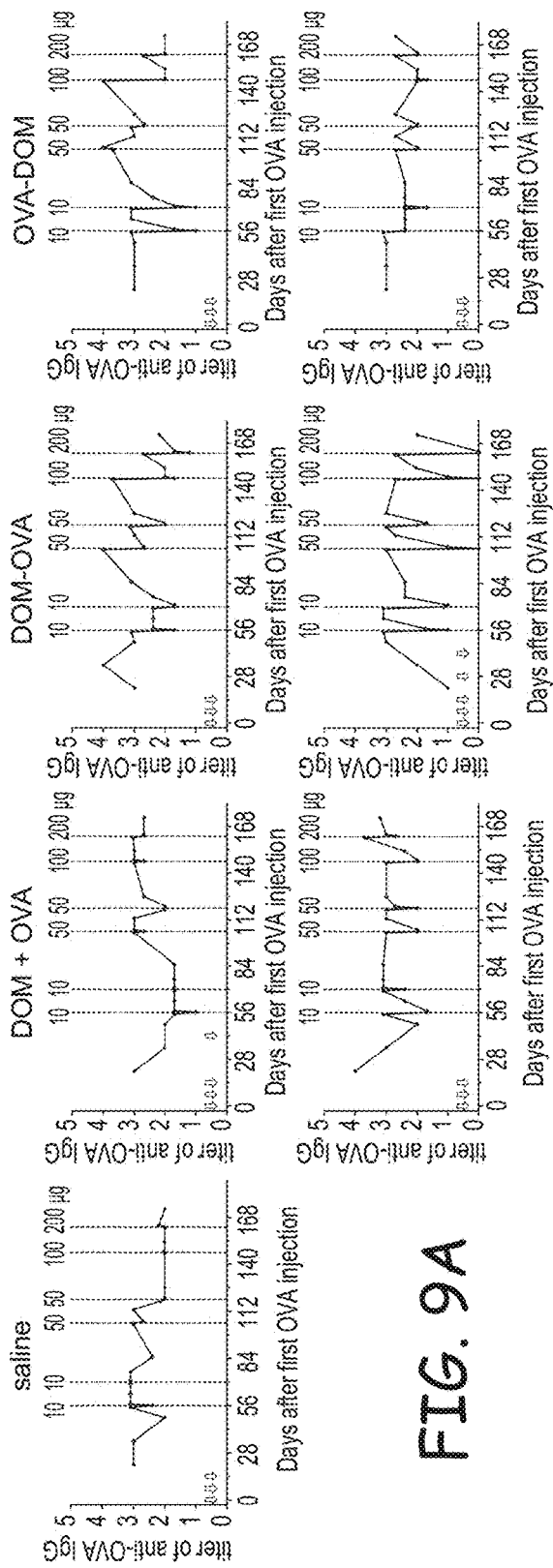

FIG. 9A is a series of graphs showing the titer of anti-OVA IgG antibodies in the circulation of individual mice after treatment with saline, DOM and OVA, DOM-OVA, or OVA-DOM. Production of anti-OVA IgG was induced by i.v. injections of OVA alone. Treatment times are indicated by vertical dashed lines. Titer is calculated as $\log_{10}$ of the maximal fold dilution of plasma with detectable anti-OVA IgG.

Figure 9B:
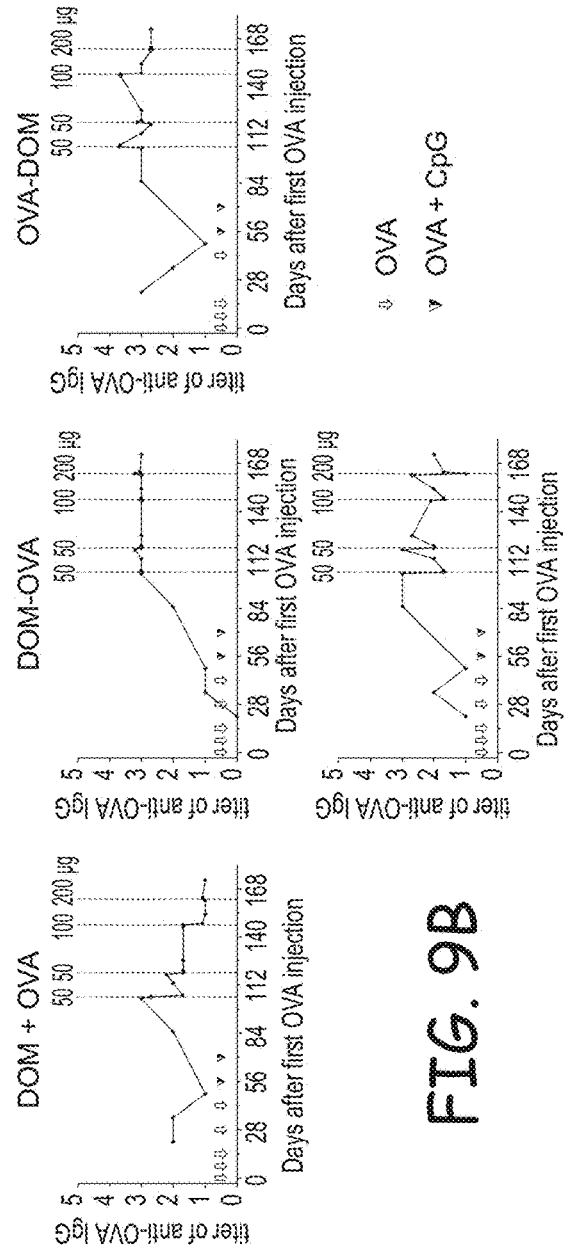

FIG. 9B is a series of graphs showing the titer of anti-OVA IgG antibodies in the circulation of individual mice after treatment with saline, DOM and OVA, DOM-OVA, or OVA-DOM. Production of anti-OVA IgG was induced by i.v. injections of OVA and CpG-B. Treatment times are indicated by vertical dashed lines. Titer is calculated as $\log_{10}$ of the maximal fold dilution of plasma with detectable anti-OVA IgG.

DETAILED DESCRIPTION

The two known asialoglycoprotein receptors ("ASGPRs") are expressed on hepatocytes and liver sinusoidal endothelial cells (or "LSECs"). Other galactose/galactosamine/N-acetylgalactosamine receptors can be found in various forms on multiple cell types [e.g., dendritic cells, hepatocytes, LSECs, and Kupffer cells]. Dendritic cells are considered "professional antigen presenting cells," because their primary function is to present antigens to the immune system for generating immune responses. Some cells within the liver are known to be able to present antigens, but the liver is more known to be involved in tolerogenesis. The liver is understood to be a tolerogenic organ. For example, lower incidences of rejection are reported in cases of multiple organ transplants when the liver is one of the organs transplanted. LSECs are much newer to the literature; consequently their role in tolerogenesis and/or moderation of inflammatory immune responses is not yet widely acknowledged or well understood. However, it is becoming clear that they also can play a significant role in the induction of antigen-specific tolerance.

One of the distinctive features of the erythrocyte surface is its glycosylation, i.e., the presence of significant numbers of glycosylated proteins. Indeed, the glycophorins (e.g., glycophorin A) have been employed as targets for erythrocyte binding. Glycophorins are proteins with many covalently attached sugar chains, the end terminus of which is sialic acid. As an erythrocyte ages and becomes ripe for clearance, the terminal sialic acid of its glycophorins tends to be lost, leaving N-acetylgalactosamine at the free end. N-acetylgalactosamine is a ligand selectively received by the ASGPR associated with hepatic cells, leading to binding of N-acetylgalactosamine-containing substances by hepatic cells and their subsequent uptake and processing in the liver.

Heretofore, it has been understood by those skilled in the art that glycosylation of a therapeutic agent in a manner that results in hepatic targeting should be avoided due to first-pass clearance by the liver resulting in poor circulation half-life of the therapeutic agent. By the same token, some monoclonal antibodies need to be specifically glycosylated at ASN297 for optimal binding to their Fc receptors. It has now surprisingly been found that galactosylation can be used in a manner that induces tolerogenesis.

The present disclosure provides certain therapeutic compositions that are targeted for delivery to (and for uptake by) the liver, particularly hepatocytes, LSECs, Kupffer cells and/or stellate cells, more particularly hepatocytes and/or LSECs, and even more particularly to specifically bind ASGPR. Liver-targeting facilitates two mechanisms of treatment: tolerization and clearance. Tolerization takes advantage of the liver's role in clearing apoptotic cells and processing their proteins to be recognized by the immune system as "self," as well as the liver's role in sampling peripheral proteins for immune tolerance. Clearance takes advantage of the liver's role in blood purification by rapidly removing and breaking down toxins, polypeptides and the like. Targeting of these compositions to the liver is accomplished by a galactosylating moiety (e.g., galactose, galactosamine and N-acetylgalactosamine, particularly conjugated at C1, C2 or C6), by another liver-targeting moiety (e.g., a monoclonal antibody, or a fragment or a scFv thereof), or by de-sialylating a polypeptide for which such liver-targeting is desired. The galactosylating or other liver-targeting moiety can be chemically conjugated or recombinantly fused to an antigen, whereas desialylation exposes a galactose-like moiety on an antigen polypeptide. The antigen can be endogenous (a self-antigen) or exogenous (a foreign antigen), including but not limited to: a foreign transplant antigen against which transplant recipients develop an unwanted immune response (e.g., transplant rejection), a foreign food, animal, plant or environmental antigen to which patients develop an unwanted immune (e.g., allergic or hypersensitivity) response, a therapeutic agent to which patients develop an unwanted immune response (e.g., hypersensitivity and/or reduced therapeutic activity), a self-antigen to which patients develop an unwanted immune response (e.g., autoimmune disease), or a tolerogenic portion (e.g., a fragment or an epitope) thereof; these compositions are useful for inducing tolerization to the antigen. Alternatively, the galactosylating or other liver-targeting moiety can be conjugated to an antibody, antibody fragment or ligand that specifically binds a circulating protein or peptide or antibody, which circulating protein or peptide or antibody is causatively involved in transplant rejection, immune response against a therapeutic agent, autoimmune disease, and/or allergy (as discussed above); these compositions are useful for clearing the circulating protein, peptide or antibody. Accordingly, the compositions of the present disclosure can be used for treating an unwanted immune response, e.g., transplant rejection, an immune response against a therapeutic agent, an autoimmune disease, and/or an allergy. Also provided are pharmaceutical compositions containing a therapeutically effective amount of a composition of the disclosure admixed with at least one pharmaceutically acceptable excipient. In another aspect, the disclosure provides methods for the treatment of an unwanted immune response, such as transplant rejection, response against a therapeutic agent, autoimmune disease or allergy.

Definitions

As used in the present specification, the following words and phrases are generally intended to have the meanings as set forth below, except to the extent that the context in which they are used indicates otherwise.

The singular forms "a," "an," and "the" include plural referents, unless the context clearly indicates otherwise.

The term "about" when used in connection with a numerical value is meant to encompass numerical values within a range typically having a lower limit that is, e.g., 5-10% smaller than the indicated numerical value and having an upper limit that is, e.g., 5-10% larger than the indicated numerical value.

An "antigen" is any substance that serves as a target for the receptors of an adaptive immune response, such as the T cell receptor, B cell receptor or an antibody. An antigen may originate from within the body ("self," "auto" or "endogenous"). An antigen may originate from outside the body ("non-self," "foreign" or "exogenous"), having entered, for example, by inhalation, ingestion, injection, or transplantation. Foreign antigens include, but are not limited to, food antigens, animal antigens, plant antigens, environmental antigens, therapeutic agents, as well as antigens present in an allograft transplant.

An "antigen-binding molecule" as used herein relates to molecules, in particular to proteins such as immunoglobulin molecules, which contain antibody variable regions providing a specific binding to an epitope. The antibody variable region can be present in, for example, a complete antibody, an antibody fragment, and a recombinant derivative of an antibody or antibody fragment. The term "antigen-binding fragment" of an antibody (or "binding portion"), as used herein, refers to one or more fragments of an antibody that retain the ability to specifically bind a target sequence. Antigen-binding fragments containing antibody variable regions include (without limitation) "Fv", "Fab", and "F(ab')$_2$" regions, "single domain antibodies (sdAb)", "nanobodies", "single chain Fv (scFv)" fragments, "tandem scFvs" (VHA-VLA-VHB-VLB), "diabodies", "triabodies" or "tribodies", "single-chain diabodies (scDb)", and "bispecific T-cell engagers (BiTEs)".

A "chemical modification" refers to a change in the naturally-occurring chemical structure of one or more amino acids of a polypeptide. Such modifications can be made to a side chain or a terminus, e.g., changing the amino-terminus or carboxyl terminus. In some embodiments, the modifications are useful for creating chemical groups that can conveniently be used to link the polypeptides to other materials, or to attach a therapeutic agent.

The term "comprising", which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics.

"Conservative changes" can generally be made to an amino acid sequence without altering activity. These changes are termed "conservative substitutions" or mutations; that is, an amino acid belonging to a grouping of amino acids having a particular size or characteristic can be substituted for another amino acid. Substitutes for an amino acid sequence can be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such substitutions are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence can undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free —NH$_2$. Yet another type of conservative substitution constitutes the case where amino acids with desired chemical reactivities are introduced to impart reactive sites for chemical conjugation reactions, if the need for chemical derivativization arises. Such amino acids include but are not limited to Cys (to insert a sulfhydryl group), Lys (to insert a primary amine), Asp and Glu (to insert a carboxylic acid group), or specialized noncanonical amino acids containing ketone, azide, alkyne, alkene, and tetrazine side-chains. Conservative substitutions or additions of free —NH$_2$ or —SH bearing amino acids can be particularly advantageous for chemical conjugation with the linkers and galactosylating moieties of Formula 1. Moreover, point mutations, deletions, and insertions of the polypeptide sequences or corresponding nucleic acid sequences can in some cases be made without a loss of function of the polypeptide or nucleic acid fragment. Substitutions can include, e.g., 1, 2, 3, 4, 5, 6, 7, 8, 9, 10, 15, 20, 25, 30, 35, 40, 45, 50 or more residues. A variant usable in the present invention may exhibit a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid residues described herein employ either the single letter amino acid designator or the three-letter abbreviation in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus.

The terms "effective amount" or "therapeutically effective amount" refer to that amount of a composition of the disclosure that is sufficient to effect treatment, as defined below, when administered to a mammal in need of such treatment. This amount will vary depending upon the subject and disease condition being treated, the weight and age of the subject, the severity of the disease condition, the particular composition of the disclosure chosen, the dosing regimen to be followed, timing of administration, manner of administration and the like, all of which can readily be determined by one of ordinary skill in the art.

An "epitope", also known as antigenic determinant, is the segment of a macromolecule, e.g. a protein, which is recognized by the adaptive immune system, such as by antibodies, B cells, or T cells. An epitope is that part or segment of a macromolecule capable of binding to an antibody or antigen-binding fragment thereof. In this context, the term "binding" in particular relates to a specific binding. In the context of the present invention it is preferred that the term "epitope" refers to the segment of protein or polyprotein that is recognized by the immune system.

The term galactose is well known in the art and refers to a monosaccharide sugar that exists both in open-chain form and in cyclic form, having D- and L-isomers. In the cyclic form there are two anomers, namely alpha and beta. In the alpha form, the C1 alcohol group is in the axial position, whereas in the beta form, the C1 alcohol group is in the equatorial position. In particular, "galactose" refers to the cyclic six-membered pyranose, more in particular the D-isomer and even more particularly the alpha-D-form (α-D-galactopyranose). The structure and numbering of galactose is illustrated below.

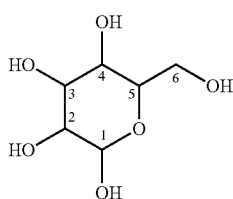

The term "galactosylating moiety" refers to a particular type of liver-targeting moiety. Galactosylating moieties include, but are not limited to a galactose, galactosamine and/or N-acetylgalactosamine residue.

The term "liver-targeting moiety", refers to moieties having the ability to direct, e.g., a polypeptide, to the liver. The liver comprises different cell types, including but not limited to hepatocytes, sinusoidal epithelial cells, Kupffer cells, stellate cells, and/or dendritic cells. Typically, a liver-targeting moiety directs a polypeptide to one or more of these cells. On the surface of the respective liver cells, receptors are present which recognize and specifically bind the liver-targeting moiety. Liver-targeting can be achieved by chemical conjugation of an antigen or ligand to a galactosylating moiety, desialylation of an antigen or ligand to expose underlying galactosyl moieties, recombinant fusion or chemical conjugation of an antigen or ligand to an ASGPR-binding moiety, or specific binding of an endogenous antibody to an antigen or ligand, where the antigen or ligand is: desialylated to expose underlying galactosyl moieties, conjugated to a galactosylating moiety, or recombinantly fused or chemically conjugated to an ASGPR-binding moiety. Naturally occurring desialylated proteins are not encompassed within the scope of the present disclosure.

The "numerical values" and "ranges" provided for the various substituents are intended to encompass all integers within the recited range. For example, when defining n as an integer representing a mixture including from about 1 to 100, particularly about 8 to 90 and more particularly about 40 to 80 ethylene glycol groups, where the mixture typically encompasses the integer specified as n±about 10% (or for smaller integers from 1 to about 25, ±3), it should be understood that n can be an integer from about 1 to 100 (e.g., 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110) and that the disclosed mixture encompasses ranges such as 1-4, 2-4, 2-6, 3-8, 7-13, 6-14, 18-23, 26-30, 42-50, 46-57, 60-78, 85-90, 90-110 and 107-113 ethylene glycol groups. The combined terms "about" and "±10%" or "±3" should be understood to disclose and provide specific support for equivalent ranges wherever used.

The term "optional" or "optionally" means that the subsequently described event or circumstance may or may not occur, and that the description includes instances where said event or circumstance occurs and instances in which it does not.

A peptide that specifically binds a particular target is referred to as a "ligand" for that target.

A "polypeptide" is a term that refers to a chain of amino acid residues, regardless of post-translational modification (e.g., phosphorylation or glycosylation) and/or complexation with additional polypeptides, and/or synthesis into multisubunit complexes with nucleic acids and/or carbohydrates, or other molecules. Proteoglycans therefore also are referred to herein as polypeptides. A long polypeptide (having over about 50 amino acids) is referred to as a "protein."

A short polypeptide (having fewer than about 50 amino acids) is referred to as a "peptide." Depending upon size, amino acid composition and three dimensional structure, certain polypeptides can be referred to as an "antigen-binding molecule," "antibody," an "antibody fragment" or a "ligand." Polypeptides can be produced by a number of methods, many of which are well known in the art. For example, polypeptides can be obtained by extraction (e.g., from isolated cells), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "purified" as used herein with reference to a polypeptide refers to a polypeptide that has been chemically synthesized and is thus substantially uncontaminated by other polypeptides, or has been separated or isolated from most other cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of a purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, a FLAG® tag, or other affinity tag) that facilitates purification or marking (e.g., capture onto an affinity matrix, visualization under a microscope). Thus a purified composition that comprises a polypeptide refers to a purified polypeptide unless otherwise indicated. The term "isolated" indicates that the polypeptides or nucleic acids of the disclosure are not in their natural environment. Isolated products of the disclosure can thus be contained in a culture supernatant, partially enriched, produced from heterologous sources, cloned in a vector or formulated with a vehicle, etc.

The term "sequence identity" is used with regard to polypeptide sequence comparisons. This expression in particular refers to a percentage of sequence identity, for example at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Particularly, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide.

"Specific binding," as that term is commonly used in the biological arts, refers to a molecule that binds to a target with a relatively high affinity as compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and certain protein-receptor interactions; while such molecules might bind tissues besides their specific targets from time to time, to the extent that such non-target binding is inconsequential, the high-affinity binding pair can still fall within the definition of specific binding.

The term "treatment" or "treating" means any treatment of a disease or disorder in a mammal, including:

preventing or protecting against the disease or disorder, that is, causing the clinical symptoms not to develop;

inhibiting the disease or disorder, that is, arresting or suppressing the development of clinical symptoms; and/or relieving the disease or disorder, that is, causing the regression of clinical symptoms.

The term "unwanted immune response" refers to a reaction by the immune system of a subject, which in the given situation is not desirable. The reaction of the immune system is unwanted if such reaction does not lead to the prevention, reduction, or healing of a disease or disorder but instead causes, enhances or worsens a disorder or disease. Typically, a reaction of the immune system causes, enhances or worsens a disease if it is directed against an inappropriate target. Exemplified, an unwanted immune response includes but is not limited to transplant rejection, immune response against a therapeutic agent, autoimmune disease, and allergy or hypersensitivity.

The term "variant" is to be understood as a protein which differs in comparison to the protein from which it is derived by one or more changes in its length, sequence, or structure. The polypeptide from which a protein variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence or structure in comparison to the parent molecule. Also encompassed modified molecules such as but not limited to post-translationally modified proteins (e.g. glycosylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Naturally occurring and artificially constructed variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active. A variant can be characterized by a certain degree of sequence identity to the parent polypeptide from which it is derived. More precisely, a protein variant in the context of the present disclosure may exhibit at least 80% sequence identity to its parent polypeptide. Preferably, the sequence identity of protein variants is over a continuous stretch of 20, 30, 40, 45, 50, 60, 70, 80, 90, 100 or more amino acids.

Compositions

One aspect of the present disclosure relates to compositions, pharmaceutical formulations, and methods of treatment employing such compositions, as represented by Formula 1:

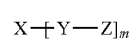

Formula 1 where:
m is an integer from about 1 to 100, particularly from about 1 to 20, and most particularly 1 to about 10;
X is an antigen moiety, particularly a foreign antigen or self-antigen against which a patient develops an unwanted immune response, or a tolerogenic portion (e.g., a fragment or an epitope) of such an antigen moiety;
Y is a linker moiety or a direct bond, or an antibody, antibody fragment, peptide or other ligand that specifically binds X; and
Z is a liver-targeting moiety, in particular galactosylating moiety.

The value for m in Formula 1 will depend upon the nature of X, in that each antigen, antibody, antibody fragment or ligand will have an individual number and density of sites (predominantly the N-terminal amine, lysine residues and cysteine residues) to which a linker or galactosylating moiety can be bound. Antigens having a limited number of such sites can be derivatized, for example, at the N or C terminus, by adding lysine or cysteine residues (optionally via a cleavable linker, particularly a linker having an immuno-proteosome cleavage site). Generally, it is preferred to provide an adequate degree of galactosylation in compositions of Formula 1 so as to facilitate uptake by liver cells. Pharmaceutical formulations and methods of the disclosure can employ a cocktail of compositions of Formula 1, respectively bearing different X moieties (e.g., several epitopes associated with a particular unwanted immune response).

The compositions of Formula 1 include the sub-genuses where X is a foreign transplant antigen against which transplant recipients develop an unwanted immune response (e.g., transplant rejection), a foreign food, animal, plant or environmental antigen against which patients develop an unwanted immune (e.g., allergic or hypersensitivity) response, a foreign therapeutic agent against which patients develop an unwanted immune response (e.g., hypersensitivity and/or reduced therapeutic activity), or a self-antigen against which patients develop an unwanted immune response (e.g., autoimmune disease); where Y is a linker of Formulae Ya through Yp; and/or where Z is galactose, galactosamine or N-acetylgalactosamine, as illustrated by Formulae 1a through 1p as described below with reference to the Reaction Schemes.

The disclosure further provides a pharmaceutically acceptable composition represented by Formula 2:

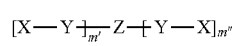

Formula 2 where:
m' is zero or an integer from about 1 to 10, m" is zero or an integer from about 1 to 10, and the sum of m'+m" is an integer from about 1 to 10 but is at least 1;

X is an antigen moiety, particularly a foreign antigen or self-antigen against which a patient develops an unwanted immune response, or a tolerogenic portion (e.g., a fragment or an epitope) of such an antigen moiety;

Y is a linker moiety or a direct bond, or an antibody, antibody fragment, peptide or other ligand that specifically binds X; and Z is a liver-targeting moiety, in particular an ASGPR-targeted antibody, an ASGPR-targeted antibody fragment, an ASGPR-targeted peptide, an ASGPR-targeted scFv, or another ASGPR ligand, such composition optionally including amino acid sequences to facilitate isolation and purification [e.g., a "His tag" or "6×His" having the sequence: HHHHHH (SEQ ID NO:1) and additional linkers [e.g., "Gly$_3$Ser" having the sequence: GGGS (SEQ ID NO:2)]. In the compositions of Formula 2 where m'+m" is greater than one, the X moieties can be the same or different, and the Y moieties can be the same or different. The value for m'+m" will be smaller (e.g., 3 or less) when X is a full protein, or larger (up to about 10) when X is a peptide. The linker(s) "Y" can advantageously comprise a cleavage site, particularly an immunoproteosome cleavage site.

The compositions of Formula 2 include the sub-genuses where X is a foreign transplant antigen against which transplant recipients develop an unwanted immune response (e.g., transplant rejection), a foreign food, animal, plant or environmental antigen against which patients develop an unwanted immune (e.g., allergic or hypersensitivity) response, a foreign therapeutic agent against which patients develop an unwanted immune response (e.g., hypersensitivity and/or reduced therapeutic activity), or a self-antigen against which patients develop an unwanted immune response (e.g., autoimmune disease).

Alternatively, in the compositions of Formula 1 and/or Formula 2, X can be an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy.

The compositions of Formula 2 can be prepared as fusion proteins and can include several components useful in their preparation and purification, such as a signal or leader sequence that directs the expressed polypeptide to a specific transport pathway and is subsequently cleaved from the polypeptide; therefore the signal sequence can be part of the expressed protein and DNA encoding it, but not part of the final composition. One example of a mammalian signal sequence used in expression systems is the Ig κ-chain sequence, which directs protein secretion: METDTLLLWV-LLLWVPGSTG (SEQ ID NO:3). Similarly, one example of a common bacterial signal sequence used in expression systems is the pelB signal sequence, which directs expressed protein into the bacterial periplasm: MKYLLPTAAAGLLL-LAAQPAMA (SEQ ID NO:4).

Antigens

The antigen employed as X in the compositions of Formula 1 and/or Formula 2 can be a protein or a peptide, e.g. the antigen may be a complete or partial therapeutic agent, a full-length transplant protein or peptide thereof, a full-length autoantigen or peptide thereof, a full-length allergen or peptide thereof, and/or a nucleic acid, or a mimetic of an aforementioned antigen.

Antigens employed in the practice of the present disclosure can be one or more of the following:

Therapeutic agents that are proteins, peptides, antibodies and antibody-like molecules, including antibody fragments and fusion proteins with antibodies and antibody fragments. These include human, non-human (such as mouse) and non-natural (i.e., engineered) proteins, antibodies, chimeric antibodies, humanized antibodies, and non-antibody binding scaffolds, such as fibronectins, DARPins, knottins, and the like.

Human allograft transplantation antigens against which transplant recipients develop an unwanted immune response.

Self-antigens that cause an unwanted, autoimmune response. Those skilled in the art will appreciate that while self-antigens are of an endogenous origin in an autoimmune disease patient, the polypeptides employed in the disclosed compositions are typically synthesized exogenously (as opposed to being purified and concentrated from a source of origin).

Foreign antigens, such as food, animal, plant and environmental antigens, against which a patient experiences an unwanted immune response. Those skilled in the art will appreciate that while a therapeutic protein can also be considered a foreign antigen due to its exogenous origin, for purposes of clarity in the description of the present disclosure such therapeutics are described as a separate group. Similarly, a plant or an animal antigen can be eaten and considered a food antigen, and an environmental antigen may originate from a plant. They are, however, all foreign antigens. In the interest of simplicity no attempt will be made to describe distinguish and define all of such potentially overlapping groups, as those skilled in the art can appreciate the antigens that can be employed in the compositions of the disclosure, particularly in light of the detailed description and examples.

The antigen can be a complete protein, a portion of a complete protein, a peptide, or the like, and can be derivatized (as discussed above) for attachment to a linker and/or galactosylating moiety, can be a variant and/or can contain conservative substitutions, particularly maintaining sequence identity, and/or can be desialylated.

In the embodiments where the antigen is a therapeutic protein, peptide, antibody or antibody-like molecule, specific antigens can be selected from: Abatacept, Abciximab, Adalimumab, Adenosine deaminase, Ado-trastuzumab emtansine, Agalsidase alfa, Agalsidase beta, Aldesluukin, Alglucerase, Alglucosidase alfa, α-1-proteinase inhibitor, Anakinra, Anistreplase (anisoylated plasminogen streptokinase activator complex), Antithrombin III, Antithymocyte globulin, Ateplase, Bevacizumab, Bivalirudin, Botulinum toxin type A, Botulinum toxin type B, C1-esterase inhibitor, Canakinumab, Carboxypeptidase G2 (Glucarpidase and Voraxaze), Certolizumab pegol, Cetuximab, Collagenase, Crotalidae immune Fab, Darbepoetin-α, Denosumab, Digoxin immune Fab, Dornase alfa, Eculizumab, Etanercept, Factor VIIa, Factor VIII, Factor IX, Factor XI, Factor XIII, Fibrinogen, Filgrastim, Galsulfase, Golimumab, Histrelin acetate, Hyaluronidase, Idursulphase, Imiglucerase, Infliximab, Insulin [including recombinant human insulin ("rHu insulin") and bovine insulin], Interferon-α2a, Interferon-α2b, Interferon-β1a, Interferon-β1b, Interferon-γ1b, Ipilimumab, L-arginase, L-asparaginase, L-methionase, Lactase, Laronidase, Lepirudin/hirudin, Mecasermin, Mecasermin rinfabate, Methoxy Natalizumab, Octreotide, Ofatumumab, Oprelvekin, Pancreatic amylase, Pancreatic lipase, Papain, Peg-asparaginase, Peg-doxorubicin HCl, PEG-epoetin-β, Pegfilgrastim, Peg-Interferon-α2a, Peg-Interferon-α2b, Pegloticase, Pegvisomant, Phenylalanine ammonia-lyase (PAL), Protein C, Rasburicase (uricase), Sacrosidase, Salmon calcitonin, Sargramostim, Streptokinase, Tenecteplase, Teriparatide, Tocilizumab (atlizumab), Trastuzumab, Type 1 alpha-interferon, Ustekinumab, vW factor. The therapeutic protein can be obtained from natural sources (e.g., concentrated and purified) or synthesized, e.g., recombinantly, and includes antibody therapeutics that are typically IgG monoclonal or fragments or fusions.

Particular therapeutic protein, peptide, antibody or antibody-like molecules include Abciximab, Adalimumab, Agalsidase alfa, Agalsidase beta, Aldeslukin, Alglucosidase alfa, Factor VIII, Factor IX, Infliximab, Insulin (including rHu Insulin), L-asparaginase, Laronidase, Natalizumab, Octreotide, Phenylalanine ammonia-lyase (PAL), or Rasburicase (uricase) and generally IgG monoclonal antibodies in their varying formats.

Another particular group includes the hemostatic agents (Factor VIII and IX), Insulin (including rHu Insulin), and the non-human therapeutics uricase, PAL and asparaginase.

Unwanted immune response in hematology and transplant includes autoimmune aplastic anemia, transplant rejection (generally), and Graft vs. Host Disease (bone marrow transplant rejection).

In the embodiments where the antigen is a human allograft transplantation antigen, specific sequences can be selected from: subunits of the various MHC class I and MHC class II haplotype proteins (for example, donor/recipient differences identified in tissue cross-matching), and single-amino-acid polymorphisms on minor blood group antigens including RhCE, Kell, Kidd, Duffy and Ss. Such compositions can be prepared individually for a given donor/recipient pair.

In the embodiments where the antigen is a self-antigen, specific antigens (and the autoimmune disease with which they are associated) can be selected from:

In type 1 diabetes mellitus, several main antigens have been identified: insulin, proinsulin, preproinsulin, glutamic acid decarboxylase-65 (GAD-65 or glutamate decarboxylase 2), GAD-67, glucose-6 phosphatase 2 (IGRP or islet-specific glucose 6 phosphatase catalytic subunit related protein), insulinoma-associated protein 2 (IA-2), and insulinoma-associated protein 2β (IA-2β); other antigens include ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestine-pancreas/pancreatic associated protein, S10013, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5. It should be noted that insulin is an example of an antigen that can be characterized both as a self-antigen and a therapeutic protein antigen. For example, rHu Insulin and bovine insulin are therapeutic protein antigens (that are the subject of unwanted immune attack), whereas endogenous human insulin is a self-antigen (that is the subject of an unwanted immune attack). Because endogenous human insulin is not available to be employed in a pharmaceutical composition a recombinant form is employed in the compositions of the disclosure.

Human insulin, including an exogenously obtained form useful in the compositions of the disclosure, has the following sequence (UNIPROT P01308):

```
                                        (SEQ ID NO: 5)
MALWMRLLPL LALLALWGPD PAAAFVNQHL CGSHLVEALY

LVGGERGFFY TPKTRREAED LQVGQVELGG GPGAGSLQPL

ALEGSLQKRG IVEQCCTSIC SLYQLENYGN.
```

GAD-65, including an exogenously obtained form useful in the compositions of the disclosure, has the following sequence (UNIPROT Q05329):

```
                                        (SEQ ID NO: 6)
MASPGSGFWS FGSEDGSGDS ENPGTARAWC QVAQKFTGGI

GNKLCALLYG DAEKPAESGG SQPPRAAARK AACACDQKPC

SCSKVDVNYA FLHATDLLPA CDGERPTLAF LQDVMNILLQ

YVVKSFDRST KVIDFHYPNE LLQEYNWELA DQPQNLEEIL

MHCQTTLKYA IKTGHPRYFN QLSTGLDMVG LAADWLTSTA

NTNMFTYEIA PVFVLLEYVT LKKMREIIGW PGGSGDGIFS

PGGAISNMYA MMIARFKMFP EVKEKGMAAL PRLIAFTSEH

SHFSLKKGAA ALGIGTDSVI LIKCDERGKM IPSDLERRIL

EAKQKGFVPF LVSATAGTTV YGAFDPLLAV ADICKKYKIW

MHVDAAWGGG LLMSRKHKWK LSGVERANSV TWNPHKMMGV

PLQCSALLVR EEGLMQNCNQ MHASYLFQQD KHYDLSYDTG

DKALQCGRHV DVFKLWLMWR AKGTTGFEAH VDKCLELAEY

LYNIIKNREG YEMVFDGKPQ HTNVCFWYIP PSLRTLEDNE

ERMSRLSKVA PVIKARMMEY GTTMVSYQPL GDKVNFFRMV

ISNPAATHQD IDFLIEEIER LGQDL.
```

IGRP, including an exogenously obtained form useful in the compositions of the disclosure, has the following sequence (UNIPROT QN9QR9):

```
                                        (SEQ ID NO: 7)
MDFLHRNGVLIIQHLQKDYRAYYTFLNFMSNVGDPRNIFFIYFPLCFQFN

QTVGTKMIWVAVIGDWLNLIFKWILFGHRPYWWVQETQIYPNHSSPCLEQ

FPTTCETGPGSPSGHAMGASCVWYVMVTAALSHTVCGMDKFSITLHRLTW

SFLWSVFWLIQISVCISRVFIATHFPHQVILGVIGGMLVAEAFEHTPGIQ

TASLGTYLKTNLFLFLFAVGFYLLLRVLNIDLLWSVPIAKKWCANPDWIH

IDTTPFAGLVRNLGVLFGLGFAINSEMFLLSCRGGNNYTLSFRLLCALTS

LTILQLYHFLQIPTHEEHLFYVLSFCKSASIPLTVVAFIPYSVHMLMKQS

GKKSQ.
```

In autoimmune diseases of the thyroid, including Hashimoto's thyroiditis and Graves' disease, main antigens include thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor.

In Addison's Disease, main antigens include 21-hydroxylase, 17α-hydroxylase, and P450 side chain cleavage enzyme (P450scc); other antigens include ACTH receptor, P450c21 and P450c17.

In premature ovarian failure, main antigens include FSH receptor and α-enolase.

In autoimmune hypophysitis, or pituitary autoimmune disease, main antigens include pituitary gland-specific protein factor (PGSF) 1a and 2; another antigen is type 2 iodothyronine deiodinase.

In multiple sclerosis, main antigens include myelin basic protein ("MBP"), myelin oligodendrocyte glycoprotein ("MOG") and myelin proteolipid protein ("PLP").

MBP, including an exogenously obtained form useful in the compositions of the disclosure, has the following sequence (UNIPROT P02686):

(SEQ ID NO: 8)
MGNHAGKRELNAEKASTNSETNRGESEKKRNLGELSRTTSEDNEVFGEAD

ANQNNGTSSQDTAVTDSKRTADPKNAWQDAHPADPGSRPHLIRLFSRDAP

GREDNTFKDRPSESDELQTIQEDSAATSESLDVMASQKRPSQRHGSKYLA

TASTMDHARHGFLPRHRDTGILDSIGRFFGGDRGAPKRGSGKDSHHPART

AHYGSLPQKSHGRTQDENPVVHFFKNIVTPRTPPPSQGKGRGLSLSRFSW

GAEGQRPGFGYGGRASDYKSAHKGFKGVDAQGTLSKIFKLGGRDSRSGSP

MARR.

MOG, including an exogenously obtained form useful in the compositions of the disclosure, has the following sequence (UNIPROT Q16653):

(SEQ ID NO: 9)
MASLSRPSLPSCLCSFLLLLLLQVSSSYAGQFRVIGPRHPIRALVGDEVE

LPCRISPGKNATGMEVGWYRPPFSRVVHLYRNGKDQDGDQAPEYRGRTEL

LKDAIGEGKVTLRIRNVRFSDEGGFTCFFRDHSYQEEAAMELKVEDPFYW

VSPGVLVLLAVLPVLLLQITVGLIFLCLQYRLRGKLRAEIENLHRTFDPH

FLRVPCWKITLFVIVPVLGPLVALIICYNWLHRRLAGQFLEELRNPF.

PLP, including an exogenously obtained form useful in the compositions of the disclosure, has the following sequence (UNIPROT P60201):

(SEQ ID NO: 10)
MGLLECCARCLVGAPFASLVATGLCFFGVALFCGCGHEALTGTEKLIETY

FSKNYQDYEYLINVIHAFQYVIYGTASFFFLYGALLLAEGFYTTGAVRQI

FGDYKTTICGKGLSATVTGGQKGRGSRGQHQAHSLERVCHCLGKWLGHPD

KFVGITYALTVVWLLVFACSAVPVYIYFNTWTTCQSIAFPSKTSASIGSL

CADARMYGVLPWNAFPGKVCGSNLLSICKTAEFQMTFHLFIAAFVGAAAT

LVSLLTFMIAATYNFAVLKLMGRGTKF.

Peptides/epitopes useful in the compositions of the disclosure for treating multiple sclerosis include some or all of the following sequences, individually in a composition of Formula 1, together in a cocktail of compositions of Formula 1, or fused in one or more compositions of Formula 2:

(SEQ ID NO: 11)
MBP13-32: KYLATASTMDHARHGFLPRH;

(SEQ ID NO: 12)
MBP83-99: ENPWHFFKNIVTPRTP;

(SEQ ID NO: 13)
MBP111-129: LSRFSWGAEGQRPGFGYGG;

(SEQ ID NO: 14)
MBP146-170: AQGTLSKIFKLGGRDSRSGSPMARR;

(SEQ ID NO: 15)
MOG1-20: GQFRVIGPRHPIRALVGDEV;

(SEQ ID NO: 16)
MOG35-55: MEVGWYRPPFSRWHLYRNGK;
and (SEQ ID NO: 17)
PLP139-154: HCLGKWLGHPDKFVGI.

In rheumatoid arthritis, main antigens include collagen II, immunoglobulin binding protein, the fragment crystallizable region of immunoglobulin G, double-stranded DNA, and the natural and cirtullinated forms of proteins implicated in rheumatoid arthritis pathology, including fibrin/fibrinogen, vimentin, collagen I and II, and alpha-enolase.

In autoimmune gastritis, a main antigen is H+,K+-ATPase.

In pernicious angemis, a main antigen is intrinsic factor.

In celiac disease, main antigens are tissue transglutaminases and the natural and deamidated forms of gluten or gluten-like proteins, such as alpha-, gamma-, and omega-gliadin, glutenin, hordein, secalin, and avenin. Those skilled in the art will appreciate, for example, that while the main antigen of celiac disease is alpha gliadin, alpha gliadin turns more immunogenic in the body through deamidation by tissue glutaminase converting alpha gliadin's glutamines to glutamic acid. Thus, while alpha gliadin is originally a foreign food antigen, once it has been modified in the body to become more immunogenic it can be characterized as a self-antigen.

In vitiligo, a main antigen is tyrosinase, and tyrosinase related protein 1 and 2.

MART1, Melanoma antigen recognized by T cells 1, Melan-A, including an exogenously obtained form useful in the compositions of the disclosure, has the following sequence (UNIPROT Q16655):

(SEQ ID NO: 18)
MPREDAHFIYGYPKKGHGHSYTTAEEAAGIGILTVILGVLLLIGCWYCRR

RNGYRALMDKSLHVGTQCALTRRCPQEGFDHRDSKVSLQEKNCEPVVPNA

PPAYEKLSAEQSPPPYSP.

Tyrosinase, including an exogenously obtained form useful in the compositions of the disclosure, has the following sequence (UNIPROT P14679):

(SEQ ID NO: 19)
MLLAVLYCLLWSFQTSAGHFPRACVSSKNLMEKECCPPWSGDRSPCGQLS

GRGSCQNILLSNAPLGPQFPFTGVDDRESWPSVFYNRTCQCSGNFMGFNC

-continued

```
GNCKFGFWGPNCTERRLLVRRNIFDLSAPEKDKFFAYLTLAKHTISSDYV

IPIGTYGQMKNGSTPMFNDINIYDLFVWMHYYVSMDALLGGSEIWRDIDF

AHEAPAFLPWHRLFLLRWEQEIQKLTGDENFTIPYWDWRDAEKCDICTDE

YMGGQHPTNPNLLSPASFFSSWQIVCSRLEEYNSHQSLCNGTPEGPLRRN

PGNHDKSRTPRLPSSADVEFCLSLTQYESGSMDKAANFSFRNTLEGFASP

LTGIADASQSSMHNALHIYMNGTMSQVQGSANDPIFLLHHAFVDSIFEQW

LRRHRPLQEVYPEANAPIGHNRESYMVPFIPLYRNGDFFISSKDLGYDYS

YLQDSDPDSFQDYIKSYLEQASRIWSWLLGAAMVGAVLTALLAGLVSLLC

RHKRKQLPEEKQPLLMEKEDYHSLYQSHL.
```

Melanocyte protein PMEL, gp100, including an exogenously obtained form useful in the compositions of the disclosure, has the following sequence (UNIPROT P40967):

```
                                         (SEQ ID NO: 20)
MDLVLKRCLLHLAVIGALLAVGATKVPRNQDWLGVSRQLRTKAWNRQLYP

EWTEAQRLDCWRGGQVSLKVSNDGPTLIGANASFSIALNFPGSQKVLPDG

QVIWVNNTIINGSQVWGGQPVYPQETDDACIFPDGGPCPSGSWSQKRSFV

YVWKTWGQYWQVLGGPVSGLSIGTGRAMLGTHTMEVTVYHRRGSRSYVPL

AHSSSAFTITDQVPFSVSVSQLRALDGGNKHFLRNQPLTFALQLHDPSGY

LAEADLSYTWDFGDSSGTLISRALVVTHTYLEPGPVTAQVVLQAAIPLTS

CGSSPVPGTTDGHRPTAEAPNTTAGQVPTTEVVGTTPGQAPTAEPSGTTS

VQVPTTEVISTAPVQMPTAESTGMTPEKVPVSEVMGTTLAEMSTPEATGM

TPAEVSIVVLSGTTAAQVTTTEWVETTARELPIPEPEGPDASSIMSTESI

TGSLGPLLDGTATLRLVKRQVPLDCVLYRYGSFSVTLDIVQGIESAEILQ

AVPSGEGDAFELTVSCQGGLPKEACMEISSPGCQPPAQRLCQPVLPSPAC

QLVLHQILKGGSGTYCLNVSLADTNSLAVVSTQLIMPGQEAGLGQVPLIV

GILLVLMAVVLASLIYRRRLMKQDFSVPQLPHSSSHWLRLPRIFCSCPIG

ENSPLLSGQQV.
```

In myasthenia gravis, a main antigen is acetylcholine receptor.

In pemphigus vulgaris and variants, main antigens are desmoglein 3, 1 and 4; other antigens include pemphaxin, desmocollins, plakoglobin, perplakin, desmoplakins, and acetylcholine receptor.

In bullous pemphigoid, main antigens include BP180 and BP230; other antigens include plectin and laminin 5.

In dermatitis herpetiformis Duhring, main antigens include endomysium and tissue transglutaminase.

In epidermolysis bullosa acquisita, a main antigen is collagen VII.

In systemic sclerosis, main antigens include matrix metalloproteinase 1 and 3, the collagen-specific molecular chaperone heat-shock protein 47, fibrillin-1, and PDGF receptor; other antigens include Scl-70, U1 RNP, Th/To, Ku, Jo1, NAG-2, centromere proteins, topoisomerase I, nucleolar proteins, RNA polymerase I, II and III, PM-Slc, fibrillarin, and B23.

In mixed connective tissue disease, a main antigen is U1snRNP.

In Sjogren's syndrome, the main antigens are nuclear antigens SS-A and SS-B; other antigens include fodrin, poly(ADP-ribose) polymerase and topoisomerase, muscarinic receptors, and the Fc-gamma receptor IIIb.

In systemic lupus erythematosus, main antigens include nuclear proteins including the "Smith antigen," SS-A, high mobility group box 1 (HMGB1), nucleosomes, histone proteins and double-stranded DNA (against which auto-antibodies are made in the disease process).

In Goodpasture's syndrome, main antigens include glomerular basement membrane proteins including collagen IV.

In rheumatic heart disease, a main antigen is cardiac myosin.

In autoimmune polyendocrine syndrome type 1 antigens include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega.

In neuromyelitis optica, a main antigen is AQP4.

Aquaporin-4, including an exogenously obtained form useful in the compositions of the disclosure, has the following sequence (UNIPROT P55087):

```
                                         (SEQ ID NO: 21)
MSDRPTARRWGKCGPLCTRENIMVAFKGVWTQAFWKAVTAEFLAMLIFVL

LSLGSTINWGGTEKPLPVDMVLISLCFGLSIATMVQCFGHISGGHINPAV

TVAMVCTRKISIAKSVFYIAAQCLGAIIGAGILYLVTPPSVVGGLGVTMV

HGNLTAGHGLLVELIITFQLVFTIFASCDSKRTDVTGSIALAIGFSVAIG

HLFAINYTGASMNPARSFGPAVIMGNWENHWIYWVGPIIGAVLAGGLYEY

VFCPDVEFKRRFKEAFSKAAQQTKGSYMEVEDNRSQVETDDLILKPGVVH

VIDVDRGEEKKGKDQSGEVLSSV.
```

In uveitis, main antigens include Retinal S-antigen or "S-arrestin" and interphotoreceptor retinold binding protein (IRBP) or retinol-binding protein 3.

S-arrestin, including an exogenously obtained form useful in the compositions of the disclosure, has the following sequence (UNIPROT P10523):

```
                                         (SEQ ID NO: 22)
MAASGKTSKS EPNHVIFKKI SRDKSVTIYL GNRDYIDHVS

QVQPVDGVVL VDPDLVKGKK VYVTLTCAFR YGQEDIDVIG

LTFRRDLYFS RVQVYPPVGA ASTPTKLQES LLKKLGSNTY

PFLLTFPDYL PCSVMLQPAP QDSGKSCGVD FEVKAFATDS

TDAEEDKIPK KSSVRLLIRK VQHAPLEMGP QPRAEAAWQF

FMSDKPLHLA VSLNKEIYFH GEPIPVTVTV TNNTEKTVKK

IKAFVEQVAN VVLYSSDYYV KPVAMEEAQE KVPPNSTLTK

TLTLLPLLAN NRERRGIALD GKIKHEDTNL ASSTIIKEGI

DRTVLGILVS YQIKVKLTVS GFLGELTSSE VATEVPFRLM

HPQPEDPAKE SYQDANLVFE EFARHNLKDA GEAEEGKRDK

NDVDE.
```

IRBP, including an exogenously obtained form useful in the compositions of the disclosure, has the following sequence (UNIPROT P10745):

(SEQ ID NO: 23)
MMREWVLLMSVLLCGLAGPTHLFQPSLVLDMAKVLLDNYCFPENLLGMQE

AIQQAIKSHEILSISDPQTLASVLTAGVQSSLNDPRLVISYEPSTPEPPP

QVPALTSLSEEELLAWLQRGLRHEVLEGNVGYLRVDSVPGQEVLSMMGEF

LVAHVWGNLMGTSALVLDLRHCTGGQVSGIPYIISYLHPGNTILHVDTIY

NRPSNTTTEIWTLPQVLGERYGADKDVVVLTSSQTRGVAEDIAHILKQMR

RAIVVGERTGGGALDLRKLRIGESDFFFTVPVSRSLGPLGGGSQTWEGSG

VLPCVGTPAEQALEKALAILTLRSALPGVVHCLQEVLKDYYTLVDRVPTL

LQHLASMDFSTVVSEEDLVTKLNAGLQAASEDPRLLVRAIGPTETPSWPA

PDAAAEDSPGVAPELPEDEAIRQALVDSVFQVSVLPGNVGYLRFDSFADA

SVLGVLAPYVLRQVWEPLQDTEHLIMDLRHNPGGPSSAVPLLLSYFQGPE

AGPVHLFTTYDRRTNITQEHFSHMELPGPRYSTQRGVYLLTSHRTATAAE

EFAFLMQSLGWATLVGEITAGNLLHTRTVPLLDTPEGSLALTVPVLTFID

NHGEAWLGGGVVPDAIVLAEEALDKAQEVLEFHQSLGALVEGTGHLLEAH

YARPEVVGQTSALLRAKLAQGAYRTAVDLESLASQLTADLQEVSGDHRLL

VFHSPGELVVEEAPPPPPAVPSPEELTYLIEALFKTEVLPGQLGYLRFDA

MAELETVKAVGPQLVRLVWQQLVDTAALVIDLRYNPGSYSTAIPLLCSYF

FEAEPRQHLYSVFDRATSKVTEVWTLPQVAGQRYGSHKDLYILMSHTSGS

AAEAFAHTMQDLQRATVIGEPTAGGALSVGIYQVGSSPLYASMPTQMAMS

ATTGKAWDLAGVEPDITVPMSEALSIAQDIVALRAKVPTVLQTAGKLVAD

NYASAELGAKMATKLSGLQSRYSRVTSEVALAEILGADLQMLSGDPHLKA

AHIPENAKDRIPGIVPMQIPSPEVFEELIKFSFHTNVLEDNIGYLRFDMF

GDGELLTQVSRLLVEHIWKKIMHTDAMIIDMRFNIGGPTSSIPILCSYFF

DEGPPVLLDKIYSRPDDSVSELWTHAQVVGERYGSKKSMVILTSSVTAGT

AEEFTYIMKRLGRALVIGEVTSGGCQPPQTYHVDDTNLYLTIPTARSVGA

SDGSSWEGVGVTPHVVVPAEEALARAKEMLQHNQLRVKRSPGLQDHL.

In the embodiments where the antigen is a foreign antigen against which an unwanted immune response can be developed, such as food antigens, specific antigens can be:
from peanut: conarachin (Ara h 1), allergen II (Ara h 2), arachis agglutinin, conglutin (Ara h 6);
  conarachin, for example has the sequence identified as UNIPROT Q6PSU6
from apple: 31 kda major allergen/disease resistance protein homolog (Mal d 2), lipid transfer protein precursor (Mal d 3), major allergen Mal d 1.03 D (Mal d 1);
from milk: α-lactalbumin (ALA), lactotransferrin; from kiwi: actinidin (Act c 1, Act d 1), phytocystatin, thaumatin-like protein (Act d 2), kiwellin (Act d 5);
from egg whites: ovomucoid, ovalbumin, ovotransferrin, and lysozyme;
from egg yolks: livetin, apovitillin, and vosvetin;
from mustard: 2S albumin (Sin a 1), 11S globulin (Sin a 2), lipid transfer protein (Sin a 3), profilin (Sin a 4);
from celery: profilin (Api g 4), high molecular weight glycoprotein (Api g 5);
from shrimp: Pen a 1 allergen (Pen a 1), allergen Pen m 2 (Pen m 2), tropomyosin fast isoform;
from wheat and/or other cerials: high molecular weight glutenin, low molecular weight glutenin, alpha-, gamma- and omega-gliadin, hordein, secalin and/or avenin;
peptides/epitopes useful in the compositions of the disclosure for treating Celiac Disease include some or all of the following sequences, individually in a composition of Formula 1, together in a cocktail of compositions of Formula 1, or fused in one or more compositions of Formula 2:
DQ-2 relevant, Alpha-gliadin "33-mer" native:

(SEQ ID NO: 24)
LQLQPFPQPQLPYPQPQLPYPQPQLPYPQPQPF

DQ-2 relevant, Alpha-gliadin "33-mer" deamidated:

(SEQ ID NO: 25)
LQLQPFPQPELPYPQPELPYPQPELPYPQPQPF

DQ-8 relevant, Alpha-gliadin:

(SEQ ID NO: 26)
QQYPSGQGSFQPSQQNPQ

DQ-8 relevant, Omega-gliadin (wheat, U5UA46):

(SEQ ID NO: 27)
QPFPQPEQPFPW from strawberry: major strawberry allergy Fra a 1-E (Fra a 1); and
from banana: profilin (Mus xp 1).
In the embodiments where the antigen is a foreign antigen against which an unwanted immune response is developed, such as to animal, plant and environmental antigens, specific antigens can, for example, be: cat, mouse, dog, horse, bee, dust, tree and goldenrod, including the following proteins or peptides derived from:
weeds, (including ragweed allergens amb a 1, 2, 3, 5, and 6, and Amb t 5; pigweed Che a 2 and 5; and other weed allergens Par j 1, 2, and 3, and Par o 1);
grass (including major allergens Cyn d 1, 7, and 12; Dac g 1, 2, and 5; Hol l 1.01203; Lol p 1, 2, 3, 5, and 11; Mer a 1; Pha a 1; Poa p 1 and 5);
pollen from ragweed and other weeds (including curly dock, lambs quarters, pigweed, plantain, sheep sorrel, and sagebrush), grass (including Bermuda, Johnson, Kentucky, Orchard, Sweet vernal, and Timothy grass), and trees (including catalpa, elm, hickory, olive, pecan, sycamore, and walnut);
dust (including major allergens from species *Dermatophagoides pteronyssinus*, such as Der p 1, 2, 3, 4, 5, 6, 7, 8, 9, 10, 11, 14, 15, 18, 20, 21, and 23; from species *Dermatophagoides farina*, such as Der f 1, 2, 3, 6, 7, 10, 11, 13, 14, 15, 16, 18, 22, and 24; from species *Blomia tropicalis* such as Blo t 1, 2, 3, 4, 5, 6, 10, 11, 12, 13, 19, and 21; also allergens Eur m 2 from *Euroglyphus maynei*, Tyr p 13 from *Tyrophagus putrescentiae*, and allergens Bla g 1, 2, and 4; Per a 1, 3, and 7 from cockroach);
pets (including cats, dogs, rodents, and farm animals; major cat allergens include Fel d 1 through 8, cat IgA, BLa g 2, and cat albumin; major dog allergens include Can f 1 through 6, and dog albumin);

bee stings, including major allergens Api m 1 through 12; and fungus, including allergens derived from, species of Aspergillus and Penicillium, as well as the species Alternaria alternata, Davidiella tassiana, and Trichophyton rubrum.

As will be appreciated by those skilled in the art, a patient can be tested to identify an antigen against which an unwanted immune response has developed, and a protein, peptide or the like can be developed based on that antigen and incorporated as X in a composition of the present disclosure.

Sialated Antigens, Antibodies, Antibody Fragments

Following are examples of antigens, antibodies, antibody fragments having sialylation that can be removed to leave glycosylation specifically targeting the ASGPR: follicle stimulating hormone (FSH), human chorionic gonadotropin (HCG), luteinizing hormone (LH), osteopontin, thyroid stimulating hormone (TSH), agalsidase alfa, agalsidase beta (FABRAZYME®; Genzyme), epoetin alfa and epoetin beta, follitropin alfa (GONAL-F®; Merck/Serono) and follitropin beta (FOLLISTIM®; Schering-Plough), insulin growth factor binding protein 6 (IGFBP-6), lutropin alfa (LUVERIS®; Merck/Serono), transforming growth factor β1, antithrombin (ATryn®/TROMBATE-III®; Genzyme/Talecris Biotherapeutics), thyrotropin alfa (THYROGEN®; Genzyme), lenograstim, sargramostim (LEUKINE®; Genzyme), interleukin-3, prourokinase, lymphotoxin, C1-esterase inhibitor (Berinert®; CSL), IgG-like antibodies, interferon beta, coagulation factor VIIa (NOVOSEVEN®; Novo Nordisk), coagulation factor VIII (moroctocog alfa), coagulation factor IX (nonacog alfa) (BENEFIX®; Wyeth), and the p55 tumor necrosis receptor fusion protein. (See: Byrne et al., Drug Discovery Today, Vol 12, No. 7/8, pages 319-326, April 2007 and Sola et al., BioDrugs. 2010; 24(1): 9-21). Pharmaceutically relevant proteins that have previously been hyperglycosylated and can be desialylated for hepatocyte-ASGPR taregeting include: interferon alfa and gamma, luteinizing hormone, Fv antibody fragments, asparaginase, cholinesterase, darbepoetin alfa (AraNESP®; Amgen), trombopoietin, leptin, FSH, IFN-α2, serum albumin, and corifollitropin alfa.

Proteins with glycans that do not normally terminate in sialic acids, including proteins produced in bacteria or yeast (such as arginase, some insulins, and uricase) would not be amenable to desialylation.

Those skilled in the art will appreciate that publicly available references, such as UNIPROT, disclose the presence and location of sites for desialylation on most if not all antigens, antibodies, antibody fragments and ligands of interest.

Antibodies and Peptide Ligands

In the embodiments employing an antibody, antibody fragment or ligand, such moieties are chosen to specifically bind a targeted circulating protein or peptide or antibody, and result in hepatic uptake of the circulating targeted moiety, possibly as an adduct with the targeting moiety, ultimately resulting in the clearance and inactivation of the circulating targeted moiety. For example, liver-targeted Factor VIII will bind and clear circulating Factor VIII antibodies. Procedures for the identification of such moieties will be familiar to those skilled in the art.

Linkers

The linkers employed in the compositions of the present disclosure ("Y" in Formula 1) can include N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, nitrophenoxy poly(ethylene glycol)ester linkers and the like.

One particular group of linkers Formula Y'-CMP below (where Y' indicates the remaining portion of the linker and $R^9$ and Z are as defined). More particularly, in the group of linkers including Formula Y'-CMP, the $R^9$ substituent is an ethylacetamido group, and even more particularly the ethylacetamido is conjugated with C1 of N-acetylgalactosamine.

Formula Y'-CMP

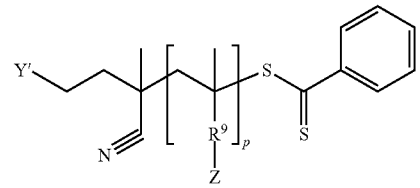

Di-thiol-containing linkers, particularly disulfanylethyl carbamate-containing linkers (named including a free amine of X, otherwise named a "disulfanyl ethyl ester" without including the free amine of X) are particularly advantageous in the present compositions as having the ability to cleave and release an antigen in its original form once inside a cell, for example as illustrated below (where Y' indicates the remaining portion of the linker and X' and Z are as defined).

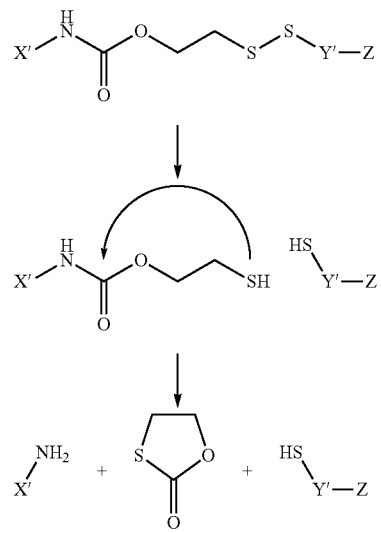

Particularly with regard to the linkers illustrated below in Formula Ya through Formula Yp:

the left bracket "(" indicates the bond between X and Y; the right or bottom bracket ")" indicates the bond between Y and Z;

n is an integer representing a mixture including from about 1 to 100, particularly about 8 to 90 (e.g., 7, 8, 9, 10, 11, 12, 13, 14, 15, 16, 17, 18, 19, 20, 25, 30, 35, 40, 45, 50, 55, 60, 65, 70, 75, 80, 85, 90 or 95), more particularly about 40 to 80 (e.g., 39, 40, 43, 45, 46, 48, 50, 52, 53, 55, 57, 60, 62, 65, 66, 68, 70, 73, 75, 78, 80 or 81) ethylene glycol groups, where the mixture typically encompasses the integer specified as n±10%;

p is an integer representing a mixture including from about 2 to 150, particularly about 20 to 100 (e.g., 18, 19, 20, 25, 30, 35, 40, 45, 50, 55, 60, 65, 70, 75, 80, 85, 90, 95, 100 or 105) and more particularly about 30 to 40 (e.g., 28, 29, 30, 31, 32, 33, 34, 35, 36, 37, 38, 39, 40, 41, 42, 43 or 44), where the mixture typically encompasses the integer specified as p±10%;

q is an integer representing a mixture including from about 1 to 44, particularly about 3 to 20 (e.g., 3, 4, 5, 6, 7, 8, 9, 10, 11, 12, 13, 14, 15, 16, 17, 18, 19, 20, 21 or 22) and more particularly about 4 to 12 (e.g., 4, 5, 6, 7, 8, 9, 10, 11, 12 or 13), where the mixture typically encompasses the integer specified as q±10%; and $R^8$ is —$CH_2$— ("methyl") or —$CH_2$—$CH_2$—$C(CH_3)(CN)$— ("1-cyano-1-methyl-propyl" or "CMP").

$R^9$ is a direct bond or —$CH_2$—$CH_2$—NH—C(O)— (an ethylacetamido group or "EtAcN"), as illustrated in the following structures of Formula 1 (where the EtAcN group is shown and the rest of the linker is referred to as Y'):

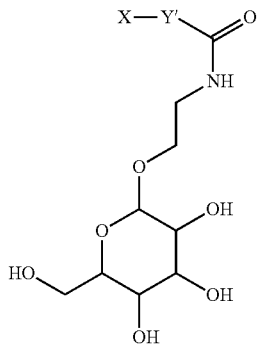

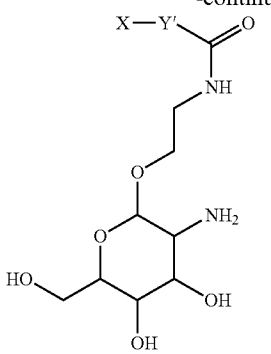

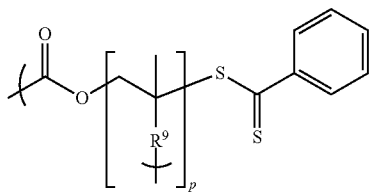

and Z is galactose, galactosamine or N-acetylgalactosamine conjugated at C1.

Formula Ya

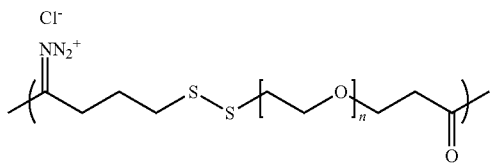

Formula Yb

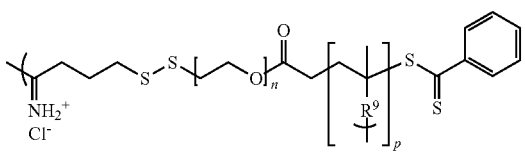

Formula Yc

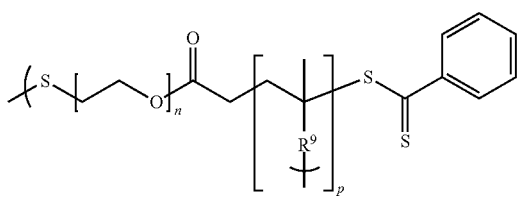

Formula Yd

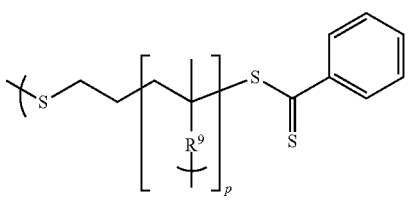

Formula Ye

Formula Yf

-continued
Formula Yg
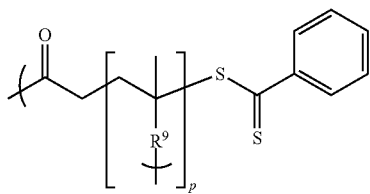
Formula Yh
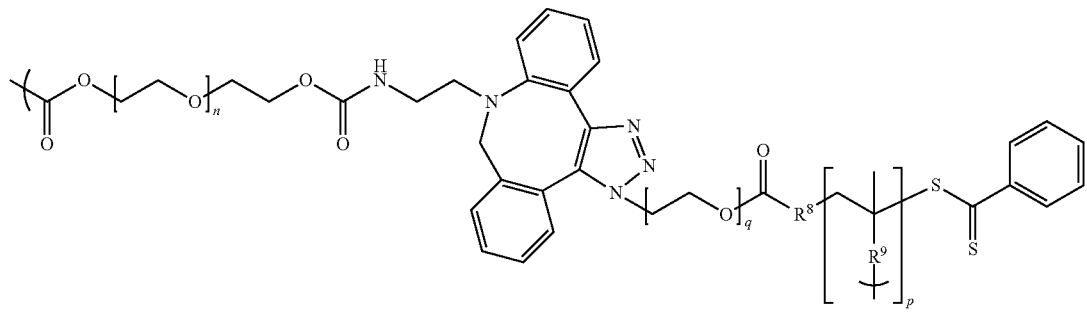
Formula Yi
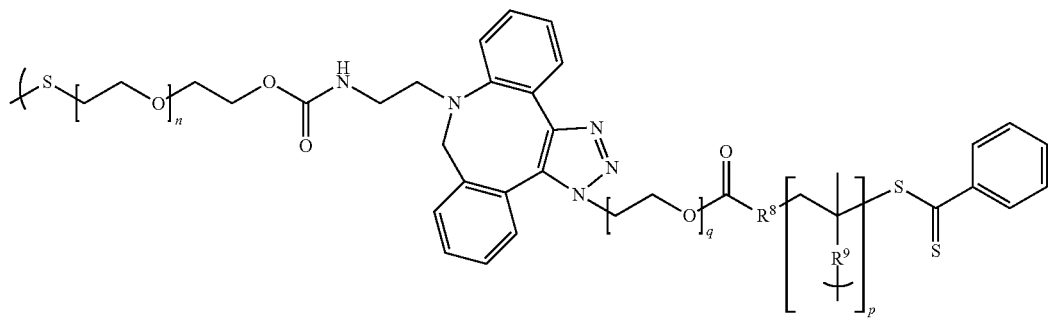
Formula Yj
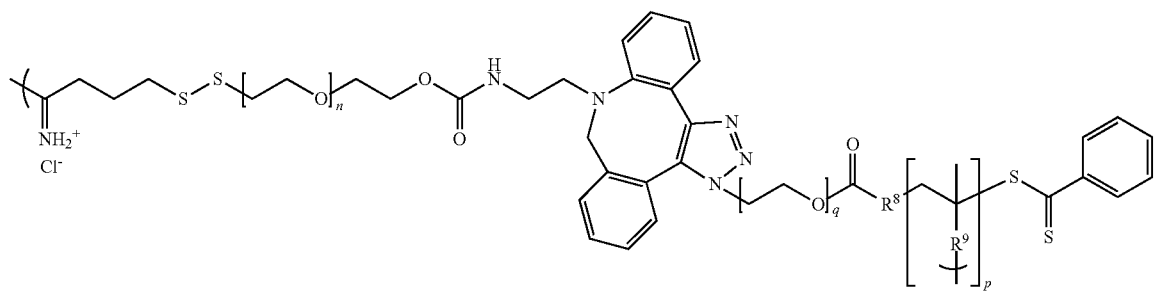
Formula Yk
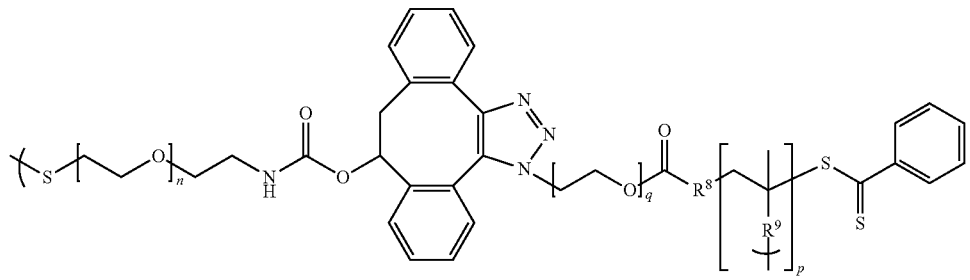

Formula YL

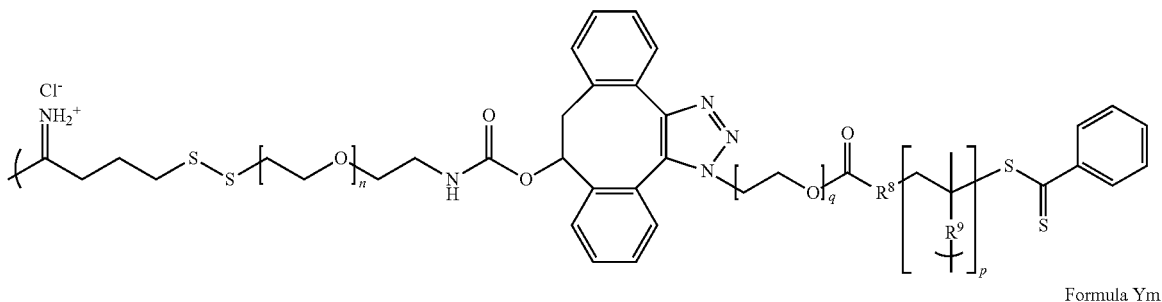

Formula Ym

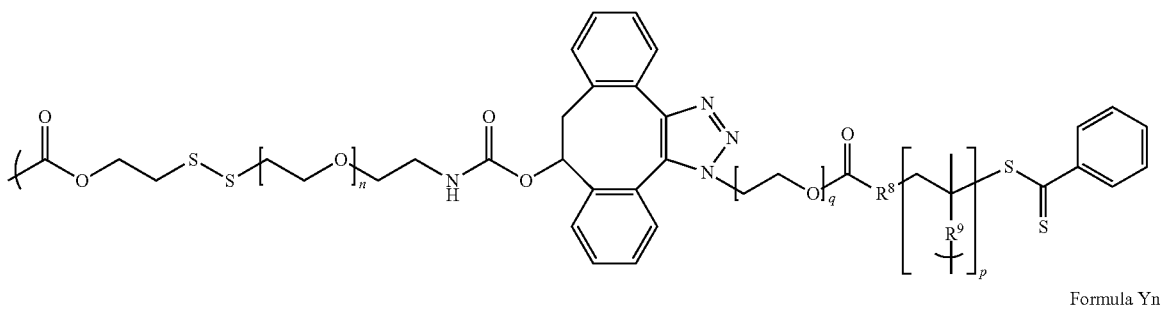

Formula Yn

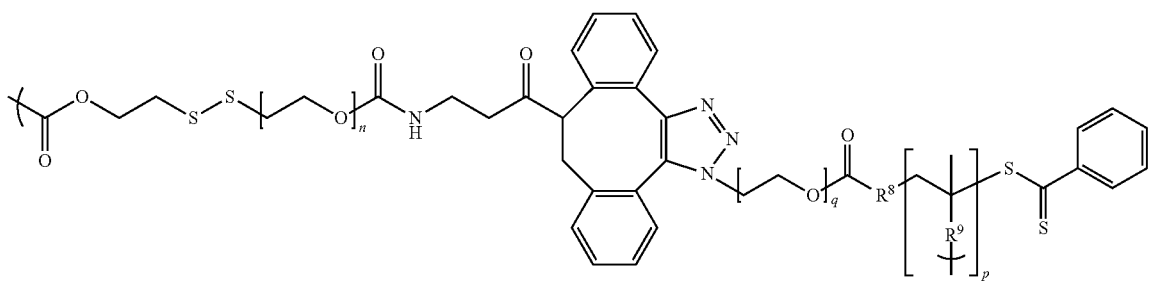

(Linkers of Formula Yn can be synthesized via certain precursors that render Yn particularly suitable for conjugation to hydrophobic antigens.)

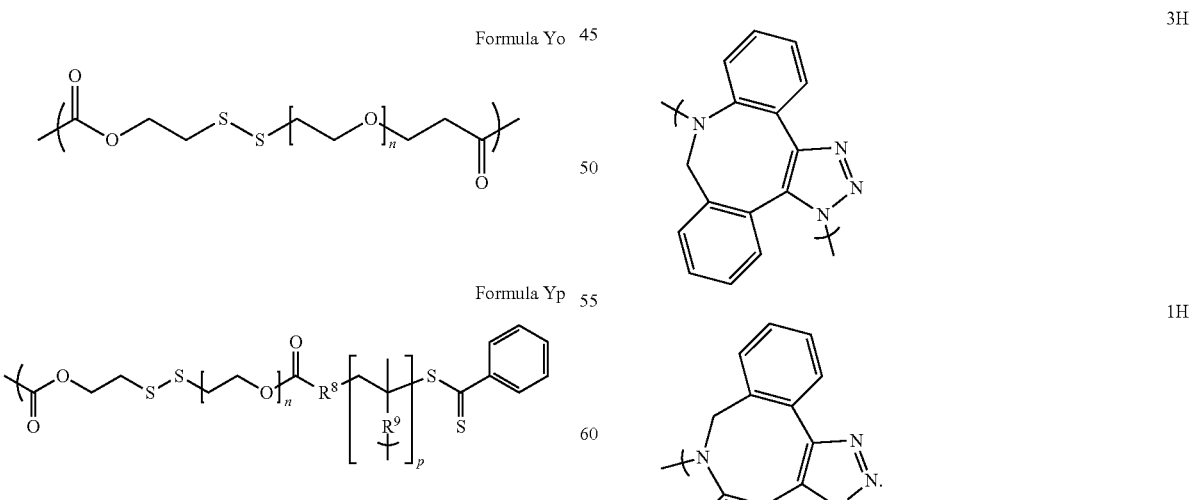

Formula Yo

Formula Yp

3H

1H triazolo[4,5-d]azocin-8yl and 8,9-dihydro-3H-dibenzo[b,f][1,2,3]triazolo[4,5-d]azocin-8yl structures illustrated below:

The linkers shown above as Formulae Yh through Yn are synthesized as isomers that are employed without separation. For example, the linkers of Formulae Yh, Yi, Yj and Yn will be a mixture of the 8,9-dihydro-1H-dibenzo[b,f][1,2,3]

The linkers of Formulae Yk, YL and Ym will be a mixture of the 8,9-dihydro-1H-dibenzo[3,4:7,8]cycloocta[1,2-d][1,2,3]triazol-8-yl and 8,9-dihydro-1H-dibenzo[3,4:7,8]cycloocta[1,2-d][1,2,3]triazol-9-yl structures illustrated below:

-8-yl

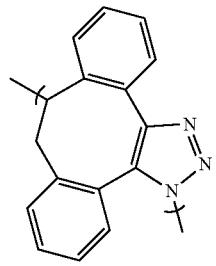

-9-yl

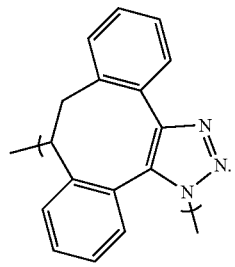

The presence of such isomeric mixtures does not impair the functionality of the compositions employing such linkers.

Galactosylating Moieties

The galactosylating moieties employed in the compositions of the present disclosure serve to target the compositions to liver cells (for example, specifically binding hepatocytes) and can be selected from: galactose, galactosamine or N-acetylgalactosamine. It has been reported that ASGPR affinity can be retained while modifying either side of galactose's C3/C4-diol anchor (Mamidyala, Sreeman K., et al., *J. Am. Chem. Soc.* 2012, 134, 1978-1981), therefore the points of conjugation are particularly at C1, C2 and C6.

Particular galactosylating moieties include galactose conjugated at C1 or C6, galactosamine conjugated at C2, and N-acetylgalactosamine conjugated at C6. Other particular galactosylating moieties include N-acetylgalactosamine conjugated at C2, more particularly conjugated to a linker bearing an $R^9$ substituent that is $CH_2$. Still other particular galactosylating moieties include galactose, galactosamine or N-acetylgalactosamine conjugated at C1, more particularly conjugated to a linker bearing an $R^9$ substituent that is an ethylacetamido group.

ASGPR Targeting Antibodies

The ASGPR-specific antibodies employed in the compositions of the present disclosure also serve to target compositions of the disclosure to liver cells and can be selected from commercially available products, such as: Anti-Asialoglycoprotein Receptor 1 antibody (ab42488) from Abcam plc, Cambridge, UK and ASGPR1/2 (FL-291) (sc28977) from Santa Cruz Biotechnology, Inc., Dallas, Tex. Alternatively, such antibodies can be expressed using any of a number of published sequences, such as the Dom26h-196-61, single-domain anti-ASGPR antibody:

(SEQ.ID.No: 6)
EVQLLESGGGLVQPGGSLRLSCAASGFTFEKYAMAWVRQAPGKGLEWVSR

ISARGVTTYYADSVKGRFTISRDNSKNTLYLQMNSLRAEDTAVYYCASHK

RHEHTRFDSWGQGTLVTVSS

[Coulstock E, et al., (2013) "Liver-targeting of interferon-alpha with tissue-specific domain antibodies." *PLoS One*. 8(2):e57263 and US 2013/0078216], or such a sequence having conservative substitutions. The above-referenced US patent application discloses liver-targeting molecules such as DOM26h-196-61 for delivering certain therapeutics [including interferon (interferon alpha 2, interferon alpha 5, interferon alpha 6, or consensus interferon), Ribavirin, Nexavar/Sorafenib, Erbitus/Cetuximab, Avastatin/bevacizumab, and Herceptin/trastuzumab] for the treatment of liver diseases. The compositions of matter corresponding to Formula 2 employing DOM26h-196-61 or another liver-targeting molecule described in US 2013/0078216 do not include interferon (interferon alpha 2, interferon alpha 5, interferon alpha 6, or consensus interferon), Ribavirin, Nexavar/Sorafenib, Erbitus/Cetuximab, Avastatin/bevacizumab, and Herceptin/trastuzumab within their scope.

New sequences for an antibody, antibody fragment, or peptide that specifically targets ASGPR can be discovered using various methods known by those skilled in the art. These methods can include, but are not limited to, vaccination technology, hybridoma technology, library display technologies (including bacterial and phage platforms), endogenous repertoire screening technologies, directed evolution and rational design.

NOMENCLATURE

The compositions of Formula 1 can be named using a combination of IUPAC and trivial names. For example, a compound corresponding to Formula 1 where X is a cyclobutyl moiety (shown instead of an antigen for illustrative purposes), Y is Formula Ya, m is 1, n is 4 and Z is N-acetylgalactosam in-2-yl:

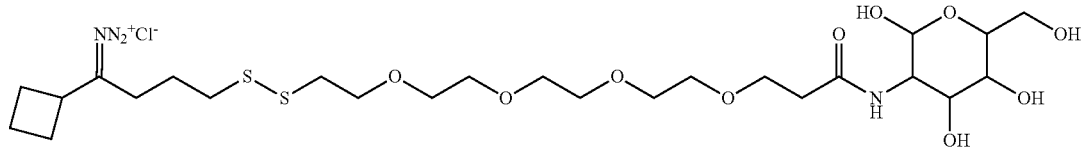

can be named (Z)-(21-cyclobutyl-1-oxo-1-((2,4,5-trihydroxy-6-(hydroxymethyl)tetrahydro-2H-pyran-3-yl)amino)-4,7,10,13-tetraoxa-16,17-dithiahenicosan-21-ylidene)triaz-1-yn-2-ium chloride, so the corresponding composition of the disclosure where X is tissue transglutaminase can be named (Z)-(21-(tissue transglutaminase)-1-oxo-1-((2,4,5-trihydroxy-6-(hydroxymethyl)tetrahydro-2H-pyran-3-yl)amino)-4,7,10,13-tetraoxa-16,17-dithiahenicosan-21- ylidene)triaz-1-yn-2-ium chloride. The corresponding composition of the disclosure where X' is tissue transglutaminase, m is 2, n is 4 and Z' is N-acetylgalactosamin-2-yl can be named (3Z)-((tissue transgultaminase)-1,3-diylbis(1-oxo-1-((2,4,5-trihydroxy-6-(hydroxymethyl)tetrahydro-2H-pyran-3-yl)amino)-4,7,10,13-tetraoxa-16,17-dithiahenicosan-21-yl-21-ylidene))bis(triaz-1-yn-2-ium) chloride.

In the interest of simplification, the compositions of Formula 1 can be named using an alternative naming system by reference to X and correspondence to one of Formulae 1a to 1p (as illustrated in the reaction schemes) followed by recitation of the integers for variables m, n, p and/or q, $R^8$, $R^9$ and identification of the galactosylating moiety and the position at which it is conjugated. Under this system, the composition of Formula 1a where X is ovalbumin, m is 2, n is 4 and Z is N-acetylgalactosamin-2-yl can be named "F1a-OVA-$m_2$-$n_4$-2NAcGAL."

Similarly, the following composition of Formula 1

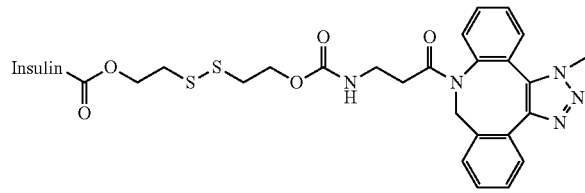

can be named "2-((2-(((3-(3-(22-((3-acetamido-4,5-dihydroxy-6-(hydroxymethyl)tetrahydro-2H-pyran-2-yl)oxy)-16-cyano-16,18-dimethyl-13,19-dioxo-18-((phenylcarbonothioyl)thio)-3,6,9,12-tetraoxa-20-azadocosyl)-3,9-dihydro-8H-dibenzo[b,f][1,2,3]triazolo[4,5-d]azocin-8-yl)-3-oxopropyl)carbamoyl)oxy)ethyl)disulfanyl)ethyl insulin carboxylate." The isomer:

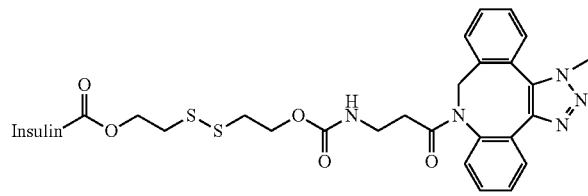

can be named "2-((2-(((3-(1-(22-((3-acetamido-4,5-dihydroxy-6-(hydroxymethyl)tetrahydro-2H-pyran-2-yl)oxy)-16-cyano-16,18-dimethyl-13,19-dioxo-18-((phenylcarbonothioyl)thio)-3,6,9,12-tetraoxa-20-azadocosyl)-1,9-dihydro-8H-dibenzo[b, t][1,2,3]triazolo[4,5-d]azocin-8-yl)-3-oxopropyl)carbamoyl)-oxy)ethyl)disulfanyl)ethyl insulin carboxylate" (bold lettering highlights added for convenience in identifying the difference between the formal names). Employing the naming system adopted for the present disclosure, both isomers can be named "F1n-insulin-$m_1$-$n_1$-$p_1$-$q_4$-CMP-EtAcN-1NAcGAL" where CMP indicates that $R^8$ is 1-cyano-1-methyl-propyl, EtAcN indicates that $R^9$ is ethylacetamido and 1NAcGAL indicates Z" is N-acetylgalactosamine conjugated at C1. Absence of the abbreviation EtAcN before the designation for Z would indicate that $R^9$ is a direct bond.

In the compositions of Formula 2, left-to-right orientation of should not be taken as specifying N to C ordering absent specific indication to the contrary. For example, the compound of Formula 2 where m' is 1, m" is 0, X is Ovalbumin, Y is Gly$_3$Ser and Z is Anti-ASGPR Dom26h-196-61, can be named OVA-Gly3Ser-DOM and read as covering both of the following:

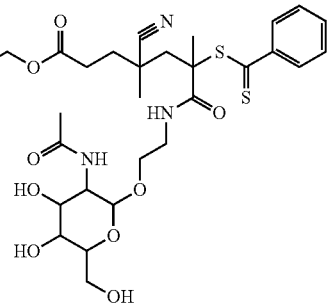

The compositions of Formula 2, for example where m' is 1, m" is 0, X is Ovalbumin, Y is Gly$_3$Ser and Z is Anti-ASGPR Dom26h-196-61 (having a purification tag attached via an additional linker) can be named as follows:

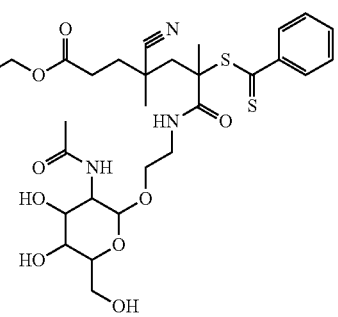

where the C' terminal Gly₃Ser-6×His group represents an amino acid sequence that facilitates isolation and purification.

The composition of Formula 2 where m' is 1, m" is 1, each X is Factor VIII, each Y is Gly₃Ser and Z is Anti-ASGPR Dom26h-196-61 (having a purification tag attached via an additional linker) can be named FVIII-Gly₃Ser-DOM-Gly₃Ser-FVIII-Gly₃Ser-6×His and covers both of the following:

N-FVIII-Gly₃Ser-DOM-Gly₃Ser-FVIII-Gly₃Ser-6xHis-C
and

N-6xHis-Gly₃Ser-FVIII-Gly₃Ser-DOM-Gly₃Ser-FVIII-C.

The composition of Formula 2 where m' is 3, m" is 0, one, the three X antigens, respectively, are Alpha-gliadin "33-mer" deamidated (SEQ ID NO:25), Alpha-gliadin (SEQ ID NO:26) and Omega-gliadin (SEQ ID NO:27), each Y is a linker having an immunoproteosome cleavage site ("IPC"), and Z is Anti-ASGPR Dom26h-196-61 can be named:

Alpha-gliadin "33-mer" deamidated-IPC-Alpha-gliadin-IPC-Omega-gliadin-IPC-DOM.

Preparation of the Compositions of the Disclosure

The compositions of Formula 1 can be prepared, for example, by adjusting the procedures described in Zhu, L., et al., *Bioconjugate Chem.* 2010, 21, 2119-2127. Syntheses of certain compositions of Formula 1 are also described below with reference to Reaction Schemes 1 to 14. Other synthetic approaches will be apparent to those skilled in the art.

Formula 101 (below) is an alternative representation of X $$X = X'\text{---}[R^1]_m \quad 101$$

where $R^1$ is a free surface amino (—NH₂) or thiol (—SH) moiety positioned on X's three-dimensional structure so as to be accessible for conjugation to a linker, and X' represents the remainder of X excluding the identified free amino group(s) [(X" is used in the reaction schemes to represent the remainder of X excluding free thiol group(s)]. Depending upon the identity of X, there will be at least one (the N-terminal amine) and can be multiple $R^1$ groups (predominantly from lysine residues or cysteine residues that are not involved in disulfide bonding), as represented by m, which is an integer from about 1 to 100, more typically 1 or from about 4 to 20, and most typically 1 to about 10.

Variables employed in the reaction schemes are as defined above, and additionally include the following, which should be understood to have these meanings absent any specific indication otherwise with respect to a particular reaction scheme or step.

$R^2$ is OH or a protecting group;
$R^3$ is OH, NH₂, NHAc, a protecting group or NH-protecting group;
$R^4$ is OH or a protecting group;
$R^5$ is OH or a protecting group;
$R^6$ is OH or a protecting group;
Z' is galactose conjugated at C1 or C6, galactosamine conjugated at C2, or N-acetylgalactosamine conjugated at C6;
$R^8$ is —CH₂— or —CH₂—CH₂—C(CH₃)(CN)—; and
$R^9$ is a direct bond and Z" is N-acetylgalactosamine conjugated at C2;

$R^9$ is an ethylacetamido group and Z" is galactose, galactosamine or N-acetylgalactosamine conjugated at C1.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present disclosure are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, centrifugal size exclusion chromatography, high-performance liquid chromatography, recrystallization, sublimation, fast protein liquid chromatography, gel electrophoresis, dialysis, or a combination of these procedures. Specific illustrations of suitable separation and isolation procedures can be had by reference to the examples hereinbelow. However, other equivalent separation or isolation procedures can, of course, also be used.

Unless otherwise specified (including in the examples), all reactions are conducted at standard atmospheric pressure (about 1 atmosphere) and ambient (or room) temperature (about 20° C.), at about pH 7.0-8.0.

Characterization of reaction products can be made by customary means, e.g., proton and carbon NMR, mass spectrometry, size exclusion chromatography, infrared spectroscopy, gel electrophoresis.

Reaction Scheme 1 illustrates the preparation of compositions of Formula 1 where Z can be galactose, galactosamine or N-acetylgalactosamine. In that regard and as defined above, Z' as employed in Reaction Scheme 1 encompasses galactose conjugated at C1 and C6 and corresponding to the following structures according to Formula 1:

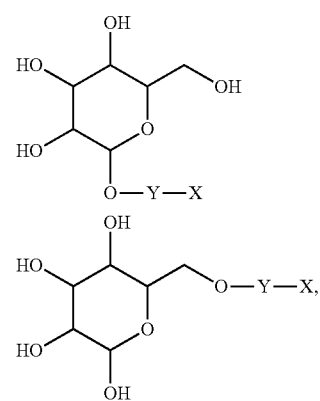

galactosamine conjugated at C2 and corresponding to the following structure according to Formula 1:
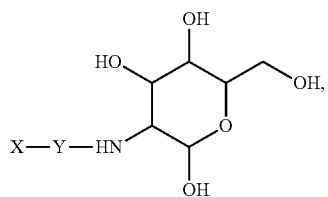
and N-acetylgalactosamine conjugated at C6 and corresponding to the following structure according to Formula 1:
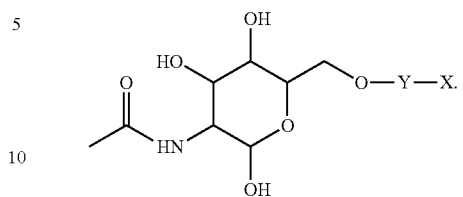
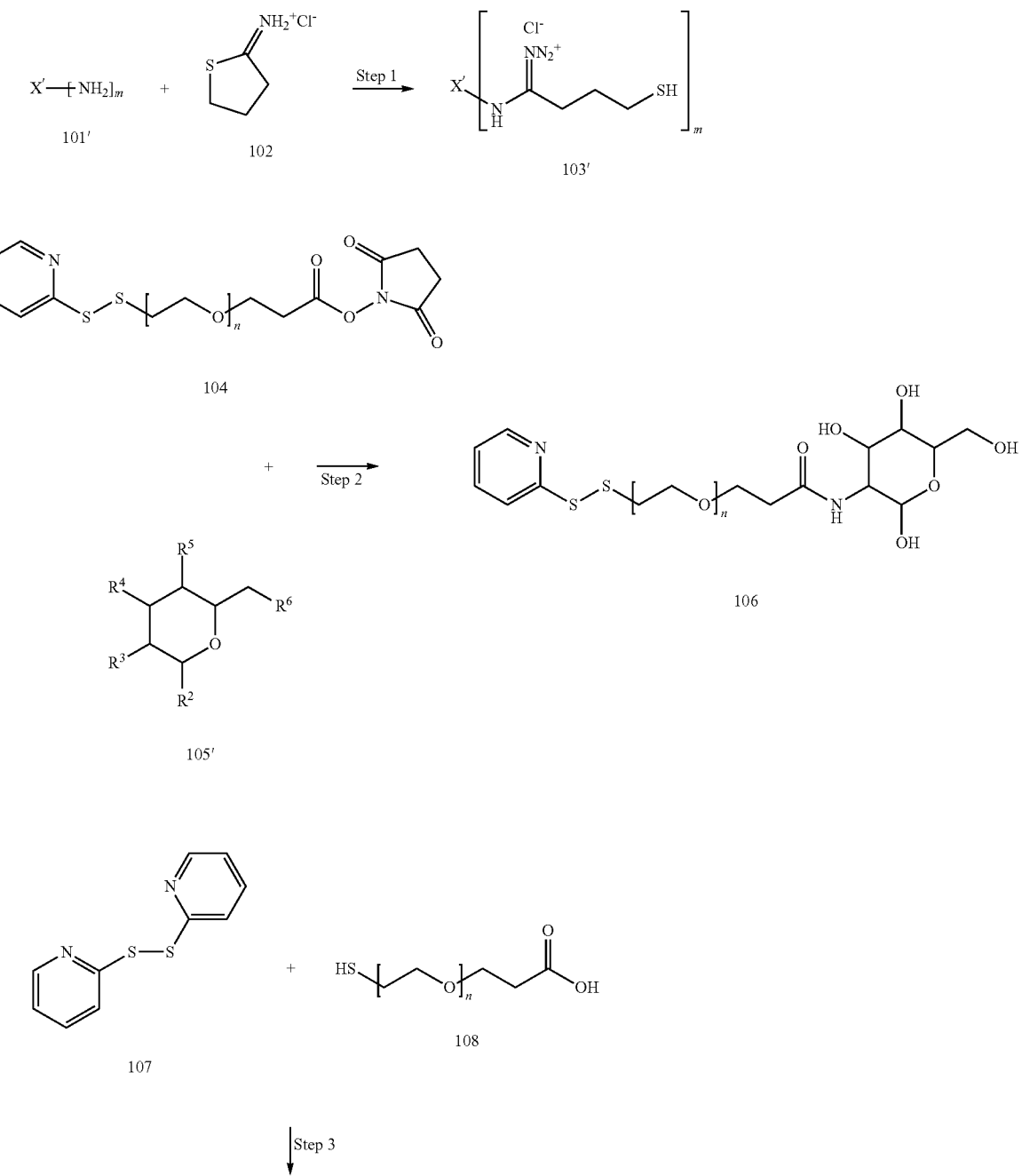

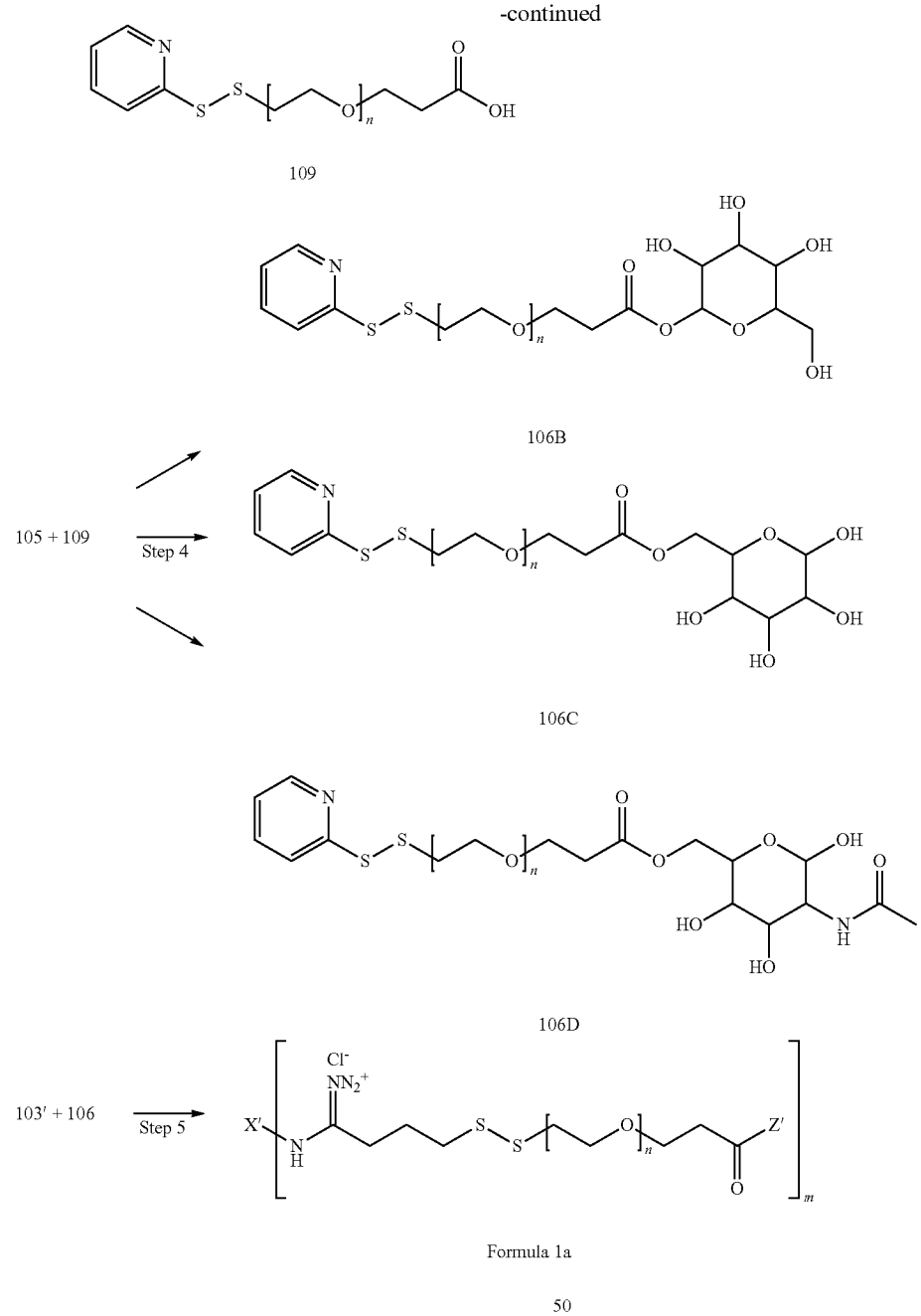

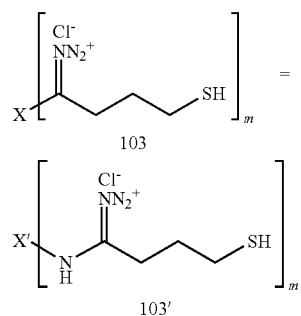

As illustrated above in Reaction Scheme 1, Step 1, surface thiol group(s) can be generated on an antigen, antibody, antibody fragment or ligand having free surface amino group(s) (Formula 101') by contact with a Traut reagent (Formula 102) at a pH of about 8.0 for about 1 hour to give the Formula 103', from which unreacted Traut's reagent is removed, e.g., via centrifugal size exclusion chromatography. The two structures shown below, illustrate the product of Reaction Scheme 1, Step 1, respectively showing the free surface amino group(s) originally found on X (i.e., Formula 103' where X' represents the remainder of X excluding the identified free surface amino groups) and omitting the free surface amino group(s) (i.e., Formula 103). This parallels the distinction illustrated as between X and Formula 101. The convention has been followed in the subsequent reaction schemes.

In Reaction Scheme 1, Step 2, a pyridyl di-thiol-poly (ethylene glycol)-NHS ester (Formula 104) is contacted with galactosamine (Formula 105 where $R^3$ is $NH_2$ and $R^2$, $R^4$, $R^5$ and $R^6$ are OH) with stirring at about pH 8 for about 1 hour to give the corresponding pyridyl di-thiol-poly(ethylene glycol)-sugar of Formula 106A, which can be used without further purification.

In Reaction Scheme 1, Step 3,4,4'-dithiodipyridine (Formula 107) is contacted with a thiol-poly(ethylene glycol) propanoic acid (Formula 108) to give the corresponding pyridyl di-thiol-poly(ethylene glycol)propanoic acid (Formula 109).

In Reaction Scheme 1, Step 4, the acid of Formula 109 is contacted with a protected galactose or N-acetylgalactosamine of Formula 105 where $R^2$ is OH and $R^3$, $R^4$, $R^5$ and $R^6$ are protecting groups ("PG"), where $R^6$ is OH and $R^2$, $R^3$, $R^4$ and $R^5$ are PG, or where $R^6$ is N-acetyl and $R^2$, $R^3$, $R^4$ and $R^5$ are PG to give the corresponding pyridyl di-thiol-poly(ethylene glycol)-sugars of Formulae 106B, 106C and 106D, which can be used following de-protection.

In Reaction Scheme 1, Step 5, to a stirred solution of the product of Step 1 (Formula 103') is added an excess (corresponding to the value of m) of the product of Step 2 or Step 4 (Formula 106, i.e., 106A, 106B, 106C or 106D) for about 1 hour, followed by centrifugal sized exclusion chromatography to remove any free remaining reactants to yield the corresponding product according to Formula 1a, respectively, Formula 1aA, Formula 1aB, Formula 1aC and Formula 1aD.

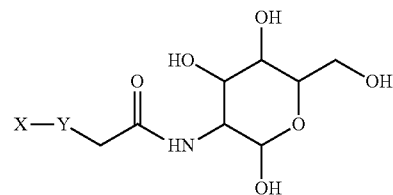

or to galactose, galactosamine or N-acetylgalactosamine conjugated at C1. It should be noted that the C1 conjugated compositions need to be protected during synthesis, for example by cyclizing the amine with the C3 hydroxyl and de-protecting following incorporation of the protected galactosamine into the adjacent portion of the linker.

The poly(galactose methacrylate) reactants of Formulae 201, 401, 501, 601, 701, 803 and 1401 can be prepared by methacrylating galactose, e.g., contacting galactosamine and methacrylate anhydride, followed by reversible addition-fragmentation chain transfer (RAFT) polymerization with a corresponding RAFT agent in the presence of azobisisobutyronitrile (AIBN) in a suitable solvent, starting with freeze-thaw cycles followed by heating at about 60-80° C., preferably 70° C. for about 5-8, preferably about 6 hours. The polymer can be precipitated in a lower alkanol, preferably methanol.

Reaction Scheme 2

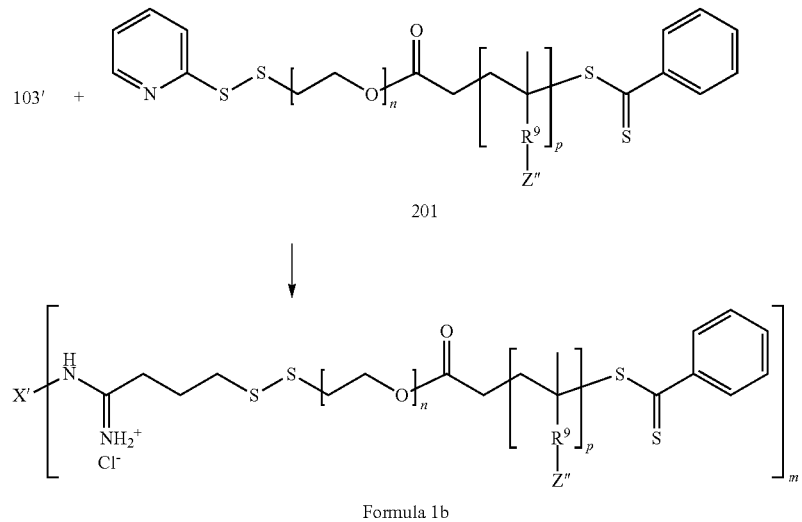

The compositions corresponding to Formula 1a can be named, respectively, e.g., as follows:

"F1aA-X'-$m_m$-$n_n$" or "F1a-X'-$m_m$-$n_n$-2NGAL"
"F1aB-X'-$m_m$-$n_n$" or "F1a-X'-$m_m$-$n_n$-1 GAL"
"F1aC-X'-$m_m$-$n_n$" or "F1a-X'-$m_m$-$n_n$-6GAL"
"F1aD-X'-$m_m$-$n_n$" or "F1a-X'-$m_m$-$n_n$-6NAcGAL"

respectively, for products made employing an intermediate according to Formulae 106A-D.

Turning to Reaction Schemes 2-14 and for the purposes of the nomenclature employed therewith, except as expressly stated otherwise, Z" refers to N-acetylgalactosamine conjugated at C2:

As illustrated in Reaction Scheme 2, an antigen, antibody, antibody fragment or ligand having free surface thiol group(s) prepared, e.g., as described with reference to Reaction Scheme 1, Step 1 (Formula 103') is contacted with an excess (corresponding to the value of m) of a pyridyl di-thiol-poly(ethylene glycol) of Formula 201 for about 1 hour to yield the corresponding product according to Formula 1b.

The compositions of Formula 1b can be named as follows:

"F1b-X'-$m_m$-$n_n$-$p_p$-2NAcGAL" or "F1b-X'-$m_m$-$n_n$-$p_p$-EtAcN-Z".

For example, the composition of Formula 1b where X' is uricase, m is 1, n is 4, p is 4 and Z" is N-acetylgalactosamine conjugated at C2 can be named "F1b-uricase-$m_1$-$n_4$-$p_4$-2NAcGAL" or "30-(uricase)-3,5,7,9-tetramethyl-12-oxo-1-phenyl-1-thioxo-3,5,7,9-tetrakis((2,4,5-trihydroxy-6-(hydroxymethyl)tetrahydro-2H-pyran-3-yl)carbamoyl)-3,16,19,22-tetraoxa-2,25,26-trithiatriacontan-30-iminium".

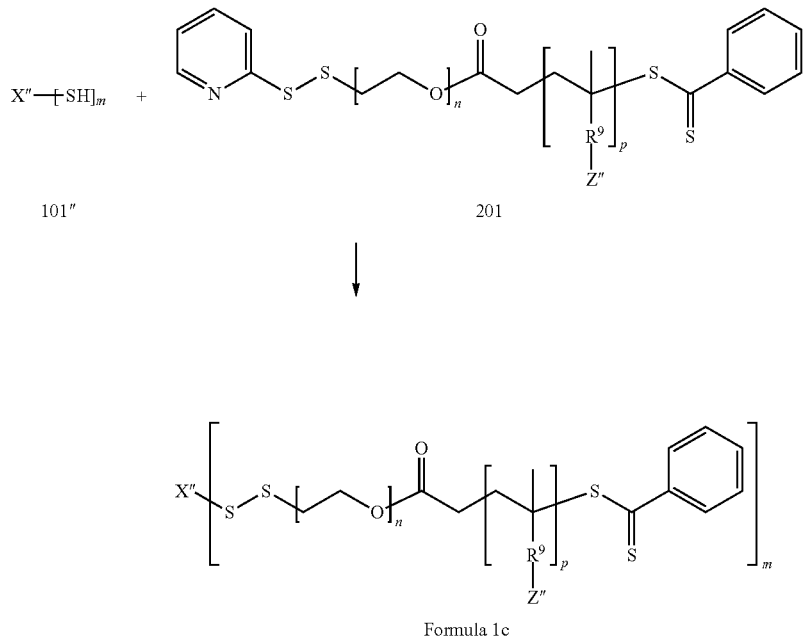

As illustrated in Reaction Scheme 3, an antigen, antibody, antibody fragment or ligand having native free surface thiol group(s) (cysteines) [Formula 101"corresponding to Formula 101 and illustrating where X", as the term will be subsequently employed, represents X excluding the identified free surface thiol group(s)] is contacted with an excess (corresponding to the value of m) of a pyridyl di-thiol-poly (ethylene glycol) of Formula 201 to yield the corresponding product according to Formula 1c.

The compositions corresponding to Formula 1c can be named as follows:

"F1c-X'-$m_m$-$n_n$-$p_p$-2NAcGAL" or "F1c-X'-$m_m$-$n_n$-$p_p$-EtAcN-Z".

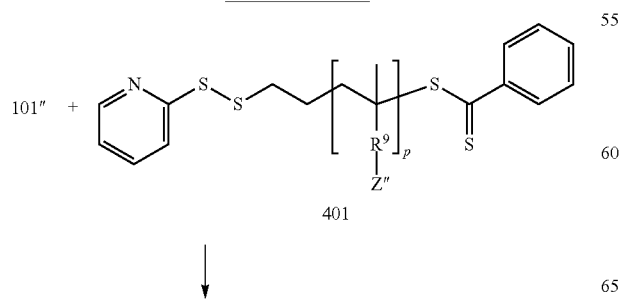

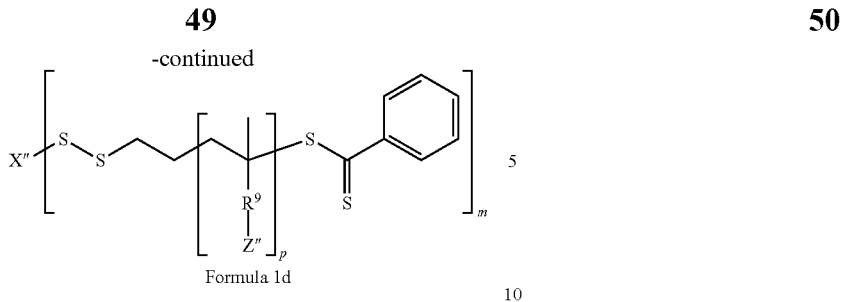

Formula 1d

As illustrated in Reaction Scheme 4, an antigen, antibody, antibody fragment or ligand having native free surface thiol group(s) of Formula 101" is contacted with an excess (corresponding to the value of m) of a pyridyl di-thiol of Formula 401 to yield the corresponding product according to Formula 1d.

The compositions corresponding to Formula 1d can be named as follows:

"F1d-X'-$m_m$-$p_p$-2NAcGAL" or "F1d-X'-$m_m$-$p_p$-EtAcN-Z".

Reaction Scheme 5

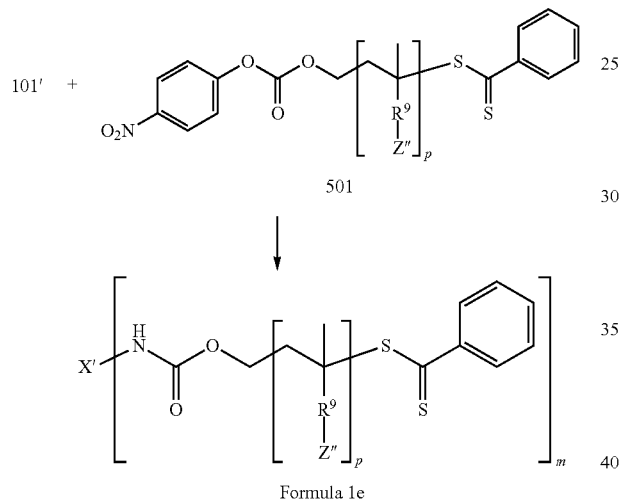

Formula 1e

As illustrated in Reaction Scheme 5, an antigen, antibody, antibody fragment or ligand having native free surface amino group(s) of Formula 101' is contacted with an excess (corresponding to the value of m) of a n-nitrophenyl carbonate of Formula 501 to yield the corresponding product according to Formula 1e.

The compositions corresponding to Formula 1e can be named as follows:

Reaction Scheme 6

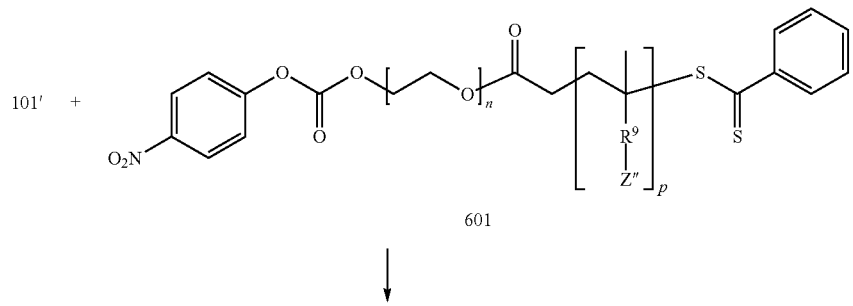

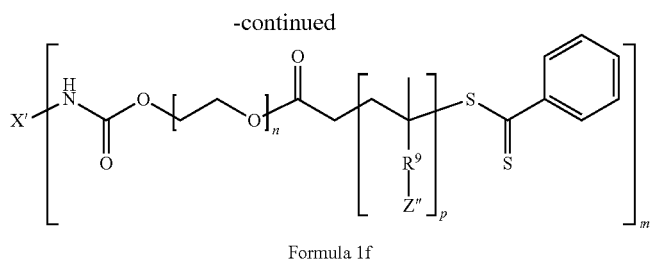

Formula 1f

As illustrated in Reaction Scheme 6, an antigen, antibody, antibody fragment or ligand having native free surface amino group(s) of Formula 101' is contacted with an excess (corresponding to the value of m) of a n-nitrophenyl carbonate poly(ethylene glycol)ester of Formula 601 to yield the corresponding product according to Formula 1f.

The compositions corresponding to Formula 1f can be named as follows: "F1f-X'-$m_m$-$n_n$-$p_p$-2NAcGAL" or "F1f-X'-$m_m$-$n_n$-$p_p$-EtAcN-Z".

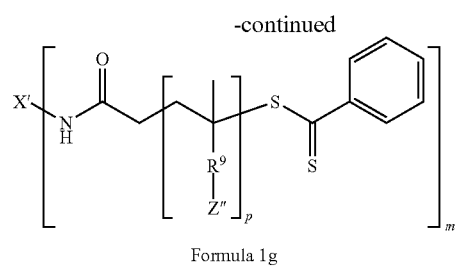

Formula 1g

Reaction Scheme 7

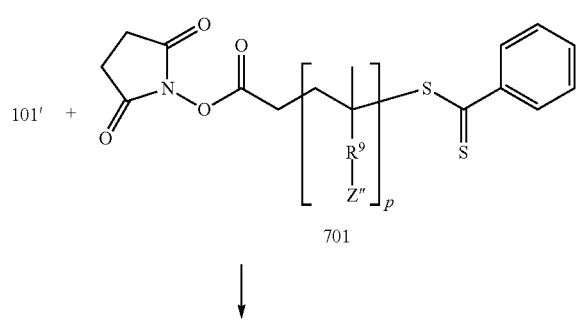

701

As illustrated in Reaction Scheme 7, an antigen, antibody, antibody fragment or ligand having native free surface amino group(s) of Formula 101' is contacted with an excess (corresponding to the value of m) of a NHS-ester poly(ethylene glycol)ester of Formula 701 to yield the corresponding product according to Formula 1g.

The compositions corresponding to Formula 1g can be named as follows:

"F1g-X'-$m_m$-$p_p$-2NAcGAL" or "F1g-X'-$m_m$-$p_p$-EtAcN-Z"

Reaction Scheme 8

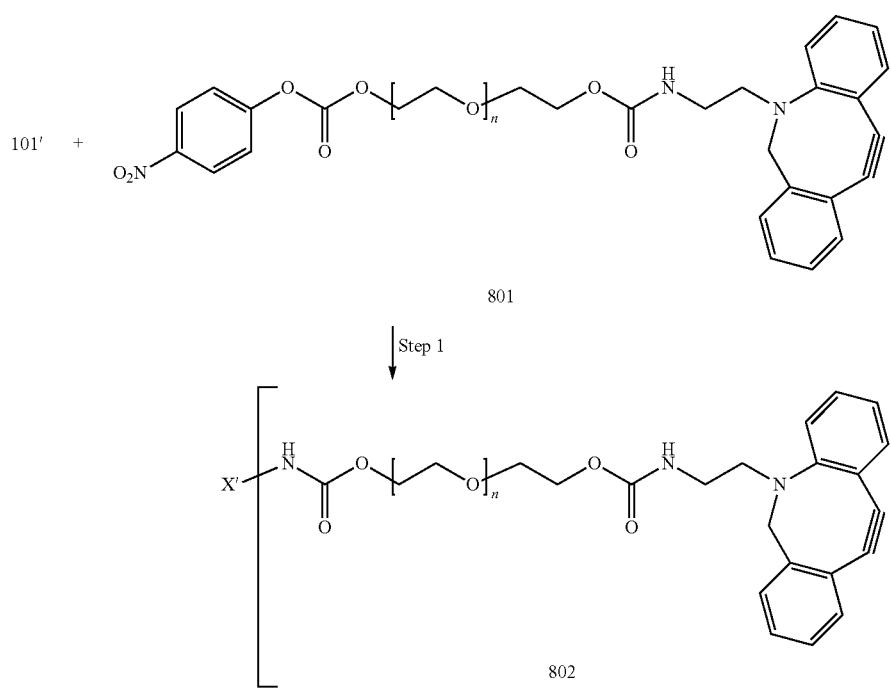

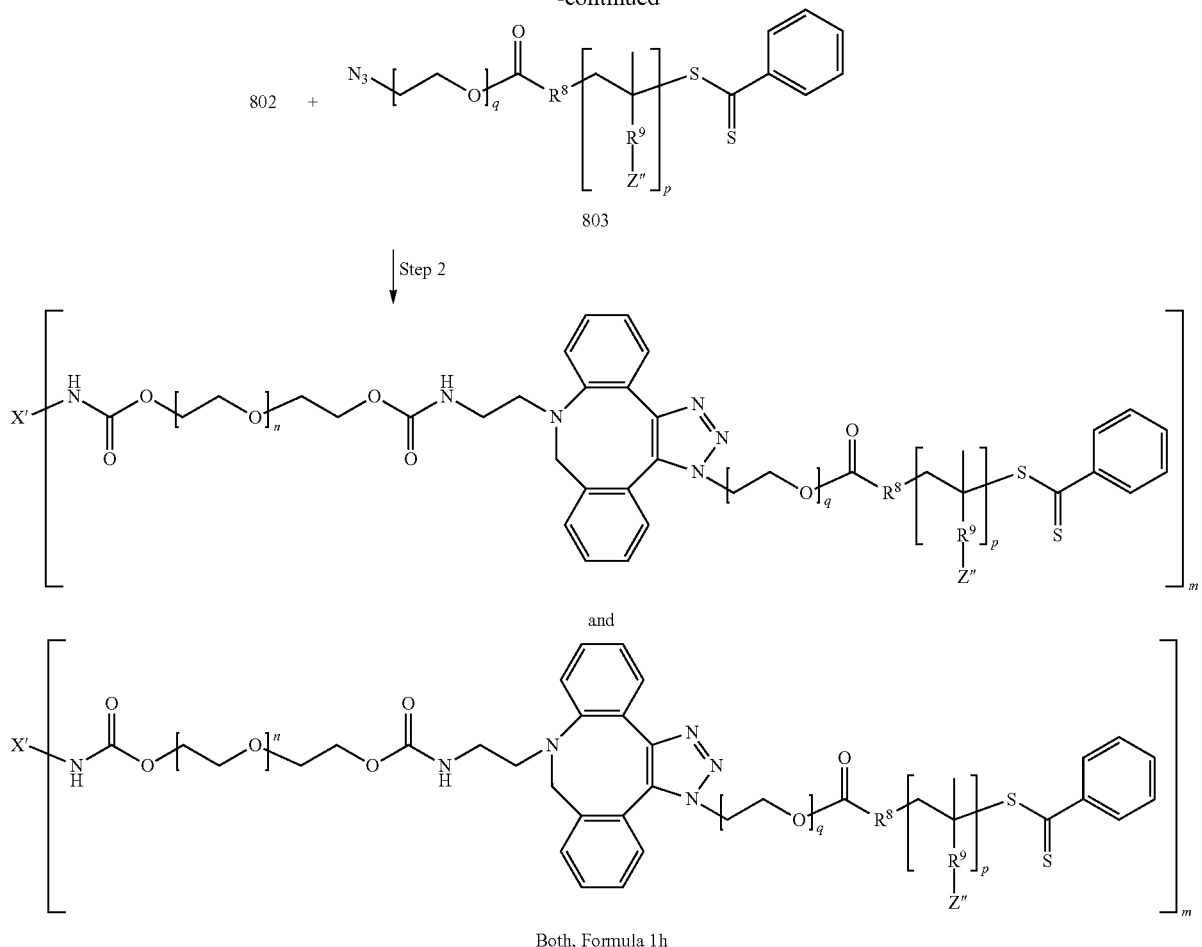

As illustrated in Reaction Scheme 8, Step 1, an antigen, antibody, antibody fragment or ligand having native free surface amino group(s) of Formula 101' is contacted with an excess (corresponding to the value of m) of an amine-reactive linker for Click chemistry of Formula 801 to yield the corresponding product according to Formula 802.

In Reaction Scheme 8, Step 2, the product of Formula 802 is then contacted with an equivalent amount (again corresponding to the value of m) of a galactos(amine) polymer of Formula 803 to yield the corresponding isomeric product according to Formula 1 h. The two isomers, illustrated above, result from non-specific cyclization of the azide of Formula 803 with the triple bond of Formula 802. Such non-specific cyclization occurs in the synthesis of other compositions where Y is selected from Formulae Yh through Yn, but will not be illustrated in each instance.

The compositions corresponding to Formula 1h can be named as follows:

"F1h-X'-m$_m$-n$_n$-p$_p$-q$_q$-2NAcGAL" or "F1h-X'-m$_m$-n$_n$-p$_p$-q$_q$-EtAcN-Z".

Reaction Scheme 9

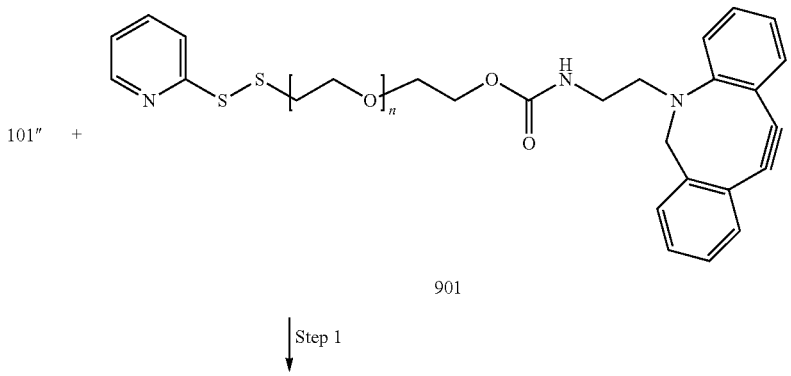

Step 1

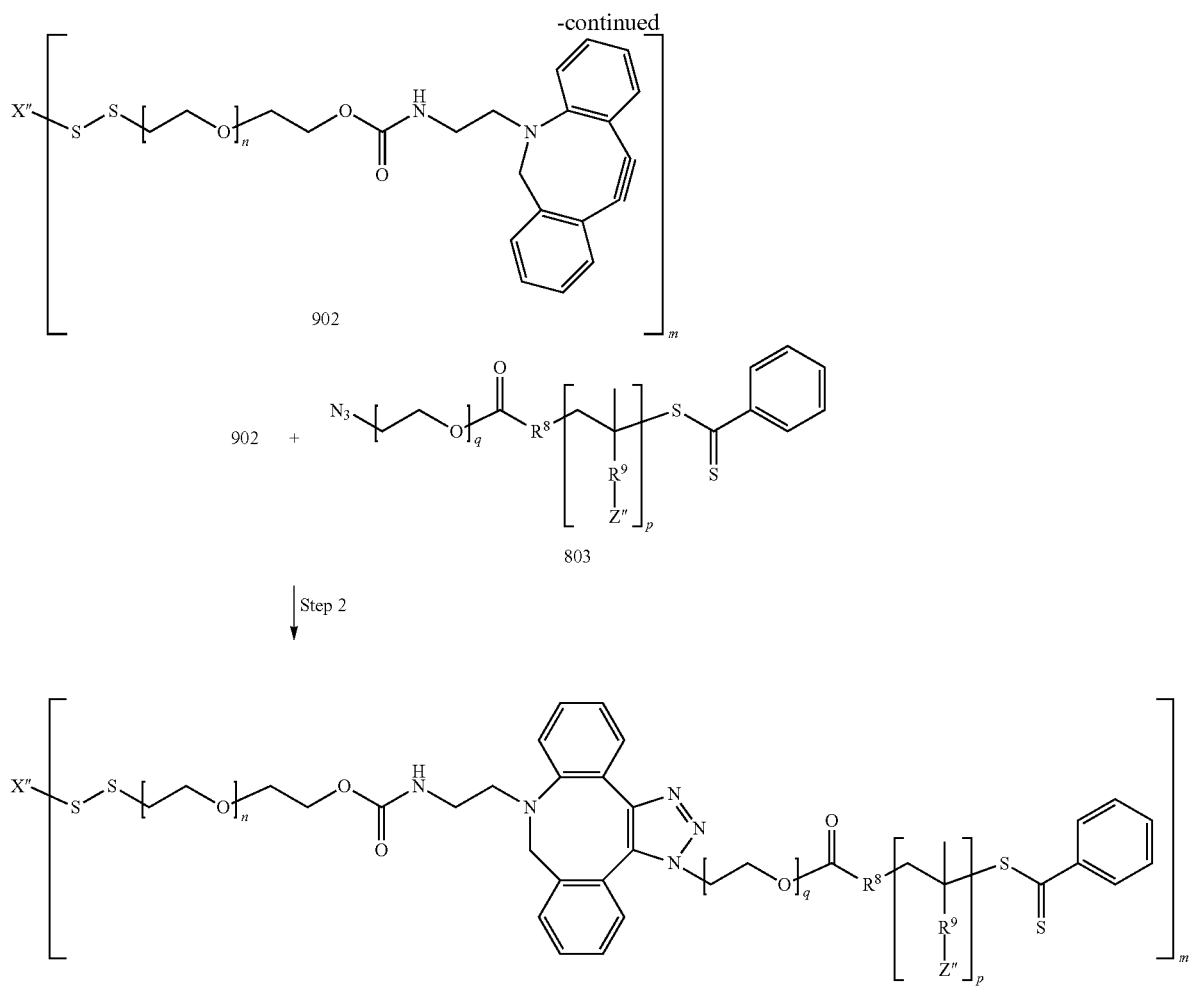

Formula 1i

As illustrated in Reaction Scheme 9, Step 1, an antigen, antibody, antibody fragment or ligand having native free surface thiol group(s) of Formula 101″ is contacted with an excess (corresponding to the value of m) of a thiol-reactive linker for Click chemistry of Formula 901 to yield the corresponding product according to Formula 902″.

In Reaction Scheme 9, Step 2, the product of Formula 902″ is then contacted with an equivalent amount (again corresponding to the value of m) of a galactos(amine) polymer of Formula 803 to yield the corresponding isomeric product according to Formula 1i.

The compositions corresponding to Formula 1i can be named as follows:

"F1i-X'-$m_m$-$n_n$-$p_p$-$q_q$-2NAcGAL" or "F1i-X'-$m_m$-$n_n$-$p_p$-$q_q$-EtAcN-Z".

By following the procedures described with regard to Reaction Scheme 9, but substituting starting material 101″ with a compound of Formula 103' (derivatized with the Traut reagent) there is obtained the corresponding isomeric product of Formula 1j as shown below.

Formula 1j

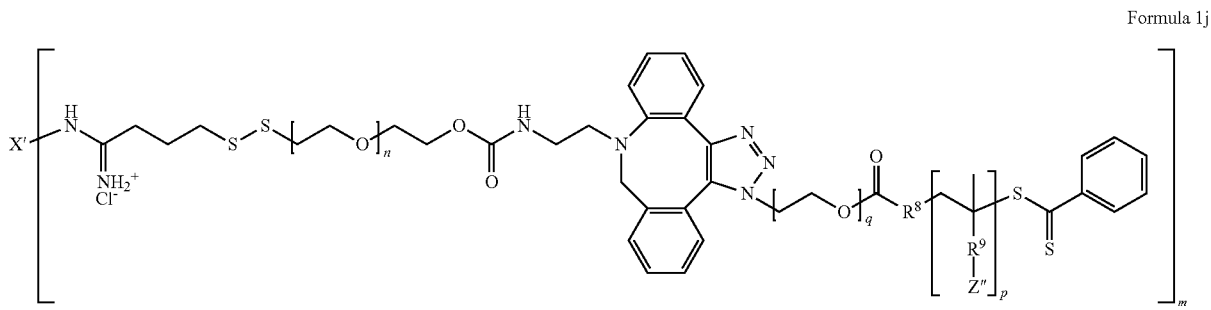

The compositions corresponding to Formula 1j can be named as follows:

"F1j-X'-$m_m$-$n_n$-$p_p$-$q_q$-2NAcGAL" or "F1j-X'-$m_m$-$n_n$-$p_p$-$q_q$-EtAcN-Z".

In Reaction Scheme 10, Step 2, the product of Formula 1002 is then contacted with an equivalent amount (again corresponding to the value of m) of a galactos(amine) polymer of Formula 803 to yield the corresponding isomeric product according to Formula 1 k.

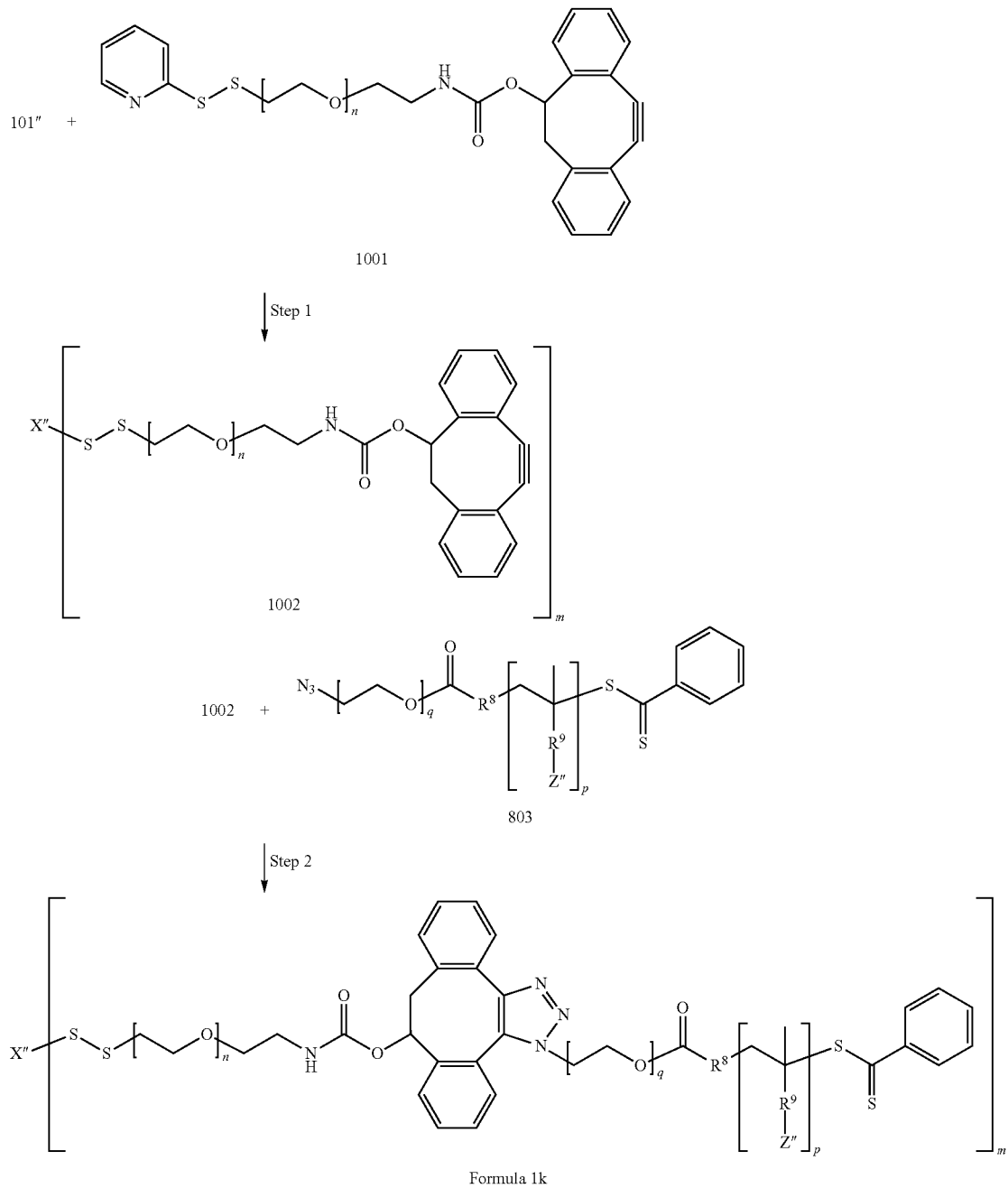

Reaction Scheme 10

Formula 1k

As illustrated in Reaction Scheme 10, Step 1, an antigen, antibody, antibody fragment or ligand having native free surface thiol group(s) of Formula 101" is contacted with an excess (corresponding to the value of m) of a thiol-reactive linker for Click chemistry of Formula 1001 to yield the corresponding product according to Formula 1002.

The compositions corresponding to Formula 1k can be named as follows:

"F1k-X'-$m_m$-$n_n$-$p_p$-$q_q$-2NAcGAL" or "F1k-X'-$m_m$-$n_n$-$p_p$-$q_q$-EtAcN-Z".

By following the procedures described with regard to Reaction Scheme 10, but substituting starting material 101" with a compound of Formula 103' (derivatized with the Traut reagent) there is obtained the corresponding isomeric product of Formula 1L as shown below.
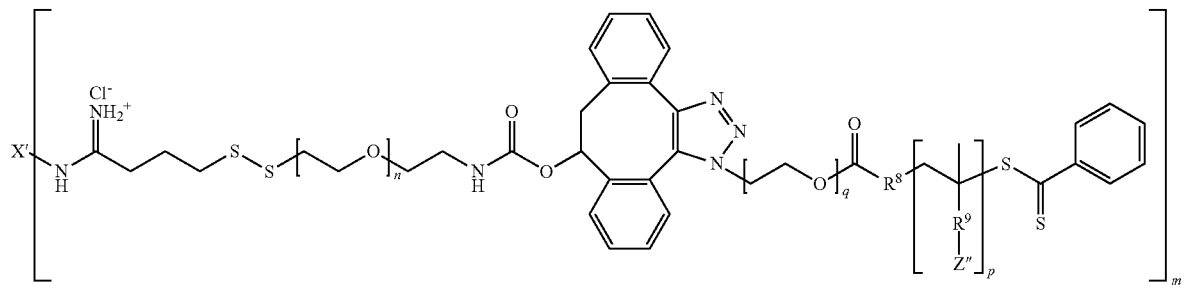
Formula 1L
The compositions corresponding to Formula 1L can be named as follows:
"F1L-X'-$m_m$-$n_n$-$p_p$-$q_q$-2NAcGAL" or "F1L-X'-$m_m$-$n_n$-$p_p$-$q_q$-EtAcN-Z".
Reaction Scheme 11
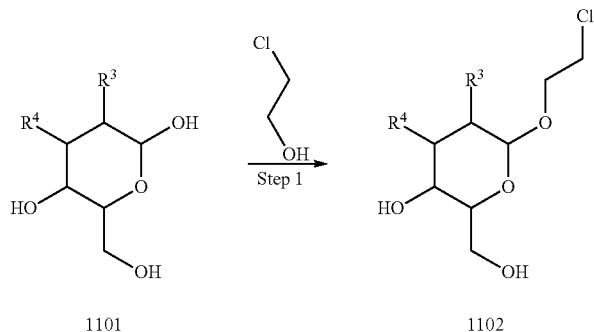
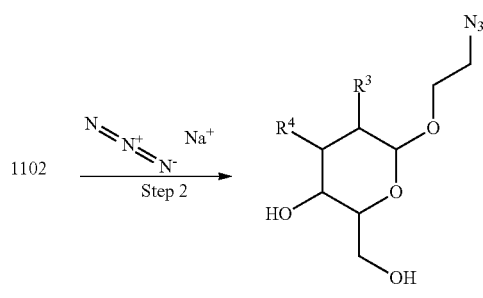
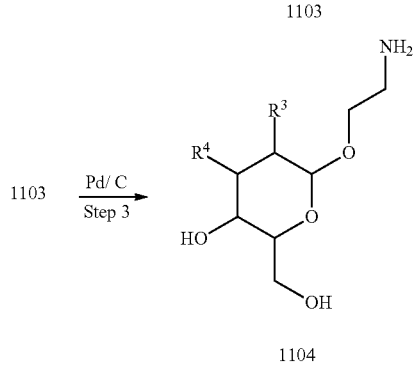

-continued
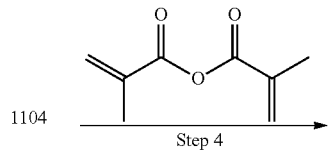 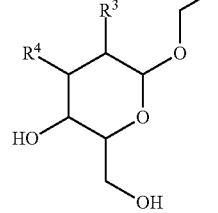
1105
1105 + 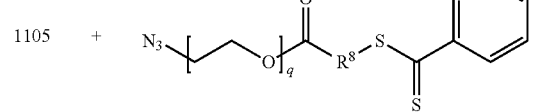
1106
↓ Step 5
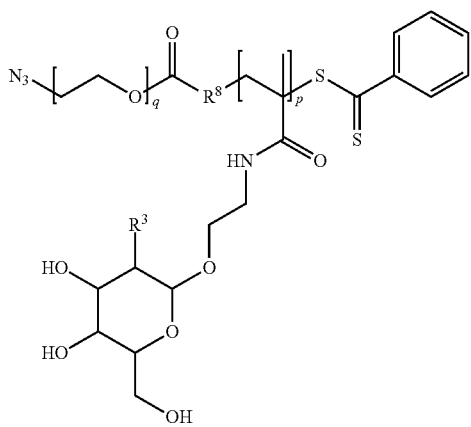
1107
101' + 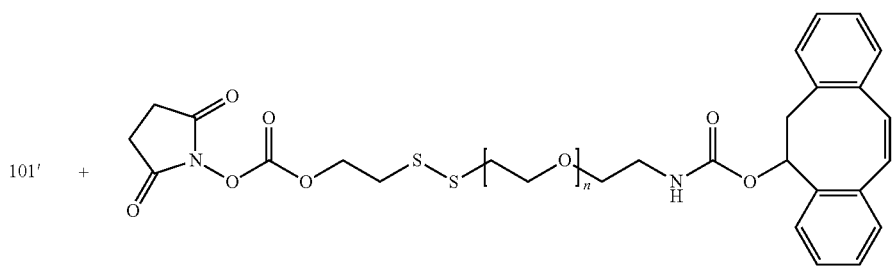
1108
↓ Step 6

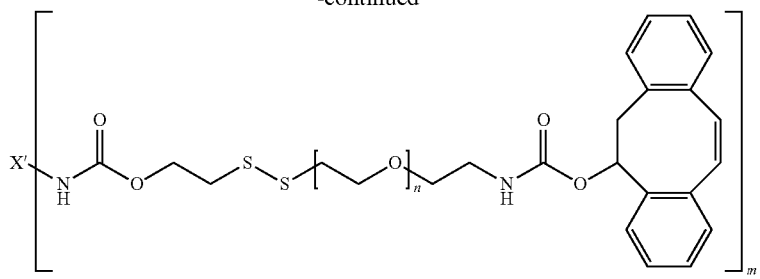

1109

1109 + 1107

Step 7

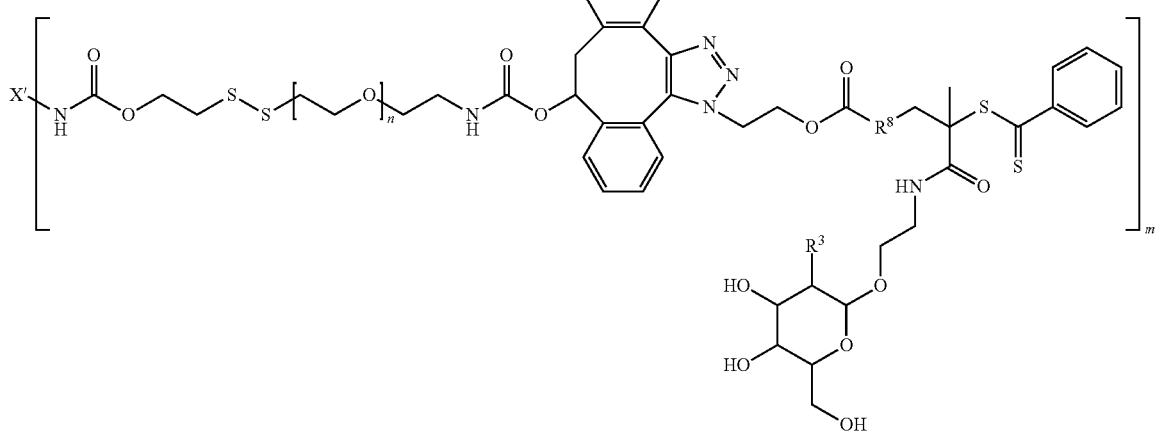

Formula 1m

As illustrated in Reaction Scheme 11, Step 1, galactose, protected galactosamine or N-Acetyl-D-galactosamine (Formula 1101 where R and $R^4$ are OH, R is NH-protecting group (e.g., cyclized with $R^4$) or $R^3$ is NHAc and $R^4$ is OH, respectively) is contacted with 2-chloroethan-1-ol followed by cooling and the dropwise addition of acetylchloride. The solution is warmed to room temperature and then heated to 70° C. for several hours. Ethanol is added to the crude product and the resulting solution is stirred in the presence of carbon and then filtered followed by solvent removal to yield the corresponding product of Formula 1102.

As illustrated in Reaction Scheme 11, Step 2, the product of Formula 1102 is added to an excess of sodium azide and heated to 90° C. for several hours, then filtered followed by solvent removal to yield the corresponding product of Formula 1103.

As illustrated in Reaction Scheme 11, Step 3, the product of Formula 1103 is added to a solution of palladium on carbon and ethanol, and stirred under hydrogen gas (3 atm) for several hours, then filtered followed by solvent removal to yield the corresponding product of Formula 1104.

As illustrated in Reaction Scheme 11, Step 4, the product of Formula 1104 is added to a solution of methacrylate anhydride. Triethylamine is added and the reaction stirred for 2 hours followed by solvent removal and isolation to yield the corresponding product of Formula 1105.

As illustrated in Reaction Scheme 11, Step 5, an azide-modified uRAFT agent (Formula 1106) is added to a solution of the product of Formula 1105 with azobisisobutyronitrile, subjected to 4 free-pump-thaw cycles and then stirred at 70° C. After several hours the corresponding polymer product of Formula 1107 is precipitated by addition of a lower alkanol followed by solvent removal. Where $R^3$ is NH-protecting group (e.g., cyclized with $R^4$) the protecting group(s) is(are) removed at this point.

As illustrated in Reaction Scheme 11, Step 6, an antigen, antibody, antibody fragment or ligand having native free surface amino group(s) of Formula 101' is added to a pH 8.0 buffer and contacted with an excess (corresponding to the value of m) of a dioxopyrrolidine of Formula 1108 with stirring. After 1 hour unreacted Formula 1108 is removed and the resulting product of Formula 1109 is used without further purification.

As illustrated in Reaction Scheme 11, Step 7, the product of Formula 1107 is added to a pH 8.0 buffer, to which is added the product of Formula 1109. After stirring for 2 hours, the excess Formula 1107 is removed to yield the corresponding isomeric product of Formula 1m.

By substituting N-(2,4,5-trihydroxy-6-(hydroxymethyl) tetrahydro-2H-pyran-3-yl)methacrylamide for the product of Formula 1105 in Step 5 and continuing with Steps 6 and 7, the corresponding isomeric product of Formula 1m where Z" is N-acetylgalactosamine conjugated at C2 are obtained.

The compositions corresponding to Formula 1m can be named as follows:

"F1m-X'-$m_m$-$n_n$-$p_p$-$q_q$-EtAcN-Z" where Z" is 1 GAL, 1 NGAL or 1 NAcGAL, or "F1m-X'-$m_m$-$n_n$-$p_p$-$q_q$-2NAc-GAL".

As illustrated in Reaction Scheme 12, Step 1, an antigen, antibody, antibody fragment or ligand having native free surface amino group(s) of Formula 101' is dissolved in an organic solvent (e.g., DMF) containing triethylamine. To this is added an amount (corresponding to the value of m) of a compound of Formula 1201 followed by stirring and the addition of t-butyl methyl ether. The corresponding product of Formula 1202 is recovered as a precipitate.

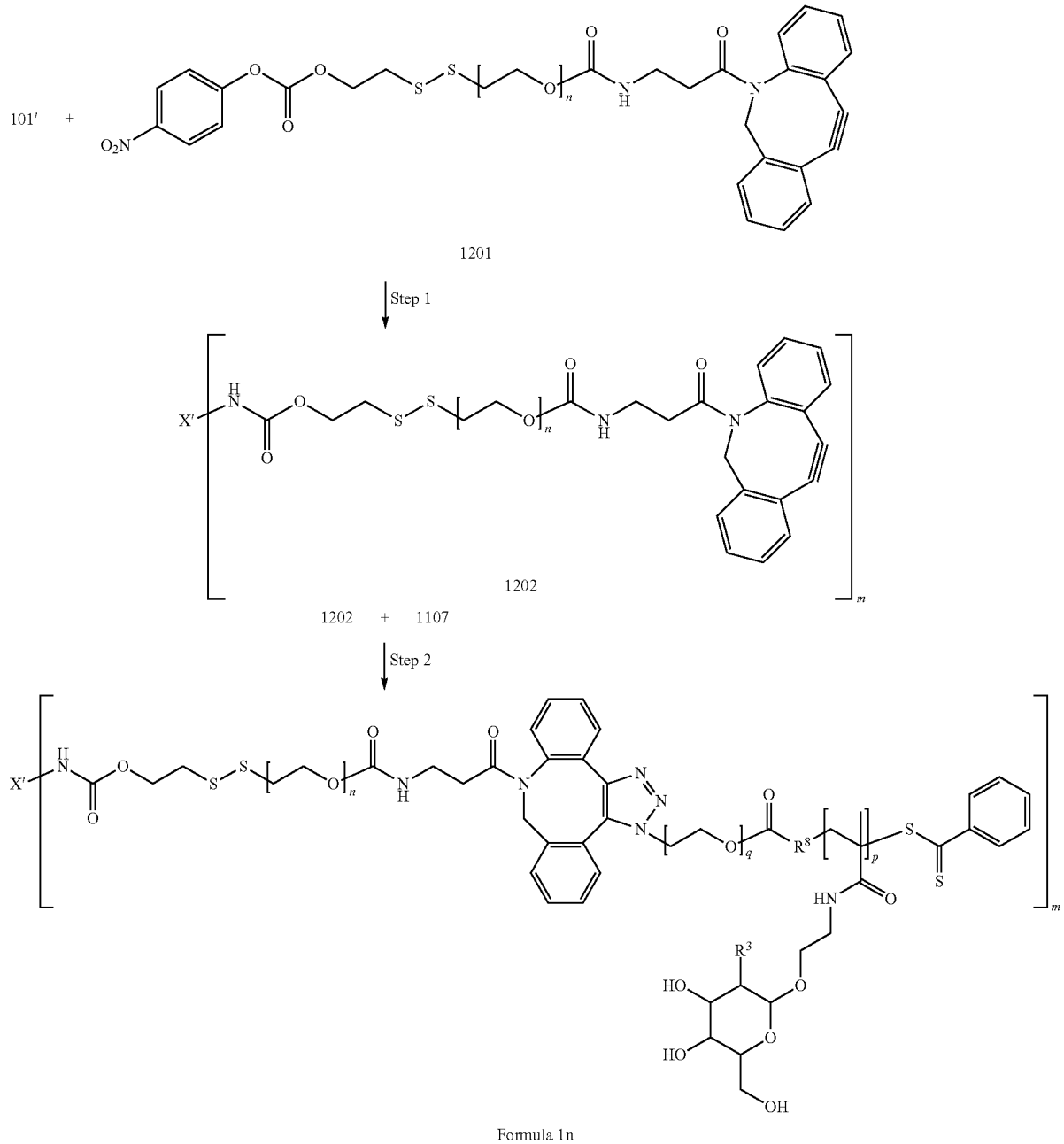

Formula 1n

The synthetic approach of Reaction Scheme 12 is particularly suitable for hydrophobic antigens, antibodies, antibody fragments and ligands (e.g., Insulin) due to the use of organic solvents.

The product of Formula 1202 is resuspended in the organic solvent and an amount (corresponding to the value of m) of Formula 1107 (obtained, e.g., as described with reference to Reaction Scheme 11) is added followed by stirring. The reaction product is precipitated via the addition of dichloromethane, followed by filtration and solvent removal. Purification (e.g., resuspension in PBS followed by centrifugal size exclusion chromatography yields the corresponding isomeric product of Formula 1n.

The compositions corresponding to Formula 1n can be named as follows:

"F1n-X'-$m_m$-$n_n$-$p_p$-$q_q$-EtAcN-Z" where Z" is 1GAL, 1NGAL or 1NAcGAL, or "F1m-X'-$n_m$-$n_n$-$p_p$-$q_q$-2NAcGAL".

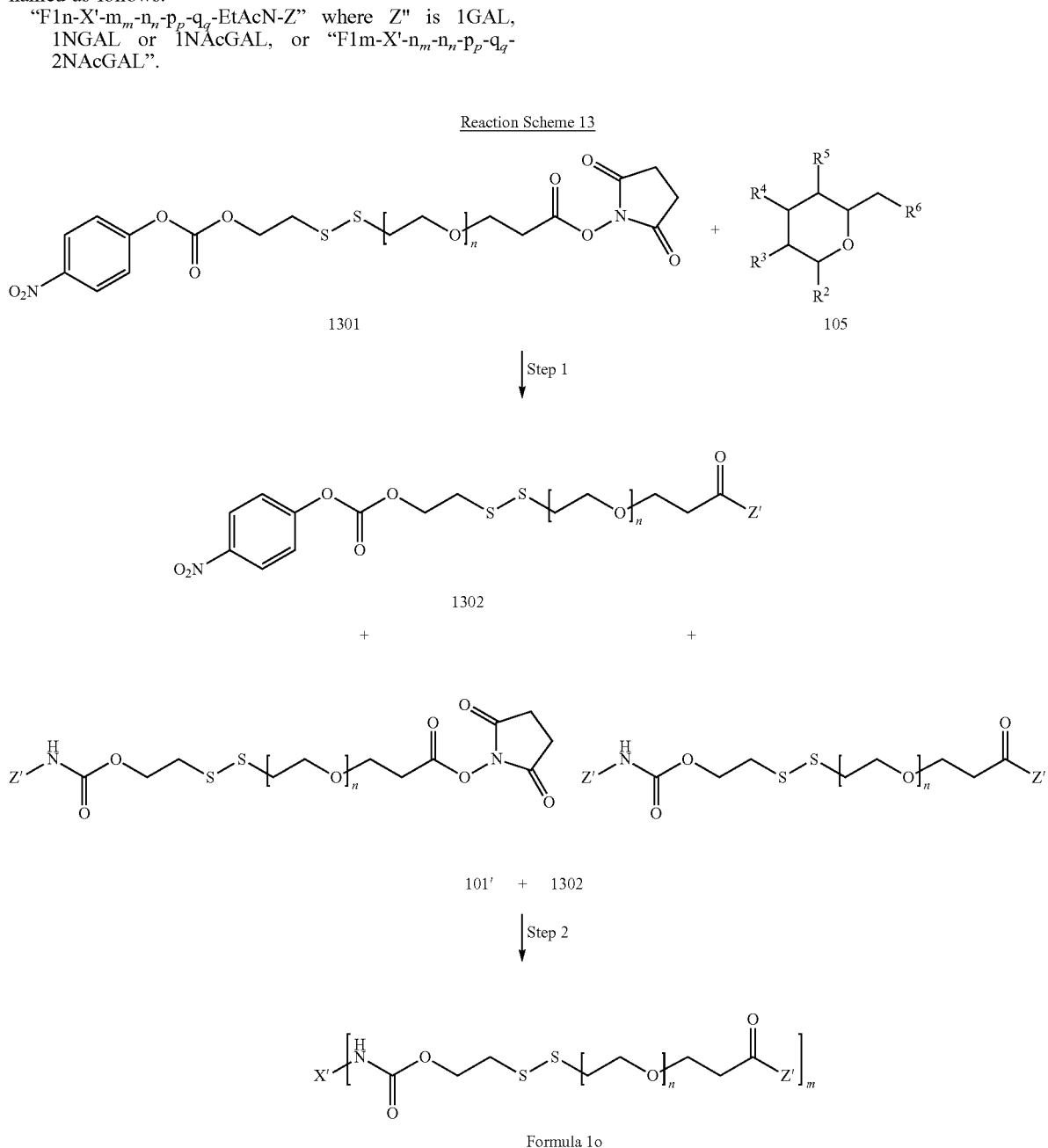

Formula 1o

In Reaction Scheme 13, Step 1, a nitrophenoxycarbonyl-oxyalkyl di-thiol-poly(ethylene glycol)-NHS ester (Formula 1301) is contacted with galactose, galactosamine or N-acetylgalactosamine (Formula 105) to give the corresponding product of Formula 1302, along with the other two illustrated products, from which the desired nitrophenoxy-carbonyl di-thiol-poly(ethylene glycol)-carboxyethyl galactose, galactosamine or N-acetylgalactosamine of Formula 1302 is isolated before proceeding to the next step.

As illustrated in Reaction Scheme 13, Step 2, an antigen, antibody, antibody fragment or ligand having native free surface amino group(s) of Formula 101' is contacted with an excess (corresponding to the value of m) of the product of Formula 1302 to yield the corresponding product according to Formula 1o.

The compositions corresponding to Formula 1o can be named as follows:

"F1o-X'-$m_m$-$n_n$-Z'."

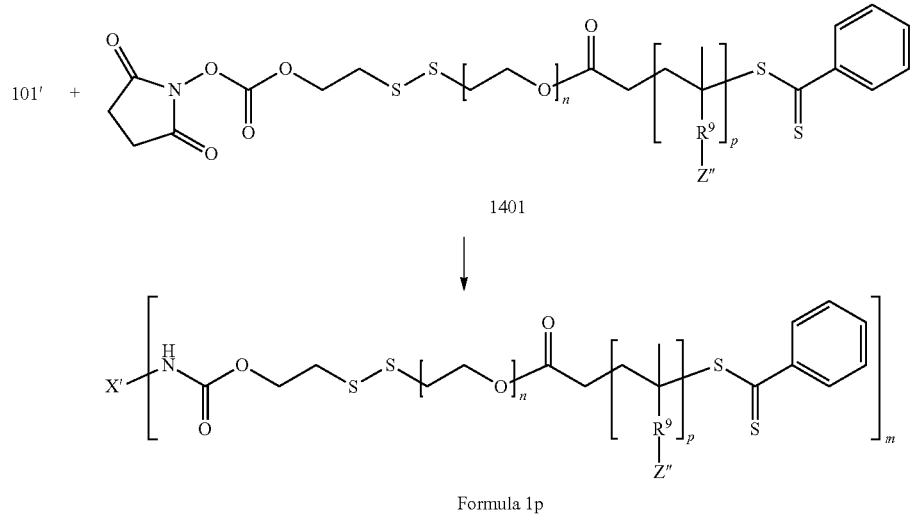

Reaction Scheme 14

Formula 1p

As illustrated in Reaction Scheme 14, an antigen, antibody, antibody fragment or ligand having native free surface amino group(s) (Formula 101') is contacted with an excess (corresponding to the value of m) of a pyridyl di-thiol-poly(ethylene glycol)-NHS ester of Formula 1401 to yield the corresponding product according to Formula 1p.

The compositions corresponding to Formula 1p can be named as follows:

"F1p-X'-$m_m$-$n_n$-$p_p$-2NAcGAL" or "F1p-X'-$m_m$-$n_n$-$p_p$-EtAcN-Z".

Preparation of Fusion Proteins

Fusion protein compositions of Formula 2 can be expressed via art-accepted methodology using commercially available mammalian, bacterial, yeast, or insect cell expression vectors, and published, discovered, or engineered gene sequences. Sequences encoding X, Y and Z together with tag sequences can be cloned into an expression vector, for example, into the mammalian expression vector pSecTag A, where the fusion protein is inserted C-terminal to the Ig κ-chain secretion leader sequence. Various other cloning techniques can be employed, including site-directed mutagenesis and variations of the QuikChange protocol (Geiser, et al.), and are known by those skilled in the art. Fusion proteins can be transiently expressed in mammalian cells [e.g., in human embryonic kidney (HEK293) cells or Chinese hamster ovary (CHO) cells] by transient transfection with the above-described vectors using polyethylenimine. Transfected cells are cultured in a suitable medium (e.g., FreeStyle 293 medium, Life Technologies) supplemented, for example, with valproic acid or DMSO for about 7 days, after which the cells are removed by centrifugation and the culture supernatants are collected and sterilized by filtration.

Alternatively, the fusion proteins can be stably expressed by creating stably transfected mammalian cell lines. Additionally, expression vectors can be used to produce fusion proteins in bacteria, such as *Escherichia coli, Corynebacterium*, or *Pseudomonas fluorescens* by using compatible media (e.g LB, 2XYT, SOB, SOC, TB and other broths), supplements (e.g. glycerol, glucose, and other supplements), and appropriate growth and expression conditions. Expression systems in yeast can commonly use *Saccharomyces cerevisiae* and *Pichia pastoris*, or other organisms for the genera *Saccharomyces, Pichia, Kluyveromyces*, and *Yarrowia*, and less commonly used organisms like the filamentous fungi *Aspergillus, Trichoderma*, or *Myceliophthora thermophila* C1. Insect expression systems can utilize baculovirus infected insect cells or non-lytic insect cell expression to achieve protein expression levels in high quantity; most common insect cells include but are not limited to Sf9 and Sf21 (from *Spodoptera frugiperda*), Hi-5 (from *Trichoplusia ni*), and Schneider 2 and 3 (from *Drosophila melanogaster*).

The expressed fusion protein products can be purified from the culture supernatants by affinity chromatography (e.g., using a HisTrap $Ni^{2+}$ sepharose column, GE Healthcare, for a His-tagged fusion protein), followed by other chromatographic polishing steps such as size exclusion chromatography (e.g., using a Superdex 75 column, GE Healthcare) or ion exchange chromatography. Protein purity can be verified, e.g., by Coomassie Brilliant Blue staining of SDS-PAGE gels and western blotting (e.g. anti-6×His tag western blotting for a His-tagged fusion protein). Protein concentration can be determined using the Beer-Lambert Law, for which the absorbance at 280 nm can be measured, e.g., using a NanoDrop 2000 (Thermo Scientific). The molecular weight and extinction coefficient can be estimated from the protein's amino acid sequence, e.g., using the ExPASy ProtParam tool. Endotoxin levels can be measured, e.g., using the HEK-Blue TLR4 reporter cell line (Invivogen) according to manufacturer's instructions.

Preparation of Desialylated Antigens, Antibodies, Antibody Fragments and Ligands Desialylated Proteins can be Produced Via Art-Accepted Methodology Using Commercially available neuraminidase (also known as acetyl-neuraminyl hydrolase or sialidase) enzyme or sulfuric acid. For enzymatic desialylation of a protein of interest, the protein can be incubated together with neuraminidase at 37° C. for 1 hour, or longer as necessary. For chemical desialylation through acid hydrolysis, a protein of interest can be treated with 0.025 N sulfuric acid at 80° C. for 1 hour, or longer as necessary. The desialylated protein can then be purified from the reaction mixture by immobilized metal ion affinity chromatography (e.g., using a HisTrap Ni2+ sepharose column, GE Healthcare), followed by size exclusion chromatography (e.g., using a Superdex 75 column, GE Healthcare). Protein purity can be verified, e.g., by Coomassie Brilliant Blue staining of SDS-PAGE gels and anti-6×His tag western blotting. Desialylation can be verified, e.g. by lectin-based detection of protein sialic acid content in western blots or colorimetric quantification of sialic acid content using commercially available kits (e.g. Abcam, ProZyme, or Sigma). Desialylated protein concentration can be determined using the Beer-Lambert Law, for which the absorbance at 280 nm can be measured, e.g., using a NanoDrop 2000 (Thermo Scientific). The molecular weight and extinction coefficient can be estimated from the protein's amino acid sequence, e.g., using the ExPASy ProtParam tool. Endotoxin levels can be measured, e.g., using the HEK-Blue TLR4 reporter cell line (Invivogen) according to manufacturer's instructions.

Particular Processes and Last Steps

A compound of Formula 103' is contacted with an excess (corresponding to the value of m) of a compound of Formula 106 to give the corresponding product of Formula 1a.

A compound of Formula 103' is contacted with an excess (corresponding to the value of m) of a compound of Formula 201 to give the corresponding product of Formula 1b.

A compound of Formula 802, 902 or 1002 is contacted with an excess (corresponding to the value of m) of a compound of Formula 803 to give the corresponding product of Formula 1h, Formula 1i or Formula 1 k, respectively.

A compound of Formula 1109 is contacted with an excess (corresponding to the value of m) of a compound of Formula 1107 to give the corresponding product of Formula 1m, particularly where n is about 80, p is about 30, q is about 4, and m being a function of the antigen is about 2 to 10.

A compound of Formula 1202 is contacted with an excess (corresponding to the value of m) of a compound of Formula 1107 to give the corresponding product of Formula 1n, particularly where n is about 1, p is about 30, q is about 4, and m being a function of the antigen is about 2 to 10.

Particular Compositions

By way of non-limiting example, a particular group preferred for the compositions, pharmaceutical formulations, methods of manufacture and use of the present disclosure are the following combinations and permutations of substituent groups of Formula 1 (sub-grouped, respectively, in increasing order of preference):

- X is a foreign transplant antigen against which transplant recipients develop an unwanted immune response, a foreign antigen to which patients develop an unwanted immune response, a therapeutic protein to which patients develop an unwanted immune response, a self-antigen to which patients develop an unwanted immune response, or a tolerogenic portion thereof.
- X is a therapeutic protein to which patients develop an unwanted immune response selected from: Abatacept, Abciximab, Adalimumab, Adenosine deaminase, Ado-trastuzumab emtansine, Agalsidase alfa, Agalsidase beta, Aldesleukin, Alglucerase, Alglucosidase alfa, α-1-proteinase inhibitor, Anakinra, Anistreplase (anisoylated plasminogen streptokinase activator complex), Antithrombin III, Antithymocyte globulin, Ateplase, Bevacizumab, Bivalirudin, Botulinum toxin type A, Botulinum toxin type B, C1-esterase inhibitor, Canakinumab, Carboxypeptidase G2 (Glucarpidase and Voraxaze), Certolizumab pegol, Cetuximab, Collagenase, Crotalidae immune Fab, Darbepoetin-α, Denosumab, Digoxin immune Fab, Dornase alfa, Eculizumab, Etanercept, Factor VIIa, Factor VIII, Factor IX, Factor XI, Factor XIII, Fibrinogen, Filgrastim, Galsulfase, Golimumab, Histrelin acetate, Hyaluronidase, Idursulphase, Imiglucerase, Infliximab, Insulin (including rHu insulin and bovine insulin), Interferon-α2a, Interferon-α2b, Interferon-β1a, Interferon-β1b, Interferon-γ1b, Ipilimumab, L-arginase, L-asparaginase, L-methionase, Lactase, Laronidase, Lepirudin/hirudin, Mecasermin, Mecasermin rinfabate, Methoxy Ofatumumab, Natalizumab, Octreotide, Oprelvekin, Pancreatic amylase, Pancreatic lipase, Papain, Peg-asparaginase, Peg-doxorubicin HCl, PEG-epoetin-3, Pegfilgrastim, Peg-Interferon-α2a, Peg-Interferon-α2b, Pegloticase, Pegvisomant, Phenylalanine ammonia-lyase (PAL), Protein C, Rasburicase (uricase), Sacrosidase, Salmon calcitonin, Sargramostim, Streptokinase, Tenecteplase, Teriparatide, Tocilizumab (atlizumab), Trastuzumab, Type 1 alpha-interferon, Ustekinumab, and vW factor.
  - Especially where X is Abciximab, Adalimumab, Agalsidase alfa, Agalsidase beta, Aldesleukin, Alglucosidase alfa, Factor VIII, Factor IX, Infliximab, L-asparaginase, Laronidase, Natalizumab, Octreotide, Phenylalanine ammonia-lyase (PAL), or Rasburicase (uricase).
    - Particularly where X is Factor VIII, Factor IX, uricase, PAL or asparaginase.
- X is a self-antigen polypeptide selected for treating type 1 diabetes mellitus, pediatric multiple sclerosis, juvenile rheumatoid arthritis, celiac disease, or alopecia universalis.
  - Especially where X is a self-antigen polypeptide selected for treating new onset type 1 diabetes mellitus, pediatric multiple sclerosis or celiac disease.
- X is a foreign antigen to which patients develop an unwanted immune response
  - From peanut, including conarachin (Ara h 1)
  - From wheat, including Alpha-gliadin "33-mer" native (SEQ ID NO:24), Alpha-gliadin "33-mer" deamidated (SEQ ID NO:25), Alpha-gliadin (SEQ ID NO:26) and Omega-gliadin (SEQ ID NO:27).
  - From cat, including Fel d 1A (UNIPROT P30438) and Cat albumin (UNIPROT P49064).
  - From dog, including Can f 1 (UNIPROT O18873) and Dog albumin (UNIPROT P49822).
- X is a foreign transplant antigen against which transplant recipients develop an unwanted immune response, e.g. a human leukocyte antigen protein.
- X is an antibody, antibody fragment or ligand that specifically binds a circulating protein or peptide or antibody, which circulating protein or peptide or antibody gives rise to transplant rejection, immune response against a therapeutic agent, autoimmune disease, and/or allergy.
  - Especially where X binds an endogenous circulating protein or peptide or antibody.
- Y is a linker selected from: Formula Ya, Formula Yb, Formula Yh, Formula Yi, Formula Yk, Formula Ym, Formula Yn, Formula Yo and Formula Yp.

Especially where n is 8 to 90±10%, p is 20 to 100±10%, and q is 3 to 20±3.
  Particularly where n is 40 to 80±10%, p is 30 to 40±10%, and q is 4 to 12±3.
Especially where Y is Formula Ya, Formula Yb, Formula Ym or Formula Yn.
  Particularly where n is 8 to 90±10%, p is 20 to 100±10% and q is 3 to 20±3.
    More particularly where n is 40 to 80±10%, p is 30 to 40±10%, and q is 4 to 12±3.
  Particularly where Z is conjugated to Y via an ethylacetamido group.
    More particularly where Z is conjugated to Y at its C1.
      More particularly where $R^8$ is CMP.
    More particularly where $R^8$ is CMP.
  Particularly where $R^8$ is CMP.
Z is galactose, galactosamine or N-acetylgalactosamine.
  Especially where Z is galactose or N-acetylgalactosamine conjugated at C1, C2 or C6.
    Particularly where Z is galactose or N-acetylgalactosamine conjugated at C1 or C2.
      More particularly where Z is N-acetylgalactosamine conjugated at C1.

Each of the above-described groups and sub-groups are individually preferred and can be combined to describe further preferred aspects of the disclosure, for example but not by way of limitation, as follows:

X is a self-antigen polypeptide selected for treating type 1 diabetes mellitus, pediatric multiple sclerosis, juvenile rheumatoid arthritis, celiac disease, or alopecia universalis.
  Especially where X is a self-antigen polypeptide selected for treating new onset type 1 diabetes mellitus, pediatric multiple sclerosis or celiac disease.
    Particularly where Y is a linker selected from: Formula Ya, Formula Yb, Formula Yh, Formula Yi, Formula Yk, Formula Ym, Formula Yn, Formula Yo and Formula Yp.
      Especially where n is 8 to 90±10%, p is 20 to 100±10%, and q is 3 to 20±3.
        Particularly where n is 40 to 80±10%, p is 30 to 40±10%, and q is 4 to 12±3.
      Especially where Y is Formula Ya, Formula Yb, Formula Ym or Formula Yn.
        Particularly where n is 8 to 90±10%, p is 20 to 100±10% and q is 3 to 20±3.
          More particularly where n is 40 to 80±10%, p is 30 to 40±10%, and q is 4 to 12±3.
          Even more particularly where Z is conjugated to Y via an ethylacetamido group.
        More particularly where Z is conjugated to Y via an ethylacetamido group.
      Particularly where Z is conjugated to Y via an ethylacetamido group.
      Especially where Z is galactose, galactosamine or N-acetylgalactosamine.
        Particularly where Z is galactose or N-acetylgalactosamine conjugated at C1, C2 or C6.
          More particularly where Z is galactose or N-acetylgalactosamine conjugated at C1 or C2.
            Even more particularly where Z is N-acetylgalactosamine conjugated at C1.
        Particularly where Z is galactose, galactosamine or N-acetylgalactosamine.
          Especially where Z is galactose or N-acetylgalactosamine conjugated at C1, C2 or C6.
            Particularly where Z is galactose or N-acetylgalactosamine conjugated at C1 or C2.
              More particularly where Z is N-acetylgalactosamine conjugated at C1.
    Especially where Y is a linker selected from: Formula Ya, Formula Yb, Formula Yh, Formula Yi, Formula Yk, Formula Ym, Formula Yn, Formula Yo and Formula Yp.
      Particularly where n is 8 to 90±10%, p is 20 to 100±10%, and q is 3 to 20±3.
        More particularly where n is 40 to 80±10%, p is 30 to 40±10%, and q is 4 to 12±3.
      Particularly where Y is Formula Ya, Formula Yb, Formula Ym or Formula Yn.
        More particularly where n is 8 to 90±10%, p is 20 to 100±10% and q is 3 to 20±3.
        More preferably where n is 40 to 80±10%, p is 30 to 40±10%, and q is 4 to 12±3.
      More particularly where Z is conjugated to Y via an ethylacetamido group.
      Especially where Z is galactose, galactosamine or N-acetylgalactosamine.
        Particularly where Z is galactose or N-acetylgalactosamine conjugated at C1, C2 or C6.
          More particularly where Z is galactose or N-acetylgalactosamine conjugated at C1 or C2.
            More preferably where Z is N-acetylgalactosamine conjugated at C1.

m is an integer from about 1 to 100.
  m is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or 110.
  Particularly m is from about 1 to 20.
    m is 1, 2, 3, 4, 5, 6, 7, 8, 9, 10, 11, 12, 13, 14, 15, 16, 17, 18, 19, 20, 21 or 22.
    More particularly m is about 10.
      m is 9, 10 or 11.
n is an integer representing a mixture including from about 1 to 100
  n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.
  Particularly n is about 8 to 90.
    Particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.
    More particularly n is about 40 to 80.
    More particularly n is 37, 40, 41, 45, 50, 54, 55, 59, 60, 65, 70, 75, 80, 82, 83 or 88.
n represents a mixture encompassing the ranges 1-4, 2-4, 2-6, 3-8, 7-13, 6-14, 15-25, 26-30, 42-50, 46-57, 60-82, 85-90, 90-110 and 107-113.
  Particularly n represents a mixture encompassing the ranges 7-13, 6-14, 15-25, 26-30, 42-50, 46-57, 60-82, 85-90 and 82-99.
    More particularly n represents a mixture encompassing the ranges 36-44, 42-50, 46-57, 60-82 and 75-85.
p is an integer representing a mixture including from about 2 to 150.
  p is 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160 or 165.

Particularly where n is an integer representing a mixture including from about 1 to 100.

Particularly n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.

More particularly where n is about 8 to 90.

More particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.

Even more particularly where n is about 40 to 80.

Even more particularly n is 37, 40, 41, 45, 50, 54, 55, 59, 60, 65, 70, 75, 80, 82, 83 or 88.

More particularly p is 18, 19, 20, 25, 30, 35, 40, 45, 50, 55, 60, 65, 70, 75, 80, 85, 90, 95, 100 or 110.

Particularly where n is an integer representing a mixture including from about 1 to 100.

Particularly n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.

More particularly where n is about 8 to 90.

More particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.

Even more particularly where n is about 40 to 80.

Even more particularly n is 37, 40, 41, 45, 50, 54, 55, 59, 60, 65, 70, 75, 80, 82, 83 or 88.

More particularly p is 27, 28, 29, 30, 31, 32, 33, 34, 35, 36, 37, 38, 39, 40, 41, 42, 43, or 44.

Particularly where n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.

More particularly where n is about 8 to 90.

More particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.

Even more particularly where n is about 40 to 80.

Even more particularly n is 37, 40, 41, 45, 50, 54, 55, 59, 60, 65, 70, 75, 80, 82, 83 or 88.

q is an integer representing a mixture including from about 1 to 44.

q is 1, 2, 3, 4, 5, 6, 7, 8, 9, 10, 11, 12, 13, 14, 15, 16, 17, 18, 19, 20, 25, 30, 35, 40, 44 or 48.

By way of non-limiting example, a particular group preferred for the compositions, pharmaceutical formulations, methods of manufacture and use of the present disclosure are the following combinations and permutations of substituent groups of Formula 2 (sub-grouped, respectively, in increasing order of preference):

X is a therapeutic protein to which patients develop an unwanted immune response selected from: Abatacept, Abciximab, Adalimumab, Adenosine deaminase, Ado-trastuzumab emtansine, Agalsidase alfa, Agalsidase beta, Aldeslukin, Alglucerase, Alglucosidase alfa, α-1-proteinase inhibitor, Anakinra, Anistreplase (anisoylated plasminogen streptokinase activator complex), Antithrombin III, Antithymocyte globulin, Ateplase, Bevacizumab, Bivalirudin, Botulinum toxin type A, Botulinum toxin type B, C1-esterase inhibitor, Canakinumab, Carboxypeptidase G2 (Glucarpidase and Voraxaze), Certolizumab pegol, Cetuximab, Collagenase, Crotalidae immune Fab, Darbepoetin-α, Denosumab, Digoxin immune Fab, Dornase alfa, Eculizumab, Etanercept, Factor VIIa, Factor VIII, Factor IX, Factor XI, Factor XIII, Fibrinogen, Filgrastim, Galsulfase, Golimumab, Histrelin acetate, Hyaluronidase, Idursulphase, Imiglucerase, Infliximab, Insulin, Interferon-α2a, Interferon-α2b, Interferon-β1a, Interferon-β1b, Interferon-γ1b, Ipilimumab, L-arginase, L-asparaginase, L-methionase, Lactase, Laronidase, Lepirudin/hirudin, Mecasermin, Mecasermin rinfabate, Methoxy Ofatumumab, Natalizumab, Octreotide, Oprelvekin, Pancreatic amylase, Pancreatic lipase, Papain, Pegasparaginase, Peg-doxorubicin HCl, PEG-epoetin-β, Pegfilgrastim, Peg-Interferon-α2a, Peg-Interferon-α2b, Pegloticase, Pegvisomant, Phenylalanine ammonia-lyase (PAL), Protein C, Rasburicase (uricase), Sacrosidase, Salmon calcitonin, Sargramostim, Streptokinase, Tenecteplase, Teriparatide, Tocilizumab (atlizumab), Trastuzumab, Type 1 alpha-interferon, Ustekinumab, and vW factor; provided that interferon (interferon alpha 2, interferon alpha 5, interferon alpha 6, or consensus interferon), Ribavirin, Nexavar/Sorafenib, Erbitus/Cetuximab, Avastatin/bevacizumab, and Herceptin/trastuzumab are excluded from the scope of Formula 2 when m'+m" equals 1 and Z is DOM 26h-196-61 or another of the liver-targeting molecules described in US 2013/0078216.

Especially where X is Abciximab, Adalimumab, Agalsidase alfa, Agalsidase beta, Aldeslukin, Alglucosidase alfa, Factor VIII, Factor IX, Infliximab, L-asparaginase, Laronidase, Natalizumab, Octreotide, Phenylalanine ammonia-lyase (PAL), or Rasburicase (uricase).

Particularly where X is Factor VIII, Factor IX, uricase, PAL or asparaginase.

X is a self-antigen polypeptide selected for treating type 1 diabetes mellitus, pediatric multiple sclerosis, juvenile rheumatoid arthritis, celiac disease, or alopecia universalis.

Especially where X is a self-antigen polypeptide selected for treating new onset type 1 diabetes mellitus, pediatric multiple sclerosis or celiac disease.

X is a foreign antigen to which patients develop an unwanted immune response

From peanut, including conarachin (Ara h 1).

From wheat, including Alpha-gliadin "33-mer" native (SEQ ID NO:24), Alpha-gliadin "33-mer" deamidated (SEQ ID NO:25), Alpha-gliadin (SEQ ID NO:26) and Omega-gliadin (SEQ ID NO:27).

From cat, including Fel d 1A (UNIPROT P30438) and Cat albumin (UNIPROT P49064).

From dog, including Can f 1 (UNIPROT O18873) and Dog albumin (UNIPROT P49822).

X s is a foreign transplant antigen against which transplant recipients develop an unwanted immune response, e.g. a human leukocyte antigen protein.

X is an antibody, antibody fragment or ligand that specifically binds a circulating protein or peptide or antibody, which circulating protein or peptide or antibody gives rise to transplant rejection, immune response against a therapeutic agent, autoimmune disease, and/or allergy.

Especially where X binds an endogenous circulating protein or peptide or antibody.

Y is Gly$_3$Ser.

Z is Anti-ASGPR Dom26h-196-61 or a conservative substitution.

m'+m" equals 1 or 2 and X is a full length protein, including protein therapeutics.

m'+m" equals 1 or 2 where m' is 1 and m" is 0 or 1.

m'+m" equals 2 to about 10 where X is a group of self-antigen peptides (epitopes) known to be associated with a particular autoimmune disease or for treatment of genetically diverse target populations.

m'+m" equals about 4 to 7 where the autoimmune disease is multiple sclerosis and X is independently selected from: MBP13-32 (SEQ ID NO:11), MBP83-99 (SEQ ID NO:12), MBP111-129 (SEQ ID NO:13), MBP146-170 (SEQ ID NO:14), MOG1-20 (SEQ ID NO:15), MOG35-55 (SEQ ID NO:16) and PLP139-154 (SEQ ID NO:17).

m'+m" equals 7 and X is, respectively, MBP13-32 (SEQ ID NO:11), MBP83-99 (SEQ ID NO:12), MBP111-129 (SEQ ID NO:13), MBP146-170 (SEQ ID NO:14), MOG1-20 (SEQ ID NO:15), MOG35-55 (SEQ ID NO:16) and PLP139-154 (SEQ ID NO:17).

As with the above discussion regarding Formula 1, each of the above-described groups and sub-groups for Formula 2 are individually preferred and can be combined to describe further preferred aspects of the disclosure.

Utility, Testing and Administration

General Utility

The compositions of the disclosure find use in a variety of applications including, as will be appreciated by those in the art, treatment of transplant rejection, immune response against a therapeutic agent, autoimmune disease, and food allergy.

In a preferred embodiment, the compositions of the disclosure are used to modulate, particularly down-regulate, antigen-specific undesirable immune response.

The compositions of the disclosure are useful to bind and clear from the circulation specific undesired proteins, including antibodies endogenously generated in a patient (i.e., not exogenous antibodies administered to a patient), peptides and the like, which cause autoimmunity and associated pathologies, allergy, inflammatory immune responses, and anaphylaxis.

In the present disclosure, antigens are targeted to the liver for presentation via antigen-presenting cells to specifically down-regulate the immune system or for clearance of unwanted circulating proteins. This is distinct from previous uses of liver targeting, for example as described in US 2013/0078216, where the purpose of liver-targeting molecules such as DOM26h-196-61 was the delivery of therapeutic agents to treat liver diseases such as fibrosis, hepatitis, Cirrhosis and liver cancer.

The present disclosure provides compositions and methods to treat unwanted immune response to self-antigens and foreign antigens, including but not limited to: a foreign transplant antigen against which transplant recipients develop an unwanted immune response (e.g., transplant rejection), a foreign antigen to which patients develop an unwanted immune (e.g., allergic or hypersensitivity) response, a therapeutic agent to which patients develop an unwanted immune response (e.g., hypersensitivity and/or reduced therapeutic activity), a self antigen to which patients develop an unwanted immune response (e.g., autoimmune disease)

Autoimmune disease states that can be treated using the methods and compositions provided herein include, but are not limited to: Acute Disseminated Encephalomyelitis (ADEM); Acute interstital allergic nephritis (drug allergies); Acute necrotizing hemorrhagic leukoencephalitis; Addison's Disease; Alopecia areata; Alopecia universalis; Ankylosing Spondylitis; Arthritis, juvenile; Arthritis, psoriatic; Arthritis, rheumatoid; Atopic Dermatitis; Autoimmune aplastic anemia; Autoimmune gastritis; Autoimmune hepatitis; Autoimmune hypophysitis; Autoimmune oophoritis; Autoimmune orchitis; Autoimmune polyendocrine syndrome type 1; Autoimmune polyendocrine syndrome type 2; Autoimmune thyroiditis; Behcet's disease; Bronchiolitis obliterans; Bullous pemphigoid; Celiac disease; Churg-Strauss syndrome; Chronic inflammatory demyelinating polyneuropathy; Cicatricial pemphigoid; Crohn's disease; Coxsackie myocarditis; Dermatitis herpetiformis Duhring; Diabetes mellitus (Type 1); Erythema nodosum; Epidermolysis bullosa acquisita, Giant cell arteritis (temporal arteritis); Giant cell myocarditis; Goodpasture's syndrome; Graves' disease; Guillain-Barre syndrome; Hashimoto's encephalitis; Hashimoto's thyroiditis; IgG4-related sclerosing disease; Lambert-Eaton syndrome; Mixed connective tissue disease; Mucha-Habermann disease; Multiple sclerosis; Myasthenia gravis; Optic neuritis; Neuromyelitis optica; Pemphigus vulgaris and variants; Pernicious angemis; Pituitary autoimmune disease; Polymyositis; Postpericardiotomy syndrome; Premature ovarian failure; Primary Biliary Cirrhosis; Primary sclerosing cholangitis; Psoriasis; Rheumatic heart disease; Sjogren's syndrome; Systemic lupus erythematosus; Systemic sclerosis; Ulcerative colitis; Undifferentiated connective tissue disease (UCTD); Uveitis; Vitiligo; and Wegener's granulomatosis.

A particular group of autoimmune disease states that can be treated using the methods and compositions provided herein include, but are not limited to: Acute necrotizing hemorrhagic leukoencephalitis; Addison's Disease; Arthritis, psoriatic; Arthritis, rheumatoid; Autoimmune aplastic anemia; Autoimmune hypophysitis; Autoimmune gastritis; Autoimmune polyendocrine syndrome type 1; Bullous pemphigoid; Celiac disease; Coxsackie myocarditis; Dermatitis herpetiformis Duhring; Diabetes mellitus (Type 1); Epidermolysis bullosa acquisita; Giant cell myocarditis; Goodpasture's syndrome; Graves' disease; Hashimoto's thyroiditis; Mixed connective tissue disease; Multiple sclerosis; Myasthenia gravis; Neuromyelitis optica; Pernicious angemis; Pemphigus vulgaris and variants; Pituitary autoimmune disease; Premature ovarian failure; Rheumatic heart disease; Systemic sclerosis; Sjogren's syndrome; Systemic lupus erythematosus; and Vitiligo.

In the embodiments employing an antigen against which an unwanted immune response is developed, such as food antigens, treatment can be provided for reactions against, for example: peanut, apple, milk, egg whites, egg yolks, mustard, celery, shrimp, wheat (and other cereals), strawberry and banana.

As will be appreciated by those skilled in the art, a patient can be tested to identify a foreign antigen against which an unwanted immune response has developed, and a composition of the disclosure can be developed based on that antigen.

Testing

In establishing the utility of the compositions and methods of the disclosure, specificity in binding to antigen-presenting cells in the liver (particularly binding to hepatocytes and specifically ASGPR) should initially be determined. This can be accomplished, for example, by employing a marker (such as the fluorescent marker phycoerythrin ("PE")) in a composition of the disclosure. The composition is administered to suitable experimental subjects. Controls, e.g., unconjugated PE or vehicle (saline) are administered to other group(s) of subjects. The composition and controls are allowed to circulate for a period of 1 to 5 hours, after which the spleens and livers of the subjects are harvested and measured for fluorescence. The specific cells in which fluorescence is found can be subsequently identified. Compositions of the disclosure, when tested in this manner, show higher levels of concentration in the antigen-presenting cells of the liver as compared with unconjugated PE or vehicle.

Effectiveness in immune modulation can be tested by measuring the proliferation of OT-I $CD8^+$ cells (transplanted into host mice) in response to the administration of a composition of the disclosure incorporating a known antigen, such as ovalbumin ("OVA"), as compared with administration of the antigen alone or just vehicle. Compositions of the disclosure, when tested in this manner, show an increase of OT1 cell proliferation as compared with antigen alone or vehicle, demonstrating increased CD8+ T-cell cross-priming. To distinguish T cells being expanded into a functional effector phenotype from those being expanded and deleted, the proliferating OT-I $CD8^+$ T cells can be phenotypically analyzed for molecular signatures of exhaustion [such as programmed death-1 (PD-1), FasL, and others], as well as annexin-V as a hallmark of apoptosis and thus deletion. The OT-I $CD8^+$ T cells can also be assessed for their responsiveness to an antigen challenge with adjuvant in order to demonstrate functional non-responsiveness, and thus immune tolerance, towards the antigen. To do so, the cells are analyzed for inflammatory signatures after administration of compositions of the disclosure into host mice followed by an antigen challenge. Compositions of the disclosure when tested in this manner demonstrate very low (e.g., background) levels of inflammatory OT-I CD8+ T cell responses towards OVA, thus demonstrating immune tolerance.

Humoral immune response can be tested by administering a composition of the disclosure incorporating a known antigen, such as OVA, as compared with the administration of the antigen alone or just vehicle, and measuring the levels of resulting antibodies. Compositions of the disclosure when tested in this manner show very low (e.g., background) levels of antibody formation responsive to their administration and the administration of vehicle, with significantly higher levels of antibody formation responsive to administration of the antigen.

Effectiveness in tolerization against an antigen can be tested as above with reference to humoral immune response, where several weeks following treatment(s) with a composition of the disclosure a group of subjects is challenged by administration of the antigen alone, followed by measuring the levels of antibodies to the antigen. Compositions of the disclosure when tested in this manner show low levels of antibody formation responsive to challenge with the antigen in groups pretreated with such compositions as compared to groups that are not pretreated.

Disease-focused experimental models are well known to those skilled in the art and include the NOD (or non-obese diabetic) mouse model of autoimmunity and tolerance and the EAE (experimental autoimmune encephalomyelitis) model for the human inflammatory demyelinating disease, multiple sclerosis. In particular, the NOD mouse develops spontaneous autoimmune diabetes (similar to type 1a diabetes in humans). Groups of NOD mice are treated with test compound or a negative control, followed by measurement of BLOOD GLUCOSE. Successful treatment corresponds to likelihood of treating diabetes in humans or proof of mechanism for approaches to the treatment of other autoimmune diseases. (See, e.g., Anderson and Bluestone, *Annu. Rev. Immunol.* 2005; 23:447-85.)

Administration

The compositions of the disclosure are administered at a therapeutically effective dosage, e.g., a dosage sufficient to provide treatment for the disease states previously described. Administration of the compounds of the disclosure or the pharmaceutically acceptable salts thereof can be via any of the accepted modes of administration for agents that serve similar utilities.

While human dosage levels have yet to be optimized for the compounds of the disclosure, these can initially be extrapolated from the about 10 μg to 100 μg doses administered for mice. Generally, an individual human dose is from about 0.01 to 2.0 mg/kg of body weight, preferably about 0.1 to 1.5 mg/kg of body weight, and most preferably about 0.3 to 1.0 mg/kg of body weight. Treatment can be administered for a single day or a period of days, and can be repeated at intervals of several days, one or several weeks, or one or several months. Administration can be as a single dose (e.g., as a bolus) or as an initial bolus followed by continuous infusion of the remaining portion of a complete dose over time, e.g., 1 to 7 days. The amount of active compound administered will, of course, be dependent on any or all of the following: the subject and disease state being treated, the severity of the affliction, the manner and schedule of administration and the judgment of the prescribing physician. It will also be appreciated that amounts administered will depend upon the molecular weight of the antigen, antibody, antibody fragment or ligand as well as the size of the linker.

The compositions of the disclosure can be administered either alone or in combination with other pharmaceutically acceptable excipients. While all typical routes of administration are contemplated, it is presently preferred to provide liquid dosage forms suitable for injection. The formulations will typically include a conventional pharmaceutical carrier or excipient and a composition of the disclosure or a pharmaceutically acceptable salt thereof. In addition, these compositions can include other medicinal agents, pharmaceutical agents, carriers, and the like, including, but not limited to the therapeutic protein, peptide, antibody or antibody-like molecule corresponding to the antigen (X) employed in the composition of the disclosure, and other active agents that can act as immune-modulating agents and more specifically can have inhibitory effects on B-cells, including anti-folates, immune suppressants, cyostatics, mitotic inhibitors, and anti-metabolites, or combinations thereof.

Generally, depending on the intended mode of administration, the pharmaceutically acceptable composition will contain about 0.1% to 95%, preferably about 0.5% to 50%, by weight of a composition of the disclosure, the remainder being suitable pharmaceutical excipients, carriers, etc. Dosage forms or compositions containing active ingredient in the range of 0.005% to 95% with the balance made up from non-toxic carrier can be prepared.

Liquid pharmaceutically administrable compositions can, for example, be prepared by dissolving, dispersing, etc. an active composition of the disclosure (e.g., a lyophilized powder) and optional pharmaceutical adjuvants in a carrier, such as, for example, water (water for injection), saline, aqueous dextrose, glycerol, glycols, ethanol or the like (excluding galactoses), to thereby form a solution or suspension. If desired, the pharmaceutical composition to be administered can also contain minor amounts of nontoxic auxiliary substances such as wetting agents, emulsifying agents, stabilizing agents, solubilizing agents, pH buffering agents and the like, for example, sodium acetate, sodium citrate, cyclodextrine derivatives, sorbitan monolaurate, triethanolamine acetate and triethanolamine oleate, etc., osmolytes, amino acids, sugars and carbohydrates, proteins and polymers, salts, surfactants, chelators and antioxidants, preservatives, and specific ligands. Actual methods of preparing such dosage forms are known, or will be apparent, to those skilled in this art; for example, see Remington: *The Science and Practice of Pharmacy*, Pharmaceutical Press, 22nd Edition, 2012. The composition or formulation to be administered will, in any event, contain a quantity of the active compound in an amount effective to treat the symptoms of the subject being treated.

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes. All references cited herein are incorporated by reference in their entirety.

Example 1

F1aA-OVA-$m_4$-$n_{80}$ (or Fla-OVA-$m_4$-$n_{80}$-2NGAL)

1A. Formula 103' where X' is OVA and m is 4

In an endotoxin-free tube, OVA (5.0 mg, 0.00012 mmol) was added to 100 µl of pH 8.0 PBS containing 5 mM EDTA and stirred. Separately, 1 mg of Traut's Reagent was dissolved in 100 µl of pH 7.0 PBS, and 16 µl (0.00119 mmol) of the Traut's Reagent solution so obtained was added to the stirred solution of OVA with continued stirring. After 1 hour, excess Traut's Reagent was removed using a centrifugal size exclusion column to afford the corresponding product of Formula 103'.

1B. Formula 106A where n is 80

In an endotoxin-free tube, galactosamine (10.0 mg, 0.04638 mmol) was dissolved with stirring in 100 µl of pH 8.0 PBS containing 5 mM EDTA. Pyridyl dithiol-poly(ethylene glycol)-NHS ester (Formula 104 where n is 80) (16.23 mg, 0.00464 mmol) dissolved in 100 µl of pH 7.0 PBS was added to the stirring solution of galactosamine. After 1 hour, the resulting pyridyl dithiol-poly(ethylene glycol)-N-acetylgalactosamine (Formula 106A) was ready to be used without further purification.

1C. Formula 1 aA where X' is OVA, m is 4, n is 80 (and Z' is C2 Galactosamine)

The purified OVA-Traut conjugate of Formula 103' prepared in Example 1A was added directly to the stirring product of Formula 106A prepared in Example 1B. After 1 hour, the resulting product of Formula 1a was purified by passing the reaction mixture through a centrifugal size exclusion column. Characterization (UHPLC SEC, gel electrophoresis) confirmed product identity. (See FIG. 5.)

1D. Other Compounds of Formula 103'

By following the procedure described in Example 1A and substituting OVA with the following:
  Abciximab,
  Adalimumab,
  Agalsidase alfa,
  Agalsidase beta,
  Aldeslukin,
  Alglucosidase alfa,
  Factor VIII,
  Factor IX,
  L-asparaginase,
  Laronidase,
  Octreotide,
  Phenylalanine ammonia-lyase,
  Rasburicase,
  Insulin (SEQ ID NO:5),
  GAD-65 (SEQ ID NO:6),
  IGRP (SEQ ID NO:7)
  MBP (SEQ ID NO:8),
  MOG (SEQ ID NO:9),
  PLP (SEQ ID NO:10),
  MBP13-32 (SEQ ID NO:11),
  MBP83-99 (SEQ ID NO:12),
  MBP111-129 (SEQ ID NO:13),
  MBP146-170 (SEQ ID NO:14),
  MOG1-20 (SEQ ID NO:15),
  MOG35-55 (SEQ ID NO:16),
  PLP139-154 (SEQ ID NO:17),
  MART1 (SEQ ID NO:18),
  Tyrosinase (SEQ ID NO:19),
  PMEL (SEQ ID NO:20),
  Aquaporin-4 (SEQ ID NO:21),
  S-arrestin (SEQ ID NO:22),
  IRBP (SEQ ID NO:23),
  Conarachin (UNIPROT Q6PSU6),
  Alpha-gliadin "33-mer" native (SEQ ID NO:24),
  Alpha-gliadin "33-mer" deamidated (SEQ ID NO:25),
  Alpha-gliadin (SEQ ID NO:26),
  Omega-gliadin (SEQ ID NO:27),
  Fel d 1A (UNIPROT P30438),
  Cat albumin (UNIPROT P49064),
  Can f 1 (UNIPROT 018873),
  Dog albumin (UNIPROT P49822), and
  RhCE example (UNIPROT P18577),
there are obtained the following corresponding compounds of Formula 103' where:
  X is Abciximab and m is 10,
  X is Adalimumab and m is 11,
  X is Agalsidase alfa and m is 14,
  X is Agalsidase beta and m is 14,
  X is Aldeslukin and m is 6,
  X is Alglucosidase alfa and m is 13,
  X is Factor VIII and m is 100,
  X is Factor IX and m is 18,
  X is L-asparaginase and m is 5,
  X is Laronidase and m is 7,
  X is Octreotide and m is 1,
  X is Phenylalanine ammonia-lyase and m is 12,
  X is Rasburicase and m is 12,
  X is Insulin (SEQ ID NO:5) and m is 2,
  X is GAD-65 (SEQ ID NO:6) and m is 8,
  X is IGRP (SEQ ID NO:7) and m is 7, X is MBP (SEQ ID NO:8) and m is 6,
X is MOG (SEQ ID NO:9) and m is 5,
X is PLP (SEQ ID NO:10) and m is 8,
X is MBP13-32 (SEQ ID NO:11) and m is 1,
X is MBP83-99 (SEQ ID NO:12) and m is 1,
X is MBP111-129 (SEQ ID NO:13) and m is 1,
X is MBP146-170 (SEQ ID NO:14) and m is 2,
X is MOG1-20 (SEQ ID NO:15) and m is 1,
X is MOG35-55 (SEQ ID NO:16) and m is 2,
X is PLP139-154 (SEQ ID NO:17) and m is 3,
X is MART1 (SEQ ID NO:18) and m is 4,
X is Tyrosinase (SEQ ID NO:19) and m is 8,
X is PMEL (SEQ ID NO:20) and m is 5,
X is Aquaporin-4 (SEQ ID NO:21) and m is 4,
X is S-arrestin (SEQ ID NO:22) and m is 12,
X is IRBP (SEQ ID NO:23) and m is 21,
X is Conarachin and m is 21,
X is Alpha-gliadin "33-mer" native (SEQ ID NO:24) and m is 1,
X is Alpha-gliadin "33-mer" deamidated (SEQ ID NO:25) and m is 1,
X is Alpha-gliadin (SEQ ID NO:26) and m is 1,
X is Omega-gliadin (SEQ ID NO:27) and m is 1,
X is Fel d 1 and m is 4,
X is Cat albumin and m is 16,
X is Can f 1 and m is 6,
X is Dog albumin and m is 23, and
X is RhCE example and m is 10.

1E. Other Compounds of Formula 1 aA

By following the procedure described in Example 1C and substituting the compounds of Formula 103', for example as obtained in Example 1 D, there are obtained the following corresponding compounds of Formula 1aA:
F1aA-Abciximab-$m_{10}$-$n_{80}$,
F1aA-Adalimumab-$m_{11}$-$n_{80}$,
F1aA-Agalsidase alfa-$m_{14}$-$n_{80}$,
F1aA-Agalsidase beta-$m_{14}$-$n_{80}$,
F1aA-Aldeslukin-$m_6$-$n_{80}$,
F1aA-Alglucosidase alfa-$m_{13}$-$n_{80}$,
F1aA-Factor VIII-$m_{100}$-$n_{80}$,
F1aA-Factor IX-$m_{18}$-$n_{80}$,
F1aA-L-asparaginase-$m_5$-$n_{80}$,
F1aA-Laronidase-$m_7$-$n_{80}$,
F1aA-Octreotide-$m_1$-$n_{80}$,
F1aA-Phenylalanine ammonia-lyase-$m_{12}$-$n_{80}$,
F1aA-Rasburicase-$m_{12}$-$n_{80}$,
F1aA-Insulin-$m_2$-$n_{80}$,
F1aA-GAD-65-$m_8$-$n_{80}$,
F1aA-IGRP-$m_7$-$n_{80}$,
F1aA-MBP-$m_6$-$n_{80}$,
F1aA-MOG-$m_5$-$n_{80}$,
F1aA-PLP-$m_8$-$n_{80}$,
F1aA-MBP13-32-$m_1$-$n_{80}$,
F1aA-MBP83-99-$m_1$-$n_{80}$,
F1aA-MBP111-129-$m_1$-$n_{80}$,
F1aA-MBP146-170-$m_2$-$n_{80}$,
F1aA-MOG1-20-$m_1$-$n_{80}$,
F1aA-MOG35-55-$m_2$-$n_{80}$,
F1aA-PLP139-154-$m_3$-$n_{80}$,
F1aA-MART1-$m_4$-$n_{80}$,
F1aA-Tyrosinase-$m_8$-$n_{80}$,
F1aA-PMEL-$m_5$-$n_{80}$,
F1aA-Aquaporin-4-$m_4$-$n_{80}$,
F1aA-S-arrestin-$m_{12}$-$n_{80}$,
F1aA-IRBP-$m_{21}$-$n_{80}$,
F1aA-Conarachin-$m_{21}$-$n_{80}$,
F1aA-Alpha-gliadin "33-mer" native-$m_1$-$n_{80}$,
F1aA-Alpha-gliadin "33-mer" deamidated-$m_1$-$n_{80}$,
F1aA-Alpha-gliadin-$m_1$-$n_{80}$,
F1aA-Omega-gliadin-$m_1$-$n_{80}$,
F1aA-Fel d 1-$m_4$-$n_{80}$,
F1aA-Cat albumin-$m_{16}$-$n_{80}$,
F1aA-Can f 1-$m_6$-$n_{80}$,
F1aA-Dog albumin-$m_{23}$-$n_{80}$, and
F1aA-RhCE-$m_{10}$-$n_{80}$.

1F. Other Compounds of Formula 106A

By following the procedure described in Example 1B and substituting the pyridyl dithiol-poly(ethylene glycol)-NHS ester (Formula 104 where n is 80) with the following:
Formula 104 where n is 12,
Formula 104 where n is 33,
Formula 104 where n is 40,
Formula 104 where n is 43,
Formula 104 where n is 50,
Formula 104 where n is 60,
Formula 104 where n is 75, and
Formula 104 where n is 80,
there are obtained the following corresponding compounds of Formula 106A where:
n is 12,
n is 33,
n is 40,
n is 43,
n is 50,
n is 60,
n is 75, and
n is 84, 1G. Other Compounds of Formula 1aA By following the procedure described in Example 1E and substituting the compound of Formula 106A with the compounds obtained in Example 1F, there are obtained the corresponding compounds of Formula 1aA where n is 12, 33, 40, 43, 50, 60, 75 and 84, such as:
F1aA-Insulin-$m_2$-$n_{12}$,
F1aA-Insulin-$m_2$-$n_{33}$,
F1aA-Insulin-$m_2$-$n_{40}$,
F1aA-Insulin-$m_2$-$n_{43}$,
F1aA-Insulin-$m_2$-$n_{50}$,
F1aA-Insulin-$m_2$-$n_{60}$,
F1aA-Insulin-$m_2$-$n_{75}$, and
F1aA-Insulin-$m_2$-$n_{84}$.

Example 2

F1b-OVA-$m_1$-$n_4$-$p_{34}$-2NAcGAL

2A. Formula 103' where X' is Ovalbumin and m is 1

In an endotoxin-free tube, OVA (6.5 mg, 0.000155 mmol) was added to 200 µl of pH 8.0 PBS containing 5 mM EDTA and stirred. Separately, 1 mg of Taut's Reagent was dissolved in 100 µl of pH 7.0 PBS, and 43 µl (0.00310 mmol) of the Traut's Reagent solution so obtained was added to the stirred solution of OVA with continued stirring. After 1 hour, non-reacted Traut's Reagent was removed using a centrifugal size exclusion column to afford the product of Formula 103'.

2B. Formula 1b where X' is Ovalbumin, m is 1, n is 4, p is 34, $R^9$ is a Direct Bond and Z" is 2NAcGAL In a micro centrifuge tube, poly(Galactosamine Methacrylate)-(pyridyl disulfide) (Formula 201) (20.0 mg, 0.0020 mmol) was solubilized in 50 µl of pH 8.0 PBS containing 5 mM EDTA. To this was added the purified OVA-Traut product from Example 2A followed by stirring for 1 hour. The resulting product of Formula 1b was purified by passing the reaction mixture through a centrifugal size exclusion column. Characterization (UHPLC SEC, gel electrophoresis) confirmed the identity of the product. (See FIG. 5.)

2C. Other Compounds of Formula 1b

By following the procedure described in Example 2B and substituting the compounds of Formula 103', for example as obtained in Example 1 D, there are obtained the following corresponding compounds of Formula 1b:

F1b-Abciximab-$m_{10}$-$n_4$-$p_{34}$-2NAcGAL,
F1b-Adalimumab-$m_{11}$-$n_4$-$p_{34}$-2NAcGAL,
F1b-Agalsidase alfa-$m_4$-$n_4$-$p_{34}$-2NAcGAL,
F1b-Agalsidase beta-$m_{14}$-$n_4$-$p_{34}$-2NAcGAL,
F1b-Aldeslukin-$m_6$-$n_4$-$p_{34}$-2NAcGAL,
F1b-Alglucosidase alfa-$m_{13}$-$n_4$-$p_{34}$-2NAcGAL,
F1b-Factor VIII-$m_{100}$-$n_4$-$p_{34}$-2NAcGAL,
F1b-Factor IX-$m_{18}$-$n_4$-$p_{34}$-2NAcGAL,
F1b-L-asparaginase-$m_5$-$n_4$-$p_{34}$-2NAcGAL,
F1b-Laronidase-$m_7$-$n_4$-$p_{34}$-2NAcGAL,
F1b-Octreotide-$m_1$-$n_4$-$p_{34}$-2NAcGAL,
F1b-Phenylalanine ammonia-lyase-$m_{12}$-$n_4$-$p_{34}$-2NAcGAL,
F1b-Rasburicase-$m_{12}$-$n_4$-$p_{34}$-2NAcGAL,
F1b-Insulin-$m_2$-$n_4$-$p_{34}$-2NAcGAL,
F1b-GAD-65-$m_8$-$n_4$-$p_{34}$-2NAcGAL,
F1b-IGRP-$m_7$-$n_4$-$p_{34}$-2NAcGAL,
F1b-MBP-$m_6$-$n_4$-$p_{34}$-2NAcGAL,
F1b-MOG-$m_8$-$n_4$-$p_{34}$-2NAcGAL,
F1b-PLP-$m_8$-$n_4$-$p_{34}$-2NAcGAL,
F1b-MBP13-32-$m_1$-$n_4$-$p_{34}$-2NAcGAL,
F1b-MBP83-99-$m_1$-$n_4$-$p_{34}$-2NAcGAL,
F1b-MBP11-129-$m_1$-$n_4$-$p_{34}$-2NAcGAL,
F1b-MBP146-170-$m_2$-$n_4$-$p_{34}$-2NAcGAL,
F1b-MOG1-20-$m_1$-$n_4$-$p_{34}$-2NAcGAL,
F1b-MOG35-55-$m_2$-$n_4$-$p_{34}$-2NAcGAL,
F1b-PLP139-154-$m_3$-$n_4$-$p_{34}$-2NAcGAL,
F1b-MART1-$m_4$-$n_4$-$p_{34}$-2NAcGAL,
F1b-Tyrosinase-$m_8$-$n_4$-$p_{34}$-2NAcGAL,
F1b-PMEL-$m_5$-$n_4$-$p_{34}$-2NAcGAL,
F1b-Aquaporin-4-$m_4$-$n_4$-$p_{34}$-2NAcGAL,
F1b-S-arrestin-$m_{12}$-$n_4$-$p_{34}$-2NAcGAL,
F1b-IRBP-$m_{21}$-$n_4$-$p_{34}$-2NAcGAL,
F1b-Conarachin-$m_{21}$-$n_4$-$p_{34}$-2NAcGAL,
F1b-Alpha-gliadin "33-mer" native-$m_1$-$n_4$-$p_{34}$-2NAcGAL,
F1b-Alpha-gliadin "33-mer" deamidated-$m_1$-$n_4$-$p_{34}$-2NAcGAL,
F1b-Alpha-gliadin-$m_1$-$n_4$-$p_{34}$-2NAcGAL,
F1b-Omega-gliadin-$m_1$-$n_4$-$p_{34}$-2NAcGAL,
F1b-Fel d 1-$m_4$-$n_4$-$p_{34}$-2NAcGAL,
F1b-Cat albumin-$m_{16}$-$n_4$-$p_{34}$-2NAcGAL,
F1b-Can f 1-$m_6$-$n_4$-$p_{34}$-2NAcGAL,
F1b-Dog albumin-$m_{23}$-$n_4$-$p_{34}$-2NAcGAL, and
F1b-RhCE-$m_{10}$-$n_4$-$p_{34}$-2NAcGAL.

Example 3

F1f-OVA-$m_1$-$n_4$-$p_{33}$-2NAcGAL

3A. Formula 1f where X' is Ovalbumin and m is 1, n is 4, p is 33, $R^9$ is a Direct Bond and Z" is 2NAcGAL In an endotoxin-free tube, OVA (4.0 mg, 0.0000952381 mmol) was added to 0.1 ml of pH 7.4 PBS and stirred. Separately, poly-(n-Acetylgalactosamine)-p-nitrophenyol carbonate of Formula 601 where n is 4 and p is 33 (33.0 mg, 0.002380952 mmol) was added to 100 µl of pH 7.5 PBS and vortexed until dissolved. The two solutions were combined and the mixture was stirred vigorously for 1 hour. The mixture was then collected and dialyzed for 3 days against pH 7.4 PBS (30 kDa molecular weight cut off) to afford the product of Formula 1f.

Example 4

F1g-PVA-$m_1$-$p_{90}$-2NAcGAL

4A. Formula 1a where X' is Ovalbumin and m is 1, p is 90, $R^9$ is a Direct Bond and Z" is 2NAcGAL In an endotoxin-free tube, OVA (5.0 mg, 0.000119048 mmol) was added to 0.2 ml of pH 7.4 PBS and stirred. To the stirring solution was added 75 mg (0.00297619 mmol) of Poly(Galactosamine Methacrylate)-NHS (Formula 701) dissolved in 0.4 ml of pH 7.4 PBS. The mixture was allowed to stir for 2 hours. The mixture was then collected and dialyzed for 3 days against pH 7.4 PBS (30 kDa molecular weight cut off) to afford the product of Formula 1g.

Example 5

F1h-OVA-$m_2$-$n_{45}$-$p_{55}$-$q_4$-2NAcGAL

5A. Formula 802' where X' is Ovalbumin, m is 2 and n is 45

In an endotoxin-free tube, OVA (3.0 mg, 0.0000714286 mmol) was added to 150 µl of pH 8.0 PBS containing 5 mM EDTA and stirred. Dibenzocyclooctyne-PEG-(p-nitrophenyl carbonate) (Formula 801) (5.265 mg, 0.002142857 mmol) dissolved in DMF was added to the OVA solution and stirred for 1 hour. The excess dibenzocyclooctyne-PEG-(p-nitrophenyl carbonate) was removed using a centrifugal size exclusion column to afford the product of Formula 802'.

5B. Formula 1h where X' is Ovalbumin, m is 2, n is 45, p is 55, q is 4, $R^8$ is $CH_2$, $R^9$ is a Direct Bond and Z" is 2NAcGAL Poly(Galactosamine Methacrylate)-N3 (Formula 803 where p is 55, q is 4 and Z" is N-acetylgalactosamine) (33 mg, 0.002142857 mmol) was dissolved in 100 µl of pH 7.4 PBS and added to the product of Example 5A with stirring.

After 1 hour, the resulting product of Formula 1h was purified by centrifugal size exclusion chromatography.

Example 6

F1j-OVA-$m_{10}$-$n_{45}$-$p_{55}$-$q_4$-2NAcGAL

6A. Formula 103' where X' is Ovalbumin and m is 10

In an endotoxin-free tube, OVA (5.0 mg, 0.00019 mmol) was added to 150 µl of pH 8.0 PBS containing 5 mM EDTA and stirred. Separately, 1 mg of Taut's Reagent was dissolved in 100 µl of pH 7.0 PBS, and 16 µl (0.0019 mmol) of the Traut's Reagent solution so obtained was added to the stirred solution of OVA with continued stirring. After 1 hour, non-reacted Traut's Reagent was removed using a centrifugal size exclusion column to afford the product of Formula 103'.

6B. Formula 902" where X' is Ovalbumin, m is 10 and n is 45

Dibenzocyclooctyne-PEG-(pyridyl disulfide) (Formula 901 where n is 45) (6.0 mg, 0.00238 mmol) was dissolved in DMF and the resulting solution was added to the OVA solution obtained in Example 6A and stirred for 1 hour. The excess dibenzocyclooctyne-PEG-(pyridyl disulfide) was removed using centrifugal size exclusion chromatography to afford the product of Formula 902".

6C. Formula 1i where X' is Ovalbumin, m is 10, n is 45, p is 55, q is 4, $R^8$ is $CH_2$, $R^9$ is a Direct Bond and Z" is 2NAcGAL Poly(Galactosamine Methacrylate)-N3 (Formula 803 where p is 55, q is 4 and Z" is N-acetylgalactosamine) (36 mg, 0.00238 mmol) was dissolved in 150 µl of pH 7.4 PBS and added to the product of Example 6B with stirring. After 1 hour, the resulting product of Formula 1j was purified (excess p(GMA)-N3 removed) by centrifugal size exclusion chromatography. Characterization (UHPLC SEC, gel electrophoresis) confirmed the identity of the product.

Example 7

F1 L-OVA-$m_2$-$n_{80}$-$p_{55}$-$q_4$-2NAcGAL

7A. Formula 1002 where X' is Ovalbumin, m is 2 and n is 80

Dibenzocyclooctyne-PEG-(pyridyl disulfide) (Formula 1001 where n is 80) (9.0 mg, 0.00238 mmol) was dissolved in DMF and the resulting solution was added to a purified OVA solution of Formula 103' (where X' is Ovalbumin and m is 2), for example prepared as described in Example 6A and stirred for 1 hour. The excess dibenzocyclooctyne-PEG-(pyridyl disulfide) was removed using centrifugal size exclusion chromatography to afford the product of Formula 1002.

7B. Formula 1L where X' is Ovalbumin, m is 2, n is 80, p is 55, q is 4, $R^8$ is $CH_2$, $R^9$ is a Direct Bond and Z" is 2NAcGAL Poly(Galactosamine Methacrylate)-N3 (Formula 803 where p is 55, q is 4 and Z" is N-Acetylgalactosamine) (36 mg, 0.00238 mmol) was dissolved in 150 µl of pH 7.4 PBS and added to the product of Example 7A with stirring. After 1 hour, the resulting product of Formula 1L was purified (excess poly(Galactosamine Methacrylate)-N3 removed) by centrifugal size exclusion chromatography. Characterization (UHPLC SEC, gel electrophoresis) confirmed the identity of the product.

Example 8

Preparation of Poly(Galactosamine Methacrylate) Polymers

8A. Galactosamine Methacrylate

To stirred galactosamine hydrochloride (2.15 g, 10.0 mmol) was added 0.5 M sodium methoxide (22 ml, 11.0 mmol). After 30 minutes, methacrylate anhydride (14.694 g, 11.0 mmol) was added and stirring continued for 4 hours. The resulting galactosamine methacrylate was loaded onto silica gel via rotovap and purified via column chromatography using DCM:MeOH (85:15).

8B. Formula 201 where n is 4 and p is 30

Galactose methacrylate (600 mg, 2.43 mmol), 2-(2-(2-(2-(pyridin-2-yldisulfanyl)ethoxy)ethoxy)ethoxy)ethyl 2-((phenylcarbonothioyl)thio)acetate (44.8 mg, 0.081 mmol) and AIBN (3.174089069 mg, 0.016 mmol) were added to 1.5 ml of DMF in a Schlenk Flask. The reaction mixture was subjected to 4 freeze-thaw cycles and then stirred at 70° C. for 6 hours. The desired polymer product of Formula 201 was precipitated in 12 ml of methanol, and excess solvent was removed under reduced pressure.

Example 9

Preparation of F1aA-PE-$m_3$-$n_{80}$

9A. Formula 103' where X' is Phycoerythrin

In an endotoxin-free tube, phycoerythrin ("PE") (purchased from Pierce) (200 µl, 0.000004 mmol) was added to 50 µl of pH 8.0 PBS containing 5 mM EDTA and stirred. Separately, 1 mg of Taut's Reagent was dissolved in 100 µl of pH 7.0 PBS, and 2 µl (0.00013 mmol) of the Traut's Reagent solution so obtained was added to the stirred solution of PE with continued stirring. After 1 hour, excess Traut's Reagent was removed using a centrifugal size exclusion column to afford the product of Formula 103'.

9B. Formula 106A where n is 80

In an endotoxin-free tube, galactosamine (7.0 mg, 0.03246 mmol) was dissolved with stirring in 100 µl of pH 8.0 PBS containing 5 mM EDTA. Pyridyl dithiol-poly (ethylene glycol)-NHS ester (Formula 104 where n is 80) (16.23 mg, 0.00464 mmol) dissolved in 50 µl of pH 7.0 PBS was added to the stirring solution of galactosamine. After 1 hour, the resulting product of Formula 106A was ready to be used without further purification.

9C. Formula 1a where X' is Phycoerythrin, m is 3, n is 80 and Z' is Galactosamine The purified PE-Traut conjugates prepared in Example 9A were added directly to the stirring product of Formula 106A prepared in Example 9B. After 1 hour, the resulting product of Formula 1a was purified by passing the reaction mixture through a centrifugal size exclusion column. Characterization (UHPLC SEC, gel electrophoresis) confirmed the identity of the product.

Example 10

OVA-DOM

10A. Preparation of Expression Vector

The mammalian cell expression vector pSecTag A was purchased from Life Technologies. The gene encoding the anti-ASGPR domain antibody, Dom26h-196-61, herein referred to as "DOM", was purchased as a codon-optimized sequence for protein expression in human cells, from the provider Genscript. Sequences encoding OVA, DOM, the flexible linker Gly3Ser, and the 6×His tag were cloned into mammalian expression vector pSecTag A, C-terminal to the Ig κ-chain secretion leader sequence, by site-directed mutagenesis, following a variation of the QuikChange protocol (Geiser, et al.)

10B. Expression and Purification of Formula 2 where m' is 1, m" is 0, X is Ovalbumin, Y is Gly$_3$Ser, Z is Anti-ASGPR Dom26h-196-61

HEK293 cells were transiently transfected with modified pSecTag A vectors, prepared for example as described in Example 10A, using polyethylenimine. Transfected cells were cultured in FreeStyle 293 medium (Life Technologies) supplemented with valproic acid for 7 days, after which the cells were removed by centrifugation and the culture supernatants were collected and sterilized by filtration. The OVA/DOM fusion proteins of Formula 2 were purified from the culture supernatants by immobilized metal ion affinity chromatography using a HisTrap Ni$^{2+}$ sepharose column (GE Healthcare), followed by size exclusion chromatography using a Superdex 75 column (GE Healthcare), having the following generalized structure:

N-OVA-Gly$_3$Ser-DOM-Gly3Ser-6×His-C and the following amino acid sequence:

```
                                            (SEQ ID NO: 28)
GSIGAASMEFCFDVFKELKVHHANENIFYCPIAIMSALAMVYLGAKDSTR

TQINKVVRFDKLPGFGDSIEAQCGTSVNVHSSLRDILNQITKPNDVYSFS

LASRLYAEERYPILPEYLQCVKELYRGGLEPINFQTAADQARELINSWVE

SQTNGIIRNVLQPSSVDSQTAMVLVNAIVFKGLWEKAFKDEDTQAMPFRV

TEQESKPVQMMYQIGLFRVASMASEKMKILELPFASGTMSMLVLLPDEVS

GLEQLESIINFEKLTEWTSSNVMEERKIKVYLPRMKMEEKYNLTSVLMAM

GITDVFSSSANLSGISSAESLKISQAVHAAHAEINEAGREVVGSAEAGVD

AASVSEEFRADHPFLFCIKHIATNAVLFFGROVSPGGGSEVQLLESGGGL

VQPGGSLRLSCAASGFTFEKYAMAWVRQAPGKGLEWVSRISARGVTTYYA

DSVKGRFTISRDNSKNTLYLQMNSLRAEDTAVYYCASHKRHEHTRFDSWGQ

GTLVTVSSGGGSHHHHHH
```

Protein purity was verified by Coomassie Brilliant Blue staining of SDS-PAGE gels and anti-6×His tag western blotting. Protein concentration was determined using the Beer-Lambert Law, for which the absorbance at 280 nm was measured using a NanoDrop 2000 (Thermo Scientific), and the molecular weight (57.3 kDa) and extinction coefficient (57,090 M$^{-1}$ cm$^{-1}$) were estimated from the protein's amino acid sequence, using the ExPASy ProtParam tool. Endotoxin levels were measured using the HEK-BLUE TLR reporter cell line (Invivogen) according to manufacturer's instructions.

10C. Other Compositions of Formula 2

By following the procedures described in Examples 10A and 10B and substituting the pSecTag A vectors accordingly, there were obtained the following fusion proteins of Formula 2:

N-DOM-Gly$_3$Ser-OVA-Gly$_3$Ser-6×His-C having the following amino acid sequence:

EVQLLESGGGLVQPGGSLRLSCAASGFTFEKYA-
MAWVRQAPGKGLEWVSRISARGVTTYYADSVKGRF
TISRDNSKNTLYLQMNSLRAEDTAVYYCASH-
KRHEHTRFDSWGQGTLVTVSSGGGSGSIGAAS-
MEFCFD VFKELKVHHANENIFYCPIAIMSALAM-
VYLGAKDSTRTQiNKVVRFDKLPGFGDSIEAQCGTSVNVHSSLR
DILNQITKPNDVYSFSLASRLYAEERYPILPEY-
LQCVKELYRGGLEPINFQTAADQARE-
LINSWVESQTNGII RNVLQPSSVDSQTAMVLVNA-
IVFKGLWEKAFKDEDTQAMPFRVTEQESKPVQMMYQIGLFRVASMASE
KMKILELPFASGTMSMLVLLPDEVSGLEQLESHN-
FEKLTEWTSSNVMEERKIKVYLPRMKMEEKYNLTSV
LMAMGITDVFSSSANLSGIS-
SAESLKISQAVHAAHAEINEAGREVVGSAE-
AGVDAASVSEEFRADHPFLFC IKHIATNAVLFF-
GRCVSPGGGSHHHHHH (SEQ ID NO:29); and N-OVA-Gly$_3$Ser-DOM-Gly$_3$Ser-OVA-Gly$_3$Ser-6× His-C having the following amino acid sequence:

```
                                            (SEQ ID NO: 30)
GSIGAASMEFCFDVFKELKVHHANENIFYCPIAIMSALAMVYLGAKDSTR

TQINKVVRFDKLPGFGDSIEAQCGTSVNVHSSLRDILNQITKPNDVYSFS

LASRLYAEERYPILPEYLQCVKELYRGGLEPINFQTAADQARELINSWVE

SQTNGIIRNVLQPSSVDSQTAMVLVNAIVFKGLWEKAFKDEDTQAMPFRV

TEQESKPVQMMYQIGLFRVASMASEKMKILELPFASGTMSMLVLLPDEVS

GLEQLESIINFEKLTEWTSSNVMEERKIKVYLPRMKMEEKYNLTSVLMAM

GITDVFSSSANLSGISSAESLKISQAVHAAHAEINEAGREVVGSAEAGVD

AASVSEEFRADHPFLFCIKHIATNAVLFFGRCVSPGGGSEVQLLESGGGL

VQPGGSLRLSCAASGFTFEKYAMAWVRQAPGKGLEWVSRISARGVTTYYA

DSVKGRFTISRDNSKNTLYLQMNSLRAEDTAVYYCASHKRHEHTRFDSWG

QGTLVTVSSGGGSGSIGAASMEFCFDVFKELKVHHANENIFYCPIAIMSA

LAMVYLGAKDSTRTQINKVVRFDKLPGFGDSIEAQCGTSVNVHSSLRDIL

NQITKPNDVYSFSLASRLYAEERYPILPEYLQCVKELYRGGLEPINFQTA

ADQARELINSWVESQTNGIIRNVLQPSSVDSQTAMVLVNAIVFKGLWEKA

FKDEDTQAMPFRVTEQESKPVQMMYQIGLFRVASMASEKMKILELPFASG

TMSMLVLLPDEVSGLEQLESIINFEKLTEWTSSNVMEERKIKVYLPRMKM

EEKYNLTSVLMAMGITDVFSSSANLSGISSAESLKISQAVHAAHAEINEA
```

-continued

GREVVGSAEAGVDAASVSEEFRADHPFLFCIKHIATNAVLFFGRCVSPGG

GSHHHHHH.

10D. Other Compositions of Formula 2

By following the procedures described in Examples 10A and 10B and substituting for Gly3Ser the vectors for a linker having an immunoproteosome cleavage site ("IPC"), and for OVA the vectors for:
  MBP13-32 (SEQ ID NO:11),
  MBP83-99 (SEQ ID NO:12),
  MBP111-129 (SEQ ID NO:13),
  MBP146-170 (SEQ ID NO:14),
  MOG1-20 (SEQ ID NO:15),
  MOG35-55 (SEQ ID NO:16), and
  PLP139-154 (SEQ ID NO:17),
or the vectors for:
  Alpha-gliadin "33-mer" deamidated (SEQ ID NO:25)
  Alpha-gliadin (SEQ ID NO:26), and
  Omega-gliadin (SEQ ID NO:27),
there are obtained the following fusion proteins of Formula 2:
  MBP13-32-IPC-MBP83-99-IPC-MBP111-129-IPC-MBP146-170-IPC-MOG1-20-IPC-MOG35-55-IPC-PLP139-154-IPC-DOM, and
  Alpha-gliadin "33-mer" deamidated-IPC-Alpha-gliadin-IPC-Omega-gliadin-IPC-DOM.

Example 11

Desialylated OVA

11A. Preparation of Expression Vector

The mammalian cell expression vector pSecTag A was purchased from Life Technologies. Sequences encoding OVA, the flexible linker Gly3Ser, and the 6×His tag were cloned into pSecTag A, C-terminal to the Ig κ-chain secretion leader sequence, by site-directed mutagenesis, following a variation of the QuikChange protocol (Geiser, et al.)

11B. Expression and Purification of OVA

HEK293 cells were transiently transfected with modified pSecTag A vector, prepared for example as described in Example 10A, using polyethylenimine. Transfected cells were cultured in FreeStyle 293 medium (Life Technologies) supplemented with valproic acid for 7 days, after which the cells were removed by centrifugation and the culture supernatants are collected and sterilized by filtration. OVA protein was purified from the culture supernatant by immobilized metal ion affinity chromatography using a HisTrap Ni2+ sepharose column (GE Healthcare), followed by size exclusion chromatography using a Superdex 75 column (GE Healthcare), having the following structure:

N'-OVA Gly3Ser 6×His-C' and the following amino acid sequence:

(SEQ ID NO: 31)
GSIGAASMEFCFDVFKELKVHHANENIFYCPIAIMSALAMVYLGAKDSTR

TQINKVVRFDKLPGFGDSIEAQCGTSVNVHSSLRDILNQITKPNDVYSFS

LASRLYAEERYPILPEYLQCVKELYRGGLEPINFQTAADQARELINSWVE

SQTNGIIRNVLQPSSVDSQTAMVLVNAIVFKGLWEKAFKDEDTQAMPFRV

TEQESKPVQMMYQIGLFRVASMASEKMKILELPFASGTMSMLVLLPDEVS

GLEQLESIINFEKLTEWTSSNVMEERKIKVYLPRMKMEEKYNLTSVLMAM

GITDVFSSSANLSGISSAESLKISQAVHAAHAEINEAGREVVGSAEAGVD

AASVSEEFRADHPFLFCIKHIATNAVLFFGRCVSPGGGSHHHHHH

Protein purity was verified by Coomassie Brilliant Blue staining of SDS-PAGE gels and anti-6×His tag western blotting. Protein concentration was determined using the Beer-Lambert Law, for which the absorbance at 280 nm was measured using a NanoDrop 2000 (Thermo Scientific), and the molecular weight (43.8 kDa) and extinction coefficient (31,525 M-1 cm-1) were estimated from the protein's amino acid sequence, using the ExPASy ProtParam tool.

11C. Desialylation

OVA is desialylated by incubation with neuraminidase for 1 hour at 37° C. (New England Biolabs). Desialylated OVA is purified from the reaction mixture by immobilized metal ion affinity chromatography (e.g., using a HisTrap Ni2+ sepharose column, GE Healthcare), followed by size exclusion chromatography (e.g., using a Superdex 75 column, GE Healthcare).

Protein purity is verified by Coomassie Brilliant Blue staining of SDS-PAGE gels and anti-6×His tag western blotting. Desialylation is verified by *Sambucus nigra* lectin-based detection of protein sialic acid content in western blots (Vector Biolabs) and by a sialic acid-mediated fluorescence assay (ProZyme). Desialylated protein concentration is determined using the Beer-Lambert Law, as described above for the protein before desialylation. Endotoxin levels are measured using the HEK-Blue TLR4 reporter cell line (Invivogen) according to manufacturer's instructions.

Example 12

Hepatic Distribution

12A. F1aA-PE-$m_3$-$n_{80}$ was Prepared, for Example, as Described in Example 9. A 30 µg/100 µl Solution in Sterile Saline was Prepared for Injection The F1aA-PE-$m_3$-$n_{80}$ solution (30 µg) was administered to one of three groups of C57 black 6 mice 3 per group) via tail vein injection. The two other groups of mice received an equivalent volume of phycoerythrin in 100 µl of saline or saline vehicle. Three hours after administration, the livers and spleens of these animals were harvested and the level of cellular fluorescents in these organs was determined by flow cytometry as an indication of cellular PE content.

As shown in FIG. 1A-1D, sinusoidal endothelial cells (LSECs), hepatocytes, kupffer cells (KC), and other antigen-presenting cells (APCs) from the livers of mice treated with F1aA-PE-$m_3$-$n_{80}$ exhibited at least a three-fold increase in fluorescence as compared with animals that received PE solution. No detectible difference in fluorescence was found in spleen cells harvested from the three groups. These results confirm that F1aA-PE-$m_3$-$n_{80}$ has sufficient specificity for binding to antigen-presenting cells in the liver.

12B. By following the procedure described in Example 12A and substituting F1aA-PE-$m_3$-$n_{80}$ with the compounds F1b-PE-$m_3$-$n_4$-$p_{34}$-2NAcGAL, F1 f-PE-$m_3$-$n_4$-$p_{33}$-2NAcGAL, F1g-PE-$m_3$-$p_{80}$-2NAcGAL, F1h-PE-$m_3$-$n_{45}$-$p_{55}$-$q_4$-2NAcGAL, F1j-PE-$m_3$-$n_{45}$-$p_{55}$-$q_4$-2NAcGAL, F1L-PE-$m_3$-$n_{80}$-$p_{55}$-$q_4$-2NAcGAL, F1m-PE-$m_3$-$n_{80}$-$p_{30}$-$q_4$-CMP-2NHAc, F1m-PE-$m_3$-$n_{62}$-$p_{80}$-$q_8$-CMP-2OH, F1n-PE-$m_3$-$n_1$-$p_{30}$-$q_4$-CMP-2NHAc and F1n-PE-$m_3$-$n_{33}$-$p_{30}$-$q_8$-CMP-2OH, prepared, for example, as described with reference to Example 9 by substitution for X in Examples 2B, 3, 4, 5B, 6B, 7B, 19G, 19L, 20B and 20F, respectively it is confirmed that the compounds F1aA-PE-$m_3$-$n_{80}$ with the compounds F1b-PE-$m_3$-$n_4$-$p_{34}$-2NAcGAL, F1f-PE-$m_3$-$n_4$-$p_{33}$-2NAcGAL, F1 g-PE-$m_3$-$p_{80}$-2NAcGAL, F1h-PE-$m_3$-$n_{45}$-$p_{55}$-$q_4$-2NAcGAL, F1j-PE-$m_3$-$n_{45}$-$p_{55}$-$q_4$-2NAcGAL, F1 L-PE-$m_3$-$n_{80}$-$p_{55}$-$q_4$-2NAcGAL, F1m-PE-$m_3$-$n_{80}$-$p_{30}$-$q_4$-CMP-2NHAc, F1m-PE-$m_3$-$n_{62}$-$p_{30}$-$q_8$-CMP-2OH, F1n-PE-$m_3$-$n_1$-$p_{30}$-$q_4$-CMP-2NHAc and F1n-PE-$m_3$-$n_{33}$-$p_{30}$-$q_8$-CMP-2OH have sufficient specificity for binding to antigen-presenting cells in the liver.

Example 13

Proliferation of Antigen-Specific OT1 CD8+ T Cells

13A. F1aA-OVA-$m_4$-$n_{80}$ synthesized, for example, as described in Example 1, was prepared as a 10 μg/100 μl saline solution for injection. On day 0, $10^6$ OT-1 T cells were fluorescently labeled and adoptively transferred into 3 groups of CD 45.2 mice (5 per group) via tail vein injection. The next day (i.e. Day 1), to each of the 3 groups of mice were administered, respectively, 10 μg of F1aA-OVA-$m_4$-$n_{80}$, OVA or saline via tail vein injection. On day 6, the animals were sacrificed and the % of splenic proliferating OT-1 cells was determined via florescence activated cell sorting.

Figure 2:
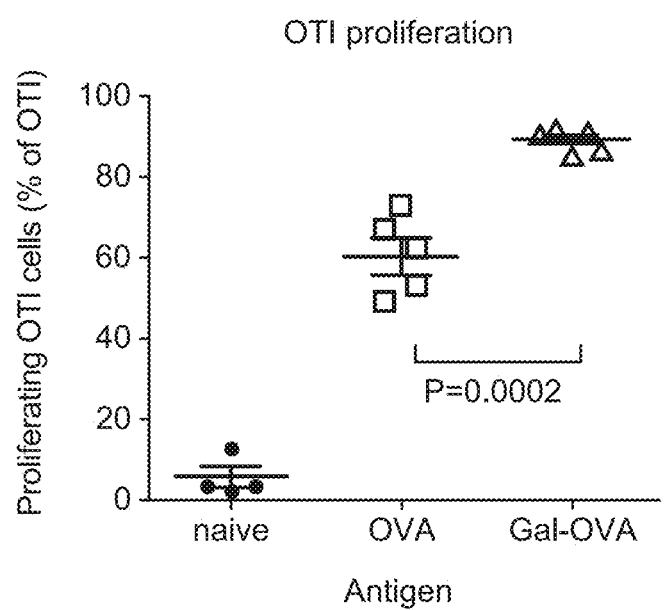

The results from this study (see FIG. 2) show that the percentage of proliferating OTI T cells in mice treated with F1aA-OVA-$m_4$-$n_{80}$ ("Gal-OVA" in FIG. 2) was significantly greater than the percentage of proliferating OTI cells in the spleens of mice treated with OVA or saline ("naïve" in FIG. 2). The increase in OTI cell-proliferation demonstrates the increased CD8+ T-cell cross-priming in animals treated with F1aA-OVA-$m_4$-$n_{80}$ versus the other therapies. In concert with the results from Example 12, these results indicate that the ability of F1aA-OVA-$m_4$-$n_{80}$ to target antigens to the liver increases OVA presentation by antigen presenting cells in the liver to OVA-specific OTI T cells.

Figures 3A, 3B:
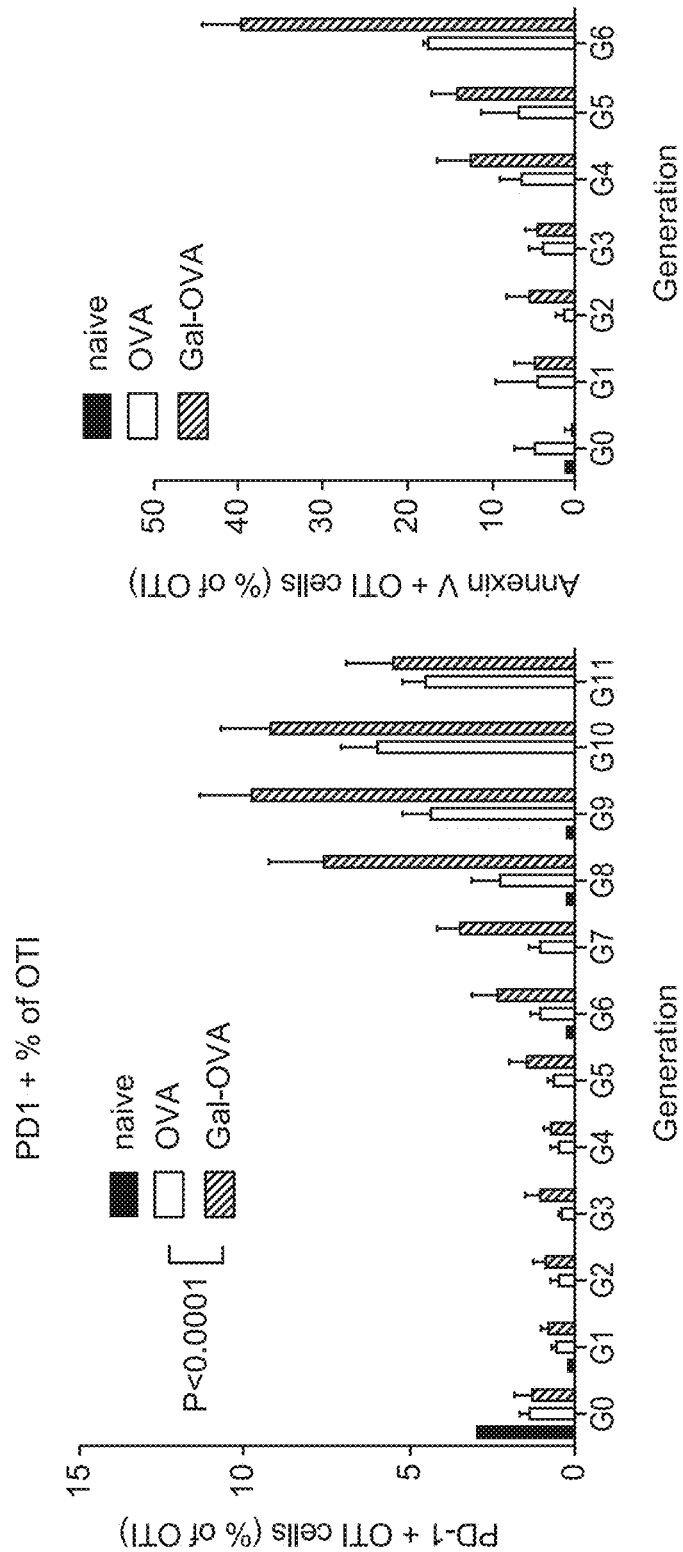

13B. To distinguish T cells being expanded into a functional effector phenotype from those being expanded and deleted, the proliferating OTI CD8+ T cells were analyzed for annexin-V, as a hallmark of apoptosis and thus deletion, as well as the exhaustion marker programmed death-1 (PD-1). As shown in FIG. 3A-3B, F1aA-OVA-$m_4$-$n_{80}$ ("Gal-OVA" in FIG. 3A-3B) induced much higher numbers of annexin-V+ and PD-1 proliferating OTI CD8+ T cells than soluble OVA.

13C. By following the procedure described in Examples 13A and 13B, and substituting F1aA-OVA-$m_4$-$n_8$ with the compounds of Formula 1 obtained, for example, as described in Examples 3A, 4A, 5B, 6C, 7B and 19G, it is shown the compounds from Examples 3A, 4A, 5B, 6C, 7B and 19G induce much higher numbers of annexin-V+ and PD-1+ proliferating OTI CD8+ T cells than soluble OVA.

13D. By following the procedure described in Examples 13A and 13B and substituting F1aA-OVA-$m_4$-$n_8$ with the compounds of Formulae 1 and 2 obtained, for example, as described in Examples 1E, 1G, 2C, 10D, 19I, 19L, 20B, 20D and 20F, and substituting OVA with the antigens corresponding to X (or X' or X"), respectively, it is shown that the compounds from Examples 1E, 1 G, 2C, 10D, 19I, 19L, 20B, 20D and 20F induce much higher numbers of annexin-V+ and PD-1+ proliferating OTI CD8+ T cells than soluble antigen X.

Example 14

F1aA-OVA-$m_4$-$n_8$ does not Induce an OVA-Specific Antibody Response

Figure 4:
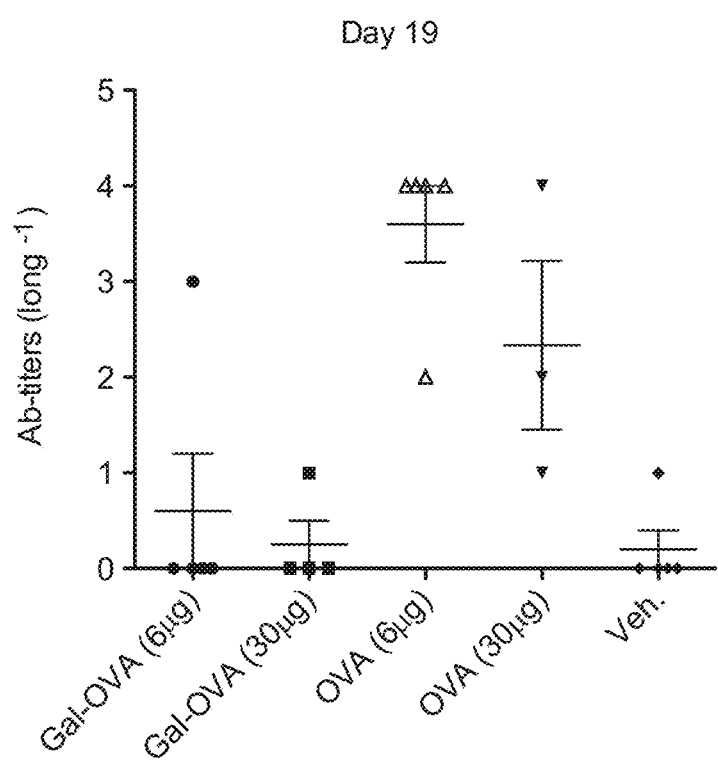

14A. In order to assess the humoral immune response to F1aA-OVA-$m_4$-$n_8$ we treated mice with a weekly i.v. injection of either F1aA-OVA-$m_4$-$n_8$ or OVA, then measured the levels of OVA-specific antibodies in the blood. On day 0, 7, and 14 of the experiment, mice were administered an i.v. injection of 100 μl of saline containing one of the following: 1.) 6 μg of OVA; 2.) 6 μg of F1aA-OVA-$m_4$-n; 3.) 30 μg of OVA; 4.) 30 μg of F1aA-OVA-$m_4$-$n_8$, or 5.) saline alone. Each group contained 5 mice. On day 19, the mice were bled via cheek puncture, and the titer of OVA-specific antibodies in each mouse's blood was determined via ELISA. The results for this study show that although mice treated with 6 and 30 μg of OVA had increased OVA-specific antibody titers, mice treated with both 6 and 30 μg of F1aA-OVA-$m_4$-$n_8$ ("Gal-OVA" in FIG. 4) had blood titers similar to mice treated with saline (i.e. vehicle treated animals) (FIG. 4). For example mice treated with 6 and 30 μg of OVA had an average antibody titer of 3.5 and 2.5, respectively; whereas, mice treated with 6 and 30 μg of OVA had an average antibody titer of 0.75 and 0.25, respectively.

14B. By following the procedure described in Example 14A and substituting F1aA-OVA-$m_4$-$n_8$ with the compounds of Formula 1 obtained, for example, as described in Examples 3A, 4A, 5B, 6C, 7B and 19G, it is shown that mice treated with the compounds from Examples 3A, 4A, 5B, 6C, 7B and 19G have OVA-specific antibody titers similar to mice treated with saline.

14C. By following the procedure described in Example 14A and substituting F1aA-OVA-$m_4$-$n_8$ with the compounds of Formulae 1 and 2 obtained, for example, as described in Examples 1E, 1G, 2C, 10D, 19I, 19L, 20B, 20D and 20F, and substituting OVA with the antigens corresponding to X (or X' or X"), respectively, it is shown that mice treated with the compounds from Examples 1E, 1G, 2C, 10D, 19I, 19L, 20B, 20D and 20F have antigen X-specific antibody titers similar to mice treated with saline.

Example 15

F1aA-OVA-$m_4$-$n_8$ Depletes OVA-Specific Antibodies

Figure 5:
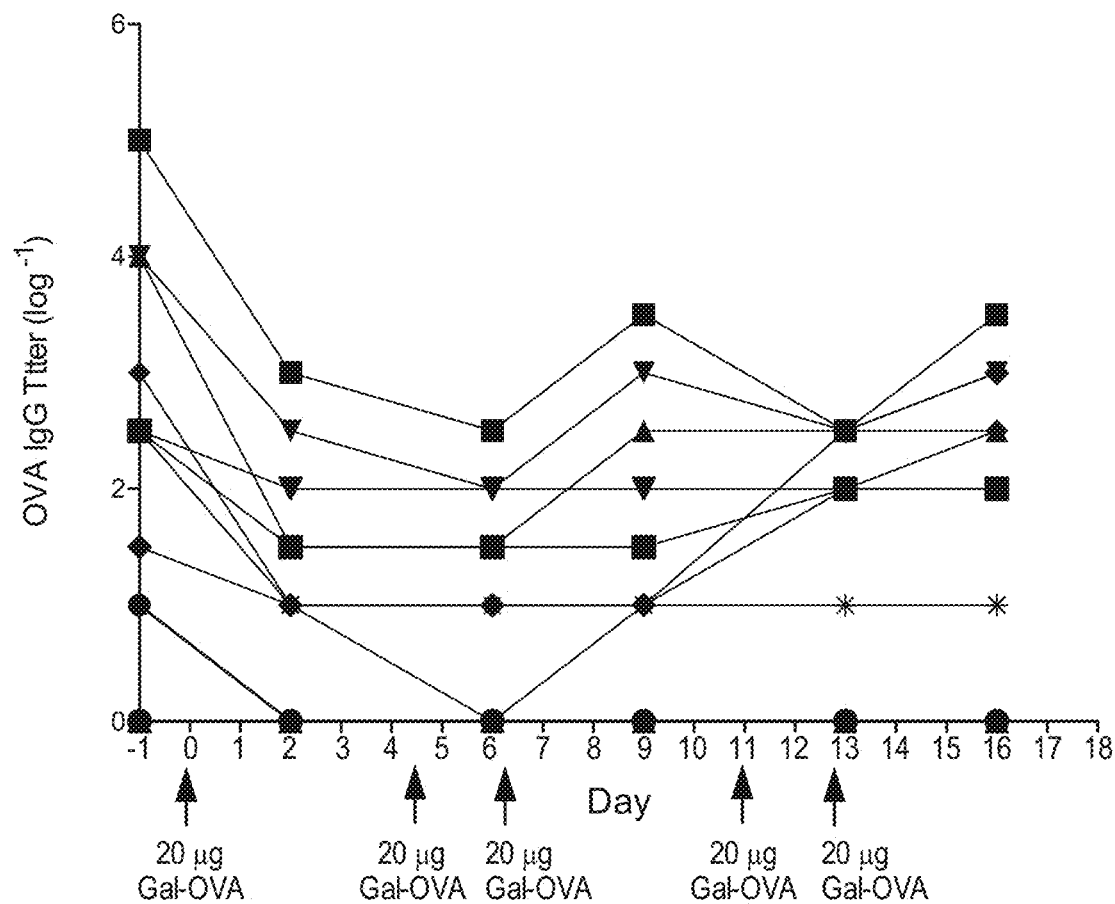

15A. We treated mice that had different OVA-antibody blood titers (each mouse had a titer from 0 to 4.5) with an i.v. injection of 20 μg of F1aA-OVA-$m_4$-$n_8$ solubilized in 100 μl saline. Mice were given i.v. injections of F1aA-OVA-$m_4$-$n_8$ on days 0, 5, 7, 12, and 14 (Injections of F1aA-OVA-$m_4$-$n_8$ are labeled as "Gal-OVA" and shown as green arrows on the x-axis of FIG. 5). In order to determine the ability of F1aA-OVA-$m_4$-$n_8$ to deplete serum OVA-specific antibodies, the mice were bled on day −1 to establish an initial antibody titer and then subsequent bleeds were carried out after each injection of F1aA-OVA-$m_4$-$n_8$ on days 2, 6, 9, 13, and 16. The antibody titer for each mouse was determined via ELISA. The results from this study show that F1aA-OVA-$m_4$-$n_8$ is able to deplete serum antibody levels in mice. For example, one day after the first F1aA-OVA-$m_4$-$n_8$ injection (i.e. day 2), mice with positive OVA-antibody titers experience a 5 to 100-fold decrease in serum antibody levels (FIG. 5). Our results show that although over the course of the 19 day experiment, antibody titers did increase for certain mice, the titer levels never reached the initial antibody titer measured on Day −1 and subsequent doses of F1aA-OVA-$m_4$-$n_8$ were effective in reducing these transient increases in antibody titers. These results demonstrate that F1aA-OVA-$m_4$-$n_8$ has the specificity to bind serum OVA-specific antibodies and the kinetics required to deplete OVA-specific serum antibodies.

15B. By following the procedure described in Example 15A and substituting F1aA-OVA-$m_4$-$n_8$ with the compounds of Formula 1 obtained, for example, as described in Examples 3A, 4A, 5B, 6C, 7B and 19G, it is shown that the compounds from Examples 3A, 4A, 5B, 6C, 7B and 19G have the specificity to bind serum OVA-specific antibodies and the kinetics required to deplete OVA-specific serum antibodies.

15C. By following the procedure described in Example 15A and substituting F1aA-OVA-$m_4$-$n_8$ with the compounds of Formulae 1 and 2 obtained, for example, as described in Examples 1E, 1G, 2C, 10D, 19I, 19L, 20B, 20D and 20F, and substituting OVA with the antigens corresponding to X (or X' or X"), respectively, it is shown that the compounds from Examples 1E, 1G, 2C, 10D, 19I, 19L, 20B, 20D and 20F have the specificity to bind serum antigen X-specific antibodies and the kinetics required to deplete antigen X-specific serum antibodies.

Example 16

OT-1 Challenge-to-Tolerance Model

16A. Using an established OTI challenge-to-tolerance model (Liu, Iyoda, et al., 2002), the ability of F1aA-OVA-$m_4$-$n_8$ (mGal-OVA), F1b-OVA-$m_1$-$n_4$-$p_{34}$ (pGal-OVA), and N-DOM-Gly$_3$Ser-OVA-Gly$_3$Ser-6×His-C (Dom-OVA) to prevent subsequent immune responses to vaccine-mediated antigen challenge were demonstrated—even with a challenge involving a very strong bacterially-derived adjuvant (i.e. lipopolysaccharide). To tolerize, 233 nmol of either F1aA-OVA-$m_4$-$n_8$, F1b-OVA-$m_1$-$n_4$-$p_{34}$, N-DOM-Gly3Ser-OVA-Gly3Ser-6×His-C, or soluble OVA were intravenously administered in 100 μl saline at 1 and 6 days following adoptive transfer of OTI CD8+(CD45.2+) T cells to CD45.1+ mice (n=5 mice per group). After 9 additional days to allow potential deletion of the transferred T cells, the recipient mice were then challenged with OVA (10 μg) adjuvanted with lipopolysaccharide (LPS) (50 ng) by intradermal injection. Characterization of the draining lymph nodes 4 d after challenge allowed a determination as to whether or not deletion actually took place.

Figure 6:
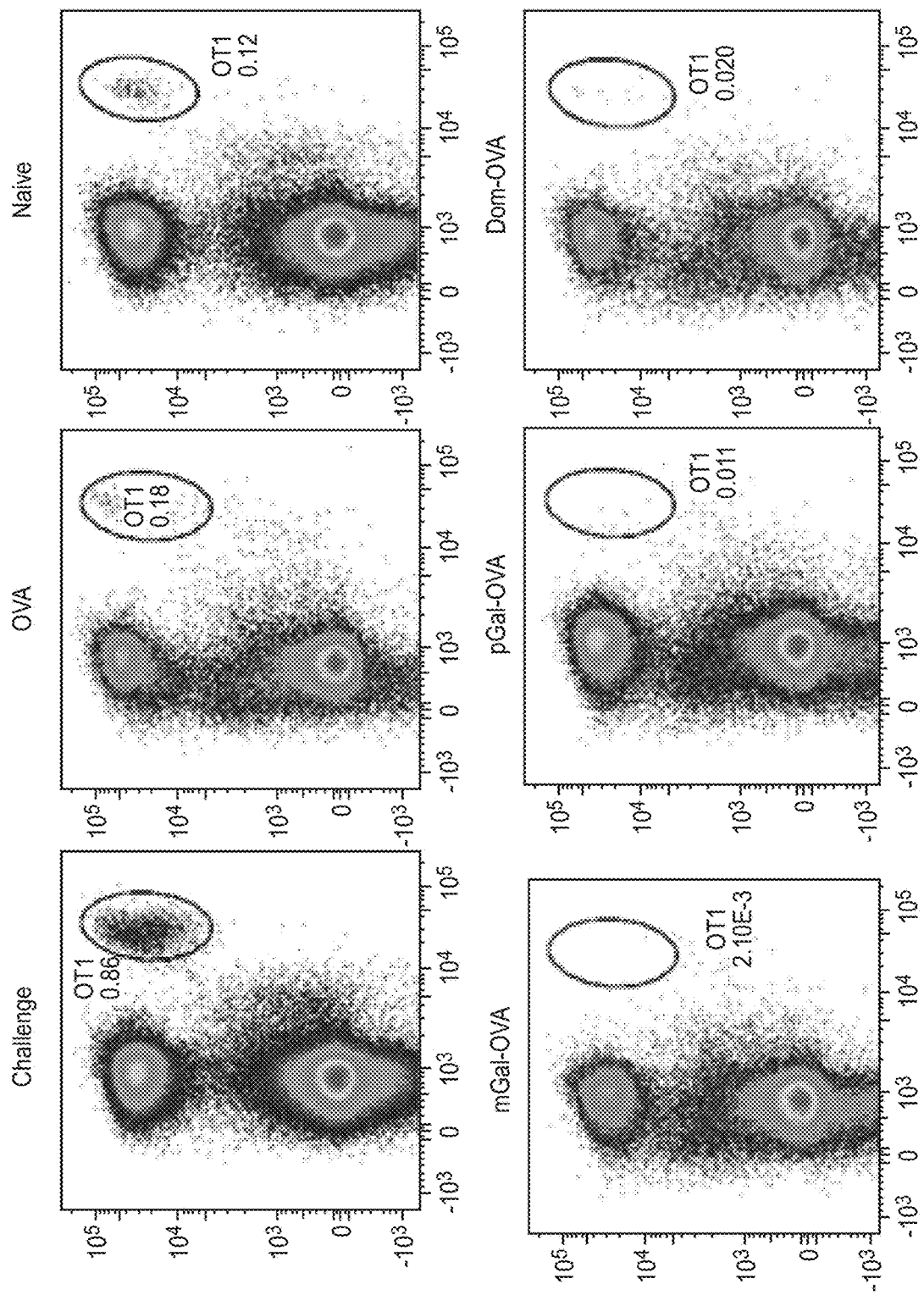
Figure 7A:
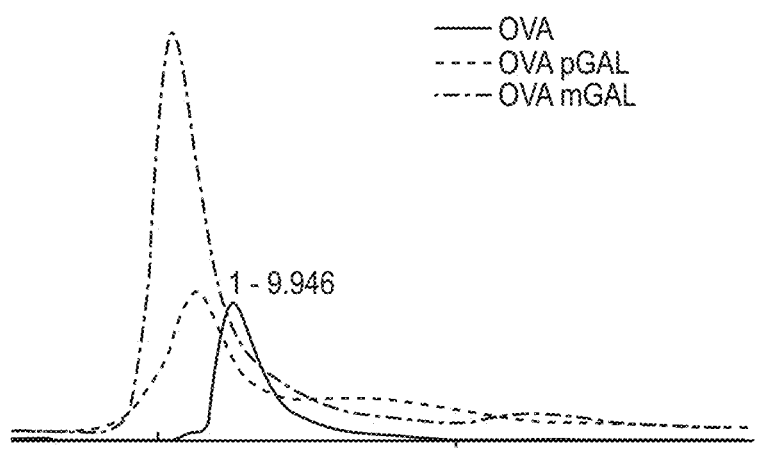
Figure 7B:
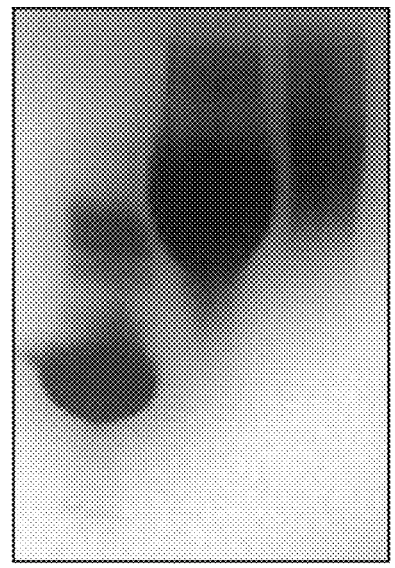

16B. Intravenous administration of F1aA-OVA-$m_4$-$n_8$, F1b-OVA-$m_1$-$n_4$-$p_{34}$, and N-DOM-Gly$_3$Ser-OVA-Gly$_3$Ser-6×His-C resulted in profound reductions in OTI CD8+ T cell populations in the draining lymph nodes as compared to mice treated with unmodified OVA prior to antigen challenge with LPS, demonstrating deletional tolerance. For example, FIG. 6 shows that the draining lymph nodes from mice treated with either F1aA-OVA-$m_4$-$n_8$ (mGal-OVA), F1b-OVA-$m_1$-$n_4$-$p_{34}$ (pGal-OVA), and N-DOM-Gly$_3$Ser-OVA-Gly$_3$Ser-6×His-C (Dom-OVA) contained over 9-fold fewer OTI CD8+ T cells as compared to OVA-treated mice, and more than 43-fold fewer than the challenge control mice that did not receive intravenous injections of antigen; responses in spleen cells were similar. These results demonstrate that F1aA-OVA-$m_4$-$n_8$, F1b-OVA-$m_1$-$n_4$-$p_{34}$, and N-DOM-Gly$_3$Ser-OVA-Gly$_3$Ser-6×His-C mitigated an OVA-specific immune response after adjuvented OVA challenge.

16C. By following the procedure described in Examples 16A and B, and substituting F1aA-OVA-$m_4$-$n_8$, F1b-OVA-$m_1$-$n_4$-$p_{34}$, and N-DOM-Gly$_3$Ser-OVA-Gly$_3$Ser-6×His-C with the compounds of Formula 1 obtained, for example, as described in Examples 3A, 4A, 5B, 6C, 7B and 19G, it is shown that the compounds from Examples 3A, 4A, 5B, 6C, 7B and 19G mitigate an OVA-specific immune response after adjuvented OVA challenge.

16D. By following the procedure described in Examples 16A and B, and substituting F1aA-OVA-$m_4$-$n_8$, F1b-OVA-$m_1$-$n_4$-$p_{34}$, and N-DOM-Gly$_3$Ser-OVA-Gly$_3$Ser-6×His-C with the compounds of Formulae 1 and 2 obtained, for example, as described in Examples 1E, 1G, 2C, 10D, 19I, 19L, 20B, 20D and 20F, and substituting OVA with the antigens corresponding to X (or X' or X"), respectively, it is shown that the compounds from Examples 1E, 1G, 2C, 10D, 19I, 19L, 20B, 20D and 20F mitigate an antigen X-specific immune response after adjuvented antigen X challenge.

Example 17

Pharmacokinetics

17A. OVA and fusion proteins N-DOM-Gly3Ser-OVA-Gly3Ser-6×His-C and N-OVA-Gly3Ser-DOM-Gly3Ser-6×His-C (prepared, e.g., as described in Example 10) are labeled with IRDye 800CW (LI-COR Biosciences) according to manufacturer's instructions. Unreacted dye is removed using Zeba desalting columns (Thermo Scientific). The labeled proteins, 50 μg in 100 μl PBS per dose, are administered i.v. or s.c into C57BL/6 mice (5 mice per group). At time=0, 0.25, 0.5, 1, 2, 4, 8, 24, 48, and 96 hours after injection, blood samples are collected from the tip of the tail into heparin-coated capillary tubes. Samples are store at 4° C., protected from light, until analysis.

On the day of analysis, blood samples are centrifuged to remove cellular components. Plasma is transferred to fresh capillary tubes and scanned using an Odyssey Infrared Imaging System (LI-COR Biosciences). Signal is acquired in the 800 nm channel. Using the image-processing program ImageJ (US National Institutes of Health), each sample is approximated as a line of width 2 and the mean intensity along the line is determined as a relative measure of the amount of circulating protein at that time point.

Figure 8:
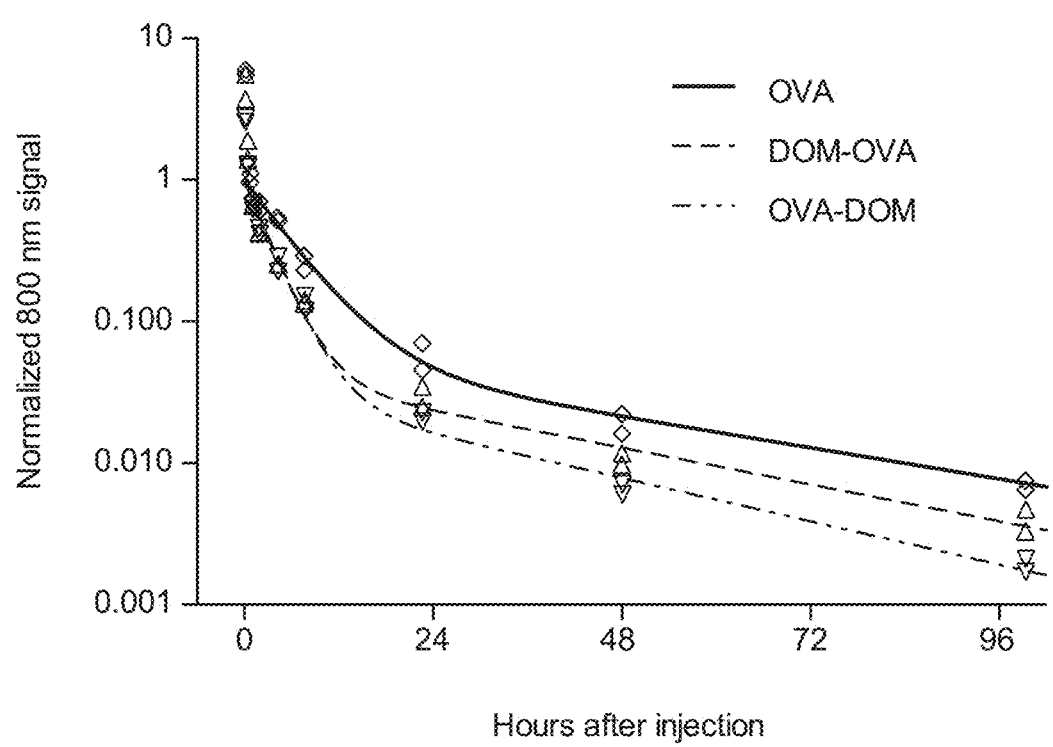

Fluorescence signals (normalized to fluorescence at time=0) vs. time for OVA and fusion proteins DOM-OVA and OVA-DOM, along with curve fits in the form of bi-exponential decays, in FIG. 8, show that the ASGPR-targeted OVA fusion proteins are cleared from circulation more quickly than unmodified OVA.

17B. By following the procedure described in Example 17A and substituting N-DOM-Gly$_3$Ser-OVA-Gly$_3$Ser-6×His-C fusion protein and OVA with asialo-Factor VIII and Factor VIII, respectively, it is shown that asialo-Factor VIII is cleared from circulation much more quickly than unmodified Factor VIII.

Example 18

Biodistribution

18A. OVA and N-DOM-Gly3Ser-OVA-Gly3Ser-6×His-C fusion protein (prepared, e.g., as described in Example 10) are labeled with Alexa Fluor 647 (Life Technologies) according to manufacturer's instructions. Unreacted dye is removed using Zeba desalting columns (Thermo Scientific). Labeled proteins, 50 μg in 100 μl PBS per dose, are administered i.v. or s.c into C57BL/6 mice (5 mice per group). Two hours after injection, mice are euthanized by $CO_2$ asphyxiation. The blood, heart, intestines, kidneys, liver, lungs, stomach, spleen, and remaining carcass are imaged using an IVIS Spectrum imaging system (Caliper Life Sciences). Data is acquired and analyzed using Living Image software (Caliper Life Sciences). Single cell suspensions of liver and spleen are prepared and stained with fluorescently conjugated antibodies against MHC class II, CD1d, CD3, CD4, CD8a, CD1 b, CD1c, CD14, CD19, CD45, CD123, and/or Lin in PBS with 0.1% (w/v) BSA. Samples are analyzed using a LSR II flow cytometer and FACS Diva software (BD Biosciences).

A histogram showing fluorescence signal densities (photons/weight) for each organ and each protein shows that in animals injected with N-DOM-$Gly_3$Ser-OVA-$Gly_3$Ser-6×His-C fusion protein the highest fluorescence signal is in the liver as compared to those treated with unmodified OVA.

A histogram showing percentages of N-DOM-$Gly_3$Ser-OVA-$Gly_3$Ser-6×His-C and OVA-positive cells shows that animals injected with N-DOM-$Gly_3$Ser-OVA-$Gly_3$Ser-6×His-C fusion proteins have a significantly higher percentage of positive hepatocytes as compared to those treated with unmodified OVA.

18B. By following the procedure described in Example 18A and substituting N-DOM-Gly3Ser-OVA-Gly3Ser-6×His-C fusion protein and OVA with asialo-Factor VIII and Factor VIII, respectively, it is shown that animals injected with asialo-Factor VIII have a significantly higher percentage of positive hepatocytes as compared to those treated with unmodified Factor VIII.

18C. By following the procedure described in Example 18A and substituting N-DOM-Gly3Ser-OVA-Gly3Ser-6×His-C fusion protein with the compounds of Formula 1 obtained, for example, as described in Examples 3A, 4A, 5B, 6C, 7B and 19G, it is shown that animals injected with the compounds from Examples 3A, 4A, 5B, 6C, 7B and 19G have a significantly higher percentage of positive hepatocytes as compared to those treated with OVA.

18D. By following the procedure described in Examples 18A and B, and substituting F1aA-OVA-$m_4$-$n_8$, F1b-OVA-$m_1$-$n_4$-$p_{34}$, and N-DOM-$Gly_3$Ser-OVA-$Gly_3$Ser-6×His-C with the compounds of Formulae 1 and 2 obtained, for example, as described in Examples 1E, 1G, 2C, 10D, 19I, 19L, 20B, 20D and 20F, and substituting OVA with the antigens corresponding to X (or X' or X"), respectively, it is shown that it is shown that animals injected with the compounds from Examples 1E, 1G, 2C, 10D, 19I, 19L, 20B, 20D and 20F have a significantly higher percentage of positive hepatocytes as compared to those treated with antigen X.

Example 19

F1m-OVA-$m_2$-$n_{80}$-$p_{30}$-$q_4$-CMP-2NHAc

19A. Formula 1102 where $R^3$ is NHAc and $R^4$ is OH

N-Acetyl-D-galactosamine (Formula 1101 where $R^3$ is NHAc and $R^4$ is OH) (5g, 22.6 mmol) was added to a stirred solution of chloroethanol (200 ml) at room temperature. The solution was cooled to 4° C. and acetylchloride was added drop-wise to the solution. The solution was brought to room temperature and then heated to 70° C. After 4 hours, the unreacted choroethanol was removed under reduced pressure. 100 ml of ethanol was added to the crude product and the resulting solution was stirred in the presence of carbon for 2 hours. The solution was filtered, and the solvent was removed under reduced pressure. The corresponding product of Formula 1102, N-(2-(2-chloroethoxy)-4,5-dihydroxy-6-(hydroxymethyl)tetrahydro-2H-pyran-3-yl)acetamide, was used without further purification.

19B. Formula 1103 where $R^3$ is NHAc and $R^4$ is OH

The N-(2-(2-chloroethoxy)-4,5-dihydroxy-6-(hydroxymethyl)tetrahydro-2H-pyran-3-yl)acetamide prepared in Example 19A (2g, 7.4 mmol) was added to a stirred solution of DMF (100 ml) and sodium azide (4g, 61.5 mmol). The solution was headed at 90° C. for 12 hours and then filtered. The residual solvent was removed under reduced pressure and the crude product was purified via flash chromatography (10% MeOH in dichloromethane) to give the corresponding product of Formula 1103, N-(2-(2-azidoethoxy)-4,5-dihydroxy-6-(hydroxymethyl)tetrahydro-2H-pyran-3-yl)acetamide.

19C. Formula 1104 where $R^3$ is NHAc and $R^4$ is OH

The N-(2-(2-azidoethoxy)-4,5-dihydroxy-6-(hydroxymethyl)tetrahydro-2H-pyran-3-yl)acetamide prepared in Example 19B (2 g, 6.9 mmol) was added to a solution of palladium on carbon and ethanol (50 ml). The solution was stirred under hydrogen gas (3 atm) for 4 hours. The resulting solution was filtered and the residual solvent was removed under reduced pressure to afford the corresponding product of Formula 1104, N-(2-(2-aminoethoxy)-4,5-dihydroxy-6-(hydroxymethyl)tetrahydro-2H-pyran-3-yl)acetamide, which was used without further purification.

19D. Formula 1105 where $R^3$ is NHAc and $R^4$ is OH

The N-(2-(2-aminoethoxy)-4,5-dihydroxy-6-(hydroxymethyl)tetrahydro-2H-pyran-3-yl)acetamide prepared in Example 19C (1.0 g, 3.78 mmol) was added to a solution of methacrylate anhydride (0.583 g, 3.78 mmol) in DMF (50 ml). Triethylamine was then added to the solution and the reaction was stirred for 2 hours at room temperature. After 2 hours, the excess solvent was removed under reduced pressure, and the corresponding product of Formula 1105, N-(2-((3-acetamido-4,5-dihydroxy-6-(hydroxymethyl)tetrahydro-2H-pyran-2-yl)oxy)ethyl)methacrylamide, was isolated via flash chromatography.

19E. Formula 1107 where p is 30, q is 4, $R^3$ is NHAc, $R^4$ is OH and $R^8$ is CMP An azide-modified uRAFT agent of Formula 1106 where q is 4 (28 mg) was added to a solution of N-(2-((3-acetamido-4,5-dihydroxy-6-(hydroxymethyl)tetrahydro-2H-pyran-2-yl)oxy)ethyl)methacrylamide prepared in Example 19D (579 mg, 1.74 mmol) and azobisisobutyronitrile (2.2 mg, 0.0116 mmol) in DMF. The reaction mixture was subjected to 4 free-pump-thaw cycles, and then stirred at 70° C. After 12 hours, the polymer product of Formula 1107, where p is 30 and q is 4 was precipitated from the reaction mixture via the addition of methanol. The solvent was decanted from the solid and the solid was collected and residual solvent was removed via reduced pressure.

19F. Formula 1109 where X' is OVA, m is 2 and n is 80

Ovalbumin (5 mg, 0.00012 mmol) was added to 100 µl of sodium phosphate buffer (pH 8.0) and stirred. To this solution was added 5 mg of the compound of Formula 1108 where n is 80. After 1 hour, the unreacted compound of Formula 1108 was removed from the solution via centrifugal size-exclusion chromatography. The resulting buffered solution containing the corresponding product of Formula 1109 was used in the next reaction without further purification.

19G. Formula 1m where X' is OVA, m is 2, n is 80, p is 30, q is 4, $R^3$ is NHAc and $R^8$ is CMP The solution prepared in Example 19F was added to 100 µl of sodium phosphate buffer (pH 8.0) which contained 10 mg of the product of Formula 1107 prepared in Example 19E. The reaction was allowed to stir for 2 hours and then the excess Formula 1107 was removed via centrifugal size exclusion chromatography to afford the corresponding isomeric product of Formula 1m in solution, which was used in biological studies without further purification. The $R^3$ substituent is shown in the name of the title compound as 2NHAc.

19H. Other Compounds of Formula 1109

By following the procedure described in Example 19F and substituting OVA with the following:
Abciximab,
Adalimumab,
Agalsidase alfa,
Agalsidase beta,
Aldeslukin,
Alglucosidase alfa,
Factor VIII,
Factor IX,
L-asparaginase,
Laronidase,
Octreotide,
Phenylalanine ammonia-lyase,
Rasburicase,
Insulin (SEQ ID NO:5),
GAD-65 (SEQ ID NO:6),
IGRP (SEQ ID NO:7)
MBP (SEQ ID NO:8),
MOG (SEQ ID NO:9),
PLP (SEQ ID NO:10),
MBP13-32 (SEQ ID NO:11),
MBP83-99 (SEQ ID NO:12),
MBP111-129 (SEQ ID NO:13),
MBP146-170 (SEQ ID NO:14),
MOG1-20 (SEQ ID NO:15),
MOG35-55 (SEQ ID NO:16),
PLP139-154 (SEQ ID NO:17),
MART1 (SEQ ID NO:18),
Tyrosinase (SEQ ID NO:19),
PMEL (SEQ ID NO:20),
Aquaporin-4 (SEQ ID NO:21),
S-arrestin (SEQ ID NO:22),
IRBP (SEQ ID NO:23),
Conarachin (UNIPROT Q6PSU6),
Alpha-gliadin "33-mer" native (SEQ ID NO:24),
Alpha-gliadin "33-mer" deamidated (SEQ ID NO:25),
Alpha-gliadin (SEQ ID NO:26),
Omega-gliadin (SEQ ID NO:27),
Fel d 1A (UNIPROT P30438),
Cat albumin (UNIPROT P49064),
Can f 1 (UNIPROT O18873),
Dog albumin (UNIPROT P49822), and
RhCE example (UNIPROT P18577),
there are obtained the following corresponding compounds of Formula 1109 where n is 80:
X is Abciximab and m is 10,
X is Adalimumab and m is 11,
X is Agalsidase alfa and m is 14,
X is Agalsidase beta and m is 14,
X is Aldeslukin and m is 6,
X is Alglucosidase alfa and m is 13,
X is Factor VIII and m is 100,
X is Factor IX and m is 18,
X is L-asparaginase and m is 5,
X is Laronidase and m is 7,
X is Octreotide and m is 1,
X is Phenylalanine ammonia-lyase and m is 12,
X is Rasburicase and m is 12,
X is Insulin (SEQ ID NO:5) and m is 2,
X is GAD-65 (SEQ ID NO:6) and m is 8,
X is IGRP (SEQ ID NO:7) and m is 7,
X is MBP (SEQ ID NO:8) and m is 6,
X is MOG (SEQ ID NO:9) and m is 5,
X is PLP (SEQ ID NO:10) and m is 8,
X is MBP13-32 (SEQ ID NO:11) and m is 1,
X is MBP83-99 (SEQ ID NO:12) and m is 1,
X is MBP111-129 (SEQ ID NO:13) and m is 1,
X is MBP146-170 (SEQ ID NO:14) and m is 2,
X is MOG1-20 (SEQ ID NO:15) and m is 1,
X is MOG35-55 (SEQ ID NO:16) and m is 2,
X is PLP139-154 (SEQ ID NO:17) and m is 3,
X is MART1 (SEQ ID NO:18) and m is 4,
X is Tyrosinase (SEQ ID NO:19) and m is 8,
X is PMEL (SEQ ID NO:20) and m is 5,
X is Aquaporin-4 (SEQ ID NO:21) and m is 4,
X is S-arrestin (SEQ ID NO:22) and m is 12,
X is IRBP (SEQ ID NO:23) and m is 21,
X is Conarachin and m is 21,
X is Alpha-gliadin "33-mer" native (SEQ ID NO:24) and m is 1,
X is Alpha-gliadin "33-mer" deamidated (SEQ ID NO:25) and m is 1,
X is Alpha-gliadin (SEQ ID NO:26) and m is 1,
X is Omega-gliadin (SEQ ID NO:27) and m is 1,
X is Fel d 1 and m is 4,
X is Cat albumin and m is 16,
X is Can f 1 and m is 6,
X is Dog albumin and m is 23, and
X is RhCE example and m is 10.

19I. Other Compounds of Formula 1m

By following the procedure described in Example 19G and substituting the compounds of Formula 1109, for example as obtained in Example 19H, there are obtained the following corresponding compounds of Formula 1m:
F1m-Abciximab-$m_{10}$-$n_{80}$-$p_{30}$-$q_4$-CMP-2NHAc,
F1m-Adalimumab-$m_{11}$-$n_{80}$-$p_{80}$-$q_4$-CMP-2NHAc,
F1m-Agalsidase alfa-$m_{14}$-$n_{80}$-$p_{30}$-$q_4$-CMP-2NHAc, F1m-Agalsidase beta-$m_{14}$-$n_{80}$-$p_{30}$-$q_4$-CMP-2NHAc,
F1m-Aldeslukin-$m_6$-$n_{80}$-$p_{30}$-$q_4$-CMP-2NHAc,
F1m-Alglucosidase alfa-$m_{13}$-$n_{80}$-$p_{30}$-$q_4$-CMP-2NHAc,
F1m-Factor VIII-$m_{100}$-$n_{80}$-$p_{80}$-$q_4$-CMP-2NHAc,
F1m-Factor IX-$m_{18}$-$n_{80}$-$p_{30}$-$q_4$-CMP-2NHAc,
F1m-L-asparaginase-$m_5$-$n_{80}$-$p_{30}$-$q_4$-CMP-2NHAc,
F1m-Laronidase-$m_7$-$n_{80}$-$p_{30}$-$q_4$-CMP-2NHAc,
F1m-Octreotide-$m_1$-$n_{80}$-$p_{30}$-$q_4$-CMP-2NHAc,
F1m-Phenylalanine ammonia-lyase-$m_{12}$-$n_{80}$-$p_{30}$-$q_4$-CMP-2NHAc,
F1m-Rasburicase-$m_{12}$-$n_{80}$-$p_{30}$-$q_4$-CMP-2NHAc,
F1m-Insulin-$m_2$-$n_{80}$-$p_{30}$-$q_4$-CMP-2NHAc,
F1m-GAD-65-$m_8$-$n_{80}$-$p_{30}$-$q_4$-CMP-2NHAc,
F1m-IGRP-$m_7$-$n_{80}$-$p_{30}$-$q_4$-CMP-2NHAc,
F1m-MBP-$m_6$-$n_{80}$-$p_{30}$-$q_4$-CMP-2NHAc,
F1m-MOG-$m_5$-$n_{80}$-$p_{30}$-$q_4$-CMP-2NHAc,
F1m-PLP-$m_8$-$n_{80}$-$p_{30}$-$q_4$-CMP-2NHAc,
F1m-MBP13-32-m-$n_{80}$-$p_{30}$-$q_4$-CMP-2NHAc,
F1m-MBP83-99-$m_1$-$n_{80}$-$p_{30}$-$q_4$-CMP-2NHAc,
F1m-MBP111-129-$m_1$-$n_{80}$-$p_{30}$-$q_4$-CMP-2NHAc,
F1m-MBP146-170-$m_2$-$n_{80}$-$p_{30}$-$q_4$-CMP-2NHAc,
F1m-MOG1-20-$m_1$-$n_{80}$-$p_{30}$-$q_4$-CMP-2NHAc,
F1m-MOG35-55-$m_2$-$n_{80}$-$p_{30}$-$q_4$-CMP-2NHAc,
F1m-PLP139-154-$m_3$-$n_{80}$-$p_{30}$-$q_4$-CMP-2NHAc,
F1m-MART1-$m_4$-$n_{80}$-$p_{30}$-$q_4$-CMP-2NHAc,
F1m-Tyrosinase-$m_8$-$n_{80}$-$p_{30}$-$q_4$-CMP-2NHAc,
F1m-PMEL-$m_5$-$n_{80}$-$p_{30}$-$q_4$-CMP-2NHAc,
F1m-Aquaporin-4-$m_4$-$n_{80}$-$p_{30}$-$q_4$-CMP-2NHAc,
F1m-S-arrestin-$m_{12}$-$n_{80}$-$p_{30}$-$q_4$-CMP-2NHAc,
F1m-IRBP-$m_{21}$-$n_{80}$-$p_{30}$-$q_4$-CMP-2NHAc,
F1m-Conarachin-$m_{21}$-$n_{80}$-$p_{30}$-$q_4$-CMP-2NHAc,
F1m-Alpha-gliadin "33-mer" native-$m_1$-$n_{80}$-$p_{30}$-$q_4$-CMP-2NHAc,
F1m-Alpha-gliadin "33-mer" deamidated-$m_1$-$n_{80}$-$p_{30}$-$q_4$-CMP-2NHAc,
F1m-Alpha-gliadin-m-$n_{80}$-$p_{30}$-$q_4$-CMP-2NHAc,
F1m-Omega-gliadin-m-$n_{80}$-$p_{30}$-$q_4$-CMP-2NHAc,
F1m-Fel d 1-$m_4$-$n_{80}$-$p_{30}$-$q_4$-CMP-2NHAc,
F1m-Cat albumin-$m_{16}$-$n_{80}$-$p_{30}$-$q_4$-CMP-2NHAc,
F1m-Can f 1-$m_6$-$n_{80}$-$p_{30}$-$q_4$-CMP-2NHAc,
F1m-Dog albumin-$m_{23}$-$n_{80}$-$p_{30}$-$q_4$-CMP-2NHAc, and
F1m-RhCE-$m_{10}$-$n_{80}$-$p_{30}$-$q_4$-CMP-2NHAc.

19J. Formula 1107 where p is 30, q is 8, $R^3$ is OH, $R^4$ is OH and $R^8$ is CMP By following the procedure described in Example 19A and substituting the N-acetyl-D-galactosamine with galactose, and following through to the procedure described in Example 19E except using an azide-modified uRAFT agent of Formula 1106 where q is 8, there is obtained the compound of Formula 1107 where p is 30, q is 8, $R^3$ is OH, $R^4$ is OH and $R^8$ is CMP.

19K. Formula 1109 where n is 62 and where X' and m are as in Example 19H

By following the procedure described in Example 19F, substituting the OVA with the compounds as described in Example 19H and employing the compound of Formula 1108 where n is 62, there are obtained the corresponding compounds of Formula 1109 where n is 62.

19L. Other Compounds of Formula 1m

By following the procedure described in Example 19G and substituting the compound of Formula 1107 with the compounds obtained in Example 19J, and substituting the compound of Formula 1109 with the compounds obtained in Example 19K, there are obtained the following corresponding compounds of Formula 1m:

F1m-Abciximab-$m_{10}$-$n_{62}$-$p_{30}$-$q_8$-CMP-2OH,
F1m-Adalimumab-$m_{11}$-$n_{62}$-$p_{30}$-$q_8$-CMP-2OH,
F1m-Agalsidase alfa-$m_{14}$-$n_{62}$-$p_{30}$-$q_8$-CMP-2OH,
F1m-Agalsidase beta-$m_{14}$-$n_{62}$-$p_{30}$-$q_8$-CMP-2OH,
F1m-Aldeslukin-$m_6$-$n_{62}$-$p_{30}$-$q_8$-CMP-2OH,
F1m-Alglucosidase alfa-$m_{13}$-$n_{62}$-$p_{30}$-$q_8$-CMP-2OH,
F1m-Factor VIII-$m_{100}$-$n_{62}$-$p_{30}$-$q_8$-CMP-2OH,
F1m-Factor IX-$m_{18}$-$n_{62}$-$p_{30}$-$q_8$-CMP-2OH,
F1m-L-asparaginase-$m_8$-$n_{62}$-$p_{30}$-$q_8$-CMP-2OH,
F1m-Laronidase-$m_7$-$n_{62}$-$p_{30}$-$q_8$-CMP-2OH,
F1m-Octreotide-$m_1$-$n_{62}$-$p_{30}$-$q_8$-CMP-2OH,
F1m-Phenylalanine ammonia-lyase-$m_{12}$-$n_{62}$-$p_{30}$-$q_8$-CMP-2OH,
F1m-Rasburicase-$m_{12}$-$n_{62}$-$p_{30}$-$q_8$-CMP-2OH,
F1m-Insulin-$m_2$-$n_{62}$-$p_{30}$-$q_8$-CMP-2OH,
F1m-GAD-65-$m_8$-$n_{62}$-$p_{30}$-$q_8$-CMP-2OH,
F1m-IGRP-$m_7$-$n_{62}$-$p_{30}$-$q_8$-CMP-2OH,
F1m-MBP-$m_6$-$n_{62}$-$p_{30}$-$q_8$-CMP-2OH,
F1m-MOG-$m_5$-$n_{62}$-$p_{30}$-$q_8$-CMP-2OH,
F1m-PLP-$m_8$-$n_{62}$-$p_{30}$-$q_8$-CMP-2OH,
F1m-MBP13-32-$m_1$-$n_{62}$-$p_{30}$-$q_8$-CMP-2OH,
F1m-MBP83-99-$m_1$-$n_{62}$-$p_{30}$-$q_8$-CMP-2OH,
F1m-MBP111-129-$m_1$-$n_{62}$-$p_{30}$-$q_8$-CMP-2OH,
F1m-MBP146-170-$m_2$-$n_{62}$-$p_{30}$-$q_8$-CMP-2OH,
F1m-MOG1-20-$m_1$-$n_{62}$-$p_{30}$-$q_8$-CMP-2OH,
F1m-MOG35-55-$m_2$-$n_{62}$-$p_{30}$-$q_8$-CMP-2OH,
F1m-PLP139-154-$m_3$-$n_{62}$-$p_{30}$-$q_8$-CMP-2OH,
F1m-MART1-$m_4$-$n_{62}$-$p_{30}$-$q_8$-CMP-2OH,
F1m-Tyrosinase-$m_8$-$n_{62}$-$p_{30}$-$q_8$-CMP-2OH,
F1m-PMEL-$m_5$-$n_{62}$-$p_{30}$-$q_8$-CMP-2OH,
F1m-Aquaporin-4-$m_4$-$n_{62}$-$p_{30}$-$q_8$-CMP-2OH,
F1m-S-arrestin-$m_{12}$-$n_{62}$-$p_{30}$-$q_8$-CMP-2OH,
F1m-IRBP-$m_{21}$-$n_{62}$-$p_{30}$-$q_8$-CMP-2OH,
F1m-Conarachin-$m_{21}$-$n_{62}$-$p_{30}$-$q_8$-CMP-2OH,
F1m-Alpha-gliadin "33-mer" native-m-$n_{62}$-$p_{30}$-$q_8$-CMP-2OH,
F1m-Alpha-gliadin "33-mer" deamidated-$m_1$-$n_{62}$-$p_{30}$-$q_8$-CMP-2OH,
F1m-Alpha-gliadin-$m_1$-$n_{62}$-$p_{30}$-$q_8$-CMP-2OH,
F1m-Omega-gliadin-$m_1$-$n_{62}$-$p_{30}$-$q_8$-CMP-2OH,
F1m-Fel d 1-$m_4$-$n_{62}$-$p_{30}$-$q_8$-CMP-2OH,
F1m-Cat album in-$m_6$-$n_{62}$-$p_{30}$-$q_8$-CMP-2OH,
F1m-Can f 1-$m_6$-$n_{62}$-$p_{30}$-$q_8$-CMP-2OH,
F1m-Dog album in-$m_{23}$-$n_{62}$-$p_{30}$-$q_8$-CMP-2OH, and
F1m-RhCE-$m_{10}$-$n_{62}$-$p_{30}$-$q_8$-CMP-2OH.

Example 20

F1n-insulin-$m_2$-$n_1$-$p_{30}$-$q_4$-CMP-2NHAc

20A. Formula 1202 where X' is Insulin, m is 2 and n is 1

Recombinant human insulin (5 mg) was added to 100 µl of DMF containing 10 µl of triethylamine and stirred until the insulin became soluble. To this solution was added 10 mg (0.0161 mmol) of a linker precursor of Formula 1201 where n is 1 and the reaction was allowed to stir. After 1 hour, 1.3 ml of tert-butyl methyl ether was added to isolate the corresponding product of Formula 1202, which was recovered as the precipitate. Residual DMF and tert-butyl methyl ether were removed under reduced pressure. Characterization via liquid chromatography, mass spectroscopy and polyacrylamide gel electrophoresis confirmed the identity of the product. The modified insulin product of Formula 1202 was used without further purification.

20B. Formula 1n where X' is Insulin, m is 2, n is 1, p is 30, q is 4 and $R^8$ is CMP The product of Formula 1202 obtained in Example 20A was resuspended in 100 μl of DMF. The polymer product of Formula 1107 obtained in Example 19E (10 mg) was added and the reaction was allowed to stir for 1 hour. After 1 hour, the reaction products were precipitated via the addition of dichloromethane (1.3 ml). The product was filtered and the residual solvent was removed under reduced pressure. The crude product was then resuspended in 500 μl of PBS, and the low molecular weight components were removed via centrifugal size exclusion chromatography to afford the corresponding isomeric product of Formula 1n. Characterization via liquid chromatography, mass spectroscopy and polyacrylamide gel electrophoresis confirmed the identity of the product. The modified insulin product of Formula 1202 was used without further purification.

20C. Other Compounds of Formula 1202

By following the procedure described in Example 19F and substituting OVA insulin the following:
Abciximab,
Adalimumab,
Agalsidase alfa,
Agalsidase beta,
Aldeslukin,
Alglucosidase alfa,
Factor VIII,
Factor IX,
L-asparaginase,
Laronidase,
Octreotide,
Phenylalanine ammonia-lyase,
Rasburicase,
GAD-65 (SEQ ID NO:6),
IGRP (SEQ ID NO:7)
MBP (SEQ ID NO:8),
MOG (SEQ ID NO:9),
PLP (SEQ ID NO:10),
MBP13-32 (SEQ ID NO:11),
MBP83-99 (SEQ ID NO:12),
MBP111-129 (SEQ ID NO:13),
MBP146-170 (SEQ ID NO:14),
MOG1-20 (SEQ ID NO:15),
MOG35-55 (SEQ ID NO:16),
PLP139-154 (SEQ ID NO:17),
MART1 (SEQ ID NO:18),
Tyrosinase (SEQ ID NO:19),
PMEL (SEQ ID NO:20),
Aquaporin-4 (SEQ ID NO:21),
S-arrestin (SEQ ID NO:22),
IRBP (SEQ ID NO:23),
Conarachin (UNIPROT Q6PSU6),
Alpha-gliadin "33-mer" native (SEQ ID NO:24),
Alpha-gliadin "33-mer" deamidated (SEQ ID NO:25),
Alpha-gliadin (SEQ ID NO:26),
Omega-gliadin (SEQ ID NO:27),
Fel d 1A (UNIPROT P30438),
Cat albumin (UNIPROT P49064),
Can f 1 (UNIPROT O18873),
Dog albumin (UNIPROT P49822), and
RhCE example (UNIPROT P18577),
there are obtained the following corresponding compounds of Formula 1202 where n is 1:
X is Abciximab and m is 10,
X is Adalimumab and m is 11,
X is Agalsidase alfa and m is 14,
X is Agalsidase beta and m is 14,
X is Aldeslukin and m is 6,
X is Alglucosidase alfa and m is 13,
X is Factor VIII and m is 100,
X is Factor IX and m is 18,
X is L-asparaginase and m is 5,
X is Laronidase and m is 7,
X is Octreotide and m is 1,
X is Phenylalanine ammonia-lyase and m is 12,
X is Rasburicase and m is 12,
X is GAD-65 (SEQ ID NO:6) and m is 8,
X is IGRP (SEQ ID NO:7) and m is 7,
X is MBP (SEQ ID NO:8) and m is 6,
X is MOG (SEQ ID NO:9) and m is 5,
X is PLP (SEQ ID NO:10) and m is 8,
X is MBP13-32 (SEQ ID NO:11) and m is 1,
X is MBP83-99 (SEQ ID NO:12) and m is 1,
X is MBP111-129 (SEQ ID NO:13) and m is 1,
X is MBP146-170 (SEQ ID NO:14) and m is 2,
X is MOG1-20 (SEQ ID NO:15) and m is 1,
X is MOG35-55 (SEQ ID NO:16) and m is 2,
X is PLP139-154 (SEQ ID NO:17) and m is 3,
X is MART1 (SEQ ID NO:18) and m is 4,
X is Tyrosinase (SEQ ID NO:19) and m is 8,
X is PMEL (SEQ ID NO:20) and m is 5,
X is Aquaporin-4 (SEQ ID NO:21) and m is 4,
X is S-arrestin (SEQ ID NO:22) and m is 12,
X is IRBP (SEQ ID NO:23) and m is 21,
X is Conarachin and m is 21,
X is Alpha-gliadin "33-mer" native (SEQ ID NO:24) and m is 1,
X is Alpha-gliadin "33-mer" deamidated (SEQ ID NO:25) and m is 1,
X is Alpha-gliadin (SEQ ID NO:26) and m is 1,
X is Omega-gliadin (SEQ ID NO:27) and m is 1,
X is Fel d 1 and m is 4,
X is Cat albumin and m is 16,
X is Can f 1 and m is 6,
X is Dog albumin and m is 23, and
X is RhCE example and m is 10.

20D. Other Compounds of Formula 1n

By following the procedure described in Example B and substituting the compounds of Formula 1202, for example as obtained in Example 20C, there are obtained the following corresponding compounds of Formula 1m:
F1n-Abciximab-$m_{10}$-$n_1$-$p_{30}$-$q_4$-CMP-2NHAc,
F1n-Adalimumab-$m_1$-$n_1$-$p_{30}$-$q_4$-CMP-2NHAc,
F1n-Agalsidase alfa-$m_{14}$-$n_1$-$p_{30}$-$q_4$-CMP-2NHAc,
F1n-Agalsidase beta-$m_{14}$-$n_1$-$p_{30}$-$q_4$-CMP-2NHAc,
F1n-Aldeslukin-$m_6$-$n_1$-$p_{30}$-$q_4$-CMP-2NHAc,
F1n-Alglucosidase alfa-$m_{13}$-$n_1$-$p_{30}$-$q_4$-CMP-2NHAc,
F1n-Factor VIII-$m_{100}$-$n_1$-$p_{30}$-$q_4$-CMP-2NHAc,
F1n-Factor IX-$m_{18}$-$n_1$-$p_{30}$-$q_4$-CMP-2NHAc,
F1n-L-asparaginase-m-$n_1$-$p_{30}$-$q_4$-CMP-2NHAc,
F1n-Laronidase-$m_7$-$n_1$-$p_{30}$-$q_4$-CMP-2NHAc,
F1n-Octreotide-$m_1$-$n_1$-$p_{30}$-$q_4$-CMP-2NHAc, F1n-Phenylalanine ammonia-lyase-$m_{12}$-$n_1$-$p_{30}$-$q_4$-CMP-2NHAc,
F1n-Rasburicase-$m_{12}$-$n_1$-$p_{30}$-$q_4$-CMP-2NHAc,
F1n-GAD-65-$m_8$-$n_1$-$p_{30}$-$q_4$-CMP-2NHAc,
F1n-IGRP-$m_7$-$n_1$-$p_{30}$-$q_4$-CMP-2NHAc,
F1n-MBP-$m_6$-$n_1$-$p_{30}$-$q_4$-CMP-2NHAc,
F1n-MOG-$m_5$-$n_1$-$p_{30}$-$q_4$-CMP-2NHAc,
F1n-PLP-$m_8$-$n_1$-$p_{30}$-$q_4$-CMP-2NHAc,
F1n-MBP13-32-$m_1$-$n_1$-$p_{30}$-$q_4$-CMP-2NHAc,
F1n-MBP83-99-$m_1$-$n_1$-$p_{30}$-$q_4$-CMP-2NHAc,
F1n-MBP111-129-$m_1$-$n_1$-$p_{30}$-$q_4$-CMP-2NHAc,
F1n-MBP146-170-$m_2$-$n_1$-$p_{30}$-$q_4$-CMP-2NHAc,
F1n-MOG1-20-$m_1$-$n_1$-$p_{30}$-$q_4$-CMP-2NHAc,
F1n-MOG35-55-$m_2$-$n_1$-$p_{30}$-$q_4$-CMP-2NHAc,
F1n-PLP139-154-$m_3$-$n_1$-$p_{30}$-$q_4$-CMP-2NHAc,
F1n-MART1-$m_4$-$n_1$-$p_{30}$-$q_4$-CMP-2NHAc,
F1n-Tyrosinase-$m_8$-$n_1$-$p_{30}$-$q_4$-CMP-2NHAc,
F1n-PMEL-$m_5$-$n_1$-$p_{30}$-$q_4$-CMP-2NHAc,
F1n-Aquaporin-4-$m_4$-$n_1$-$p_{30}$-$q_4$-CMP-2NHAc,
F1n-S-arrestin-$m_{12}$-$n_1$-$p_{30}$-$q_4$-CMP-2NHAc,
F1n-IRBP-$m_{21}$-$n_1$-$p_{30}$-$q_4$-CMP-2NHAc,
F1n-Conarachin-$m_{21}$-$n_1$-$p_{30}$-$q_4$-CMP-2NHAc,
F1n-Alpha-gliadin "33-mer" native-$m_1$-$n_1$-$p_{30}$-$q_4$-CMP-2NHAc,
F1n-Alpha-gliadin "33-mer" deamidated-m-$n_1$-$p_{30}$-$q_4$-CMP-2NHAc,
F1n-Alpha-gliadin-$m_1$-$n_1$-$p_{30}$-$q_4$-CMP-2NHAc,
F1n-Omega-gliadin-$m_1$-$n_1$-$p_{30}$-$q_4$-CMP-2NHAc,
F1n-Fel d 1-$m_4$-$n_1$-$p_{30}$-$q_4$-CMP-2NHAc,
F1n-Cat albumin-$m_{16}$-$n_1$-$p_{30}$-$q_4$-CMP-2NHAc,
F1n-Can f 1-$m_6$-$n_1$-$p_{30}$-$q_4$-CMP-2NHAc,
F1n-Dog albumin-$m_{23}$-$n_1$-$p_{30}$-$q_4$-CMP-2NHAc, and
F1n-RhCE-$m_{10}$-$n_1$-$p_{30}$-$q_4$-CMP-2NHAc.

20E. Formula 1202 where n is 33 and where X' and m are as in Example 20C

By following the procedure described in Example 19F, substituting the insulin with the compounds as described in Example 20C and employing the compound of Formula 1201 where n is 33, there are obtained the corresponding compounds of Formula 1202 where n is 33.

20F. Other Compounds of Formula 1n

By following the procedure described in Example 20B and substituting the compound of Formula 1107 with the compounds obtained in Example 19J, and substituting the compound of Formula 1202 with the compounds obtained in Example 20E, there are obtained the following corresponding compounds of Formula 1n:
F1n-Abciximab-$m_{10}$-$n_{33}$-$p_{30}$-$q_8$-CMP-2OH,
F1n-Adalimumab-$m_{11}$-$n_{33}$-$p_{30}$-$q_8$-CMP-2OH,
F1n-Agalsidase alfa-$m_{14}$-$n_{33}$-$p_{30}$-$q_8$-CMP-2OH,
F1n-Agalsidase beta-$m_4$-$n_{33}$-$p_{30}$-$q_8$-CMP-2OH,
F1n-Aldeslukin-$m_6$-$n_{33}$-$p_{30}$-$q_8$-CMP-2OH,
F1n-Alglucosidase alfa-$m_{13}$-$n_{33}$-$p_{30}$-$q_8$-CMP-2OH,
F1n-Factor VIII-$m_{100}$-$n_{33}$-$p_{30}$-$q_8$-CMP-2OH,
F1n-Factor IX-$m_{18}$-$n_{33}$-$p_{30}$-$q_8$-CMP-2OH,
F1n-L-asparaginase-$m_5$-$n_{33}$-$p_{30}$-$q_8$-CMP-2OH,
F1n-Laronidase-$m_7$-$n_{33}$-$p_{30}$-$q_8$-CMP-2OH,
F1n-Octreotide-$m_1$-$n_{33}$-$p_{30}$-$q_8$-CMP-2OH,
F1n-Phenylalanine ammonia-lyase-$m_2$-$n_{33}$-$p_{30}$-$q_8$-CMP-2OH,
F1n-Rasburicase-$m_2$-$n_{33}$-$p_{30}$-$q_8$-CMP-2OH,
F1n-GAD-65-$m_8$-$n_{33}$-$p_{30}$-$q_8$-CMP-2OH,
F1n-IGRP-$m_7$-$n_{33}$-$p_{30}$-$q_8$-CMP-2OH,
F1n-MBP-$m_6$-$n_{33}$-$p_{30}$-$q_8$-CMP-2OH,
F1n-MOG-$m_5$-$n_{33}$-$p_{30}$-$q_8$-CMP-2OH,
F1n-PLP-$m_8$-$n_{33}$-$p_{30}$-$q_8$-CMP-2OH,
F1n-MBP13-32-$m_1$-$n_{33}$-$p_{30}$-$q_8$-CMP-2OH,
F1n-MBP83-99-$m_1$-$n_{33}$-$p_{30}$-$q_8$-CMP-2OH,
F1n-MBP111-129-$m_1$-$n_{33}$-$p_{30}$-$q_8$-CMP-2OH,
F1n-MBP146-170-$m_2$-$n_{33}$-$p_{30}$-$q_8$-CMP-2OH,
F1n-MOG1-20-$m_1$-$n_{33}$-$p_{30}$-$q_8$-CMP-2OH,
F1n-MOG35-55-$m_2$-$n_{33}$-$p_{30}$-$q_8$-CMP-2OH,
F1n-PLP139-154-$m_3$-$n_{33}$-$p_{30}$-$q_8$-CMP-2OH,
F1n-MART1-$m_4$-$n_{33}$-$p_{30}$-$q_8$-CMP-2OH,
F1n-Tyrosinase-$m_8$-$n_{33}$-$p_{30}$-$q_8$-CMP-2OH,
F1n-PMEL-$m_5$-$n_{33}$-$p_{30}$-$q_8$-CMP-2OH,
F1n-Aquaporin-4-$m_4$-$n_{33}$-$p_{30}$-$q_8$-CMP-2OH,
F1n-S-arrestin-$m_{12}$-$n_{33}$-$p_{30}$-$q_8$-CMP-2OH,
F1n-IRBP-$m_{21}$-$n_{33}$-$p_{30}$-$q_8$-CMP-2OH,
F1n-Conarachin-$m_{21}$-$n_{33}$-$p_{30}$-$q_8$-CMP-2OH,
F1n-Alpha-gliadin "33-mer" native-$m_1$-$n_{33}$-$p_{30}$-$q_8$-CMP-2OH,
F1n-Alpha-gliadin "33-mer" deamidated-m-$n_{33}$-$p_{30}$-$q_8$-CMP-2OH,
F1n-Alpha-gliadin-$m_1$-$n_{33}$-$p_{30}$-$q_8$-CMP-2OH,
F1n-Omega-gliadin-$m_1$-$n_{33}$-$p_{30}$-$q_8$-CMP-2OH,
F1n-Fel d 1-$m_4$-$n_{33}$-$p_{30}$-$q_8$-CMP-2OH,
F1n-Cat albumin-$m_{16}$-$n_{33}$-$p_{30}$-$q_8$-CMP-2OH,
F1n-Can f 1-$m_6$-$n_{33}$-$p_{30}$-$q_8$-CMP-2OH,
F1n-Dog albumin-$m_{23}$-$n_{33}$-$p_{30}$-$q_8$-CMP-2OH, and
F1n-RhCE-$m_{10}$-$n_{33}$-$p_{30}$-$q_8$-CMP-2OH.

Example 21

Clearance of OVA-Specific Antibodies from Circulation

To induce production of OVA-specific antibodies for subsequent depletion, C57BL/6 mice were injected i.v. with up to five doses of 10 μg OVA until a titer of anti-OVA IgG in plasma, as determined by ELISA, reached 3 (FIG. 9A). Plasma samples were prepared by centrifugation of blood collected into EDTA-coated tubes at 2000×g for 10 minutes at room temperature and stored at −20° C. until analysis. Titer is defined as the $\log_{10}$ of the maximal fold dilution of plasma with detectable anti-OVA IgG. Here, plasma samples were assayed at dilutions of 10-, 50-, 100-, 500-, 1,000-, 5,000-, 10,000-, and 50,000-fold, yielding potential titer measurements of 0, 1, 1.7, 2, 2.7, 3, 3.7, 4, and 4.7. Mice with titers below 3 after five doses of 10 μg OVA were given two additional doses of 10 μg OVA adjuvanted with 10 μg CpG-B to boost anti-OVA IgG production and hence the amount of circulating anti-OVA IgG available for depletion (FIG. 9B).

To evaluate the efficacy of hepatocyte ASGPR-targeted OVA for anti-OVA antibody clearance, mice with circulating anti-OVA IgG were injected i.v. with saline or saline containing molar equivalents of DOM and OVA, DOM-OVA, or OVA-DOM. In particular, mice were treated with molar equivalents of 10, 50, 100, or 200 μg OVA, as indicated in FIG. 9A-9B. At times t=−1 day, +3 hours, +1 day, and +7 days, relative to the time of treatment injection, blood samples were collected to assess, by ELISA analysis of plasma, the amount of anti-OVA IgG in circulation. Clearance of anti-OVA IgG from circulation is expected to decrease the amount of anti-OVA IgG in plasma and hence decrease plasma anti-OVA IgG titer as determined by ELISA. In mice immunized with OVA alone and treated with DOM-OVA or OVA-DOM, titers of anti-OVA IgG decreased by up to 3 or 2, respectively, representing decreases in the amount of circulating anti-OVA IgG by 1000- or 100-fold, which is up to 50-fold more effective than control treatment using saline or DOM and OVA (FIG. 9A). In mice immunized with OVA adjuvanted with CpG-B, clearance of circulating anti-OVA IgG was not observed (FIG. 9B).

Example 22

NOD Mouse

Non-obese diabetic (NOD) mice are susceptible to the spontaneous onset of autoimmune diabetes mellitus, which is the result of an autoimmune response to various pancreatic auto-antigens. Diabetes develops in NOD mice as a result of insulitis, characterized by the infiltration of various leukocytes into the pancreatic islets.

In order to evaluate the efficacy of a treatment for diabetes mellitus, starting at 6-weeks of age, NOD mice are divided into control or test groups and treated, respectively, with weekly intravenous injections of a test composition (10 μg) or an inactive control such as saline. The injections continue for 18 consecutive weeks.

The blood glucose concentration of the mice is measured weekly. Mice that maintain a blood glucose concentration of less than 300 mg/ml during the experiment are considered non-diabetic. In addition, at the end of the study the pancreases of the mice are harvested and T cell infiltration in the pancreas is determined via immunohistochemistry as an assessment of insulitis. Tolerance induction is assessed by the depletion of auto-antigen specific CD8 T cells as compared to mice that are treated with saline and develop diabetes. The existence of auto-antigen specific CD8 T cells is determined via ELISpot assay.

When tested as described above, compositions of Formulae 1 and 2 where X is insulin, such as F1m-insulin-$m_2$-$n_1$-$p_{30}$-$q_4$-2NAcGAL, show efficacy for treating diabetes mellitus.

While the present disclosure has been described with reference to the specific embodiments thereof, it should be understood by those skilled in the art that various changes can be made and equivalents can be substituted without departing from the true spirit and scope of the disclosure. In addition, many modifications can be made to adapt a particular situation, material, composition of matter, process, process step or steps, to the objective, spirit and scope of the present disclosure. All such modifications are intended to be within the scope of the claims appended hereto. All patents and publications cited above are hereby incorporated by reference.

The invention claimed is:

1. A composition comprising a compound of Formula 1:

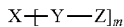

Formula 1 where:

m is an integer from 1 to 100;

X comprises a self-antigen which induces an unwanted immune response;

where Y comprises one or more structures represented by one or more of the following Formulae:

Formula Ya

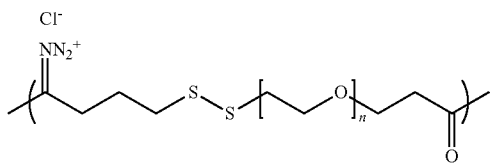

Formula Yb

Formula Yd

Formula Ye

Formula Yf

Formula Yg

-continued

Formula Yh

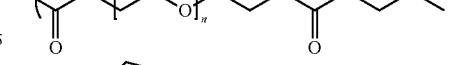

Formula Yi

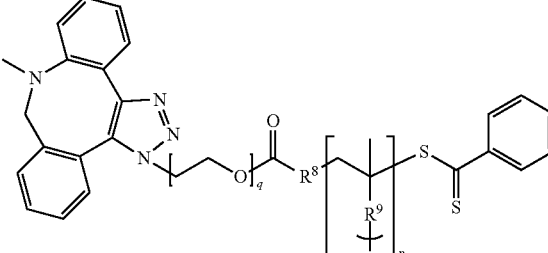

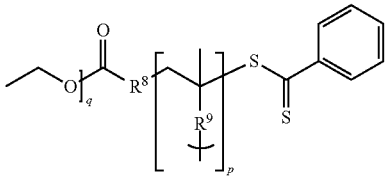

Formula Yj

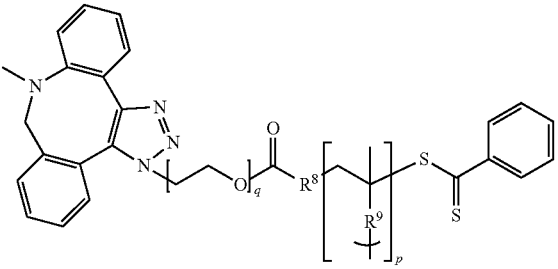

Formula Yk

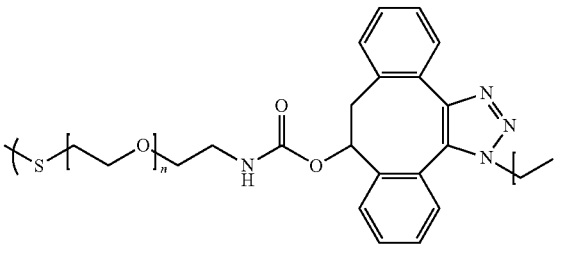

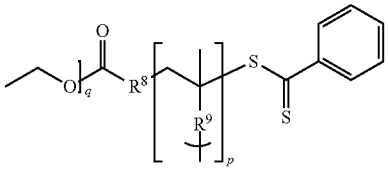

-continued

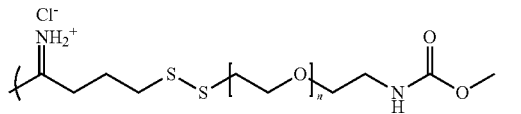

Formula YL

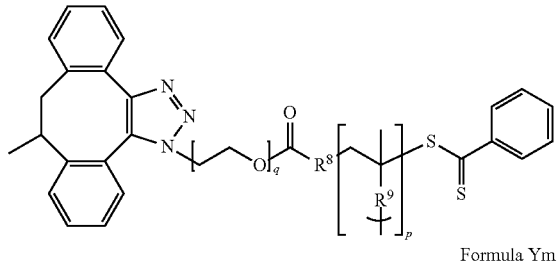

Formula Ym

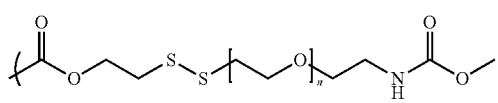

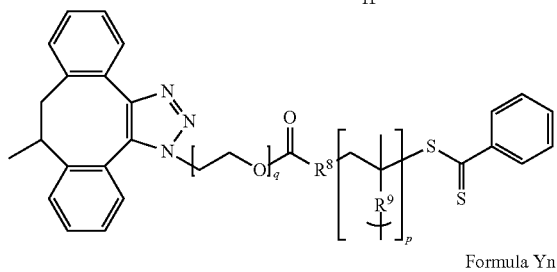

Formula Yn

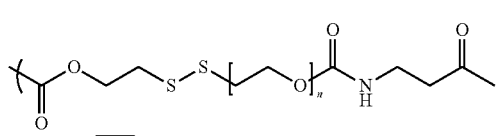

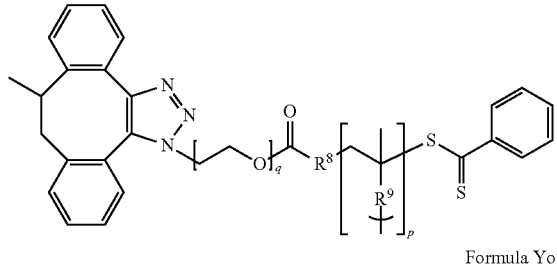

Formula Yo

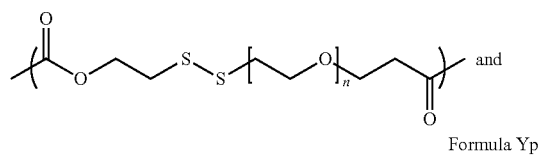

and

Formula Yp

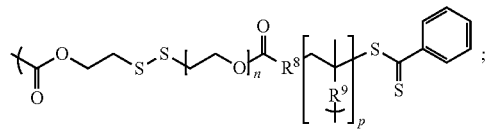

;

where:
the left bracket "(" indicates the bond between X and Y;
the right or bottom bracket and ")" indicates the bond between Y and Z;
n, where present, is an integer from 1 to 100;
p, where present, is an integer from 2 to 150;
q, where present, is an integer from 1 to 44;

$R^8$, where present, is —CH₂— or —CH₂—CH₂—C(CH₃)(CN)—; and $R^9$, where present, is a direct bond or —C(O)—NH—CH₂—CH₂—; and Z comprises one or more liver-targeting moieties.

2. The composition of claim 1 where:

n, where present, is 40 to 80;

p, where present, is 10 to 100;

q, where present, is 3 to 20;

$R^8$, where present, is —CH₂—CH₂—C(CH₃)(CN)—; and $R^9$, where present, is —C(O)—NH—CH₂—CH₂—, Z is galactose or N-acetylgalactosamine conjugated at its C1.

3. The composition of claim 1 wherein X comprises a synthetic self-antigen against the endogenous version of which patients develop an unwanted immune response.

4. The composition of claim 1, wherein X is selected from the group consisting of insulin, proinsulin, preproinsulin, glutamic acid decarboxylase-65 (GAD-65), GAD-67, glucose-6 phosphatase 2, insulinoma-associated protein 2, and insulinoma-associated protein 213.

5. The composition of claim 1, wherein X is selected from the group consisting of myelin basic protein, myelin oligodendrocyte glycoprotein, myelin proteolipid protein, SEQ ID NO:11, SEQ ID NO:12, SEQ ID NO:13, SEQ ID NO:14, SEQ ID NO:15, SEQ ID NO:16, and SEQ ID NO:17.

6. The composition of claim 1, wherein X is transglutaminase.

7. The composition of claim 1, where Y further comprises the following group:

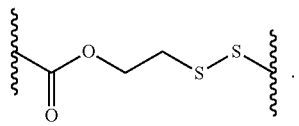 [SMILES: *SSCCOC(*)=O]

8. The composition of claim 1, wherein Z comprises galactose, galactosamine or N-acetylgalactosamine.

9. The composition of claim 8, wherein Z is conjugated at its C1, C2 or C6 to Y.

10. The composition of claim 1, wherein Y is prepared using N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NETS-ester linkers, or nitrophenoxy poly(ethylene glycol)ester linkers.

11. The composition of claim 1 where Y comprises Formula Ym.

12. The composition of claim 11, wherein X is a synthetic self-antigen against the endogenous version of which patients develop an unwanted immune response.

13. The composition of claim 11, wherein Z is N-acetylgalactosamine conjugated at its C1 position.

14. The composition of claim 11, wherein Z is galactose conjugated at its C1 position.

15. The composition of claim 11, wherein n is 40 to 80; and p is 10 to 100.

16. The composition of claim 11, wherein X is associated with an autoimmune disease selected from the group consisting of Type I diabetes, multiple sclerosis, rheumatoid arthritis, vitiligo, uveitis, pemphigus vulgaris and neuromyelitis optica.

17. A compound represented by Formula 1:

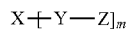

Formula 1 where:
m is an integer from 1 to 100;
X comprises a self-antigen, wherein the self-antigen is capable of inducing an unwanted immune response;
Y comprises a linker moiety comprising one or more of the following Formulae:

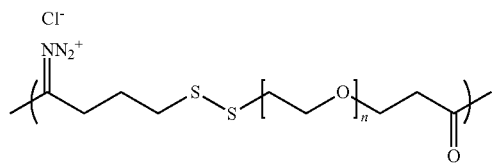

Formula Ya

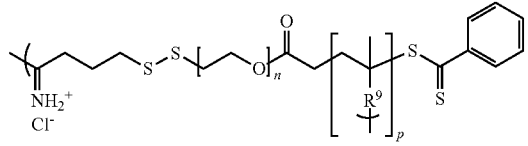

Formula Yb

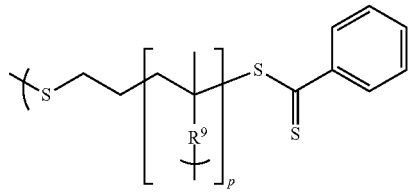

Formula Yd

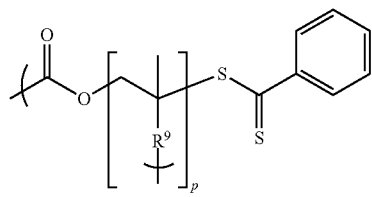

Formula Ye

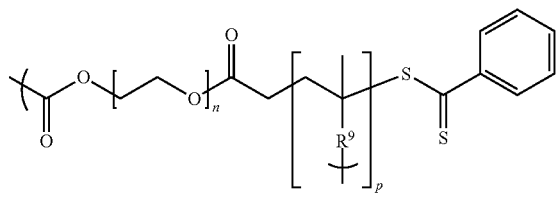

Formula Yf

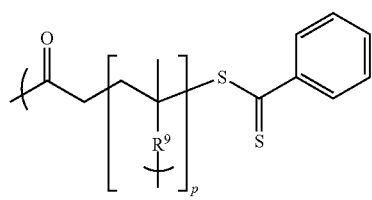

Formula Yg

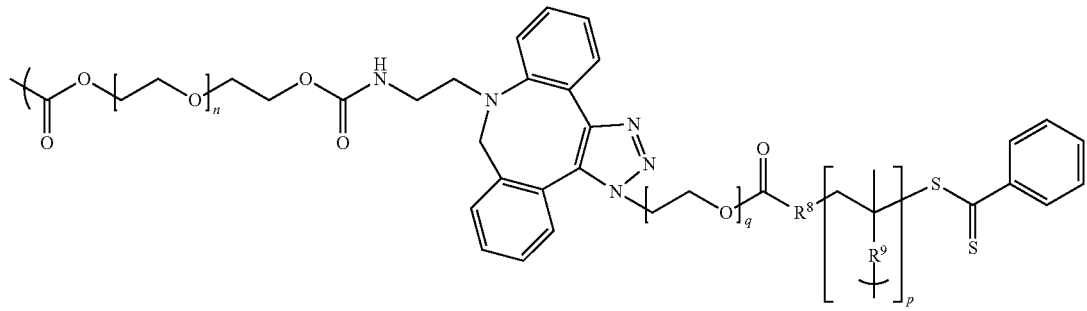

Formula Yh

Formula Yi
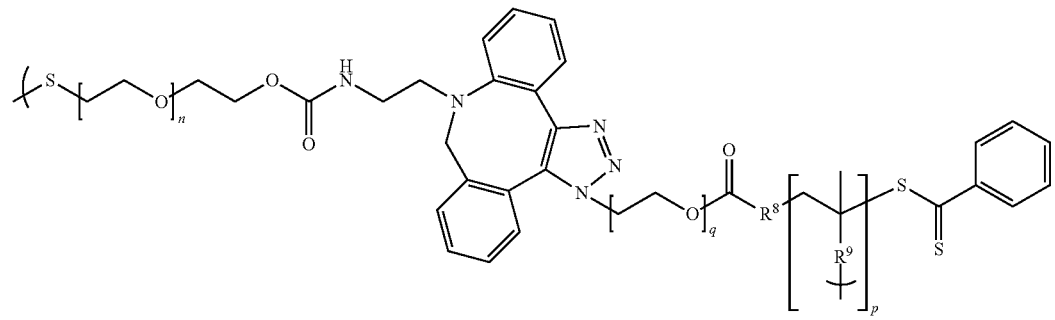
Formula Yj
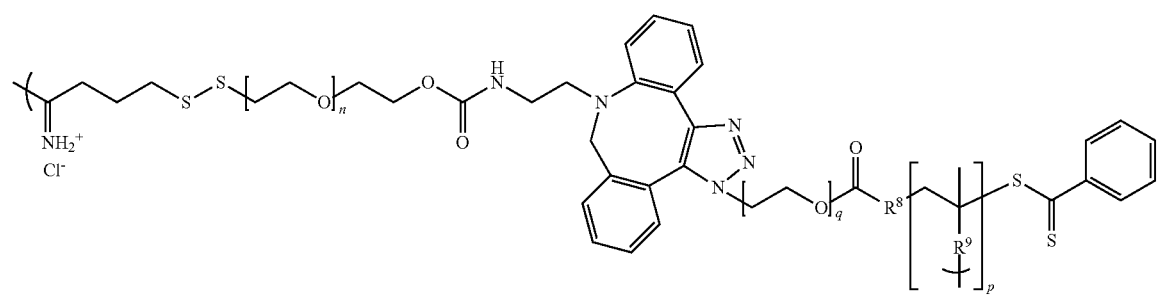
Formula Yk
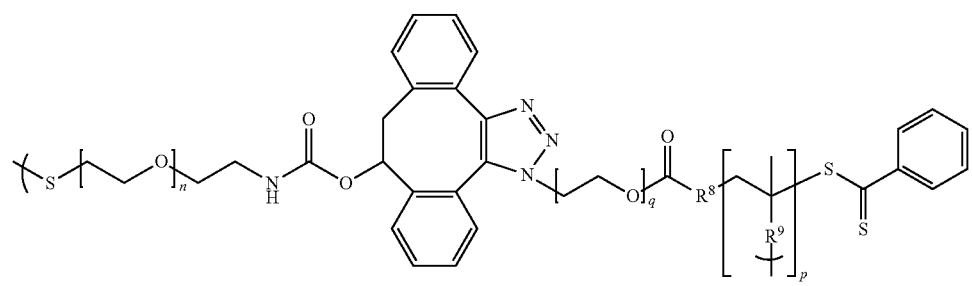
Formula YL
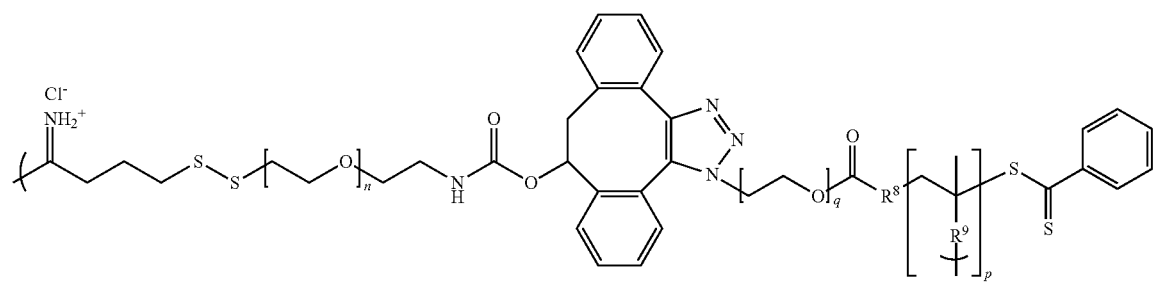
Formula Ym
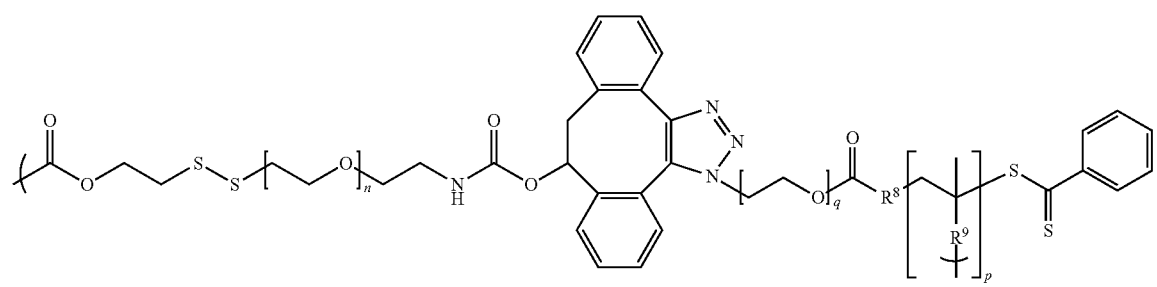

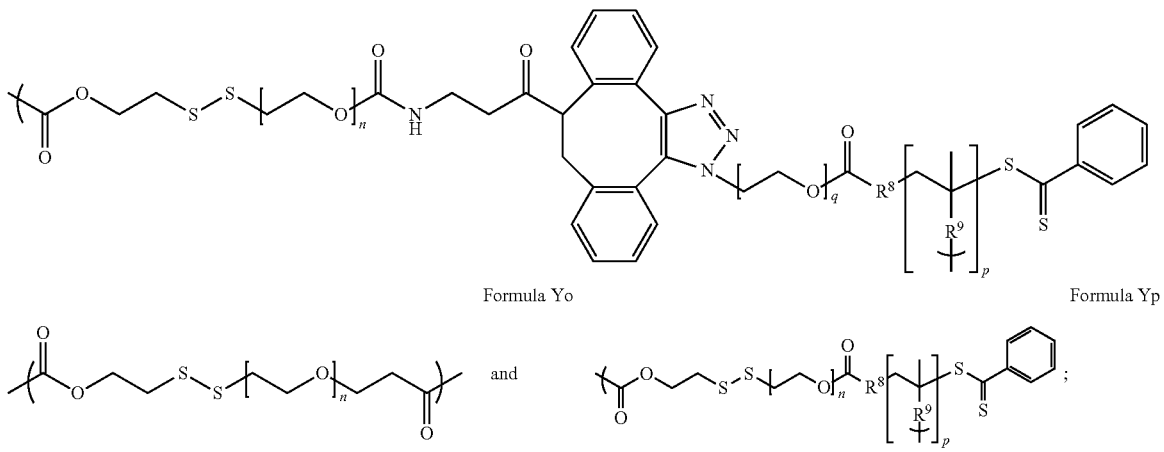

Formula Yn, Formula Yo, Formula Yp where:
the left bracket "(" indicates the bond between X and Y;
the right or bottom bracket and ")" indicates the bond between Y and Z;
n, where present, is an integer from 1 to 100;
p, where present, is an integer from 2 to 150;
q, where present, is an integer from 1 to 44;
$R^8$, where present, is —$CH_2$— or —$CH_2$—$CH_2$—C($CH_3$)(CN)—; and
$R^9$, where present, is a direct bond or —C(O)—NH—$CH_2$—$CH_2$—; and
Z comprises one or more liver-targeting moieties.

18. The compound of claim 17, wherein the self-antigen is selected from the group consisting of insulin, proinsulin, preproinsulin, glutamic acid decarboxylase-65 (GAD-65), GAD-67, glucose-6 phosphatase 2, insulinoma-associated protein 2, and insulinoma-associated protein 213.

19. The compound of claim 17, wherein X is associated with an autoimmune disease selected from the group consisting of Type I diabetes, multiple sclerosis, rheumatoid arthritis, vitiligo, uveitis, pemphigus vulgaris and neuromyelitis optica.

20. The compound of claim 17, wherein X is selected from the group consisting of myelin basic protein, myelin oligodendrocyte glycoprotein, myelin proteolipid protein, SEQ ID NO:11, SEQ ID NO:12, SEQ ID NO:13, SEQ ID NO:14, SEQ ID NO:15, SEQ ID NO:16, and SEQ ID NO:17.

21. The compound of claim 17, wherein Z comprises galactose, galactosamine or N-acetylgalactosamine.

22. The compound of claim 21, comprising Z conjugated at its C1, C2 or C6 to Y.

23. The compound of claim 22, wherein X is associated with Type I diabetes.

24. The compound of claim 22, wherein X is associated with multiple sclerosis.

25. The compound of claim 22, wherein Y is Ym.

26. The compound of claim 21, wherein Z is N-acetylgalactosamine conjugated at its C1 position.

* * * * *